United States Patent
Yokota et al.

(10) Patent No.: US 11,834,421 B2
(45) Date of Patent: Dec. 5, 2023

(54) SATURATED-RING-FUSED DIHYDROPYRIMIDINONE OR DIHYDROTRIAZINONE COMPOUNDS AND PHARMACEUTICAL USE THEREOF

(71) Applicant: Japan Tobacco Inc., Tokyo (JP)

(72) Inventors: Masahiro Yokota, Osaka (JP); Noriyoshi Seki, Osaka (JP); Eiichi Watanabe, Osaka (JP); Shingo Fujioka, Osaka (JP)

(73) Assignee: Japan Tobacco Inc., Tokyo (JP)

( * ) Notice: Subject to any disclaimer, the term of this patent is extended or adjusted under 35 U.S.C. 154(b) by 155 days.

(21) Appl. No.: 17/334,517

(22) Filed: May 28, 2021

(65) Prior Publication Data

US 2022/0119355 A1 Apr. 21, 2022

Related U.S. Application Data

(63) Continuation of application No. 16/287,871, filed on Feb. 27, 2019, now abandoned.

(30) Foreign Application Priority Data

Feb. 28, 2018 (JP) .................. 2018-035601

(51) Int. Cl.

| | | |
|---|---|---|
| *A61K 31/519* | (2006.01) | |
| *A61K 31/517* | (2006.01) | |
| *A61K 31/53* | (2006.01) | |
| *C07D 239/80* | (2006.01) | |
| *C07D 239/82* | (2006.01) | |
| *C07D 239/70* | (2006.01) | |
| *C07D 253/10* | (2006.01) | |
| *C07D 253/06* | (2006.01) | |
| *C07D 471/04* | (2006.01) | |
| *C07D 487/04* | (2006.01) | |
| *C07D 491/048* | (2006.01) | |
| *C07D 491/052* | (2006.01) | |
| *C07D 498/04* | (2006.01) | |
| *A61P 9/10* | (2006.01) | |
| *A61P 9/12* | (2006.01) | |
| *A61P 27/02* | (2006.01) | |
| *A61P 35/00* | (2006.01) | |
| *A61P 37/00* | (2006.01) | |
| *A61P 37/08* | (2006.01) | |

(52) U.S. Cl.
CPC ......... *C07D 239/82* (2013.01); *C07D 239/70* (2013.01); *C07D 487/04* (2013.01); *C07D 491/048* (2013.01); *C07D 498/04* (2013.01)

(58) Field of Classification Search
CPC .... A61K 31/519; A61K 31/517; A61K 31/53; C07D 239/80; C07D 239/82; C07D 239/70; C07D 253/10; C07D 253/06; C07D 471/04; C07D 487/04; C07D 491/048; C07D 491/052; C07D 498/04; A61P 1/02; A61P 9/10; A61P 9/12; A61P 27/02; A61P 35/00; A61P 37/00; A61P 37/08; Y02A 50/30

See application file for complete search history.

(56) References Cited

U.S. PATENT DOCUMENTS

| | | |
|---|---|---|
| 7,868,000 B2 | 1/2011 | Zhu et al. |
| 8,426,403 B2 | 4/2013 | Zhu et al. |
| 8,450,331 B2 | 5/2013 | Zhu et al. |
| 8,541,427 B2 | 9/2013 | Stamford et al. |
| 8,822,456 B2 | 9/2014 | Brodney et al. |
| 9,045,498 B2 | 6/2015 | Brodney et al. |

(Continued)

FOREIGN PATENT DOCUMENTS

| | | |
|---|---|---|
| CN | 101809016 A | 8/2010 |
| JP | 2011518225 A | 6/2011 |

(Continued)

OTHER PUBLICATIONS

Baeten, D. et al. (Nov. 23, 2013; e-pub. Sep. 13, 2013). "Anti-Interleukin-17A Monoclonal Antibody Secukinumab in Treatment of Ankylosing Spondylitis: A Randomised, Double-Blind, Placebo-Controlled Trial," Lancet 382(9906):1705-1713.

(Continued)

*Primary Examiner* — Brenda L Coleman
(74) *Attorney, Agent, or Firm* — MORRISON & FOERSTER LLP

(57) ABSTRACT

The present invention relates to saturated-ring-fused dihydropyrimidinone or dihydrotriazinone compounds, or pharmaceutically acceptable salts having RORγ antagonist activity, pharmaceutical compositions comprising the same, and pharmaceutical use thereof. A compound of Formula [I] or a pharmaceutically acceptable salt thereof, a pharmaceutical composition comprising the same, and pharmaceutical use thereof are provided:

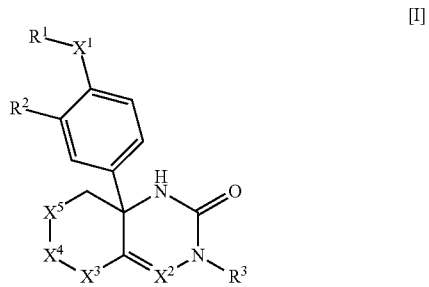

wherein each substituent is defined as defined in the description.

28 Claims, No Drawings

(56) References Cited

U.S. PATENT DOCUMENTS

| | | |
|---|---|---|
| 9,198,917 B2 | 12/2015 | Brodney et al. |
| 9,266,886 B2 | 2/2016 | Lotesta et al. |
| 9,624,217 B2 | 4/2017 | Claremon et al. |
| 10,047,085 B2 | 8/2018 | Claremon et al. |
| 10,047,098 B2 | 8/2018 | Dai et al. |
| 10,196,363 B2 | 2/2019 | Yokota et al. |
| 10,399,976 B2 | 9/2019 | Claremon et al. |
| 10,807,980 B2 | 10/2020 | Claremon et al. |
| 11,008,340 B2 | 5/2021 | Claremon et al. |
| 11,535,614 B2 | 12/2022 | Claremon et al. |
| 2007/0060575 A1 | 3/2007 | Zhu et al. |
| 2010/0256128 A1 | 10/2010 | Zhu et al. |
| 2011/0110927 A1 | 5/2011 | Stamford et al. |
| 2011/0110957 A1 | 5/2011 | Stamford et al. |
| 2014/0163015 A1 | 6/2014 | Brodney et al. |
| 2014/0323474 A1 | 10/2014 | Brodney et al. |
| 2015/0218160 A1 | 8/2015 | Claremon et al. |
| 2015/0231144 A1 | 8/2015 | Brodney et al. |
| 2016/0194290 A1 | 7/2016 | Yokota et al. |
| 2016/0200724 A1 | 7/2016 | Claremon et al. |
| 2017/0260180 A1 | 9/2017 | Claremon et al. |
| 2017/0362248 A1 | 12/2017 | Dai et al. |
| 2018/0370968 A1 | 12/2018 | Claremon et al. |
| 2019/0300490 A1 | 10/2019 | Yokota et al. |
| 2019/0322687 A1 | 10/2019 | Claremon et al. |
| 2019/0359575 A1 | 11/2019 | Yokota et al. |
| 2020/0172535 A1 | 6/2020 | Claremon et al. |
| 2021/0130300 A1 | 5/2021 | Yokota et al. |
| 2021/0238174 A1 | 8/2021 | Claremon et al. |

FOREIGN PATENT DOCUMENTS

| | | |
|---|---|---|
| JP | 2016502978 A | 2/2016 |
| WO | 2016093342 A1 | 6/2006 |
| WO | 2006138264 A2 | 12/2006 |
| WO | 2006138264 A3 | 3/2007 |
| WO | 2013064231 A1 | 5/2013 |
| WO | 2015116904 A1 | 8/2015 |
| WO | 2016085780 A1 | 6/2016 |
| WO | 2017087608 A1 | 5/2017 |

OTHER PUBLICATIONS

Crispin, J.C. et al. (2010). "Interleukin-17-Producing T Cells In Lupus," Current Opinion in Rheumatology 22(5):499-503.

Dutzan, N. et al. (Oct. 17, 2018). "A Dysbiotic Microbiome Triggers TH17 Cells to Mediate Oral Mucosal Immunopathology in Mice and Humans," Sci. Transl. Med. 10(463):eaat0797, 13 pages.

Emamaullee, J.A. et al. (Jun. 2009). "Inhibition of Th17 Cells Regulates Autoimmune Diabetes in NOD Mice," Diabetes 58:1302-1311.

Extended European Search Report, dated Jun. 7, 2021, for European Patent Application No. 19761273.2, 6 pages.

Feagan, B.G. et al. (Apr. 29, 2017; e-pub. Apr. 12, 2017). "Induction Therapy With the Selective Interleukin-23 Inhibitor Risankizumab in Patients With Moderate-to-Severe Crohn's Disease: A Randomised, Double-Blind, Placebo-Controlled Phase 2 Study," The Lancet 389(10080):1699-1709.

Fulton, L.M. et al. (2012; e-pub. Jul. 9, 2012). "Attenuation of Acute Graft-versus-Host Disease in the Absence of the Transcription Factor RORγt," Journal of Immunology 189(4):1765-1772.

Havrdova, E. et al. (Jul. 2016; e-pub. May 3, 2016). "Activity of Secukinumab, an Anti-IL-17A Antibody, on Brain Lesions in RRMS: Results From a Randomized, Proof-of-Concept Study," J. Neurol. 263(7):1287-1295.

Hueber, W. et al. (Oct. 6, 2010). "Effects of AIN457, a Fully Human Antibody to Interleukin-HA, on Psoriasis, Rheumatoid Arthritis, and Uveitis," Science Translational Medicine 2(52):52ra72, 11 pages.

International Search Report, dated May 7, 2019, for PCT Application No. PCT/JP2019/007435, filed Feb. 27, 2019, 2 pages.

Ivanov, I.I. et al. (Sep. 22, 2006). "The Orphan Nuclear Receptor RORγt Directs the Differentiation Program of Proinflammatory IL-17+ T Helper Cells," Cell 126(6):1121-1133.

Jetten, A.M. (2009; e-pub. Apr. 3, 2009). "Retinoid-Related Orphan Receptors (RORs): Critical Roles in Development, Immunity, Circadian Rhythm, and Cellular Metabolism," Nucl. Recept. Signal. 7:e003, 32 pages.

Kelchtermans, H. et al. (Aug. 17, 2009). "Effector Mechanisms of Interleukin-17 in Collagen-Induced Arthritis in the Absence of Interferon-γ and Counteraction by Interferon-γ," Arthritis Research & Therapy 11(4):R122, 13 pages.

Koenders, M.I. et al. (Dec. 2006). "Potential New Targets in Arthritis Therapy: Interleukin (IL)-17 And 15 its Relation to Tumour Necrosis Factor and IL-1 in Experimental Arthritis," Ann. Rheum. Dis. 65 (Suppl. III):iii29-iii33.

Leppkes, M. et al. (2009). "RORγ-Expressing Th17 Cells Induce Murine Chronic Intestinal Inflammation via Redundant Effects of IL-17A and IL-HF," Gastroenterology 136(1):257-267.

Liao, Y.H. et al. (Jan. 24, 2012). "Interleukin-17A Contributes to Myocardial Ischemia/Reperfusion Injury by Regulating Cardiomyocyte Apoptosis and Neutrophil Infiltration," J. Am. Coll. Cardiol. 59(4):420-429.

Meissburger, B. et al. (2011). "Adipogenesis and Insulin Sensitivity in Obesity are Regulated by Retinoid-Related Orphan Receptor Gamma," EMBO Mol. Med. 3:637-651.

Mi, S. et al. (2011; e-pub. Aug. 11, 2011). "Blocking IL-17 A Promotes the Resolution of Pulmonary Inflammation and Fibrosis Via TGF-β1-Dependent and -Independent Mechanisms," Journal of Immunology 187:3003-3014.

Nakae, S. et al. (2003). "Suppression of Immune Induction of Collagen-Induced Arthritis in IL-17-Deficient Mice," J. Immunol. 171:6173-6177.

Rutz, S. et al. (2016, e-pub. Jul. 25, 2016). "Post-Translational Regulation of RORγt-A Therapeutic Target For The Modulation of Interleukin-17-Mediated Responses in Autoimmune Diseases," Cytokine & Growth Factor Reviews 30:1-17.

Saleh, M.A. et al. (2016). "Inhibition of Interleukin 17-A But Not Interleukin-17F Signaling Lowers Blood Pressure and Reduces End-organ Inflammation in Angiotensin II-induced Hypertension," JACC Basic Transl. Sci. 1(7):606-616.

Sanford, M. et al. (2015, e-pub. Feb. 4, 2015). "Secukinumab: First Global Approval," Drugs 75(3):329-338.

Schmidt-Weber, C.B. et al. (Aug. 2007). "TH17 Cells in the Big Picture of Immunology," J. Allergy Clin. Immunol. 120(2):247-254.

Shi, W. et al. (2013). "Anti-IL-17 Antibody Improves Hepatic Steatosis by Suppressing Interleukin-17-Related Fatty Acid Synthesis and Metabolism," Clin. Dev. Immunol. 2013(Article ID 253046):1-9.

Speeckaert, R. et al. (Nov. 2016; e-pub. Apr. 26, 2016). "The Many Faces of Interleukin-17 In Inflammatory Skin Diseases," Br. J. Dermatol. 175(5):892-901.

Steinmetz, O.M. et al. (2011). "The Th17-Defining Transcription Factor RORγt Promotes Glomerulonephritis," Journal of the American Society of Nephrology 22(3):472-483.

Tilley, S.L. et al. (Mar. 1, 2007). "Retinoid-Related Orphan Receptor γ Controls Immunoglobulin Production and Th1/Th2 Cytokine Balance in the Adaptive Immune Response to Allergen," J. Immunol. 178(5):3208-3218.

U.S. Nat. Inst. Health. ClinicalTrials.gov Identifier: NCT02443298. (May 13, 2015). "Efficacy & Safety of BI 655066/ABBV-066 (Risankizumab) in Patients With Severe Persistent Asthma. (Official Title)—Phase IIa, Randomized, Double-blind, Placebo Controlled, Parallel Group Study to Assess the Safety and Efficacy of Subcutaneously Administered BI 655066/ABBV-066 (Risankizumab) as . . . ", 9 pages.

U.S. National Inst. of Health . . . ClinicalTrials.gov Identifier: NCT02044848. (Jan. 24, 2014). Study of Secukinumab in Patients With Newly-diagnosed Type 1 Diabetes Mellitus. (Official Title)—A Randomized, Double-blind, Multiple Dose, Placebo-controlled Study to Evaluate the Safety, Tolerability, Immunogenicity, Pharmacokinetics, and Efficacy of Secukinumab in Adult and Pediatric . . . 5 pages.

U.S. National Institutes of Health. ClinicalTrials.gov ID: NCT01389973. (Jul. 8, 2011). "A Study of Efficacy and Safety of Ustekinumab in

(56) References Cited

OTHER PUBLICATIONS

Patients w/ Primary Biliary Cirrhosis (PBC) Who Had an Inadequate Response to Ursodeoxycholic Acid," located at https://clinicaltrials.gov/ct2/show/NCT01389973?term=NCT01389973&rank=1, last visited on May 2, 2019.

U.S. National Institutes of Health. ClinicalTrials.gov Identifier: NCT01250171. (Nov. 30, 2010). "The Effects of a Single Intravenous Administration of Secukinumab (AIN457) or Canakinumab (ACZ885) in Dry Eye Patients," 8 pages.

U.S. National Institutes of Health. ClinicalTrials.gov Identifier: NCT02594098 (Nov. 2, 2015). "Secukinumab for Treatment of Atopic Dermatitis—(Official Title)—A Pilot Study to Evaluate the Efficacy and Safety of Secukinumab in the Treatment of Moderate to Severe Atopic Dermatitis ," located at https://clinicaltrials.gov/ct2/show/ NCT02594098?. . . , last visited on May 2, 2019, 9 pages.

U.S. National Institutes of Health. ClinicalTrials.gov Identifier: NCT02599129. (Nov. 6, 2015). "A Study of Secukinumab for the Treatment of Alopecia Areata. (Official Title)—An Exploratory Study to Evaluate the Safety and Efficacy of Secukinumab in the Treatment of Extensive Alopecia Areata," located at https://clinicaltrials.gov/ct2/show/ . . . , last visited on May 2, 2019, 7 pages.

U.S. National Institutes of Health. ClinicalTrials.gov Identifier: NCT02733094. (Apr. 11, 2016). "Single-arm Study to Assess a Potential Effect of Anti-IL-17 (Secukinumab) in the Treatment of Pyoderma Gangrenosum," located at https://clinicaltrials.gov/ct2/show/NCT02733094?term=NCT02733094&rank=1, last visited on May 2, 2019, 6 pages.

U.S. National Institutes of Health. ClinicalTrials.gov Identifier: NCT03137160. (May 2, 2017). "An Open-Label, Proof-of-Concept Study of Ixekizumab in the Treatment of Pyoderma Gangrenosum," located at https://clinicaltrials.gov/ct2/show/NCT03137160?term=NCT03137160&rank=1, last visited on May 2, 2019, 7 pages.

Xu, R. et al. (Sep. 2013; e-pub. Jun. 19, 2013). "Neutralization of Interleukin-17 Attenuates High Fat Diet-Induced Non-Alcoholic Fatty Liver Disease in Mice," Acta Biochim. Biophys. Sin. 45(9):726-733.

Zhang, Q. et al. (Jun. 2017; e-pub. Feb. 27, 2017). "Targeting Th17-IL-17 Pathway in Prevention of Micro-Invasive Prostate Cancer in a Mouse Model," Prostate 77(8):888-899, 18 pages.

Zigeuner, G. et al. (1970). "Heterocycles. XXVI. Hexahydro-2(1H)-Quinazolines and -Thiones," Montash. Chem. 101(6):1745-1750, (with English Abstract only).

SATURATED-RING-FUSED DIHYDROPYRIMIDINONE OR DIHYDROTRIAZINONE COMPOUNDS AND PHARMACEUTICAL USE THEREOF

CROSS REFERENCE TO RELATED APPLICATIONS

This application is a continuation application of U.S. patent application Ser. No. 16/287,871, filed Feb. 27, 2019, which claims priority to and benefit of Japanese Patent Application No. 2018-035601, filed Feb. 28, 2018, the disclosure of which is incorporated herein by reference in its entirety.

TECHNICAL FIELD

The present invention relates to saturated-ring-fused dihydropyrimidinone or dihydrotriazinone compounds, or pharmaceutically acceptable salts thereof, having RORγ antagonist activity, pharmaceutical compositions comprising the same, and pharmaceutical use thereof.

BACKGROUND ART

RORγ (i.e., Retinoid-related Orphan Receptor gamma) is nuclear receptor which is important for the differentiation and activation of Th17 cells. RORγt is also known as a splicing variant of RORγ (Non patent literature 1). RORγ and RORγt differ only in their N-terminal domains and share the same ligand-binding domain and DNA-binding domain. It is reported that RORγ is expressed in other tissues besides Th17 cells (Non Patent Literature 1).

Inhibition of RORγ can inhibit the differentiation and activation of Th17 cells. IL-17 produced in Th17 cells is involved in the induction of a variety of chemokines, cytokines, metalloproteases, and other inflammatory mediators and the migration of neutrophil, and therefore, inhibition of IL-17 may lead to inhibit such induction and migration (Non Patent Literatures 2 and 3). It is known that Th17 cells are involved in autoimmune diseases (such as rheumatoid arthritis, psoriasis, inflammatory bowel disease (such as Crohn's disease and ulcerative colitis), multiple sclerosis, systemic lupus erythematosus (SLE), Behcet's disease, sarcoidosis, Harada disease, ankylosing spondylitis, uveitis, polymyalgia rheumatica, type I diabetes, draft-versus-host disease, alopecia areata, and vitiligo), allergic diseases, dry eye, fibrosis (such as lung fibrosis and primary biliary cirrhosis), and cancers (such as malignant melanoma and prostate cancer).

RORγ in adipose tissues is related to the regulation of adipogenesis and inhibition of RORγ can ameliorate insulin resistance (Non Patent Literature 4). It is known that adipose tissues are involved in metabolic diseases (such as hepatic steatosis).

It also known that IL-17 and Th17 cells are involved in ischemia, cardiomyopathy, hypertension, and periodontitis.

For example, as for rheumatoid arthritis, it is reported that administration of anti-IL-17 antibody can ameliorate swelling and joint destruction associated with collagen-induced arthritis (Non Patent Literature 5). It is also reported that swelling and joint destruction with associated collagen-induced arthritis can be ameliorated in experiments using IL-17-deficient mice (Non Patent Literature 6).

As for psoriasis, it is reported that administration of anti-IL-17 antibody is effective in treating psoriasis in clinical trials (Non Patent Literature 7). Anti IL-17 antibodies have been placed on the market for use in psoriasis (Non Patent Literature 8).

As for inflammatory bowel diseases such as Crohn's disease and ulcerative colitis, adaptive transfer of T cells derived from RORγ-KO mice does not increase IL-17 in the mucosa in a colitis model induced by the adaptive transfer of T cells, thereby the onset of colitis can be inhibited (Non Patent Literature 9). It is also reported that an anti-IL-23 antibody, an antibody against IL-23 which activates Th17 cells, was effective in treating Crohn's disease in clinical trials (Non Patent Literature 20).

As for multiple sclerosis, the disease state of a mouse experimental autoimmune encephalomyelitis model which is an animal model of multiple sclerosis can be inhibited in RORγ-KO mice (Non Patent Literature 10). It is also reported that an anti-IL-17A antibody can ameliorate MRI observation in relapsing remitting multiple sclerosis in clinical trials (Non Patent Literature 21).

As for systemic lupus erythematosus, it is reported that administration of anti-IL-17 antibody can inhibit onset of GBM nephritis model in RORγt-KO mice which is an animal model of glomerulenephritis (Non Patent Literature 11). Administration of anti-IL-17 antibody potentially inhibits nephritis associated with SLE as well (Non Patent Literature 12).

As for ankylosng spondylitis, it is reported that administration of anti-IL-17 antibody is effective in treating ankylosing spondylitis (Non Patent Literature 13).

As for uveitis, it is reported that administration of anti-IL-17 antibody is effective in treating uveitis associated with Behcet's disease, sarcoidosis, and Harada disease (Non Patent Literature 7).

As for polymyalgia rheumatica, efficacy of anti-17 antibody is currently assessed an clinical trials for polymyalgia rheumatica.

As for type I diabetes, administration of anti-IL-17 antibody can inhibit progression of disease states in a NOD mouse model which is a type I diabetes model (Non Patent Literature 14). Efficacy of anti-IL-17A antibody is currently assessed in clinical trials (Non Patent Literature 22).

As for graft-versus-host disease, it is reported that transfection of RORγ-KO-mouse-derived cells can ameliorate survival rates and rejections in a host in mouse transplant model (Non Patent Literature 19).

As for alopecia areata, efficacy of anti-IL-17A antibody is currently assessed in clinical trials (Non Patent Literature 25).

As for vitiligo, increases of IL-17 and Th17 cells are recognized in patient sera and pathological tissues, respectively (Non Patent Literature 34).

As for allergic diseases such as asthma, attenuated eosinophilic pulmonary inflammation, the reduced number of CD4+ lymphocytes, and the decrease of Th2 cytokines/chemokines levels are exhibited in RORγ-KO mice in an OVA-sensitized model, which then allergic reactions can be inhibited (Non Patent Literature 15). Efficacy of anti-IL17A antibody is currently assessed in clinical trials for atopic dermatitis (Non Patent Literature 23). Efficacy of anti-IL-23 antibody is currently assessed in clinical trials for asthma (Non Patent Literature 24).

As for dry eye, it is reported that Th17 cells increase in an animal model of dry eye, and efficacy of anti-IL-17 antibody is currently assessed in clinical trials for dry eye patients (Non Patent Literature 16).

As for fibrosis, administration of anti-IL-17 antibody can inhibit inflammation and fibrosis in lung and extend survival of animals in a bleomycin-induced lung fibrosis model which is an animal model of lung fibrosis (Non Patent Literature 17).

As for primary biliary cirrhosis, it is reported that Th17 cells increase in the lesion area of patients with primary biliary cirrhosis, and efficacy of anti-IL-23 antibody is currently assessed in clinical trials (Non Patent Literature 18).

As for malignant melanoma, efficacy of anti-IL-17 antibody is currently assessed in clinical trials (Non Patent Literatures 26 and 27).

As for prostate cancer, it is recognized that anti-IL-17 antibody treatment decreased the formation of micro-invasive prostate cancer in Pten-null mice (Non Patent Literature 28).

As for insulin resistance, the insulin resistance induced by feeding high-fat diets can be inhibited in RORγ KO mice (Non Patent Literature 4).

As for hepatic steatosis, it is recognized that anti-IL-17 antibody ameliorated steatosis on pathological tissues in an alcoholic liver-disease model (Non Patent Literature 29).

As for non-alcoholic fatty liver disease, it is recognized that anti-IL-17 antibody treatment improved liver function, attenuated hepatic lipid accumulation, suppressed Kupffer cells activation, and decreased proinflammatory cytokines levels in a high fat diet-induced non-alcoholic fatty liver disease model (Non Patent Literature 30).

As for ischemia and cardiomyopathy, it is reported that IL-17A contributes to myocardial ischemia/reperfusion injury by regulating cardiomyocyte apoptosis and neutrophil infiltration. It is recognized that anti-IL-17A antibody treatment or IL-17A knockout reduced infarct size, improved cardiac function, and thus, ameliorated ischemia/reperfusion injury (Non Patent Literature 31).

As for hypertension, it is reported that treatment with antibody against IL-17A or IL-17RA suppressed increased blood pressure by administration of angiotensin IIT (Non Patent Literature 32).

As for periodontitis, increase of Th17 cells or IL-17 was recognized in an experimental periodontitis model. It is reported that treatment with RORγ antagonist, GSK805, or anti-IL-17A antibody diminished bone loss in the model (Non Patent Literature 33).

On the basis of these findings, RORγ antagonists are deemed to be beneficial for preventing or treating autoimmune diseases, allergic diseases, dry eye, fibrosis, cancers (such as malignant melanoma and prostate cancer), metabolic disease, ischemia, cardiomyopathy, hypertension, and periodontal disease.

[Non Patent Literature 1] JETTEN, "Retinoid-related orphan receptors (RORs): critical roles in development, immunity, circadian rhythm, and cellular metabolism", Nucl. Recept. Signal., 7: e003 (2009).

[Non Patent Literature 2] KOENDERS, et al., "Potential new targets in arthritis therapy: interleukin (IL)-17 and its relation to tumour necrosis factor and IL-1 in experimental arthritis", Ann. Rheum. Dis., 65: iii29-33 (2006).

[Non Patent Literature 3] SCHMIDT-WEBER, et al., "Th17 cells in the big picture of immunology", J. Allergy Clin. Immunol., 120: 247-54 (2007).

[Non Patent Literature 4] MEISSBURGER, et al., "Adipogenesis and insulin sensitivity in obesity are regulated by retinoid related orphan receptor gamma", EMBO Mol. Med., 3: 637-51 (2011).

[Non Patent Literature 5] KELCHTERMANS et al., "Effector mechanisms of interleukin-17 in collagen-induced arthritis in the absence of interferon-γ and counteraction by interferon-γ", Arthritis Res. Ther., 11(4): R122 (2009).

[Non Patent Literature 6] NAKAE, et al., "Suppression of Immune Induction of Collagen-Induced Arthritis in IL-17-Deficient Mice", J. Immunol., 171: 6173-6177 (2003).

[Non Patent Literature 7] HUEBER et al., "Effects of AIN457, a Fully Human Antibody to Interleukin-17A, on Psoriasis, Rheumatoid Arthritis, and Uveitis", Sci. Transl. Med., 2(52): 52ra72 (2010).

[Non Patent Literature 8] SANFORD et al., "Secukinumab: first global approval", Drugs, 75(3): 329-338 (2015).

[Non Patent Literature 9] LEPPKES, et al, "RORγ-Expressing Th17 Cells Induce MurineChronic Intestinal Inflammation via Redundant Effects of IL-17A and IL-17F", Gastroenterology, 136(1): 257-267 (2009).

[Non Patent Literature 10] IVANOV et al., "The Orphan Nuclear Receptor RORγt Directs the Differentiation Program of Proinflammatory IL-17+ T Helper Cells", Cell, 126 (6): 1121-1133 (2006).

[Non Patent Literature 11] STEINMETZ et al., "The Th17-Defining Transcription Factor RORγt Promotes Glomerulonephritis", J. Am. Soc. Nephrol., 22(3): 472-483 (2011).

[Non Patent Literature 12] CRISPIN et al., "Interleukin-17-producing T cells in lupus", Curr. Opin. Rheumatol., 22(5): 499-503 (2010).

[Non Patent Literature 13] BAETEN et. al., "Anti-interleukin-17A monoclonal antibody secokinumab in treatment of ankylosing spondylitis: a randomised, double-blind, placebo-controlled trial", Lancet, 382(9906): 1705-1713 (2013).

[Non Patent Literature 14] EMAMAULLEE et al., "Inhibition of Th17 Cells Regulates Autoimmune Diabetes in NOD Mice", Diabetes, 58: 1302-1311 (2009).

[Non Patent Literature 15] TILLEY, et al., "Retinoid-Related Orphan Receptor γ Controls Immunoglobulin Production and Th1/Th2 Cytokine Balance in the Adaptive Immune Response to Allergen", J. Immunol., 178: 3208-3218 (2007).

[Non Patent Literature 16] U.S. NATIONAL INSTITUTES OF HEALTH, "The Effects of Single Intravenous Administration of Secukinumab (AIN457) or Canakinumab (ACZ885) in Dry Eye Patients", ClinicalTrials.gov information for Clinical Trials Identifier NCT01250171 (Dec. 4, 2012).

[Non Patent Literature 17] M I et al., "Blocking IL-17A Promotes the Resolution of Pulmonary Inflammation and Fibrosis Via TGF-β1-Dependent and -Independent Mechanisms", J. Immunol., 187: 3003-3014 (2011).

[Non Patent Literature 18] U.S. NATIONAL INSTITUTES OF HEALTH, "A Study of Efficacy and Safety of Ustekinumab in Patients With Primary Biliary Cirrhosis (PBC) Who Had an Inadequate Response to Ursodeoxycholic Acid", ClinicalTrials.gov information for Clinical Trials Identifier NCT01389973 (Apr. 2, 2015).

[Non Patent Literature 19] FULTON et al., "Attenuation of Acute Graft-versus-Host Disease in the Absence of the Transcription Factor RORγt", Immunol., 189(4): 1765-1772 (2012).

[Non Patent Literature 20] Brian G Feagan et al., "Induction therapy with the selective interleukin-23 inhibitor risankizumab in patients with moderate-to-severe Crohn's disease: a randomised, double-blind, placebo-controlled phase 2 study", The Lancet, 389(10080): 1699-1709 (2017).

[Non Patent Literature 21] Eva Havrdova et al., "Activity of secukinumab, an anti-IL-17A antibody, on brain lesions in RRMS: results from a randomized, proof-of-concept study", J. Neurol., 263(7): 1287-1295 (2016).

[Non Patent Literature 22] U.S. NATIONAL INSTITUTES OF HEALTH, "Study of Secukinumab in Patients With Newly-diagnosed Type I Diabetes Mellitus", ClinicalTrials.gov information for Clinical Trials Identifier NCT02044848.

[Non Patent Literature 23] U.S. NATIONAL INSTITUTES OF HEALTH, "Secukinumab for Treatment of Atopic Dermatitis", ClinicalTrials.gov information for Clinical Trials identifier NCT02594098.

[Non Patent Literature 24] U.S. NATIONAL INSTITUTES OF HEALTH, "Efficacy and Safety of BI 655066/ABBV-066 (Risankizumab) in Patients With Severe Persistent Asthma", ClinicalTrials.gov information for Clinical Trials Identifier NCT02443998.

[Non Patent Literature 25] U.S. NATIONAL INSTITUTES OF HEALTH, "A Study of Secukinumab for the Treatment of Alopecia Areata", ClinicalTrials.gov information for Clinical Trials Identifier NCT02599129.

[Non Patent Literature 26] U.S. NATIONAL INSTITUTES OF HEALTH, "An Open-Label, Proof-of-Concept Study of Ixekizumab in the Treatment of Pyoderma Gangrenosum", ClinicalTrials.gov information for Clinical Trials Identifier NCT03137160.

[Non Patent Literature 27] U.S. NATIONAL INSTITUTES OF HEALTH, "Single-arm Study to Assess a Potential Effect of Anti-IL-17 (Secukinumab) in the Treatment of Pyoderma Gangrenosum", ClinicalTrials.gov information for Clinical Trials identifier NCT02733094.

[Non Patent Literature 28] Q Zhang et al., "Targeting Th17-IL-17 Pathway in Prevention of Micro-Invasive Prostate Cancer in a Mouse Model", Prostate, 77(8): 888-899 (2017).

[Non Patent Literature 29] W Shi et al., "Anti-IL-17 Antibody Improves Hepatic Steatosis by Suppressing Interleukin-17-Related Fatty Acid Synthesis and Metabolism", Clin. Dev. Immunol., Volume 2013, Article ID 253046 (2013).

[Non Patent Literature 30] R Xu et al., "Neutralization of interleukin-17 attenuates high fat diet-induced non-alcoholic fatty liver disease in mice", Acta Biochim. Biophys. Sin. (Shanghai), 45(9): 726-733 (2013).

[Non Patent Literature 31] Y. H. Lial et. al., "Interleukin-17A Contributes to Myocardial Ischemia/Reperfusion Injury by Regulating Cardiomyocyte Apoptosis and Neutrophil Infiltration", J. Am. Coll. Cardiol. 59(4): 420-429 (2012).

[Non Patent Literature 32] M. A. Saleh et al., "Inhibition of Interleukin 17-A but not Interleukin-17F Signaling Lowers Blood Pressure and Reduces End-organ Inflammation in Angiotensin II-induced Hypertension", JACC Basic Transl. Sci. 1(7): 606-616 (2016).

[Non Patent Literature 33] N. Dutzan et al., "A dysbiotic microbiome triggers TH17 cells to mediate oral mucosal immunopathology in mice and humans", Sci. Transl. Med. 10(463): eaat0797 (2018).

[Non Patent Literature 34] R Speeckaert et al., "The many faces of interleukin-17 in inflammatory skin diseases", Br. J. Dermatol. 175(5): 892-901 (2016).

SUMMARY OF INVENTION

The present invention provides saturated-ring-fused dihydropyrimidinone or dihydrotriazinone compounds, or pharmaceutically acceptable salts thereof, having RORγ antagonist activity, pharmaceutical compositions comprising the same, and their medical use. One aspect of the present invention includes the following illustrative embodiments.

[Item 1]

A compound of Formula [I]:

[I]

wherein $R^1$ is
(1) $C_{1-8}$ alkyl,
(2) halo-$C_{1-8}$ alkyl,
(3) cycloalkyl optionally substituted with the same or different 1 to 3 substituents selected from Group $A^1$, or
(4) $C_{3-8}$ cycloalkyl-$C_{1-4}$ alkyl wherein the $C_{3-8}$ cycloalkyl moiety may be optionally substituted with the same or different 1 to 3 substituents selected from Group $A^1$,
Group $A^1$ is
(1) halogen,
(2) $C_{1-4}$ alkyl, and
(3) halo-$C_{1-4}$ alkyl,
$X^1$ is
(1) a bond, or
(2) —O—,
$R^2$ is
(1) hydrogen, or
(2) halogen,
$R^3$ is
(1) hydrogen, or
(2) —$Y^3$—COO—$R^{30}$,
$Y^3$ is
(1) $C_{1-8}$ alkylene,
(2) $C_{3-8}$ cycloalkylene,
(3) bridged $C_{5-8}$ cycloalkylene, or
(4) $C_{6-14}$ arylene,
$R^{30}$ is
(1) hydrogen, or
(2) $C_{1-4}$ alkyl,
$X^2$ is
(1) =C($R^4$)—, or
(2) =N—,
$R^4$ is
(1) hydrogen, or
(2) $C_{1-4}$ alkyl,
$X^3$ is
(1) —C($R^5$)($R^6$)—,
$X^4$ is
(1) a bond, or
(2) —C($R^7$)($R^8$)—,
$X^5$ is
(1) —C($R^9$)($R^{10}$)—,
(2) —N($R^{11}$)—, or
(3) —O—,
$R^5$ and $R^6$ are each independently
(1) hydrogen,
(2) $C_{1-4}$ alkyl,
(3) halo-$C_{1-4}$ alkyl, (4) cyano-$C_{1-4}$ alkyl, or
(5) $C_{1-4}$ alkyl substituted with one substituent selected from the group consisting of —O—$R^{51}$, —CO—$R^{61}$, —COO—$R^{52}$, —N($R^{71}$)($R^{72}$), —CO—N($R^{73}$)($R^{74}$), —N($R^{75}$)—CO—$R^{62}$, —N($R^{76}$)—COO—$R^{53}$, and —O—S(O)$_2$—$R^{63}$, $R^7$, $R^8$, $R^9$ and $R^{13}$ are each independently
(1) hydrogen,
(2) halogen,
(3) cyano,
(4) hydroxy,
(5) $C_{1-4}$ alkyl,
(6) halo-$C_{1-4}$ alkyl,
(7) cyano-$C_{1-4}$ alkyl,
(8) $C_{1-4}$ alkoxy, or
(9) $C_{1-4}$ alkyl substituted with one substituent selected from the group consisting of —O—$R^{51}$, —CO—$R^{61}$, —COO—$R^{52}$, —N($R^{71}$)($R^{72}$), —CO—N($R^{73}$)($R^{74}$), —N($R^{75}$)—CO—$R^{62}$, —N($R^{76}$)—COO—$R^{53}$, and —O—S(O)$_2$—$R^{63}$, $R^{51}$, $R^{52}$, and $R^{53}$ are each independently
(1) hydrogen,
(2) $C_{1-4}$ alkyl, or
(3) $C_{5-14}$ aryl-$C_{1-4}$ alkyl, $R^{61}$, $R^{62}$, and $R^{63}$ are each independently
(1) $C_{1-4}$ alkyl, $R^{71}$, $R^{72}$, $R^{73}$, $R^{74}$, $R^{75}$, and $R^{76}$ are each independently
(1) hydrogen, or
(2) $C_{1-4}$ alkyl, $R^{11}$ is
(1) —CO—$R^{111}$, or
(2) —COO—$R^{112}$, $R^{111}$ is
(1) $C_{1-4}$ alkyl, $R^{112}$ is
(1) $C_{1-4}$ alkyl, or a pharmaceutically acceptable salt thereof.

[Item 2]
The compound according to Item 1, having a structure of Formula [II]:

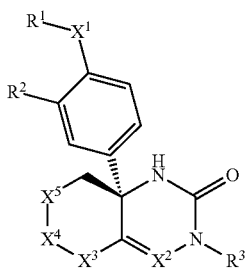

[II]

wherein each variable is defined as defined in Item 1, or a pharmaceutically acceptable salt thereof.

[Item 3]
The compound according to item 1 or 2, wherein $X^2$ is =N—, or a pharmaceutically acceptable salt thereof.

[Item 4]
The compound according to Item 1 or 2, wherein $X^2$ is =C($R^4$)— and $R^4$ is hydrogen, or a pharmaceutically acceptable salt thereof.

[Item 5]
The compound according to any one of Items 1 to 4, wherein $R^3$ is hydrogen, or a pharmaceutically acceptable salt thereof.

[Item 6]
The compound according to any one of Items 1 to 4, wherein $R^3$ is —$Y^3$—COO—$R^{30}$, $Y^3$ is
(1) $C_{1-8}$ alkylene,
(2) $C_{3-8}$ cycloalkylene, or
(3) bridged $C_{5-8}$ cycloalkylene, $R^{30}$ is hydrogen or $C_{1-4}$ alkyl, or a pharmaceutically acceptable salt thereof.

[Item 7]
The compound according to any one of Items 1 to 6, wherein $R^2$ is halogen, or a pharmaceutically acceptable salt thereof.

[Item 8]
The compound according to any one of Items 2 to 7, wherein $R^1$ is $C_{1-8}$ alkyl and $X^1$ is a bond, or a pharmaceutically acceptable salt thereof.

[Item 9]
The compound according to any one of Items 1 to 8, wherein $R^5$ and $R^6$ are each independently hydrogen or $C_{1-4}$ alkyl, or a pharmaceutically acceptable salt thereof.

[Item 10]
The compound according to any one of Items 1 to 9, wherein $X^4$ is a bond or —C($R^7$)($R^8$)— and both of $R^7$ and $R^8$ are hydrogen, or a pharmaceutically acceptable salt thereof.

[Item 11]
The compound according to any one of Items 1 to 10, wherein $X^5$ is —C($R^9$))($R^{10}$)— or —O— and both of $R^9$ and $R^{10}$ are hydrogen, or a pharmaceutically acceptable salt thereof.

[Item 12]
The compound according to Item 1, selected from the following compound group:

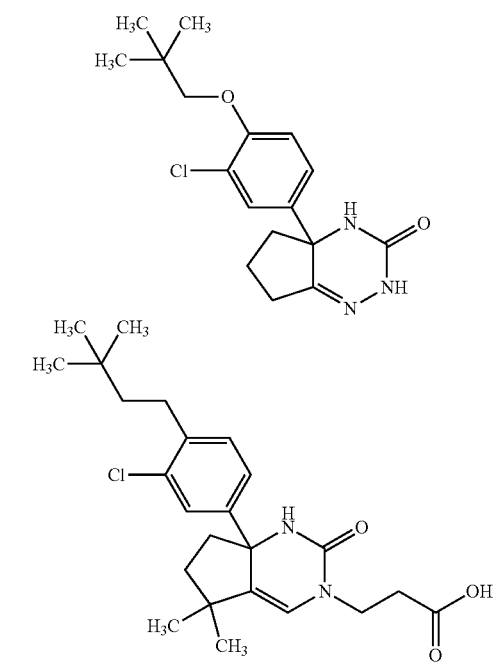

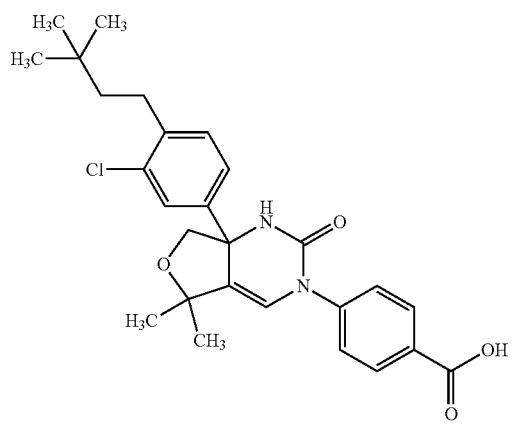
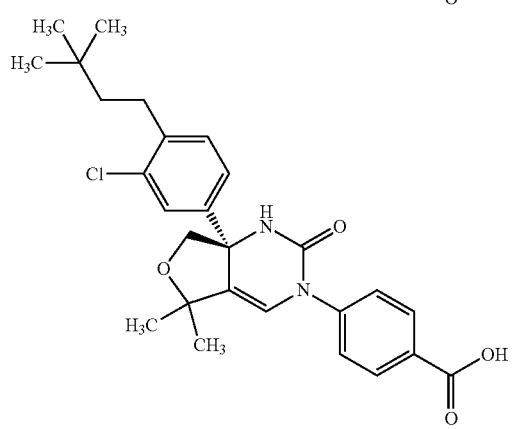
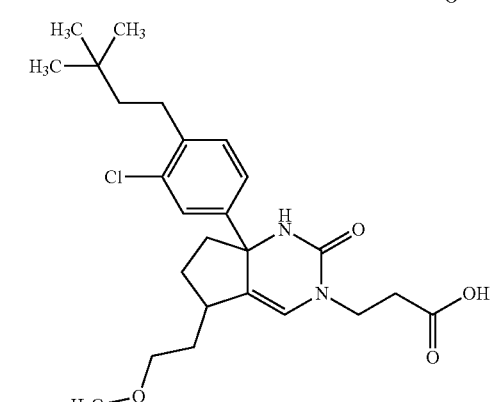
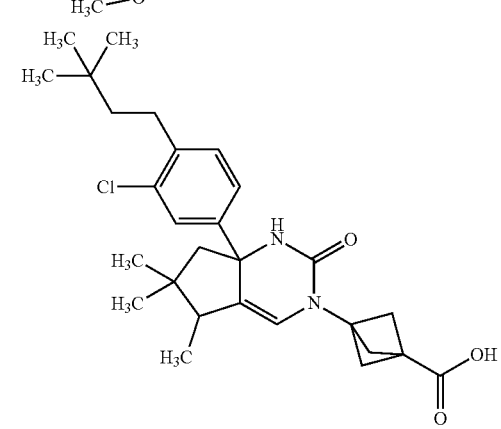
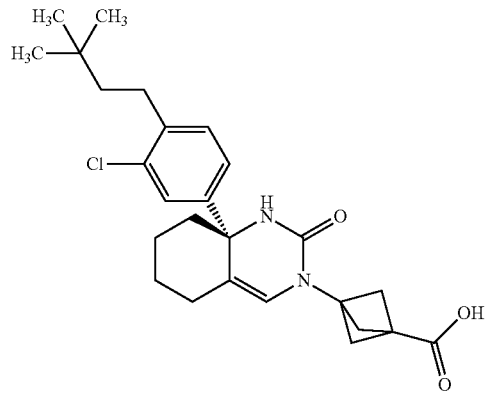
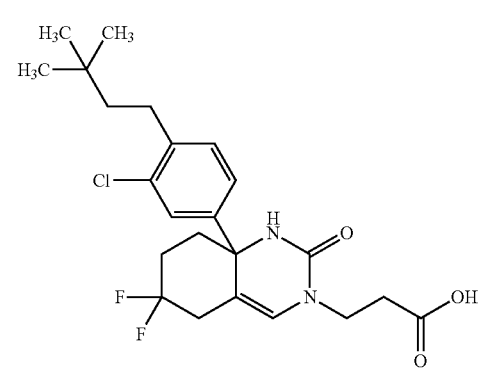
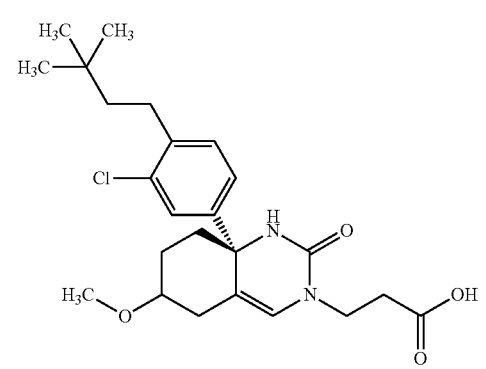

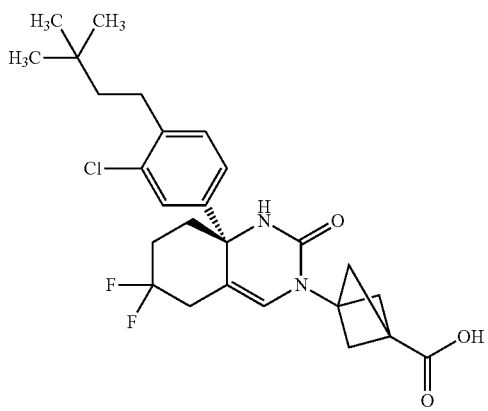

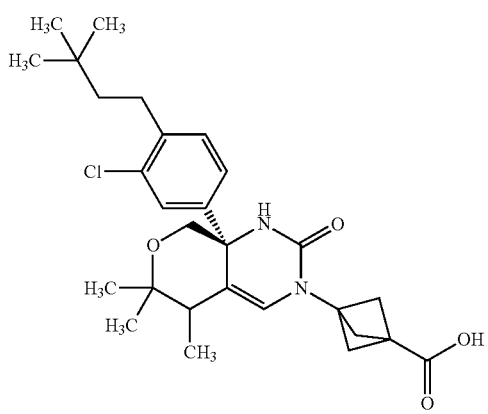

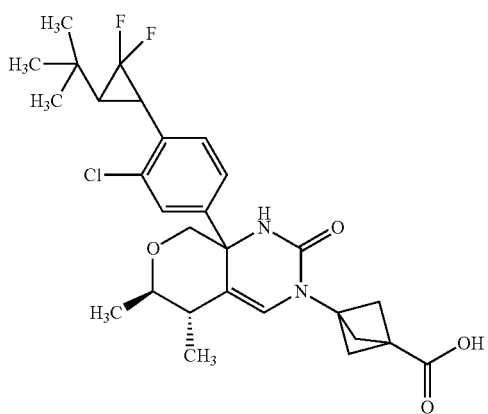

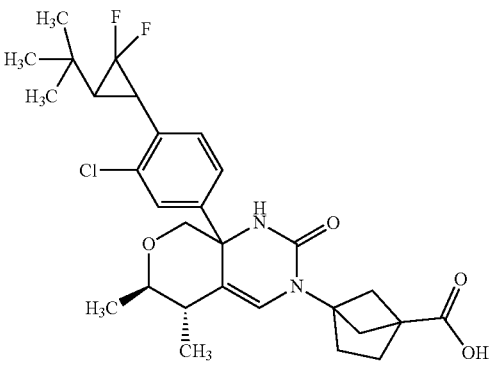

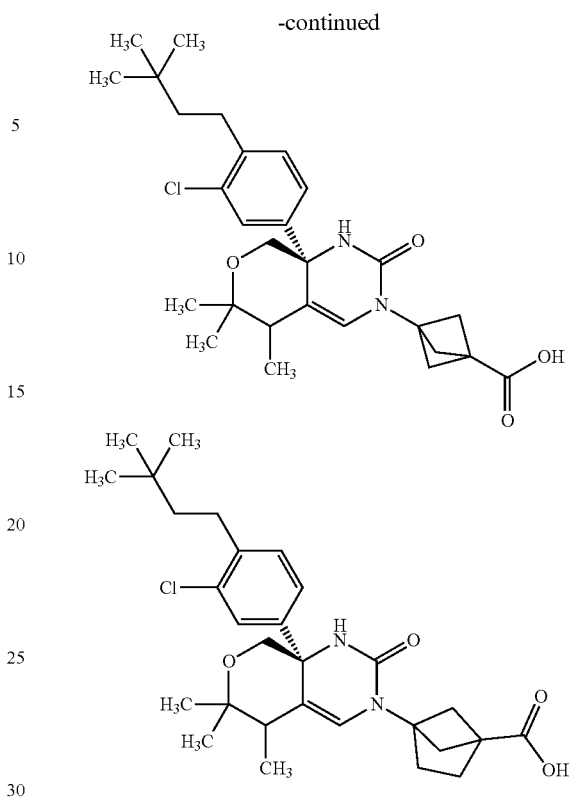

or a pharmaceutically acceptable salt thereof.

[Item 13]

A pharmaceutical composition comprising a compound according to any one of items 1 to 12 or a pharmaceutically acceptable salt thereof and a pharmaceutically acceptable carrier.

[Item 14]

An RORγ antagonist comprising a compound according to any one of Items 1 to 12 or a pharmaceutically acceptable salt thereof.

[Item 15]

A therapeutic or preventive agent for a disease selected from the group consisting of autoimmune diseases, allergic diseases, dry eye, fibrosis, cancers, metabolic disease, ischemia, cardiomyopathy, hypertension, and periodontal disease, comprising a compound according to any one of Items 1 to 12 or a pharmaceutically acceptable salt thereof.

[Item 16]

A method of antagonizing RORγ, comprising administering a therapeutically effective amount of a compound according to any one of Items 1 to 12 or a pharmaceutically acceptable salt thereof to a mammal.

[Item 17]

A method of treating or preventing a disease selected from the group consisting of autoimmune diseases, allergic diseases, dry eye, fibrosis, cancers, metabolic disease, ischemia, cardiomyopathy, hypertension, and periodontal disease, comprising administering a therapeutically effective amount of a compound according to any one of Items 1 to 12 or a pharmaceutically acceptable salt thereof to a mammal.

[Item 18]

Use of a compound according to any one of Items 1 to 12 or a pharmaceutically acceptable salt thereof in the manufacture of an RORγ antagonist.

[Item 19]
Use of a compound according to any one of Items 1 to 12 or a pharmaceutically acceptable salt thereof in the manufacture of a therapeutic or preventive agent for a disease selected from the group consisting of autoimmune diseases, allergic diseases, dry eye, fibrosis, cancers, metabolic disease, ischemia, cardiomyopathy, hypertension, and periodontal disease.

[Item 20]
A compound according to any one of Items 1 to 12 or a pharmaceutically acceptable salt thereof for use in an RORγ antagonist.

[Item 21]
A compound according to any one Items 1 to 12 or a pharmaceutically acceptable salt thereof for use in treating or preventing a disease selected from the group consisting of autoimmune diseases, allergic diseases, dry eye, fibrosis, cancers, metabolic disease, ischemia, cardiomyopathy, hypertension, and periodontal disease.

[Item 22]
A commercial package comprising a pharmaceutical composition according to Item 13 and a package insert concerning the pharmaceutical composition describing that the pharmaceutical composition can be used for treating or preventing a disease selected from the group consisting of autoimmune diseases, allergic diseases, dry eye, fibrosis, cancers, metabolic disease, ischemia, cardiomyopathy, hypertension, and periodontal disease.

[Item 23]
A kit comprising a pharmaceutical composition according to Item 13 and a package insert concerning the pharmaceutical composition describing that the pharmaceutical composition can be used for treating or preventing a disease selected from the group consisting of autoimmune diseases, allergic diseases, dry eye, fibrosis, cancers, metabolic disease, ischemia, cardiomyopathy, hypertension, and periodontal disease.

DESCRIPTION OF EMBODIMENTS

Definitions of terms used herein are shown as follows.
A wavy line as follows:
in a partial structure shows a binding site.
The term "halogen" includes fluoro, chloro, bromo, and iodo. A preferable "halogen" is fluoro, chloro, or bromo.
The term "$C_{1-4}$ alkyl" means a straight- or branched-chain saturated hydrocarbon group with 1 to 4 carbon atoms. The "$C_{1-4}$ alkyl" group includes methyl, ethyl, n-propyl, isopropyl, n-butyl, isobutyl, sec-butyl, and tert-butyl.
The term "$C_{1-8}$ alkyl" means a straight- or branched-chain saturated hydrocarbon group with 1 to 8 carbon atoms. The "$C_{1-8}$ alkyl" group includes, for example, methyl, ethyl, n-propyl, isopropyl, n-butyl, isobutyl, sec-butyl, tert-butyl, n-pentyl, isopentyl, neopentyl, 1,1-dimethylpropyl, 1-ethylpropyl, n-hexyl, isohexyl, 3,3-dimethylbutyl, 2,2-dimethylbutyl, 1,1-dimethylbutyl, 2-ethylbutyl, n-heptyl, 5-methylhexyl, 4-methylhexyl, 4,4-dimethylpentyl, 3,3-dimethylpentyl, 3,4-dimethylpentyl, 2,3-dimethylpentyl, 3-ethylpentyl, 2-ethylpentyl, heptan-4-yl, n-octyl, 6-methylheptyl, 5,5-dimethylhexyl, 4,5-dimethylhexyl, 4-ethylhexyl, 3-ethylhexyl, 2-propylpentyl, and octan-4-yl.
The term "$C_{1-8}$ alkylene" means a divalent group derived from straight- or branched-chain saturated hydrocarbon with 1 to 8 carbon atoms. The "$C_{1-8}$ alkylene" group includes, for example, the following groups:

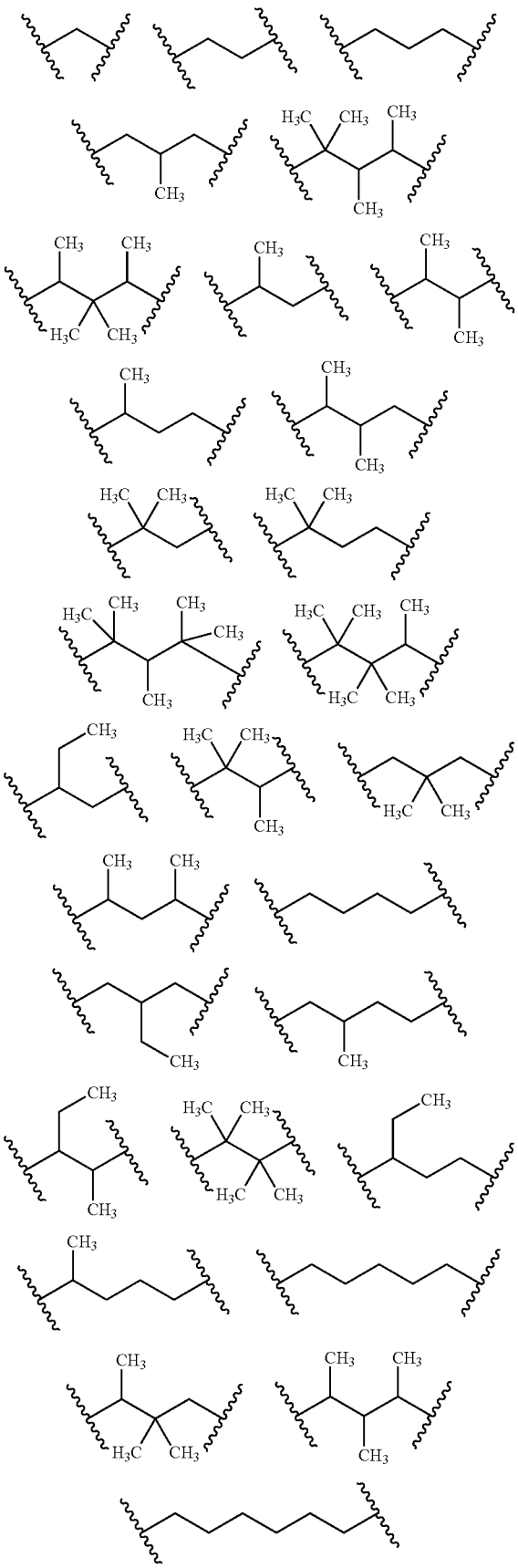

-continued

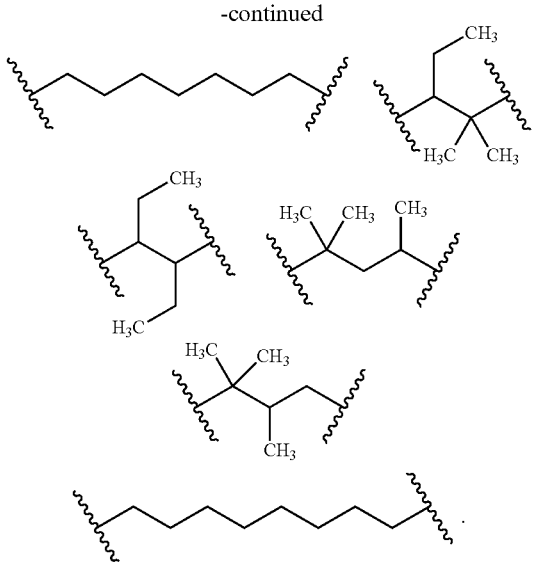

The term "halo-$C_{1-4}$ alkyl" means the "$C_{1-4}$ alkyl" group substituted with 1 to 5 halogen atoms independently selected from the group of the term "halogen". The "halo-$C_{1-4}$ alkyl" group includes, for example, monofluoromethyl, difluoromethyl, trifluoromethyl, 2-fluoroethyl, 2-chloroethyl, 2-bromoethyl, 1,1-difluoroethyl, 2,2,2-trifluoroethyl, pentafluoroethyl, 3-fluoropropyl, 3-chloropropyl, 1,1-difluoropropyl, 3,3,3-trifluoropropyl, 4-fluorobutyl, and 4,4,4-trifluorobutyl.

The term "halo-$C_{1-8}$ alkyl" means the "$C_{1-8}$ alkyl" group substituted with 1 to 9 halogen atoms independently selected from the group of the term "halogen". The "halo-$C_{1-8}$ alkyl" group includes, for example, monofluoromethyl, difluoromethyl, trifluoromethyl, 2-fluoroethyl, 2-chloroethyl, 2-bromoethyl, 1,1-difluoroethyl, 2,2,2-trifluoroethyl, pentafluoroethyl, 3-fluoropropyl, 3-chloropropyl, 1,1-difluoropropyl, 3,3,2-trifluoropropyl, 4-fluorobutyl, 4,4,4-trifluorobutyl, 5-fluoropentyl, 5,5,5-trifluoropentyl, 4,4,5,5,5-pentafluoropentyl, 3,3,4,4,5,5,5-heptafluoropentyl, 6-fluorohexyl, 6,6,6-trifluorohexyl, 7-fluoroheptyl, 7,7,7-trifluoroheptyl, 8-fluorooctyl, 8,8,8-trifluorooctyl, and 7,7,8,8,8-pentafluorooctyl.

The term "cyano-$C_{1-4}$ alkyl" means the "$C_{1-4}$ alkyl" group substituted with one cyano group. The "cyano-$C_{1-4}$ alkyl" group includes, for example, cyanomethyl, 1-cyanoethyl, 2-cyanoethyl, 2-cyanopropyl, 3-cyanopropyl, 4-cyanobutyl, and 2-cyano-2-methylpropyl.

The term "$C_{1-4}$ alkoxy" means those which the "$C_{1-4}$ alkyl" group binds to an oxygen atom and the group binds to another group via the oxygen atom. The "$C_{1-4}$ alkoxy" group includes methoxy, ethoxy, n-propoxy, isopropoxy, n-butoxy, isobutoxy, sec-butoxy, and tert-butoxy.

The term "$C_{3-8}$ cycloalkyl" means a monocyclic saturated hydrocarbon group with 3 to 8 carbon atoms. The "$C_{3-8}$ cycloalkyl" group includes cyclopropyl, cyclobutyl, cyclopentyl, cyclohexyl, cycloheptyl, and cyclooctyl.

The term "$C_{3-8}$ cycloalkyl-$C_{1-4}$ alkyl" means the "$C_{1-4}$ alkyl" group substituted with one cycloalkyl group selected from the group of the "$C_{3-8}$ cycloalkyl". The "$C_{3-8}$ cycloalkyl-$C_{1-4}$ alkyl" group includes, for example, cyclopropylmethyl, cyclobutylmethyl, cyclopentylmethyl, cyclohexylmethyl, cycloheptylmethyl, cyclooctylmethyl, 2-cyclopropylethyl, 2-cyclobutylethyl, 2-cyclopentylethyl, 2-cyclohexylethyl, 2-cycloheptylethyl, 2-cyclooctylethyl, 1-cyclopropylethyl, 1-cyclobutylethyl, 1-cyclopentylethyl, 1-cyclohexylethyl, 1-cycloheptylethyl, 1-cyclooctylethyl, 3-cyclopropylpropyl, 3-cyclobutylpropyl, 3-cyclopentylpropyl, 3-cyclohexylpropyl, 3-cycloheptylpropyl, and 3-cyclooctylpropyl.

The term "$C_{3-8}$ cycloalkylene" means a divalent group derived from a monocyclic saturated hydrocarbon group with 3 to 8 carbon atoms. The "$C_{3-8}$ cycloalkylene" group includes, for example, the following groups:

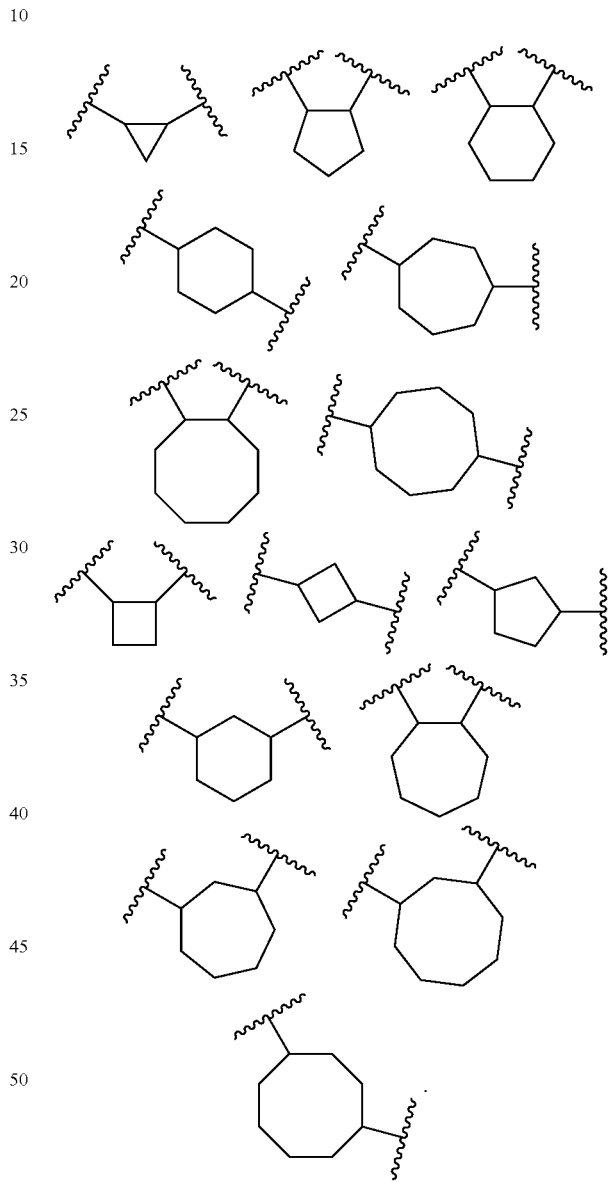

The term "bridged $C_{5-8}$ cycloalkylene" means a divalent group derived from a bridged cyclic saturated hydrocarbon group with 5 to 8 carbon atoms. The "bridged $C_{5-8}$ cycloalkylene" group includes, for example, the following groups:

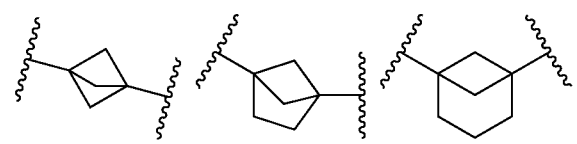

-continued

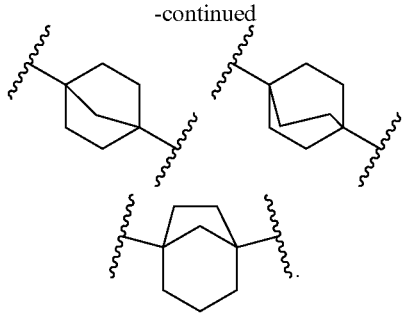
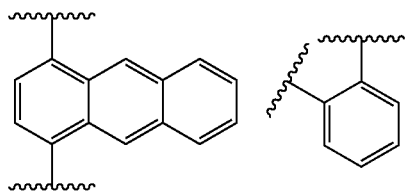

The term "$C_{6-14}$ aryl" means an aromatic hydrocarbon group with 6 to 14 carbon atoms. The "$C_{6-14}$ aryl" group includes, for example, phenyl, naphthyl, anthryl, indenyl, azulenyl, fluorenyl, phenanthryl, and pentalenyl.

The term "$C_{6-14}$ aryl-$C_{1-4}$ alkyl" means the "$C_{1-4}$ alkyl" group substituted with one aryl group selected from the group of the "$C_{6-14}$ aryl". The "$C_{6-14}$ aryl-$C_{1-4}$ alkyl" group includes, for example, benzyl, phenethyl, 3-phenylpropyl, 4-phenylbutyl, naphthalen-1-ylmethyl, naphthalen-2-ylmethyl, anthracen-1-ylmethyl, anthracen-2-ylmethyl, and anthracen-9-ylmethyl.

The term "$C_{6-14}$ arylene" means a divalent group derived from an aromatic hydrocarbon group with 6 to 14 carbon atoms. The "$C_{6-14}$ arylene" group includes, for example, the following groups:

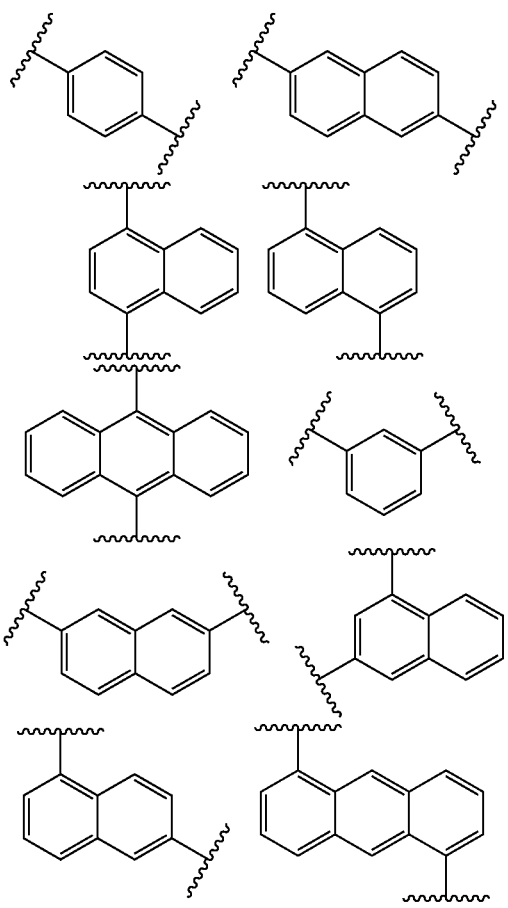

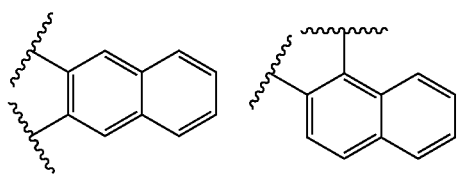

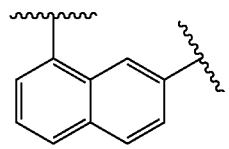

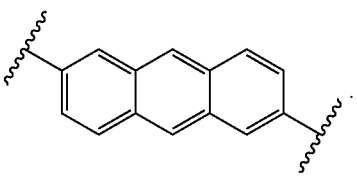

As for the term "substituted", for example, the phrase "$C_{3-8}$ cycloalkyl optionally substituted with the same or different 1 to 3 substituents selected from Group $A^1$" in $R^1$ means unsubstituted $C_{3-8}$ cycloalkyl or a group where any of replaceable hydrogen atoms in $C_{3-8}$ cycloalkyl are substituted with the same or different 1 to 3 substituents selected from Group $A^1$, i.e., the group consisting of (1) halogen, (2) $C_{1-4}$ alkyl, and (3) halo-$C_{1-4}$ alkyl. Such a substituted $C_{3-8}$ cycloalkyl group includes, for example, the following groups:

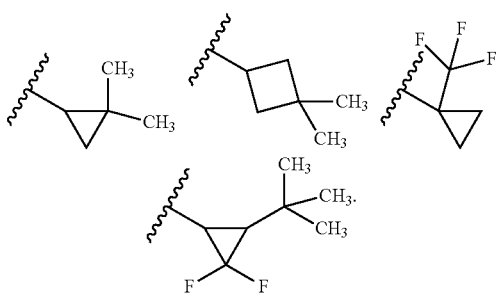

The term "a compound of Formula [I]" herein may also be referred to as "Compound [I]". In one embodiment, Compound [I] is a compound of Formula [II]:

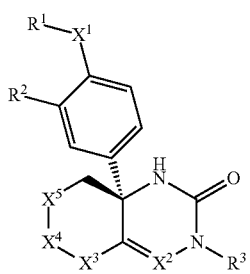

wherein each variable is defined as defined above. The term "a compound of Formula [II]" herein may also be referred to as "Compound [II]".

Embodiments of partial structures and substituents of Compound [I] and Compound [II] are illustrated as below, but each partial structure or substituent of Compound [I] and Compound [II] is not limited to those embodiments; Compound [I] and Compound [II] include any combinations of two or more embodiments optionally selected from the embodiments in each partial structure or substituent.

The following partial structure of Compound [I]:

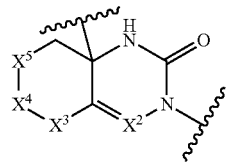

means either of the following partial structures:

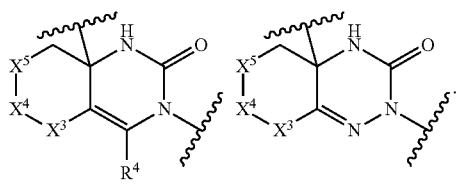

A preferable structure is any of the following partial structures:

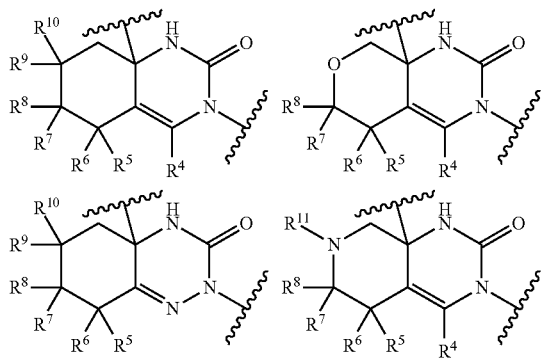

A more preferable one is any of the following partial structures:

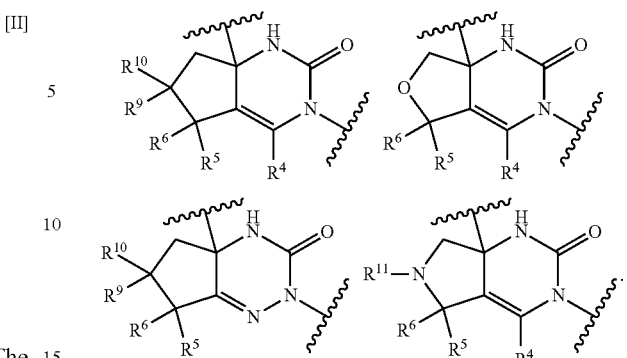

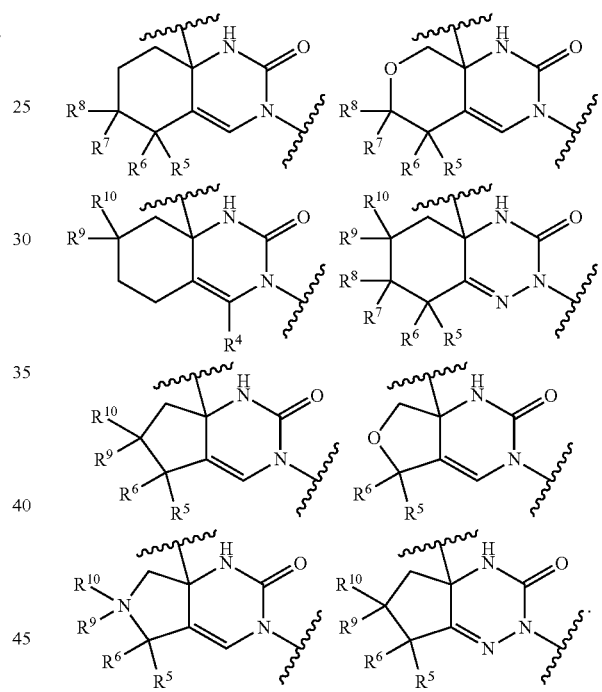

A further preferable one is any of the following partial structures:

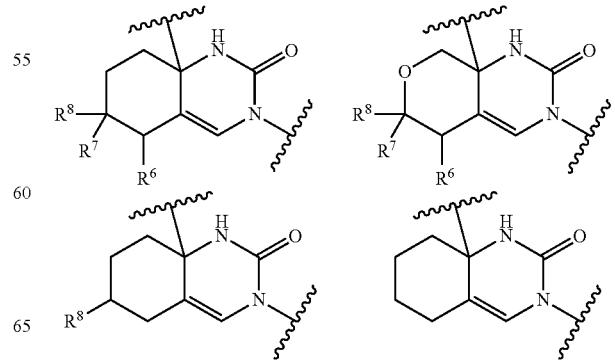

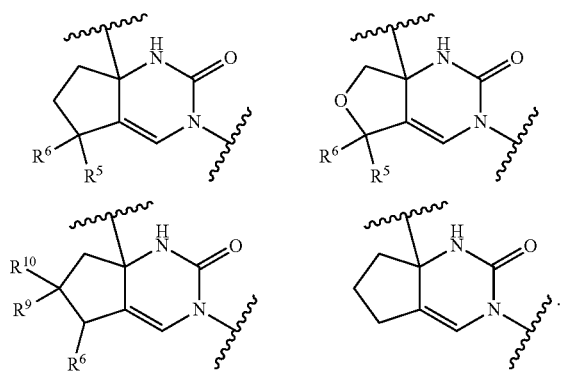
The following partial structure of Compound [II]:
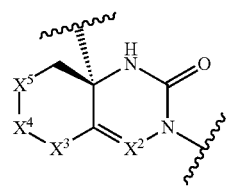
means either of the following partial structures:
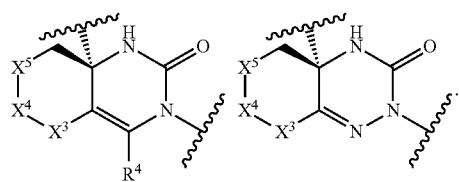
A preferable structure is any of the following partial structures:
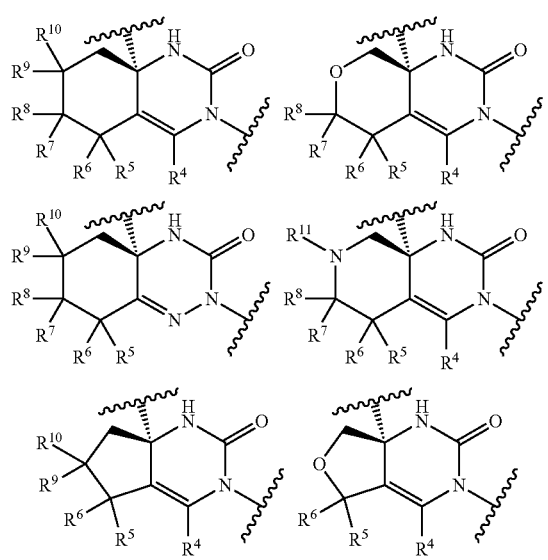
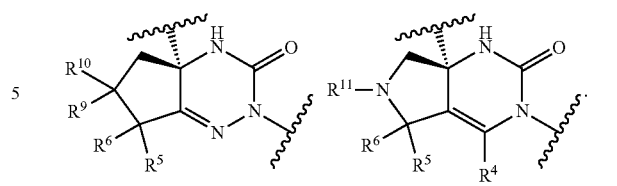
A more preferable one is any of the following partial structures:
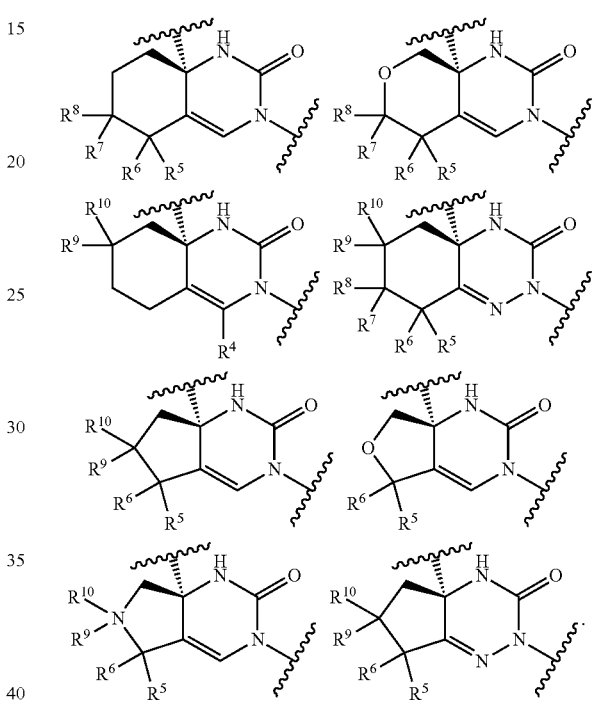
A further preferable one any of the following partial structures:
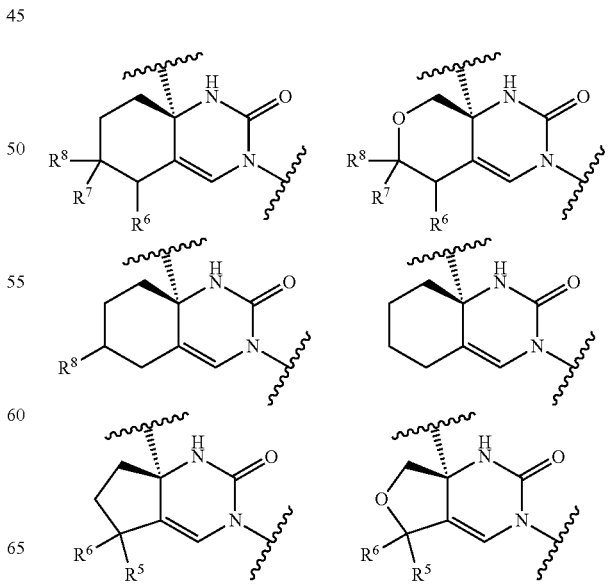

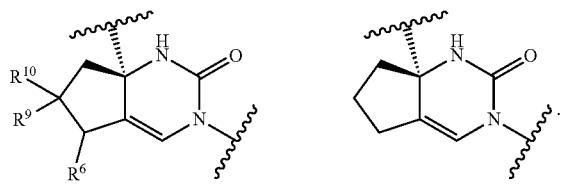

Another embodiment of the following partial structure of Compound [I]:

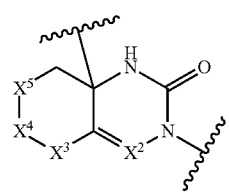

includes the following partial structure:

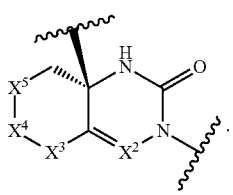

Such a partial structure means either of the following partial structures:

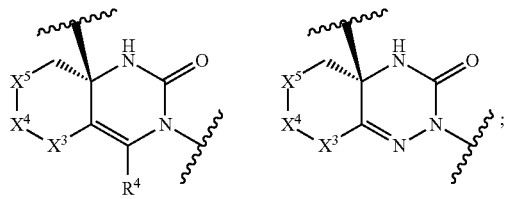

a preferable one is any of the following partial structures:

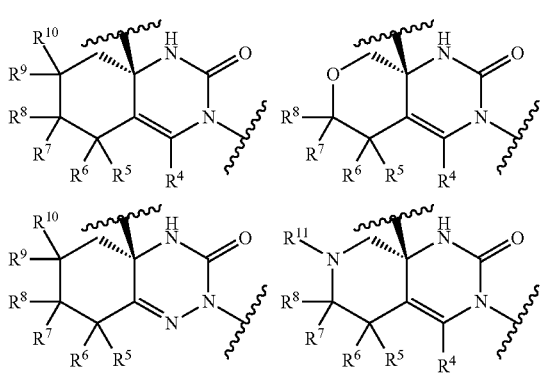

A more preferable one is any of the following partial structures:

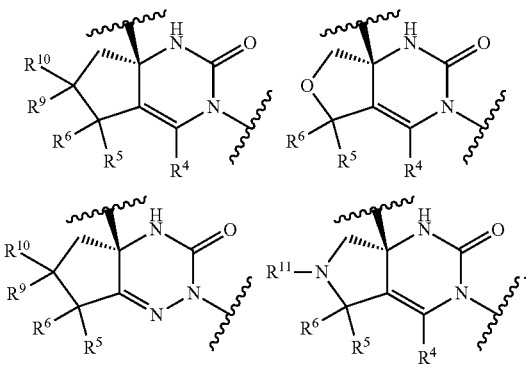

A further preferable one is any of the following partial structures:

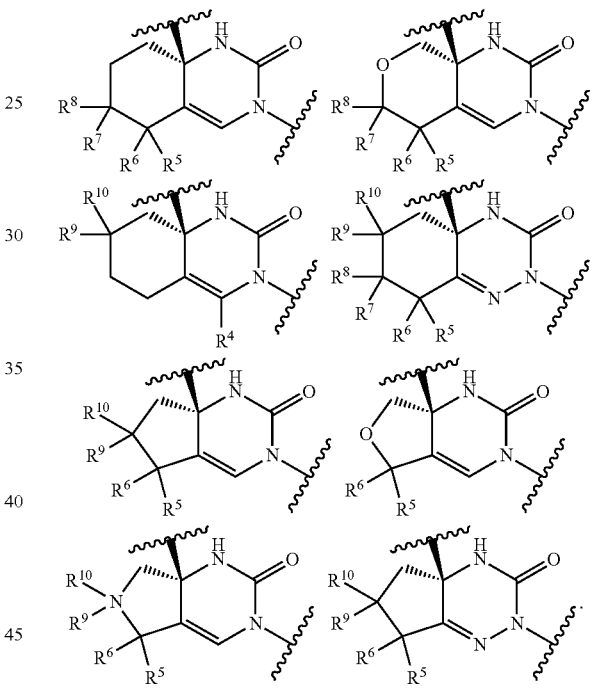

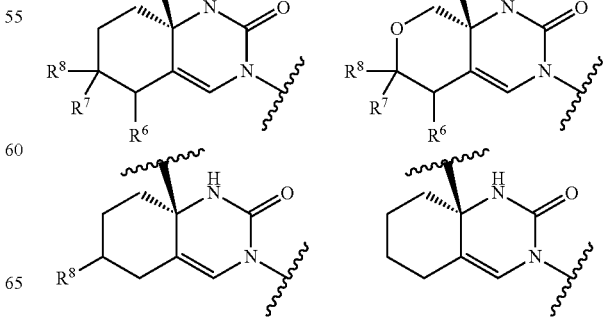

-continued

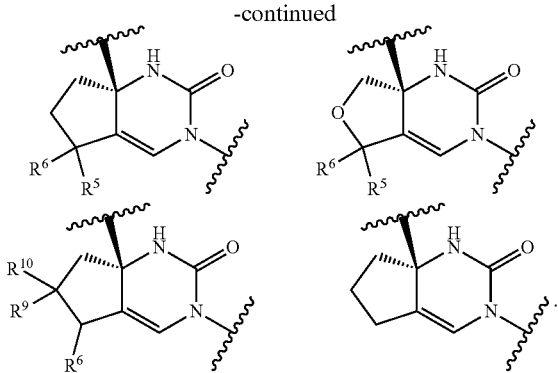

R¹ is preferably $C_{1-8}$ alkyl, or $C_{3-8}$ cycloalkyl substituted with the same or different 1 to 3 substituents selected from Group $A^1$, and is more preferably $C_{1-8}$ alkyl.

Group $A^1$ is preferably halogen and $C_{1-4}$ alkyl.

$X^1$ is preferably a bond.

A partial structure of —$X^1$—$R^1$ is preferably any one of the following structures:

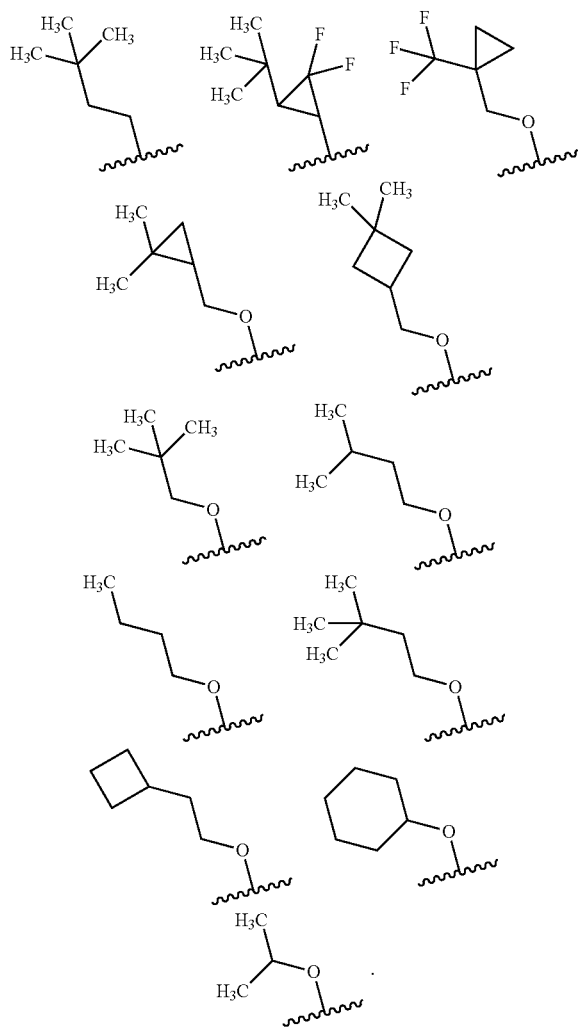

$R^2$ is preferably halogen and more preferably chloro.
$R^3$ is preferably —$Y^3$—COO—$R^{30}$.

$Y^3$ is preferably $C_{1-8}$ alkylene, $C_{3-8}$ cycloalkylene, or bridged $C_{5-8}$ cycloalkylene, and more preferably $C_{3-8}$ cycloalkylene or bridged $C_{5-8}$ cycloalkylene.

$C_{1-8}$ alkylene in $Y^3$ is preferably any one of the following groups:

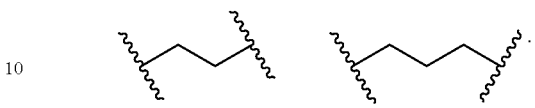

$C_{3-8}$ cycloalkylene in $Y^3$ is preferably the following group:

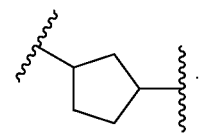 [SMILES: *C1CCC(*)C1]

Bridged $C_{5-8}$ cycloalkylene in $Y^3$ is preferably any one of the following groups:

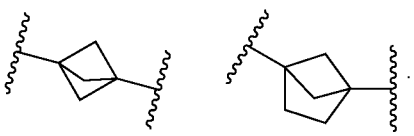 [SMILES: *C12CC(*)(C1)C2 ; *C12CCC(*)(C1)C2]

$C_{6-14}$ arylene in $Y^3$ is preferably the following group:

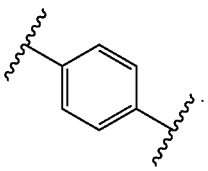 [SMILES: *c1ccc(*)cc1]

$R^{30}$ is preferably hydrogen or ethyl, and more preferably hydrogen.

$R^4$ is preferably hydrogen or methyl, and more preferably hydrogen.

$R^5$ and $R^6$ are preferably each independently hydrogen, $C_{1-4}$ alkyl, cyano-$C_{1-4}$ alkyl, or $C_{1-4}$ alkyl substituted with one substituent selected from the group consisting of —O—$R^{51}$, —COO—$R^{52}$, —N($R^{71}$)($R^{72}$), —CO—N($R^{73}$)($R^{74}$), —N($R^{75}$)—CO—$R^{62}$, and —O—S(O)$_2$—$R^{63}$ and are more preferably each independently hydrogen or $C_{1-4}$ alkyl.

In one embodiment, $R^5$ and $R^6$ are selected from the following options:

(A) both are hydrogen;
(B) one is hydrogen and the other is $C_{1-4}$ alkyl, preferably methyl;
(C) both are $C_{1-4}$ alkyl, preferably methyl for both;
(D) one is hydrogen and the other is cyano-$C_{1-4}$ alkyl, preferably cyanomethyl; or
(E) one is hydrogen and the other is $C_{1-4}$ alkyl, preferably methyl or ethyl, substituted with one substituent selected from the group consisting of —O—$R^{51}$, —COO—$R^{52}$, —N($R^{71}$)($R^{72}$), —CO—N($R^{73}$)($R^{74}$), —N($R^{75}$)—CO—$R^{62}$, and —O—S(O)$_2$—$R^{63}$.

R⁷ and R⁸ are preferably each independently hydrogen, halogen, cyano, $C_{1-4}$ alkyl, halo-$C_{1-4}$ alkyl, $C_{1-4}$ alkoxy, or $C_{1-4}$ alkyl substituted with and more preferably, both of them are hydrogen.

In one embodiment, R⁷ and R⁸ are selected from the following options:
(A) both are hydrogen;
(B) both are halogen, preferably fluoro for both;
(C) both are $C_{1-4}$ alkyl, preferably methyl for both; or
(D) one is hydrogen and the other is cyano, $C_{1-4}$ alkyl (preferably methyl, ethyl, or isopropyl), halo-$C_{1-4}$ alkyl (preferably trifluoromethyl), $C_{1-4}$ alkoxy (preferably methoxy), or $C_{1-4}$ alkyl, preferably methyl, substituted with one —O—R⁵¹.

R⁹ and R¹⁰ are preferably each independently hydrogen or $C_{1-4}$ alkyl, and more preferably, both of them are hydrogen.

In one embodiment, R⁹ and R¹⁰ are selected from the following options:
(A) both are hydrogen; or
(B) both are methyl.

In one embodiment, X² is =N— and R³ is hydrogen.
In another embodiment, X² is =C(R⁴)— and R³ is Y³—COO—R³⁰.

The term "pharmaceutically acceptable salt" may be any salts without excess toxicity known in the art. Specifically, it includes, for example, salts with inorganic acids, salts with organic acids, salts with inorganic bases, and salts with organic bases. Various forms of pharmaceutically acceptable salts are well known in the art and are listed, for example, in the following references:
(a) Berge et al., J. Pharm. Sci., 66, p 1-19 (1977);
(b) Stahl et al., "Handbook of Pharmaceutical Salts: Properties, Selection, and Use" (Wiley-VCH, Weinheim, Germany, 2002);
(c) Paulekuhn et al., J. Med. Chem., 50, p 6665-6672 (2007).

According to known methods, Compound [I] may be reacted with an inorganic acid, organic acid, inorganic base, or organic base to give each pharmaceutically acceptable salt thereof.

Such salts with inorganic acids include, for example, salts with hydrofluoric acid, hydrochloric acid, hydrobromic acid, hydroiodic acid, nitric acid, phosphoric acid, and sulfuric acid. Preferable salts include salts with hydrochloric acid, nitric acid, sulfuric acid, phosphoric acid, and hydrobromic acid.

Such salts with organic acids include, for example, salts with acetic acid, adipic acid, alginic acid, 4-aminosalicyclic acid, anhydromethylenecitric acid, benzoic acid, benzenesulfonic acid, camphor acid, camphor-10-sulfonic acid, carbonic acid, citric acid, edetic acid, ethane-1,2-disulfonic acid, dodecylsulfonic acid, ethanesulfonic acid, fumaric acid, glucoheptonic acid, gluconic acid, glucuronic acid, glucoheptonic acid, glycollylarsanilic acid, hydroxynaphthoic acid, 2-hydroxy-1-ethanesulfonic acid, lactic acid, lactobionic acid, malic acid, maleic acid, mandelic acid, methanesulfonic acid, methylsulfuric acid, methylnitric acid, methylenebis(salicylic acid), galactaric acid, naphthalene-2-sulfonic acid, 2-naphthoic acid, 1,5-naphthalenedisulfonic acid, oleic acid, oxalic acid, pamoic acid, pantothenic acid, pectic acid, picric acid, propionic acid, polygalacturonic acid, salicylic acid, stearic acid, succinic acid, tannic acid, tartaric teoclic acid, thiocyanic acid, trifluoroacetic acid, p-toluenesulfonic acid, undecanoic acid, asparaginic acid, and glutamic acid. Preferable salts include salts with oxalic acid, maleic acid, citric acid, fumaric acid, lactic acid, malic acid, succinic acid, tartaric acid, acetic acid, trifluoroacetic acid, benzoic acid, glucuronic acid, oleic acid, pamoic acid, methanesulfonic acid, benzenesulfonic acid, p-toluenesulfonic acid, and 2-hydroxy-1-ethanesulfonic acid.

Such salts with inorganic bases include, for example, salts with lithium, sodium, potassium, magnesium, calcium, barium, aluminum, zinc, bismuth, and ammonium. Preferable salts include salts with sodium, potassium, calcium, magnesium, and zinc.

Such salts with organic bases include, for example, salts with arecoline, betaine, choline, clemizole, ethylenediamine, N-methylglucamine, N-benzylphenethylamine, tris (hydroxymethyl)methylamine, arginine, and lysine. Preferable salts include salts with tris(hydroxymethyl) methylamine, N-methylglucamine, and lysine.

A preferable "pharmaceutically acceptable salt" includes hydrochloride and sodium salt.

Compound [I] or a pharmaceutically acceptable salt thereof may exist in a solvate form.

The term "solvate" means Compound [I] or a pharmaceutically acceptable salt thereof coordinate with a solvent molecule and includes a hydrate. Such a solvate is preferably a pharmaceutically acceptable solvate and includes hydrates, ethanolates, and solvates with dimethylsufoxide of Compound [I] or a pharmaceutically acceptable salt thereof.

Specifically, such a solvate includes a hemihydrate, monohydrate, dihydrate, or monoethanolate of Compound [I], or a monohydrate of a hydrochloride salt of Compound [I] or a ⅔ ethanolate of a dihydrochloride salt thereof. Such a solvate may be obtained according to known methods.

Compound [I] or a pharmaceutically acceptable salt thereof may exist in its tautomeric form. Such Compound [I] or a pharmaceutically acceptable salt thereof may exist in each tautomeric form or in the form of a mixture of its tautomers.

Compound [I] or a pharmaceutically acceptable salt thereof may have stereoisomers recognized as cis/trans isomers. Such Compound [I] or pharmaceutically acceptable salt thereof may exist in its cis or trans form, or in the form of a mixture of its cis and trans isomers.

Compound [I] or a pharmaceutically acceptable salt thereof may have one or more asymmetric carbon atoms. Such Compound [I] or a pharmaceutically acceptable salt thereof may exist in a single enantiomeric form or a single diastereomeric form, or in the form of a mixture of its enantiomers or diastereomers.

Compound [I] or a pharmaceutically acceptable salt thereof may exist in its atropisomeric form. Such Compound [I] or a pharmaceutically acceptable salt thereof may exist in each atropisomeric form or in the form of a mixture of its atropisomers.

Compound [I] or a pharmaceutically acceptable salt thereof may simultaneously comprise multiple structural features responsible for the above isomers. Compound [I] or a pharmaceutically acceptable salt thereof may comprise the above isomers in any ratios.

Formulae, chemical structures, or compound names herein without stereochemistry specified include any of the above isomers available, unless otherwise specified. For example, the following structure:

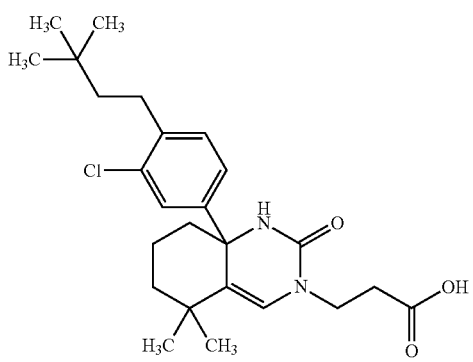 [SMILES: CC(C)(C)CCc1ccc(C23CCCC(C)(C)C2=CN(CCC(=O)O)C(=O)N3)cc1Cl]

includes, unless otherwise specified, all of:
(1) a racemate of the following two (i.e., S- and R-) enantiomers:

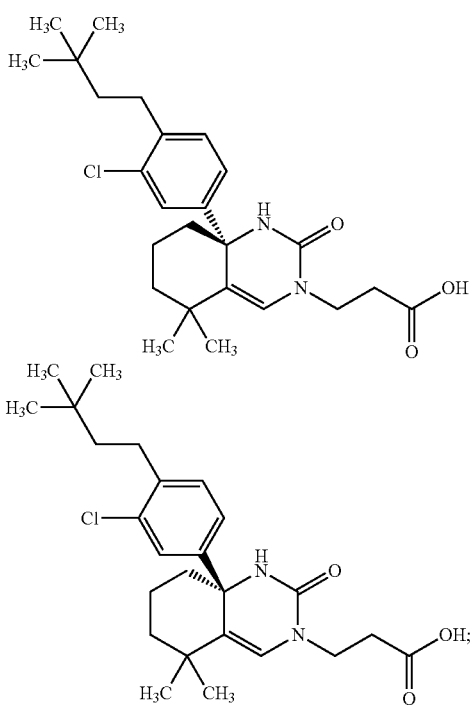

(2) the S-enantiomer; and
(3) the R-enantiomer.

A diastereomeric mixture may be separated into each diastereomer by conventional methods such as chromatography and crystallization. Each diastereomer may also be prepared with a stereochemically-single starting material or by synthetic methods with stereoselective reactions.

An enantiomeric mixture may be separated into each single enantiomer by methods well known in the art.

For example, an enantiomeric mixture may be reacted with a substantially pure enantiomer that is known as a chiral auxiliary to form a diastereomeric mixture, followed by separation from the diastereomeric mixture by ordinary methods such as fractional crystallization and chromatography to give a single diastereomer with an enhanced isomeric ratio or a substantially pure single diastereomer. Then, the separated diastereomer may be converted into a desired enantiomer by removal of the added chiral auxiliary in a cleavage reaction.

An enantiomeric mixture may also be directly separated into each enantiomer by chromatography methods with a chiral stationary phase well known in the art. Alternatively, either of enantiomers may be obtained with a substantially-pure optically-active starting material or by stereoselective synthesis, i.e., asymmetric induction, for a prochiral intermediate with a chiral auxiliary or asymmetric catalyst.

Absolute configurations may be determined by X-ray crystallography for crystalline products or intermediates. Crystalline products or intermediates derivatized with a reagent with a known configuration and an asymmetric center may optionally be used in the determination.

Compound [I] or a pharmaceutically acceptable salt thereof may be labeled with an isotope atom such as $^2$H, $^3$H, $^{14}$C, and $^{35}$S.

For example, any hydrogen atoms of Compound [I] include protium $^1$H (H), deuterium $^2$H (D), and tritium $^3$H (T). For example, when $C_{1-8}$ alkyl of $R^1$ is ethyl, the ethyl group includes —$CD_2CD_3$ and —$CT_2CT_3$ besides —$CH_2CH_3$.

Compound [I], or a pharmaceutically acceptable salt thereof is preferably Compound [I], or a pharmaceutically acceptable salt thereof, substantially purified. More preferable one is Compound [I], or a pharmaceutically acceptable salt thereof, having 80% or more of purity.

According to known methods in the art of pharmaceutical formulations, a pharmaceutical composition herein may be prepared by, for example, mixing Compound [I] or a pharmaceutically acceptable salt thereof with at least one or more pharmaceutically acceptable carrier(s) in an appropriate amount. The content (also referred to as "a therapeutically effective amount" herein) of Compound [I] or a pharmaceutically acceptable salt thereof in the pharmaceutical composition varies depending on dosage forms and doses and is, for example, 0.1 to 100% by weight of the composition.

A dosage form of Compound [I] or a pharmaceutically acceptable salt thereof includes an oral preparation such as tablets, capsules, granules, powders, lozenges, syrups, emulsions, and suspensions and a parenteral preparation such as external preparations, suppositories, injections, eye drops, nasal preparations, and pulmonary preparations.

The term "pharmaceutically acceptable carrier" includes various conventional organic or inorganic carrier substances for formulation materials such as excipients, disintegrants, binders, fluidizers, and lubricants in solid formulations; solvents, solubilizing agents, suspending agents, tonicity agents, buffers, and soothing agents in liquid formulations; and bases, emulsifying agents, wetting agents, stabilizers, stabilizing agents, dispersants, plasticizers, pH regulators, absorption promoters, gelators, preservatives, fillers, solubilizers, solubilizing agents, and suspending agents in semisolid formulations. A preserving agent, an antioxidant agent, a colorant, or a sweetening agent may also be optionally used as an additive.

Such an "excipient" includes, for example, lactose, white soft sugar, D-mannitol, D-sorbitol, cornstarch, dextrin, microcrystalline of crystalline cellulose, carmellose, carmellose calcium, sodium carboxymethyl starch, low substituted hydroxypropyl cellulose, and gum arabic.

Such a "disintegrant" includes, for example, carmellose, carmellose calcium, carmellose sodium, sodium carboxymethyl starch, croscarmellose sodium, crospovidone, low substituted hydroxypropyl cellulose, hydroxypropyl methylcellulose, and crystalline cellulose.

Such a "binder" includes, for example, hydroxypropyl cellulose, hydroxypropyl methylcellulose, povidone, crystalline cellulose, white soft sugar, dextrin, starch, gelatin, carmellose sodium, and gum arabic.

Such a "fluidizer" includes, for example, light anhydrous silicic acid and magnesium stearate.

Such a "lubricant" includes, for example, magnesium stearate, calcium stearate, and talc.

Such a "solvent" includes, for example, purified water, ethanol, propyleneglycol, macrogol, sesame oil, corn oil, and olive oil.

Such a "solubilizing agent" includes, for example, propyleneglycol, D-mannitol, benzyl benzoate, ethanol, triethanolamine, sodium carbonate, and sodium citrate.

Such a "suspending agent" includes, for example, benzalkonium chloride, carmellose, hydroxypropyl cellulose, propyleneglycol, povidone, methylcellulose, and glyceryl monostearate.

Such a "tonicity agent" includes, for example, glucose, D-sorbitol, sodium chloride, and D-mannitol.

Such a "buffer" includes, for example, sodium hydrogen phosphate, sodium acetate, sodium carbonate, and sodium citrate.

Such a "soothing agent" includes, for example, benzyl alcohol.

Such a "base" includes, for example, water, animal or vegetable oils such as olive oil, corn oil, arachis oil, sesame oil, and castor oil, lower alcohols such as ethanol, propanol, propylene glycol, 1,3-butylene glycol, and phenol, higher fatty acids and esters thereof, waxes, higher alcohols, polyalcohols, hydrocarbons such white petrolatum, liquid paraffin, and paraffin, hydrophilic petrolatum, purified lanolin, absorptive ointment, hydrous lanolin, hydrophilic ointment, starch, pullulan, gum arabic, tragacanth gum, gelatin, dextran, cellulose derivatives such as methylcellulose, carboxymethylcellulose, hydroxyethyl cellulose, and hydroxypropyl cellulose, synthetic polymers such as carboxyvinyl polymers, sodium polyacrylate, polyvinyl alcohol, and polyvinylpyrrolidone, propylene glycol, macrogol such as macrogol 200 to 600, and a combination of any two or more of them.

Such a "preserving agent" includes, for example, ethyl parahydroxybenzoate, chlorobutanol, benzyl alcohol, sodium dehydroacetate, and sorbic acid.

Such an "antioxidant agent" includes, for example, sodium sulfite and ascorbic acid.

Such a "colorant" includes, for example, food dye such as Food Red No. 2 and No. 3, and Food Yellow No. 4 and No. 5, and β-carotene.

Such a "sweetening agent" includes, for example saccharin sodium, dipotassium glycyrrhizate, and aspartame.

A pharmaceutical composition herein may be administered orally or parenterally such as locally, rectally, intravenously, intramuscularly, and subcutaneously to human as well as mammals other than human such as mice, rats, hamsters, guinea pigs, rabbits, cats, dogs, pigs, cattle, horses, sheep, and monkeys. A dose may vary depending on subjects to be administered, diseases, symptoms, dosage forms, routes of administration, etc. For example, in oral administration to an adult patient, the dose of Compound [I], the active ingredient, ranges generally from about 0.01 mg to about 1 g per day, which may be administered once or several times in a divided amount.

A kit such as kits for administration, treatment, and/or prevention, a package such as packaged goods, and a set and/or case of medicine which comprises a pharmaceutical composition comprising Compound [I] or a pharmaceutically acceptable salt thereof as the active ingredient or active agent and a written matter concerning the composition indicating that the composition may or should be used for treatment and/or prevention are also useful. Such a kit, package, and set of medicine may comprise one or more containers filled with the pharmaceutical composition or one or more active ingredients and other drugs or medicines (or ingredients) used for the composition. Examples of such a kit, package, and set of medicine include commercial kits, commercial packages, and commercial medicine set for appropriate use in the treatment and/or prevention of intended diseases. The written matter comprised in such a kit, package, and set of medicine includes a cautionary note or package insert in the form designated by the government organization that regulates manufactures, use, or sales of pharmaceutical or biological products which ensures an approval by the government organization on manufactures, use, or sales of products concerning administration to humans. The kit, package, and set of medicine may include packaged products as well as structures configured for appropriate administration steps and configured so as to be able to achieve more preferable medical treatment and/or prevention including treatment and/or prevention of intended diseases.

Compound [I] or a pharmaceutically acceptable salt thereof has RORγ antagonism and is useful for an RORγ antagonist.

The term "having RORγ antagonist activity", "having RORγ antagonism", or "antagonizing RORγ" means that the function of RORγ is antagonized, preferably specifically antagonized, to disappear or reduce its activity, and includes, for example, antagonizing, preferably specifically antagonizing, the function of RORγ according to the conditions described in Test Example 1 below.

The term "RORγ antagonist" means any substances that antagonize the function of RORγ, preferably any substances that specifically antagonize the function of RORγ.

The term "RORγ" is preferably "human RORγ".

Compound [I] or a pharmaceutically acceptable salt thereof has RORγ antagonism, and is expected to be effective against diseases that involve the function of RORγ.

Specifically, Compound [I] or a pharmaceutically acceptable salt thereof is expected to be useful for treating or preventing a disease selected from the group consisting of autoimmune diseases, allergic diseases, dry eye, fibrosis, cancers, metabolic disease, ischemia, cardiomyopathy, hypertension, and periodontal disease.

The term "autoimmune diseases" means a generic name of diseases where an immune system of a subject overreacts to and attacks even normal cells and tissues thereof to cause symptoms, and includes, specifically, rheumatoid arthritis, psoriasis, inflammatory bowel diseases such as Crohn's disease and ulcerative colitis, multiple sclerosis, systemic lupus erythematosus (SLE), Behcet's disease, sarcoidosis, Harada disease, ankylosing spondylitis, uveitis, polymyalgia rheumatica, type I diabetes, graft-versus-host disease, alopecia areata, and vitiligo.

The term "allergic diseases" means diseases derived front the condition where an immune reaction excessively occurs against a certain antigen, and includes, specifically, atopic dermatitis, allergic rhinitis such as pollen allergy, allergic conjunctivitis, allergic gastroenteritis, asthma such as bronchial asthma and infantile asthma, food allergy, medication allergy, and hives.

The term "fibrosis" means a condition with increased fibroconnective tissues, and includes, specifically, lung fibrosis and primary biliary cirrhosis.

The term "cancer" includes malignant melanoma and prostate cancer.

The term "metabolic disease" means a disease caused by abnormality of metabolic turnover or a disease which includes metabolic abnormality as an element that constitutes pathogenesis, and includes, for example, diabetes such as type I diabetes and type II diabetes, hepatic steatosis, and non-alcoholic fatty liver disease.

The term "treating" used herein also includes ameliorating symptoms, preventing from becoming severe, maintaining remission, preventing exacerbation, and preventing relapse.

The term "preventing" used herein means suppressing pathogenesis of symptoms.

As long as an embodiment disclosed herein is compatible with another embodiment disclosed in another portion of the description, any two or more combinations of these embodiments are also intended to be included in the invention.

A general method of preparing Compound [I] or a pharmaceutically acceptable salt thereof is illustrated as below. A method of preparing Compound [I] or a pharmaceutically acceptable salt thereof, however, is not intended to be limited thereto. Salts of each compound in the general method may be selected from the above "pharmaceutically acceptable salt" unless otherwise specified.

Each compound obtained in each step may be isolated and/or purified by known methods such as distillation, recrystallization, and column chromatography, if necessary, but each reaction may optionally proceed to a sequential step without isolation and/or purification.

The room temperature herein means a temperature under no control, and includes 1° C. to 40° C. as one embodiment.

Abbreviations used herein are defined as follows.
IPA: Isopropyl alcohol
Hex.: n-Hexane
DMSO: Dimethyl sulfoxide
NOE: Nuclear overhauser effect
DsPhSO$_3$N$_3$: p-Dodecylbenzenesulfonylazide
DMEAD: Di-2-methoxyethyl azodicarboxylate
TBAI: Tetrabutylammonium iodide
PPTS: Pyridinium p-toluenesulfonate
THF: Tetrahydrofuran
WSC·HCl: 1-(3-Dimethylaminopropyl)-3-ethylcarbodiimide hydrochloride
DMF: Dimethylaminopyridine
LDA: Lithium diisopropylamide
DMF: N,N-Dimethylformamide
DIBAL-H: Diisobutylaluminum hydride
TFA: Trifluoroacetic acid
NaHMDS: Sodium bis(trimethylsilyl)amide
HMDS: Bis(trimethylsilyl)amine
TEMPO: 2,2,6,6-Tetramethylpiperidin-1-oxyl
TBAF: Tetrabutylammonium fluoride

[Preparation Method 1]: Preparation of Compound [I-1] or a Salt Thereof

Compound [I] wherein X$^2$ is =C(R$^4$)—, or a salt thereof, may be obtained by, for example, the following Preparation method 1.

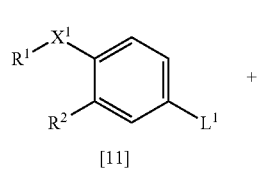

[11]

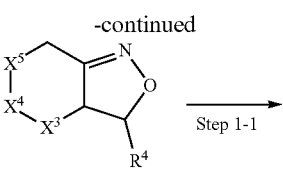

[12]

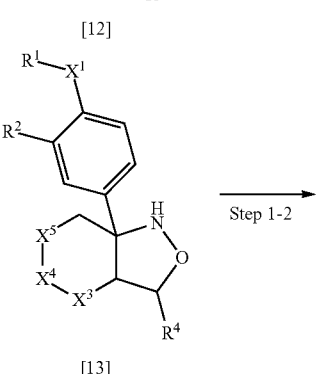

[13]

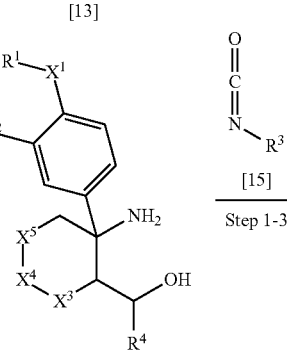

[14]

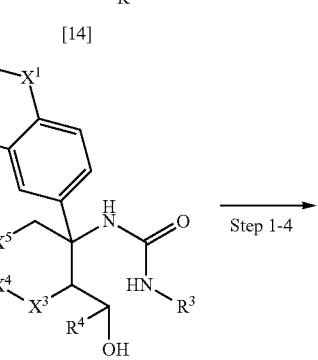

[16]

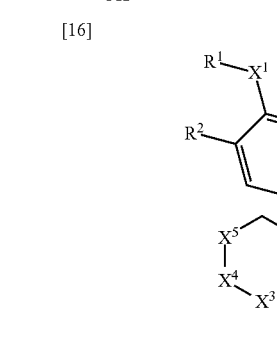

[I-1]

In the scheme, R$^1$, R$^2$, R$^3$, R$^4$, X$^1$, X$^3$, X$^4$, and X$^5$ are defined as defined above, and L$^1$ is halogen, for example, selected from chloro, bromo, and iodo.

(Step 1-1)

Compound [13] or a salt thereof may be prepared by reaction of Compound [11] with Compound [12] or a salt thereof in a solvent in the presence of an organometallic reagent and Lewis acid.

Such a solvent includes, for example, ether solvents such as tetrahydrofuran; hydrocarbon solvents such as toluene; and a mixed solvent of any of them. A preferable solvent herein is tetrahydrofuran.

Such an organometallic reagent includes, for example, n-butyllithium and tert-butyllithium. A preferable organometallic reagent herein is n-butyllithium.

Such Lewis acid includes a boron trifluoride-diethyl ether complex.

The reaction temperature herein ranges, for example, from −102° C. to −69° C., preferably from −78° C. to −70° C.

Compound [11] commercially available or may be prepared by known methods from commercially available products.

Compound [12] or a salt thereof may be prepared by, for example, any of Preparation methods 1A to 1R below.

(Step 1-2)

Compound [14] or a salt thereof may be prepared by reduction of Compound [13] or a salt thereof in a solvent in the presence of a metal reagent and an acid.

Such a metal reagent includes, for example, zinc and iron. A preferable metal reagent herein is zinc.

Such an acid includes, for example, acetic acid, trifluoroacetic acid, hydrochloric acid, and sulfuric acid. A preferable acid herein is acetic acid or hydrochloric acid.

Such a solvent includes, for example, ether solvents such as tetrahydrofuran; alcohol solvents such as methanol; water; and a mixed solvent of any of them. A preferable solvent herein is tetrahydrofuran, methanol, or water.

The reaction temperature herein ranges, for example, from 0° C. to 80° C., preferably from room temperature to 80° C.

Compound [14] or a salt thereof may also prepared by hydrogenation of Compound [13] or a salt thereof in a solvent in the presence of a catalytic amount of palladium. Such a solvent includes, for example, ether solvents such as tetrahydrofuran; alcohol solvents such as ethanol; ester solvents such as ethyl acetate; and a mixed solvent of any of them. A preferable solvent herein is tetrahydrofuran, ethanol, or ethyl acetate. The reaction temperature herein is room temperature.

(Step 1-3)

Compound [16] or a salt thereof may be prepared by reaction of Compound [14] or a salt thereof with Compound [15] or a salt thereof in a solvent.

Such a solvent includes, for example, hydrocarbon solvents such as toluene; ether solvents such as tetrahydrofuran; halogenated solvents such as dichloromethane; and a mixed solvent of any of them. A preferable solvent herein is toluene, tetrahydrofuran, or dichloromethane.

The reaction temperature herein ranges, for example, from 0° C. to 80° C., preferably from 0° C. to room temperature.

The reaction may also be carried out with optional addition of triethylamine.

(Step 1-4)

Compound [I-1] or a salt thereof may be prepared by oxidation of Compound [16] or a salt thereof in a solvent in the presence of an oxidizing agent, followed by cyclization.

Such a solvent includes, for example, halogenated solvents such as chloroform; ester solvents such as ethyl acetate; nitrile solvents such as acetonitrile; ether solvents such as cyclopentyl methyl ether; carboxylic acid solvents such as acetic acid; and a mixed solvent of any of them. A preferable solvent herein is dichloromethane, chloroform, cyclopentyl methyl ether, or acetic acid.

Such an oxidizing agent includes, for example, 2-azaadamantan-N-oxyl, 2,2,6,6-tetramethylpiperidin-1-oxyl radical, and Dess-Martin reagent. The reaction may also be carried out with optional addition of a co-oxidizing agent such as (diacetoxyiodo)benzene and sodium hypochlorite. A preferable oxidizing agent herein is a mixture of 2,2,6,6-tetramethylpiperidin-1-oxyl radical and (diacetoxyiodo)benzene.

An acid in the cyclization includes hydrochloric acid, trifluoroacetic acid, and p-toluenesulfonic acid. A preferable acid herein is trifluoroacetic acid.

The reaction temperature herein ranges, for example, from 0° C. to 80° C., preferably from 0° C. to room temperature.

[Preparation Method 1A]: Preparation of Compound [I-1A] or a Salt Thereof

Compound [I] wherein $X^2$ is =C($R^4$)— and $R^4$ is hydrogen (Compound [I-1A]):

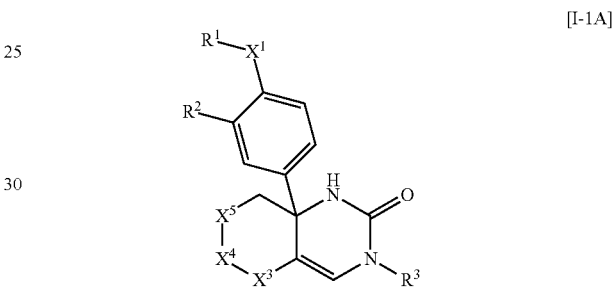

wherein $R^1$, $R^2$, $R^3$, $X^1$, $X^3$, $X^4$, and $X^5$ are defined as defined above, or a salt thereof, may be obtained by, for example, using Compound [12a] or a salt thereof obtained in Preparation method 1A as follows, instead of Compound [12] or a salt thereof in Preparation method 1.

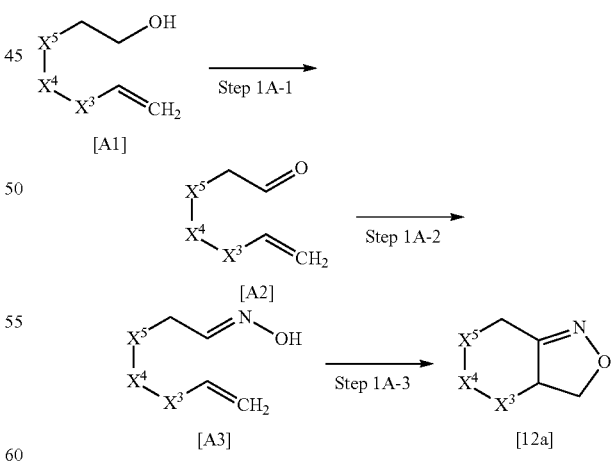

In the scheme, $X^3$, $X^4$, and $X^5$ are defined as defined above.

(Step 1A-1)

Compound [A2] or a salt thereof may be prepared by oxidation of Compound [A1] or a salt thereof in a solvent.

Such a solvent includes, for example, ester solvents such as ethyl acetate; hydrocarbon solvents such as toluene;

sulfoxide solvents such as dimethyl sulfoxide; ether solvents such as tetrahydrofuran; and halogenated solvents such as chloroform. A preferable solvent herein is chloroform or dichloromethane.

The oxidizing agent herein includes, for example, 2,2,6,6-tetramethylpiperidin-1-oxyl radical, dimethyl sulfoxide, a sulfur trioxide-pyridine complex, iodoxybenzoic acid, pyridinium chlorochromate, and Dess-Martin reagent. A preferable oxidizing agent herein is 2,2,6,6-tetramethylpiperidin-1-oxyl radical.

The reaction temperature herein ranges, for example, from −78° C. to room temperature, preferably from 0° C. to room temperature.

The reaction may also be carried out with optional addition of (diacetoxyiodo)benzene.

(Step 1A-2)

Compound [A3] or a salt thereof may be prepared by reaction of Compound [A2] or a salt thereof with hydroxylamine hydrochloride in a solvent.

Such a solvent includes, for example, alcohol solvents such as ethanol; hydrocarbon solvents such as toluene; halogenated solvents such as dichloromethane; ether solvents such as tetrahydrofuran; amide solvents such as dimethylformamide; nitrile solvents such as acetonitrile; water; and a mixed solvent of any of them. A preferable solvent herein is ethanol, toluene, tetrahydrofuran, or water.

The reaction temperature herein ranges from room temperature to 120° C.

The reaction may also be carried out with optional addition of sodium acetate.

(Step 1A-3)

Compound [12a] or a salt thereof may be prepared by cyclization of Compound [A3] or a salt thereof in a solvent in the presence of an oxidizing agent.

Such an oxidizing agent includes, for example, (diacetoxyiodo)benzene, sodium hypochlorite, chloramine T, and N-chlorosuccinimide. A preferable oxidizing agent herein is (diacetoxyiodo)benzene or sodium hypochlorite.

When (diacetoxyiodo)benzene as used for the oxidizing agent, an acid is used for an additive. Such an acid includes trifluoroacetic acid. A solvent used herein includes, for example, alcohol solvents such as methanol; halogenated solvents such as dichloromethane; and a mixed solvent of any of them. A preferable solvent herein is methanol or dichloromethane. The reaction temperature herein ranges from 0° C. to room temperature.

When aqueous sodium hypochlorite solution is used for the oxidizing agent, a base is used for an additive. Such a base includes, for example, triethylamine and pyridine. A preferable base herein is triethylamine. A solvent used herein includes, for example, halogenated solvents such as dichloromethane; alcohol solvents such as ethanol; nitrile solvents such as acetonitrile; ether solvents such as tert-butyl methyl ether; and a mixed solvent of any of them. A preferable solvent herein is dichloromethane. The reaction temperature herein ranges, for example, from 0° C. to room temperature and is preferably room temperature.

[Preparation Method 1B]: Preparation of Compound [I-1B] or a Salt Thereof

Compound [I] wherein $X^2$ is =C($R^4$)—, $R^4$ is hydrogen, $X^4$ is a bond, and $X^5$ is —O— (Compound [I-1B]):

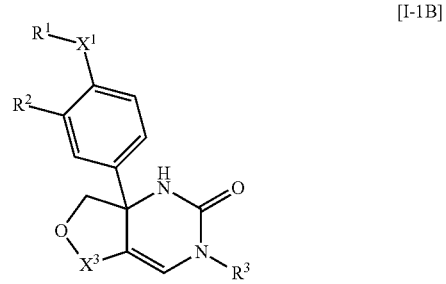

[I-1B]

wherein $R^1$, $R^2$, $R^3$, $X^1$, and $X^3$ are defined as defined above, or a salt thereof, may be obtained by, for example, using Compound [12b] or a salt thereof obtained in Preparation method 1B as follows, instead of Compound [12] or a salt thereof in the above Preparation method 1.

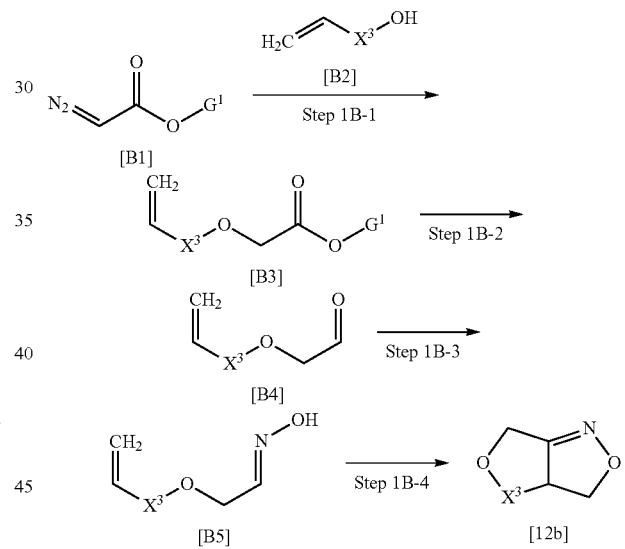

In the scheme, $X^3$ is defined as defined above, and $G^1$ is a protective group of carboxy, for example, selected from methyl, ethyl, isopropyl, tert-butyl, or benzyl.

(Step 1B-1)

Compound [B3] or a salt thereof may be prepared by reaction of Compound [B1] with Compound [B2] or a salt thereof in a solvent or without any solvents in the presence of a catalyst.

Such a solvent includes, for example, halogenated solvents such as dichloromethane; ester solvents such as ethyl acetate; ether solvents such as diethyl ether; hydrocarbon solvents such as benzene; and a mixed solvent of any of them. Herein, no solvent or dichloromethane is preferable.

Such a catalyst includes, for example, rhodium (II) acetate dimer dihydrate, indium (III) chloride, and iron (III) chloride. A preferable catalyst herein is rhodium (II) acetate dimer dihydrate.

The reaction temperature herein is room temperature.

(Step 1B-2)

Compound [B4] or a salt thereof may be prepared by reduction of Compound [B3] or a salt thereof in a solvent.

Such a solvent includes, for example, ether solvents such as tetrahydrofuran; halogenated solvents such as dichloromethane; hydrocarbon solvents such as toluene; and a mixed solvent of any of them. A preferable solvent herein is tetrahydrofuran, dichloromethane, or toluene.

A reducing agent used herein includes, for example, diisobutylaluminum hydride, and lithium aluminum hydride. A preferable reducing agent herein is diisobutylaluminum hydride.

The reaction temperature herein ranges, for example, from −78° C. to room temperature, preferably from −78° C. to 0° C.

(Step 1B-3)

Compound [B5] or a salt thereof may be prepared from Compound [B4] or a salt thereof in a similar manner to Step 1A-2.

(Step 1B-4)

Compound [12b] or a salt thereof may be prepared from Compound [B5] or a salt thereof in a similar manner to Step 1A-3.

[Preparation Method 1C]: Preparation of Compound [I-1C] or a Salt Thereof

Compound [I] wherein $X^2$ is $=C(R^4)-$, $R^4$ is hydrogen, $X^4$ is a bond, $X^5$ is $-C(R^9)(R^{10})-$, and both of $R^9$ and $R^{10}$ are hydrogen (Compound [I-1C]):

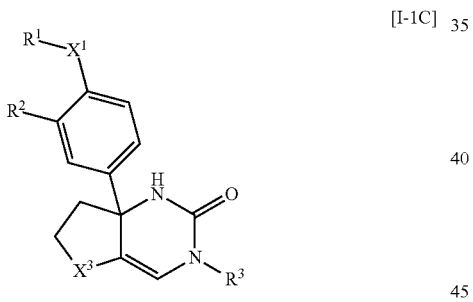

wherein $R^1$, $R^2$, $R^3$, $X^1$, and $X^3$ are defined as defined above, or a salt thereof, may be obtained by, for example, using Compound [12c] or a salt thereof obtained in Preparation method 1C as follows, instead of Compound [12] or a salt thereof in the above Preparation method 1.

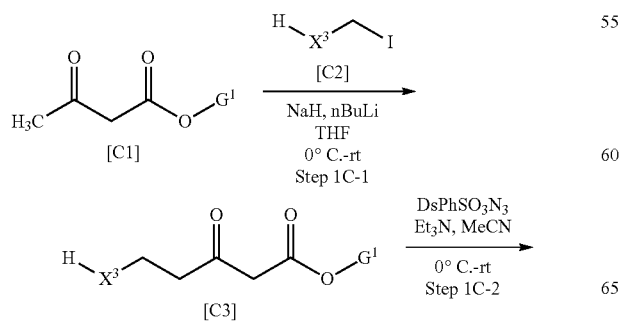

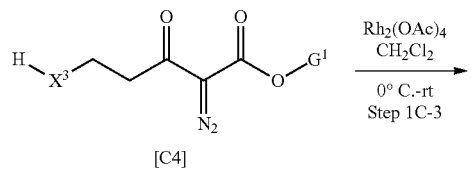

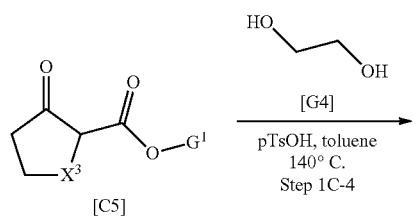

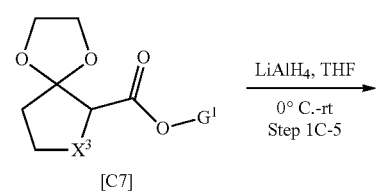

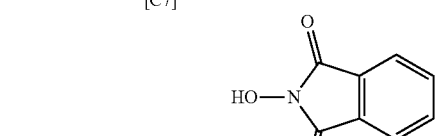

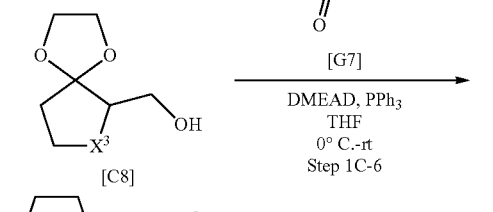

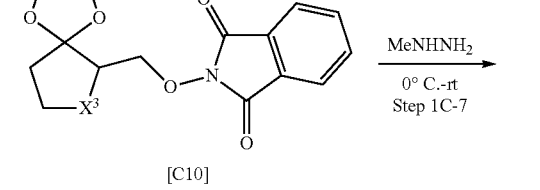

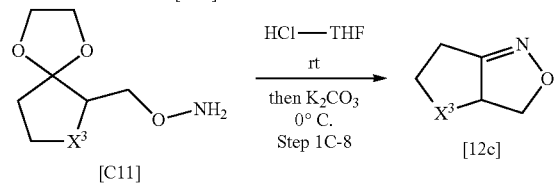

In the scheme, $X^3$ and $G^1$ are defined as defined above.

[Preparation Method 1D]: Preparation of Compound [I-1D] or a Salt Thereof

Compound [I] wherein $X^2$ is $=C(R^4)-$, $R^4$ is hydrogen, $X^3$ is $-C(R^5)(R^6)-$, $R^5$ is hydrogen, $R^6$ is $C_{1-4}$ alkyl, $X^4$ is $-C(R^7)(R^8)-$, $R^7$ and $R^8$ are each independently hydrogen or $C_{1-4}$ alkyl, $X^5$ is $-C(R^9)(R^{10})-$, and both of $R^9$ and $R^{10}$ are hydrogen (Compound [I-1D]):

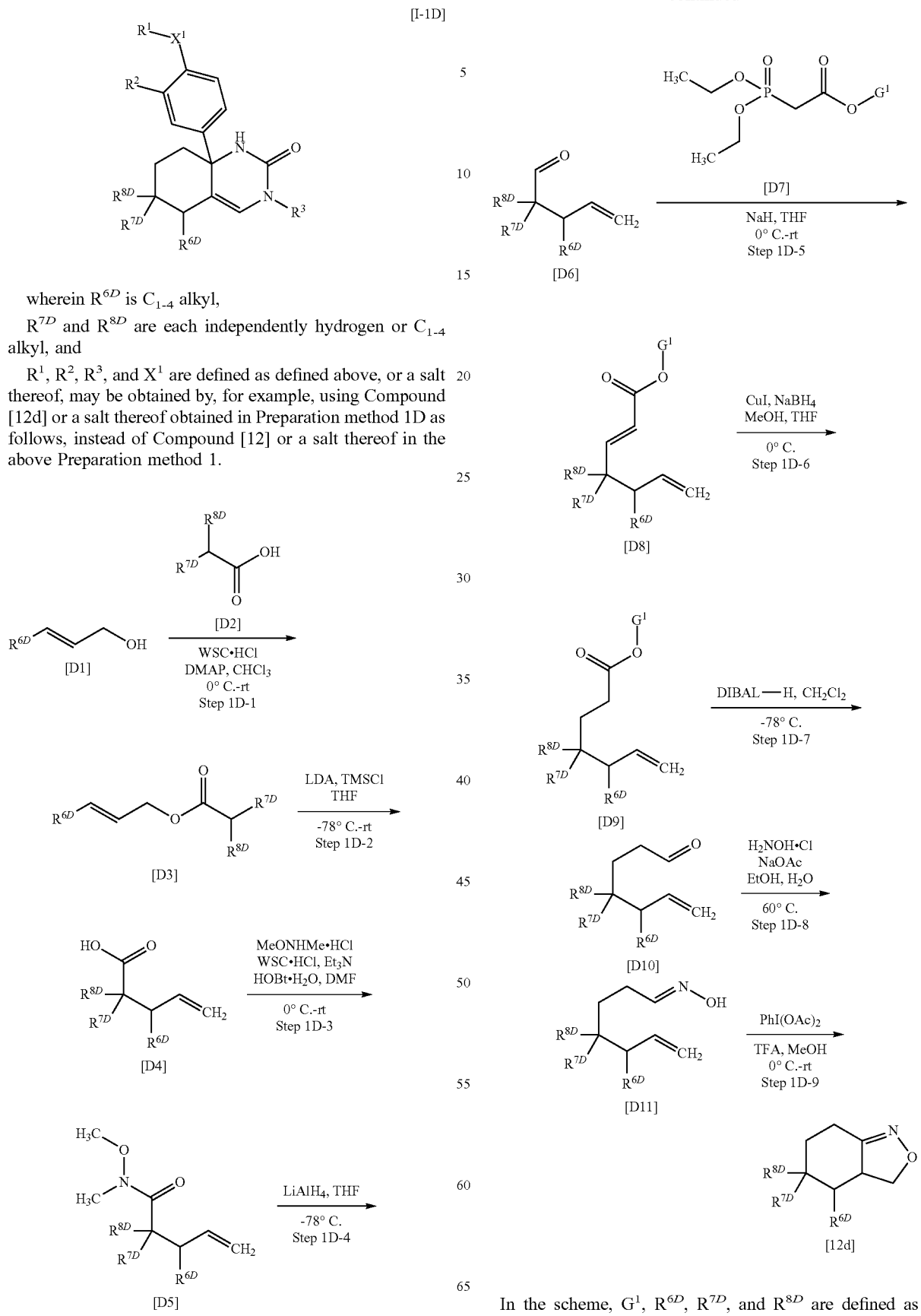

wherein $R^{6D}$ is $C_{1-4}$ alkyl, $R^{7D}$ and $R^{8D}$ are each independently hydrogen or $C_{1-4}$ alkyl, and $R^1$, $R^2$, $R^3$, and $X^1$ are defined as defined above, or a salt thereof, may be obtained by, for example, using Compound [12d] or a salt thereof obtained in Preparation method 1D as follows, instead of Compound [12] or a salt thereof in the above Preparation method 1.

In the scheme, $G^1$, $R^{6D}$, $R^{7D}$, and $R^{8D}$ are defined as defined above.

[Preparation Method 1E]: Preparation of Compound [I-1E] or a Salt Thereof

Compound [I] wherein $X^2$ is $=C(R^4)—$, $R^4$ is hydrogen, and $X^5$ is —O— (Compound [I-1E]):

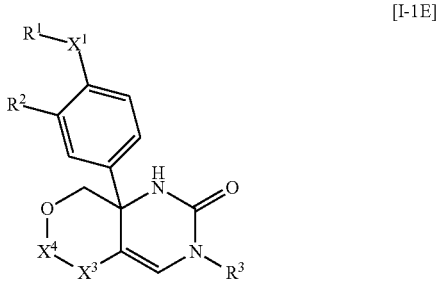

wherein $R^1$, $R^2$, $R^3$, $X^1$, $X^3$, and $X^4$ are defined as defined above, or a salt thereof, may be obtained by, for example, using Compound [12e] or a salt thereof obtained in Preparation method 1E as follows, instead or Compound [12] or a salt thereof in the above Preparation method 1.

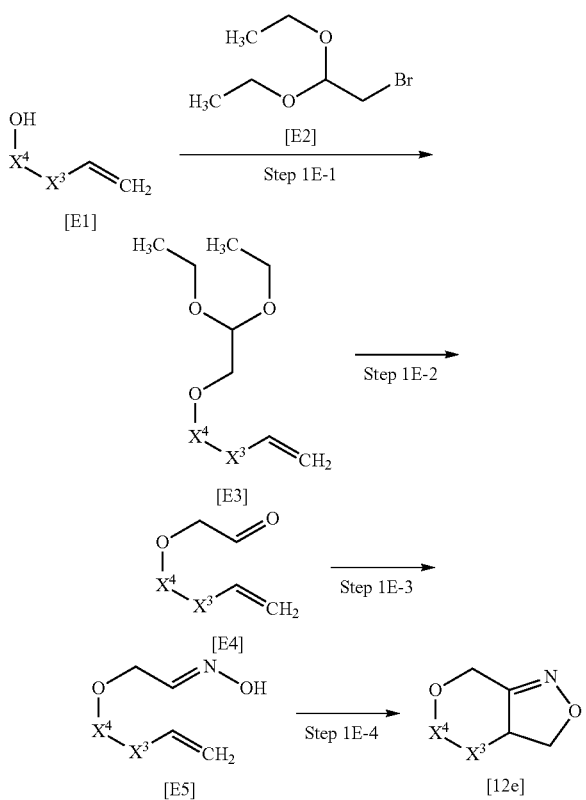

In the scheme, $X^3$ and $X^4$ are defined as defined above.

(Step 1E-1)

Compound [E3] may be prepared by reaction of Compound [E1] with Compound [E2] in a solvent in the presence of a base.

Such a solvent includes, for example, ether solvents such as tetrahydrofuran; hydrocarbon solvents such as toluene; alcoholic solvents such as methanol; amide solvents such as dimethylformamide; sulfoxide solvents such as dimethylsulfoxide; and a mixed solvent of any of them. A preferable solvent herein is tetrahydrofuran.

Such a base includes, for example, sodium hydride, sodium hydroxide, sodium tert-butoxide, sodium bis(trimethylsilyl)amide, lithium diisopropylamide, and n-butyllithium. A preferable base herein is sodium hydride.

The reaction temperature herein ranges, for example, from 0° C. to 140° C., preferably from 0° C. to room temperature.

(Step 1E-2)

Compound [E4] may be prepared by treatment of Compound [E3] in a solvent in the presence of an acid.

Such a solvent includes, for example, ether solvents such as tetrahydrofuran; halogen solvents such as dichloromethane; alcoholic solvents such as methanol; water; and a mixed solvent of any of them. A preferable solvent herein is tetrahydrofuran or water.

Such an acid includes, for example, hydrochloric acid, sulfuric acid, acetic acid, phosphoric acid, boron trifluoride-diethyl ether complex, trimethylsilyl iodide, iodine, and ion-exchange resin. A preferable acid herein is hydrochloric acid.

The reaction temperature herein ranges, for example, from 0° C. to 120° C. and is preferably 60° C.

(Step 1E-3)

Compound [E5] or a salt thereof may be prepared from Compound [E4] in a similar manner to Step 1A-2.

(Step 1E-4)

Compound [12e] or a salt thereof may be prepared from Compound [E5] or a salt thereof in a similar manner to Step 1A-3.

[Preparation Method 1F]: Preparation of Compound [I-1F] or a Salt Thereof

Compound [I] wherein $X^2$ is $=C(R^4)—$, $R^4$ is hydrogen, $X^3$ is $—C(R^5)(R^6)—$, $R^5$ is hydrogen, $R^6$ is alkyl, $X^4$ is a bond, $X^5$ is $—C(R^9)(R^{10})—$, and $R^9$ and $R^{10}$ are each independently hydrogen or $C_{1-4}$ alkyl (Compound [I-1F]):

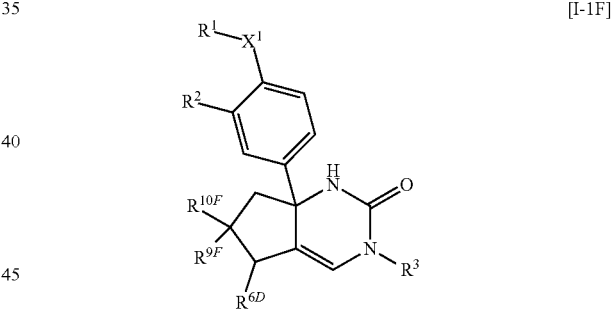

wherein $R^{9F}$ and $R^{10F}$ are each independently hydrogen or $C_{1-4}$ alkyl, and $R^1$, $R^2$, $R^3$, $R^{6D}$, and $X^1$ are defined as defined above, or a salt thereof, may be obtained by, for example, using Compound [12f] or a salt thereof obtained in Preparation method 1F as follows, instead of Compound [12] or a salt thereof in the above Preparation method 1.

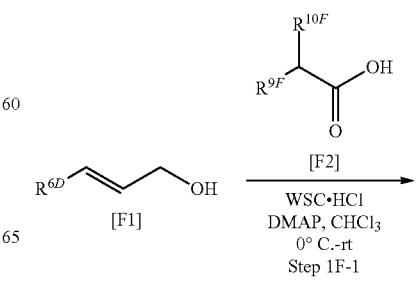

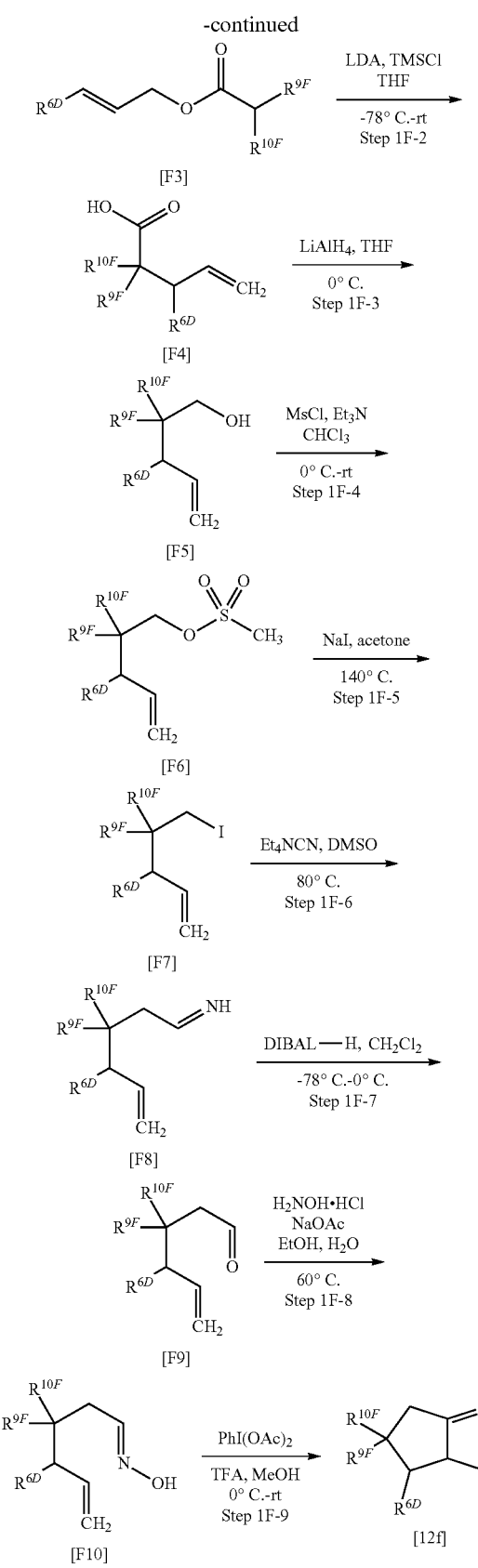

In the scheme, $R^{6D}$, $R^{9F}$, and $R^{10F}$ are defined as defined above.

[Preparation Method 1G]: Alternative Preparation of Compound [I-1A] or a Salt Thereof Compound [I] wherein $X^2$ is =C($R^4$)— and $R^4$ is hydrogen (Compound [I-1A]):

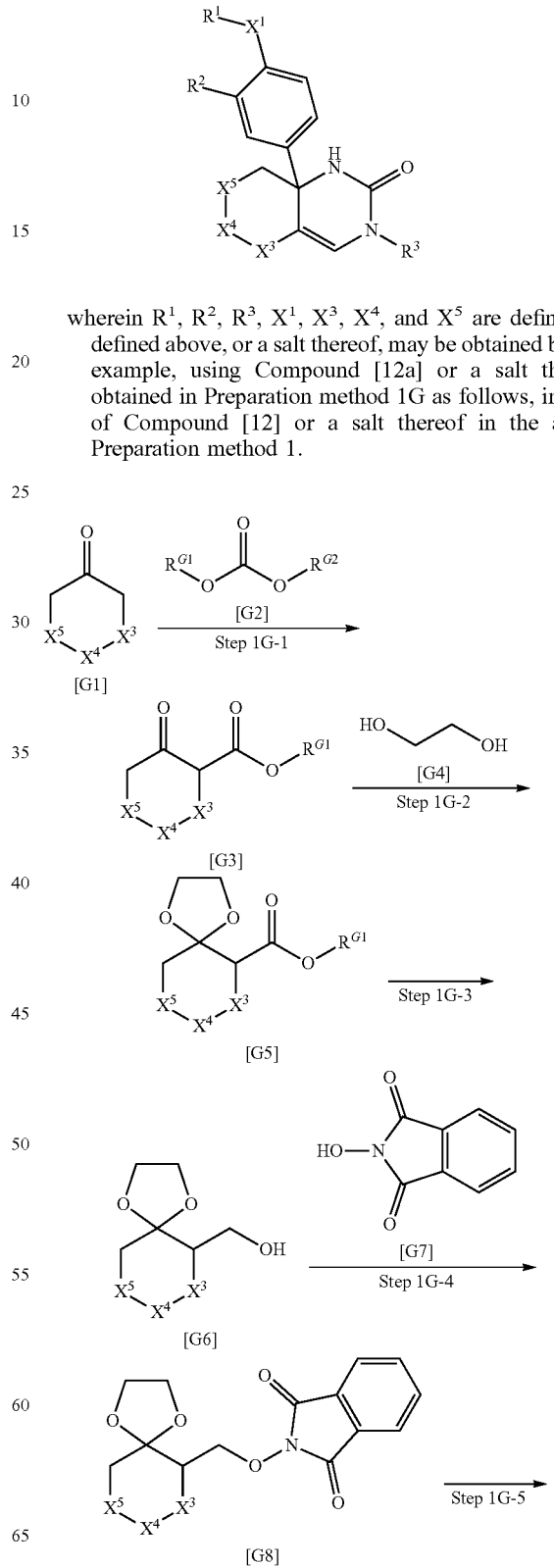

wherein $R^1$, $R^2$, $R^3$, $X^1$, $X^3$, $X^4$, and $X^5$ are defined as defined above, or a salt thereof, may be obtained by, for example, using Compound [12a] or a salt thereof obtained in Preparation method 1G as follows, instead of Compound [12] or a salt thereof in the above Preparation method 1.

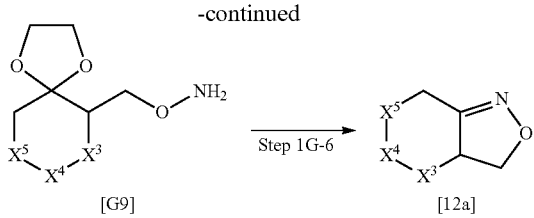

In the scheme, $R^{G1}$ and $R^{G2}$ each independently $C_{1-4}$ alkyl, and $X^3$, $X^4$, and $X^5$ are defined as defined above.

(Step 1G-1)

Compound [G3] or a salt thereof may be prepared by reaction of Compound [G1] or a salt thereof with Compound [G2] in a solvent in the presence of a base.

Such a solvent includes, for example, ether solvents such as tetrahydrofuran; hydrocarbon solvents such as toluene; sulfoxide solvents such as dimethyl sulfoxide; and a mixed solvent of any of them. A preferable solvent herein is tetrahydrofuran.

Such a base includes sodium hydride and lithium diisopropylamide.

The reaction temperature herein ranges, for example, from −78° C. to 110° C., preferably from −78° C. to 65° C.

The reaction may also be carried out with optional addition of 18-crown-6-ether.

(Step 1G-2)

Compound [G5] or a salt thereof may be prepared by protection of a carbonyl group of Compound [G3] or a salt thereof with Compound [G4] in a solvent in the presence of an acid.

Such a solvent includes, for example, hydrocarbon solvents such as toluene; halogenated solvents such as dichloromethane; nitrile solvents such as acetonitrile; and a mixed solvent of any of them. A preferable solvent herein is toluene.

Such an acid includes, for example, p-toluenesulfonic acid, and pyridinium p-toluenesulfonate. A preferable acid herein is p-toluenesulfonic acid.

The reaction temperature herein ranges, for example, from room temperature to 120° C., preferably from 100° C. to 120° C.

(Step 1G-3)

Compound [G6] or a salt thereof may be prepared by reduction of Compound [G5] or a salt thereof in a solvent.

Such a solvent includes, for example, ether solvents such as tetrahydrofuran; hydrocarbon solvents such as toluene; halogenated solvents such as dichloromethane; and a mixed solvent of any of them. A preferable solvent herein is tetrahydrofuran or toluene.

A reducing agent used herein includes, for example, lithium aluminum hydride and diisobutylaluminum hydride. A preferable reducing agent herein is diisobutylaluminum hydride.

The reaction temperature herein ranges, for example, from −78° C. to 65° C., preferably from −78° C. to room temperature.

(Step 1G-4)

Compound [G8] or a salt thereof may be prepared by Mitsunobu reaction of Compound [G6] or a salt thereof with Compound [G7] in a solvent.

Such a solvent includes, for example, ether solvents such as tetrahydrofuran; halogenated solvents such as dichloromethane; hydrocarbon solvents such as toluene; and a mixed solvent of any of them. A preferable solvent herein is tetrahydrofuran or dichloromethane.

A reagent used in Mitsunobu reaction includes, for example, a mixture of triphenylphosphine or tributylphosphine with diethyl azodicarboxylate or dipiperidineamide azodicarboxylate. A preferable reagent used in Mitsunobu reaction is a mixture of triphenylphosphine with diethyl azodicarboxylate.

The reaction temperature herein ranges, for example, from 0° C. to 80° C., preferably from 0° C. to room temperature.

(Step 1G-5)

Compound [G9] or a salt thereof may be prepared by removal of a phthaloyl group of Compound [G8] or a salt thereof in a solvent.

Such a solvent includes, for example, alcohol solvents such as ethanol; halogenated solvents such as dichloromethane; ether solvents such as diethyl ether; and a mixed solvent of any of them. A preferable solvent herein is ethanol or dichloromethane.

A reagent used for removal of the phthaloyl group includes, for example, methylhydrazine, hydrazine, and ethanolamine. A preferable reagent used for removal of the phthaloyl group is methylhydrazine or hydrazine.

The reaction temperature herein ranges, for example, from 0° C. to 100° C., preferably from room temperature to 100° C.

(Step 1G-6)

Compound [12a] or a salt thereof may be prepared by removal of an acetal group of Compound [G9] or a salt thereof in a solvent in the presence of an acid, followed by intramolecular cyclization in the presence of a base.

Such a solvent includes, for example, alcohol solvents such as methanol; ether solvents such as tetrahydrofuran; halogenated solvents such as dichloromethane; and a mixed solvent of any of them. A preferable solvent herein is methanol or tetrahydrofuran.

Such an acid includes, for example, hydrochloric acid, acetic acid, and p-toluenesulfonic acid. A preferable acid herein is hydrochloric acid or p-toluenesulfonic acid.

Such a base includes, for example, potassium carbonate, sodium acetate, and triethylamine. A preferable base herein is potassium carbonate.

The reaction temperature herein ranges, for example, from 0° C. to 120° C., preferably from 0° C. to room temperature.

[Preparation Method 1H]: Preparation of Compound [I-1H] or a Salt Thereof

Compound [I] wherein $X^2$ is $=C(R^4)-$, $R^4$ is hydrogen, $X^3$ is $-C(R^5)(R^6)-$, $R^5$ is hydrogen, $R^6$ is $C_{1-4}$ alkyl, $X^4$ is $-C(R^7)(R^8)-$, $R^7$ is $C_{1-4}$ alkyl, $R^8$ is hydrogen, $X^5$ is $-C(R^9)(R^{10})-$, and both of $R^9$ and $R^{10}$ are hydrogen (Compound [I-1H]):

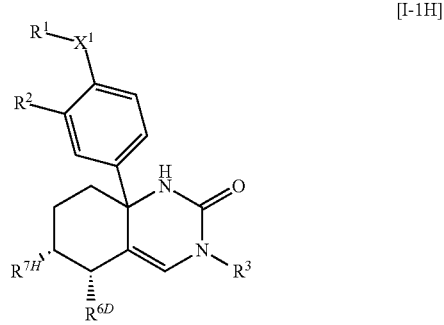

wherein $R^{7H}$ is $C_{1-4}$ alkyl, and $R^1$, $R^2$, $R^3$, $R^{6D}$, and $X^1$ are defined as defined above, or salt thereof, may be obtained by, for example, using Compound [12h] or a salt thereof obtained in Preparation method 1H as follows, instead of Compound [12] or a salt thereof in the above Preparation method 1.

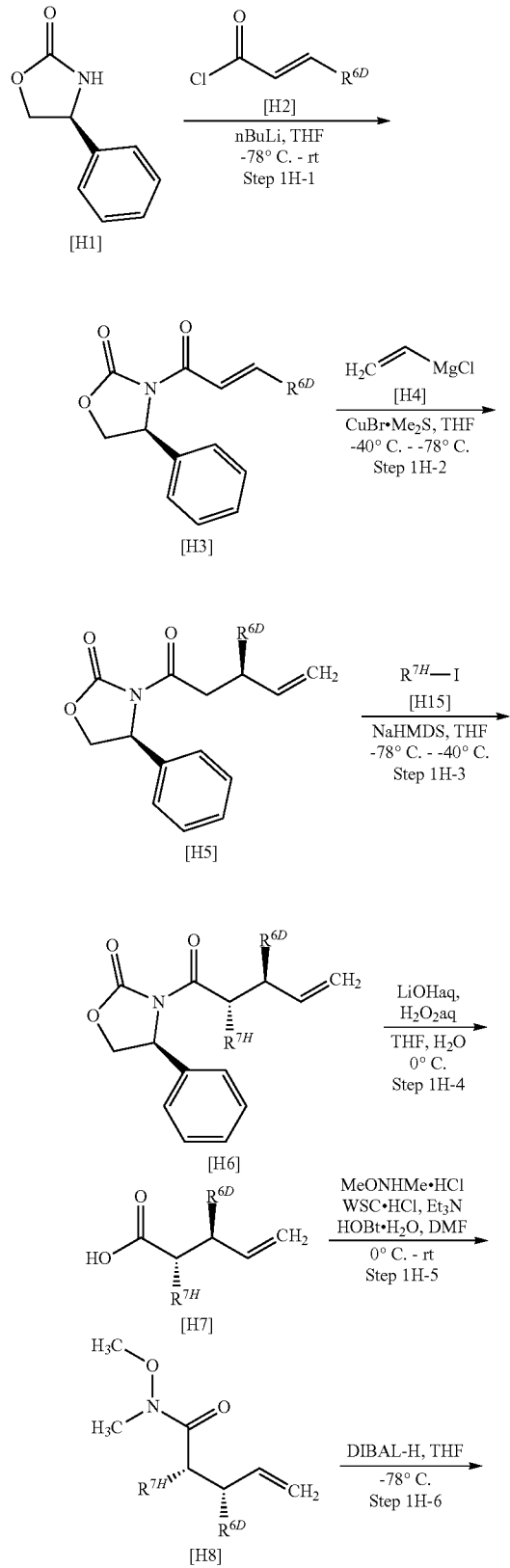

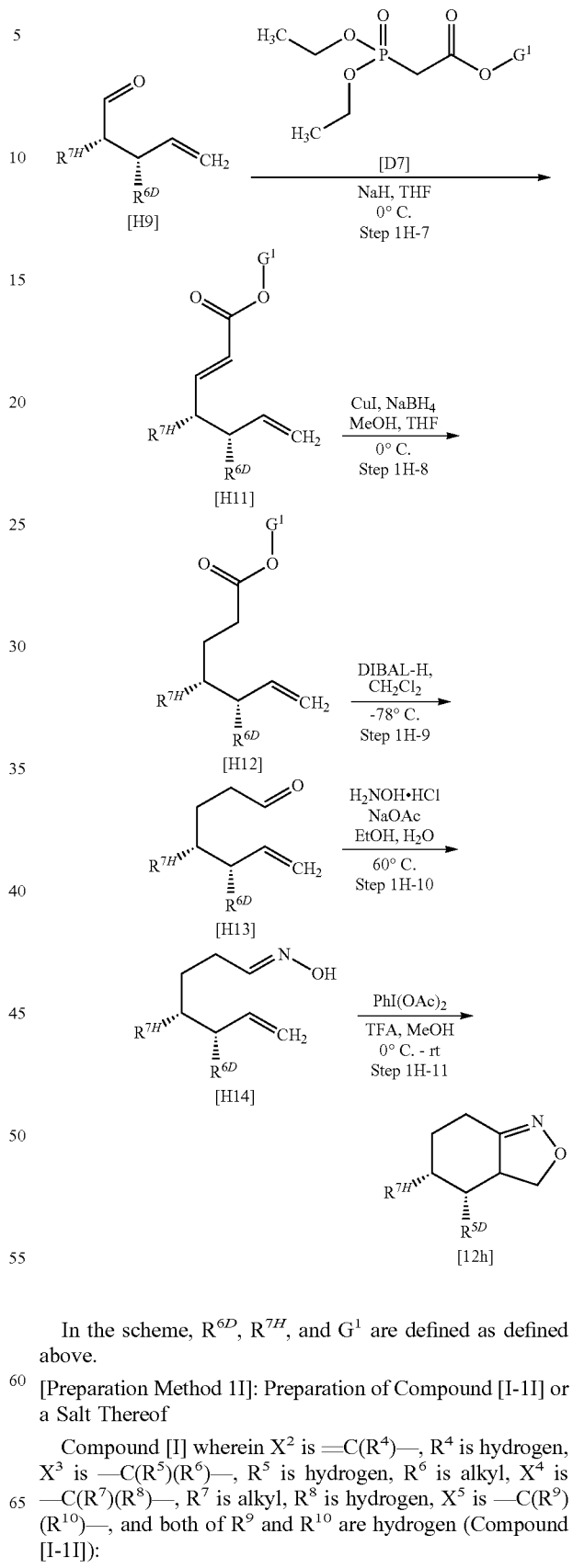

In the scheme, $R^{6D}$, $R^{7H}$, and $G^1$ are defined as defined above.

[Preparation Method 1I]: Preparation of Compound [I-1I] or a Salt Thereof

Compound [I] wherein $X^2$ is =C($R^4$)—, $R^4$ is hydrogen, $X^3$ is —C($R^5$)($R^6$)—, $R^5$ is hydrogen, $R^6$ is alkyl, $X^4$ is —C($R^7$)($R^8$)—, $R^7$ is alkyl, $R^8$ is hydrogen, $X^5$ is —C($R^9$)($R^{10}$)—, and both of $R^9$ and $R^{10}$ are hydrogen (Compound [I-1I]):

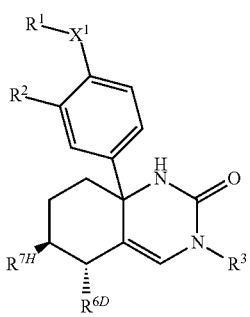
wherein R¹, R², R³, R$^{6D}$, R$^{7H}$, and X¹ are defined as defined above, or a salt thereof, may be obtained by, for example, using Compound [12i] or a salt thereof obtained in Preparation method 1I as follows, instead of Compound [12] or a salt thereof in the above Preparation method 1.
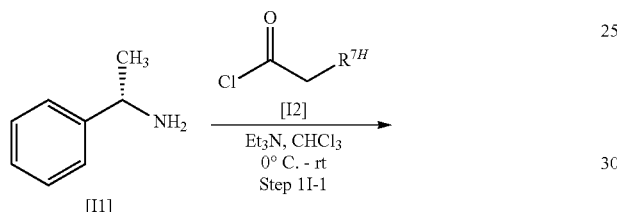
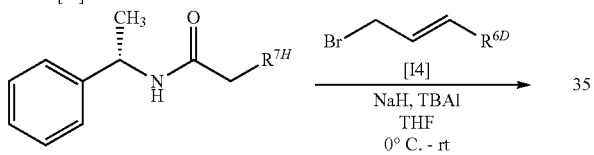
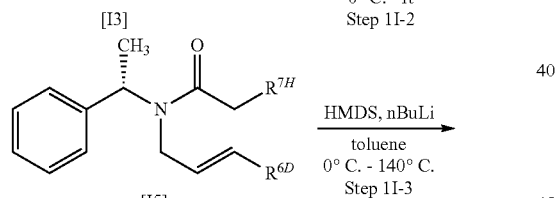
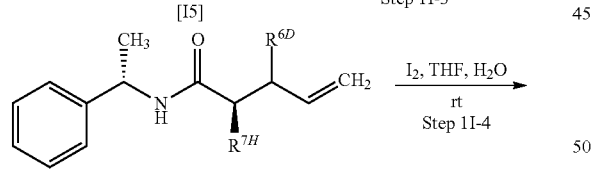
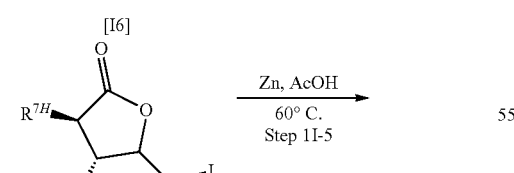
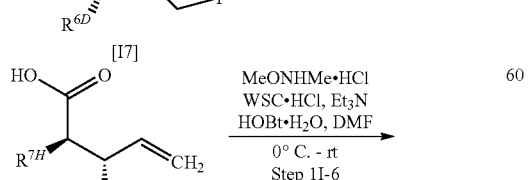
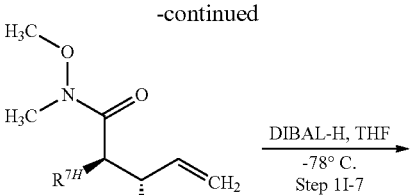
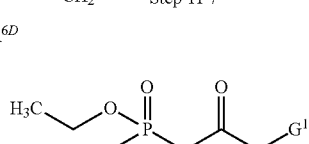
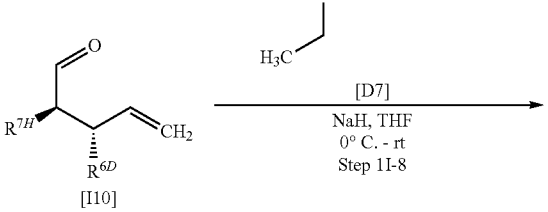
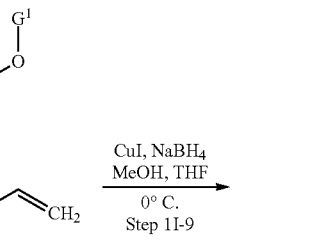
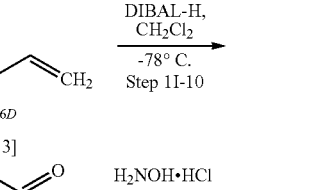
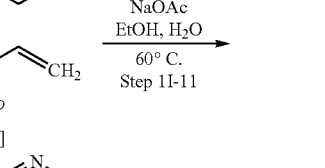
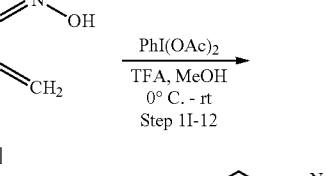
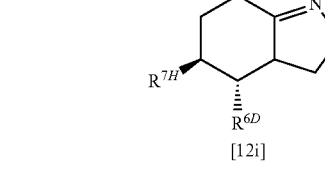
In the scheme, R$^{6D}$, R$^{7H}$, and G¹ are defined as defined above.

[Preparation Method 1J]: Preparation of Compound [I-1J] or a Salt Thereof

Compound [I] wherein $X^2$ is =C($R^4$)— and $R^4$ is $C_{1-4}$ alkyl (Compound [I-1J]):

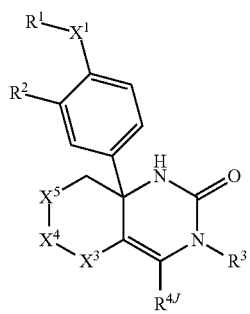

wherein $R^{4J}$ is $C_{1-4}$ alkyl, and $R^1$, $R^2$, $R^3$, $X^1$, $X^3$, $X^4$, and $X^5$ are defined as defined above, or a salt thereof, may be obtained by, for example, using Compound [12j] or a salt thereof obtained in Preparation method 1J as follows, instead of Compound [12] or a salt thereof in the above Preparation method 1.

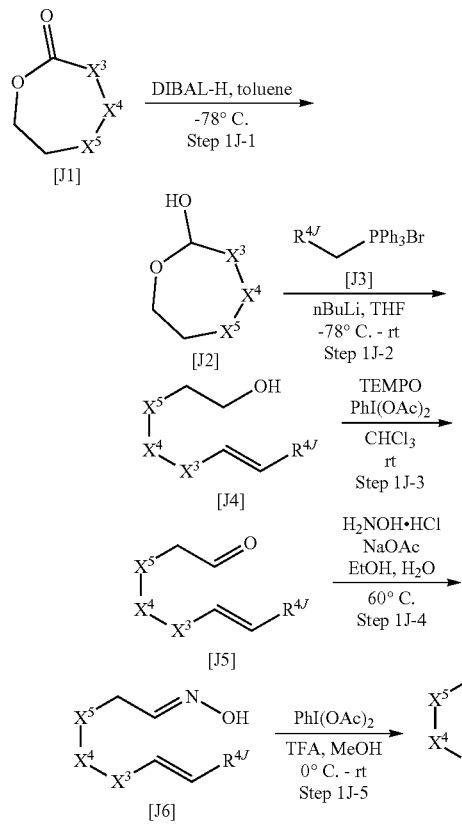

In the scheme, $X^3$, $X^4$, $X^5$, and $R^{4J}$ are defined as defined above.

[Preparation Method 1K]: Preparation of Compound [I-1K] or a Salt Thereof

Compound [I] wherein $X^2$ is =C($R^4$)—, $R^4$ is hydrogen, $X^3$ is —C($R^5$)($R^6$)—, $R^5$ is hydrogen, and $R^6$ is:

(1) halo-$C_{1-4}$ alkyl, (2) cyano-$C_{1-4}$ alkyl, or (3) $C_{1-4}$ alkyl substituted with one substituent selected from the group consisting of —O—$R^{51}$, —CO—$R^{61}$, —COO—$R^{52}$, —N($R^{71}$)($R^{72}$), —CO—N($R^{73}$)($R^{74}$), —N($R^{75}$)—CO—$R^{62}$, —N($R^{76}$)—COO—$R^{53}$, and —O—S(O)$_2$—$R^{63}$ (Compound [I-1K]):

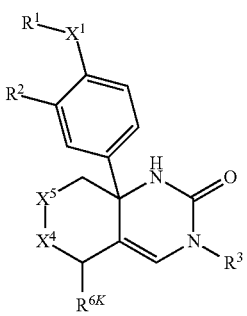

wherein $R^{6K}$ is:

(1) halo-$C_{1-4}$ alkyl, (2) cyano-$C_{1-4}$ alkyl, or (3) $C_{1-4}$ alkyl substituted with one substituent selected from the group consisting of —O—$R^{51}$, —CO—$R^{61}$, —COO—$R^{52}$, —N($R^{71}$)($R^{72}$), —CO—N($R^{73}$)($R^{74}$), —N($R^{75}$)—CO—$R^{62}$, —N($R^{76}$)—COO—$R^{53}$, and —O—S(O)$_2$—$R^{63}$, and $R^1$, $R^2$, $R^3$, $X^1$, $X^4$, and $X^5$ are defined as defined above, or a part of salts thereof, may be obtained by, for example, using Compound [12k] or a salt thereof obtained in Preparation method 1K as follows, instead of Compound [12] or a salt thereof in the above Preparation method 1, or by converting a benzyl ether moiety of the resulting compound into various substituents.

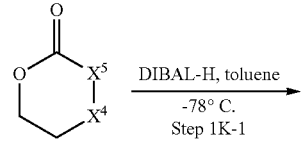

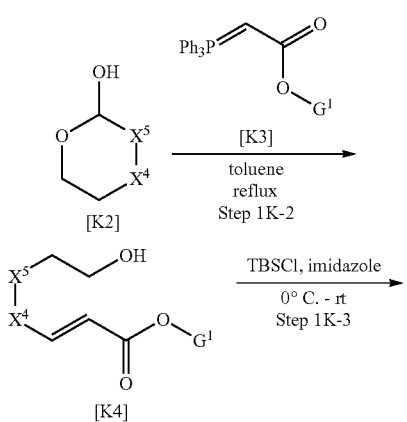

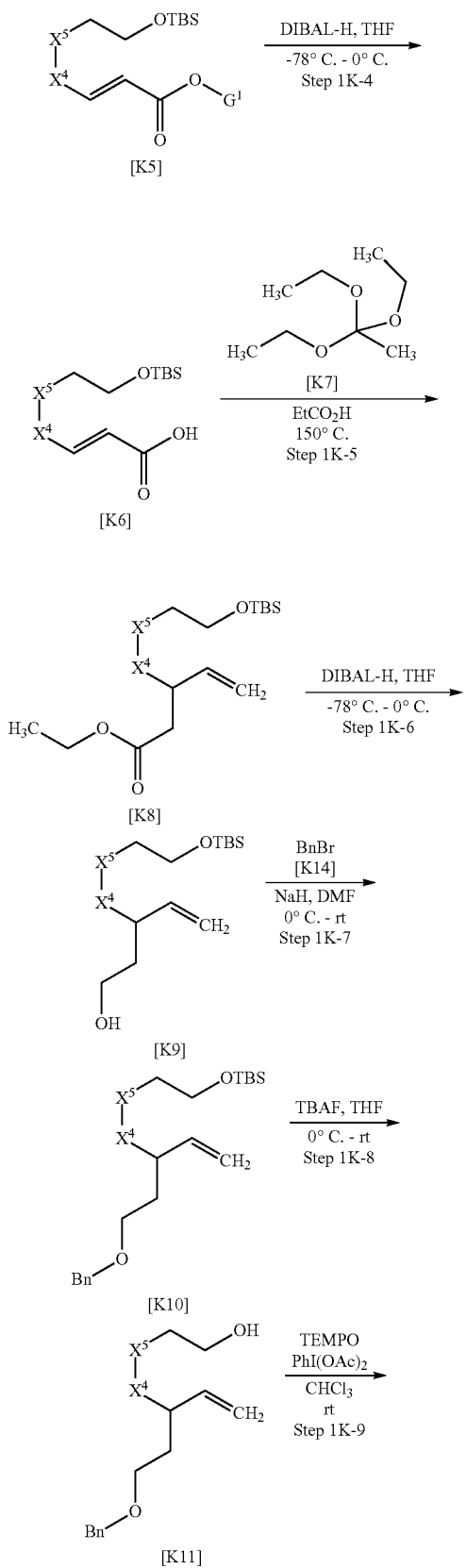

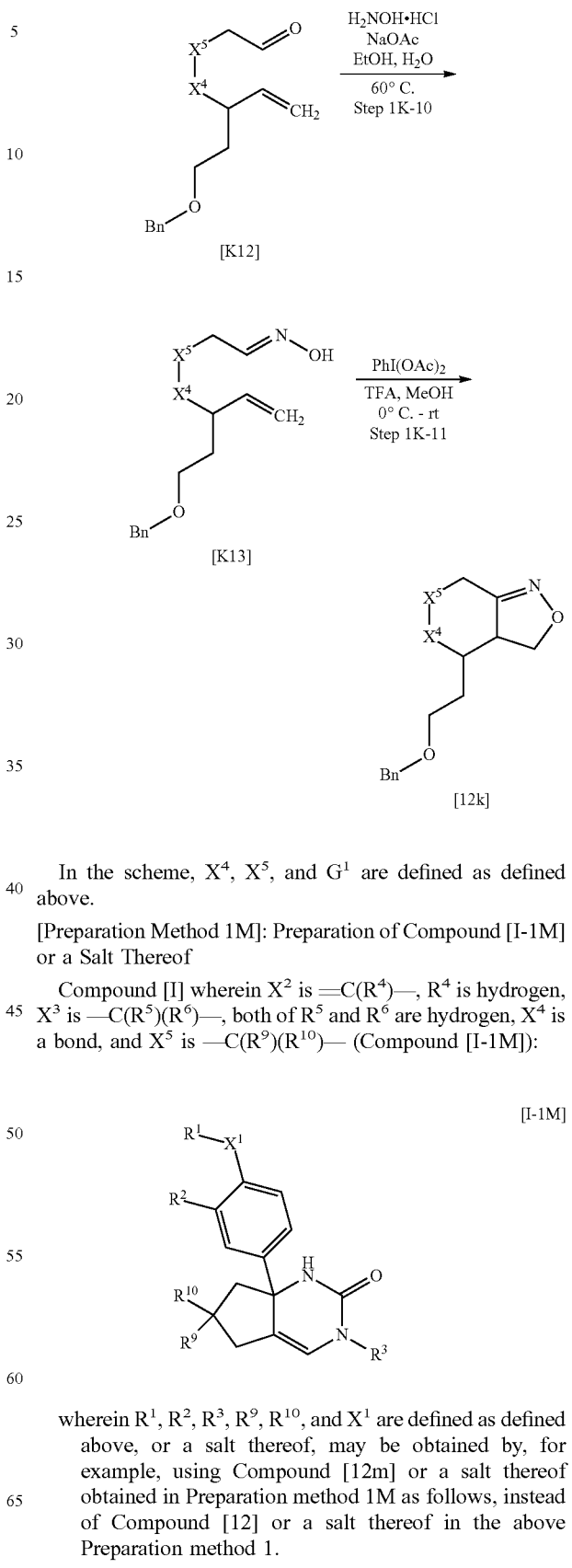

In the scheme, $X^4$, $X^5$, and $G^1$ are defined as defined above.

[Preparation Method 1M]: Preparation of Compound [I-1M] or a Salt Thereof

Compound [I] wherein $X^2$ is $=C(R^4)-$, $R^4$ is hydrogen, $X^3$ is $-C(R^5)(R^6)-$, both of $R^5$ and $R^6$ are hydrogen, $X^4$ is a bond, and $X^5$ is $-C(R^9)(R^{10})-$ (Compound [I-1M]):

wherein $R^1$, $R^2$, $R^3$, $R^9$, $R^{10}$, and $X^1$ are defined as defined above, or a salt thereof, may be obtained by, for example, using Compound [12m] or a salt thereof obtained in Preparation method 1M as follows, instead of Compound [12] or a salt thereof in the above Preparation method 1.

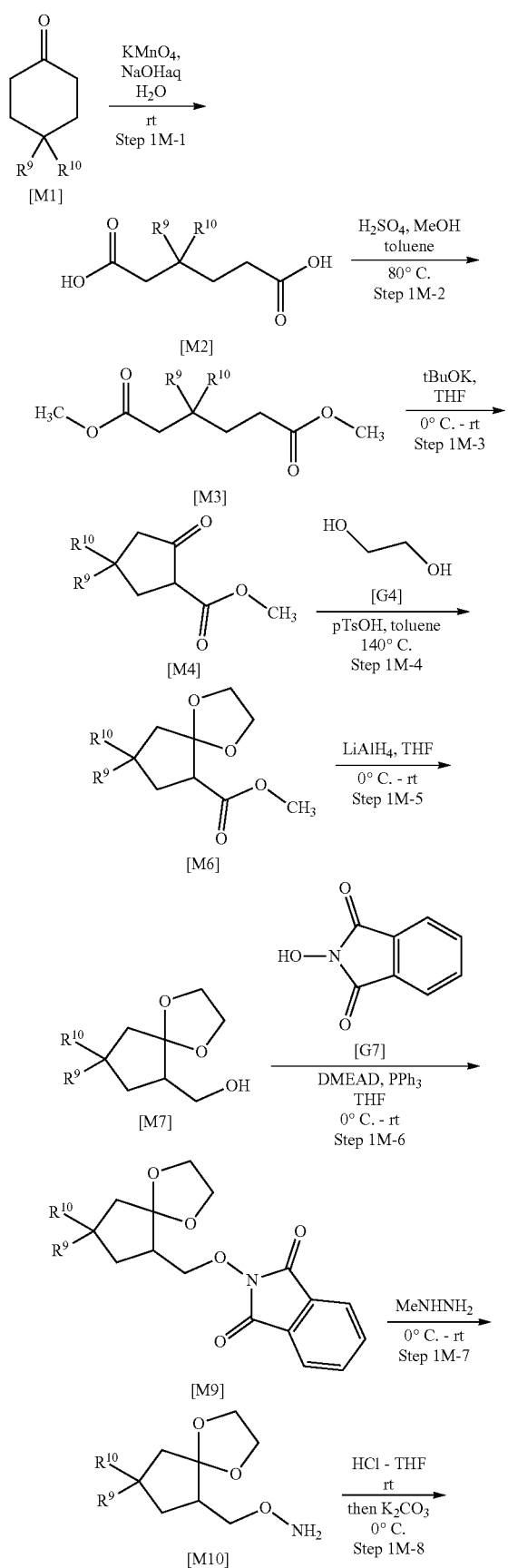

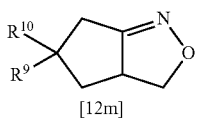

In the scheme, $R^9$ and $R^{10}$ are defined as defined above.

[Preparation Method 1N]: Preparation of Compound [I-1N] or a Salt Thereof

Compound [I] wherein $X^2$ is =C($R^4$)—, $R^4$ is hydrogen, $X^3$ is —C($R^5$)($R^6$)—, $R^5$ is hydrogen, $R^6$ is:
(1) halo-$C_{1-4}$ alkyl,
(2) cyano-$C_{1-4}$ alkyl, or
(3) $C_{1-4}$ alkyl substituted with one substituent selected from the group consisting of —O—$R^{51}$, —CO—$R^{61}$, —COO—$R^{52}$, —N($R^{71}$)($R^{72}$), —CO—N($R^{73}$)($R^{74}$), —N($R^{75}$)—CO—$R^{62}$, —N($R^{76}$)—COO—$R^{53}$, and —O—S(O)$_2$—$R^{63}$, and $X^4$ is a bond (Compound [I-1N]):

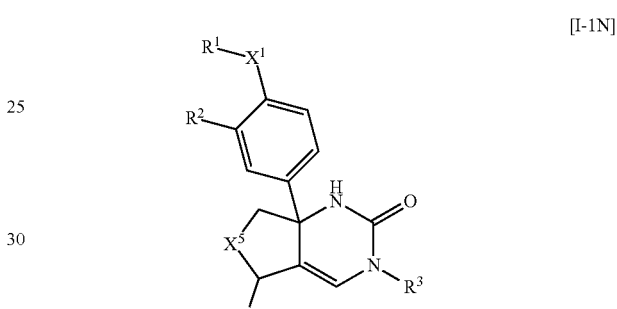

wherein $R^1$, $R^2$, $R^3$, $R^{6K}$, $X^1$, and $X^5$ are defined as defined above, or a part of salts thereof, may be obtained by, for example, using Compound [12n] or a salt thereof obtained in Preparation method 1N as follows, instead of Compound [12] or a salt thereof in the above Preparation method 1, or by converting a benzyl ether moiety of the resulting compound into various substituents.

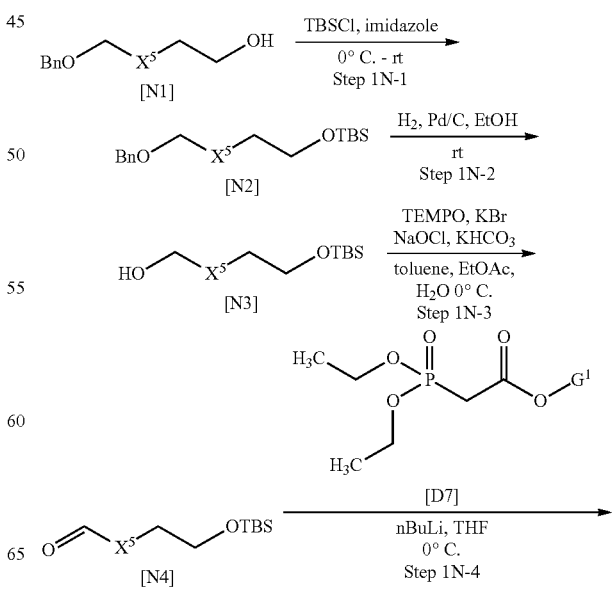

59
-continued

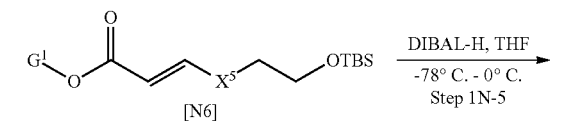
[N6]

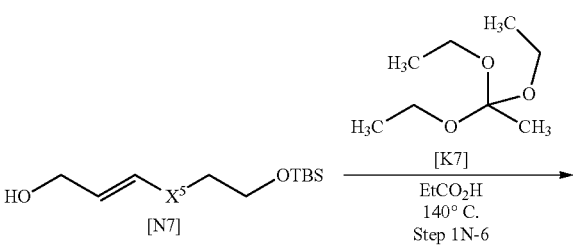
[N7]

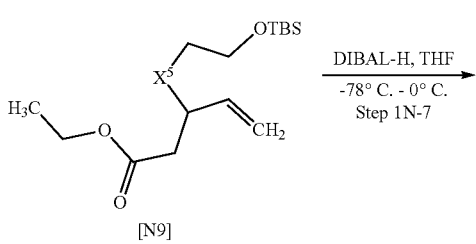
[N9]

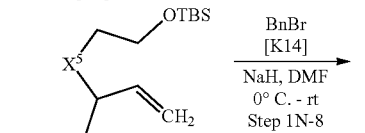
[N10]

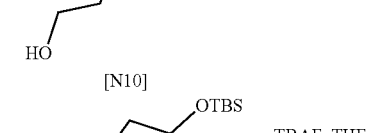
[N11]

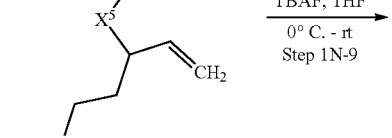
[N12]

[N13]

60
-continued

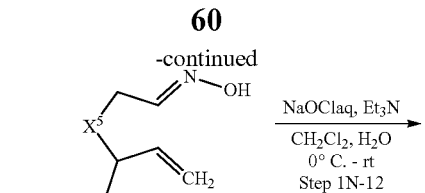
[N14]

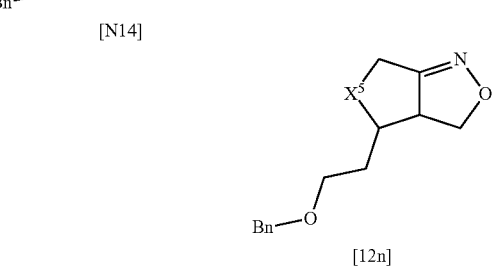
[12n]

In the scheme, $X^5$ and $G^1$ are defined as defined above.

[Preparation Method 1P]: Preparation of Compound [I-1P] or a Salt Thereof

Compound [I] wherein $X^2$ is =C($R^4$)—, $R^4$ is hydrogen, $X^4$ is a bond, and $X^5$ is —N($R^{11}$)— (Compound [I-1P]):

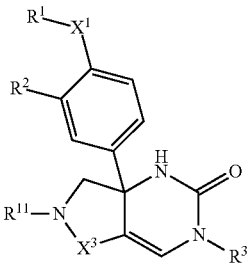
[I-1P]

wherein $R^1$, $R^2$, $R^3$, $R^{11}$, $X^1$, and $X^3$ are defined as defined above, or a salt thereof, may be obtained by, for example, using Compound [12p] or a salt thereof obtained in Preparation method 1P as follows, instead of Compound [12] or a salt thereof in the above Preparation method 1.

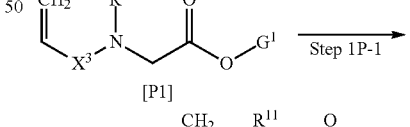
[P1]

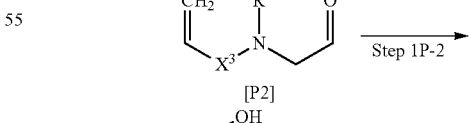
[P2]

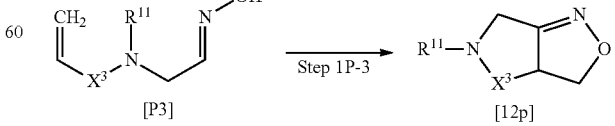 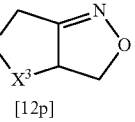
[P3] [12p]

In the scheme, $R^{11}$, $X^3$, and $G^1$ are defined as defined above.

(Step 1P-1)

Compound [P2] or a salt thereof may be prepared from Compound [P1] or a salt thereof in a similar manner to Step 1B-2.

(Step 1P-2)

Compound [P3] or a salt thereof may be prepared from Compound [P2] or a salt thereof in a similar manner to Step 1A-2.

(Step 1P-3)

Compound [12p] or a salt thereof may be prepared from Compound [P3] or a salt thereof in a similar manner to Step 1A-3.

[Preparation Method 1Q]: Preparation of Compound [I-1Q] or a Salt Thereof

Compound [I] wherein $X^2$ is =C($R^4$)—, $R^4$ is hydrogen, $X^3$ is —C($R^5$)($R^6$)—, $R^5$ and $R^6$ are each independently $C_{1-4}$ alkyl, $X^4$ is a bond, $X^5$ is —C($R^9$)($R^{10}$)—, and both of $R^9$ and $R^{10}$ are hydrogen (Compound [I-1Q]):

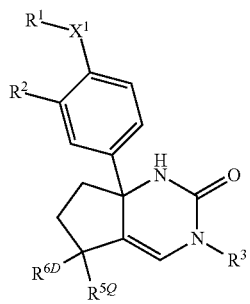

wherein $R^{5Q}$ is $C_{1-4}$ alkyl, and $R^1$, $R^2$, $R^3$, $R^{6D}$, and $X^1$ are defined as defined above, or a salt thereof, may be obtained by, for example, using Compound [12q] or a salt thereof obtained in Preparation method 1Q as follows, instead of Compound [12] or a salt thereof in the above Preparation method 1.

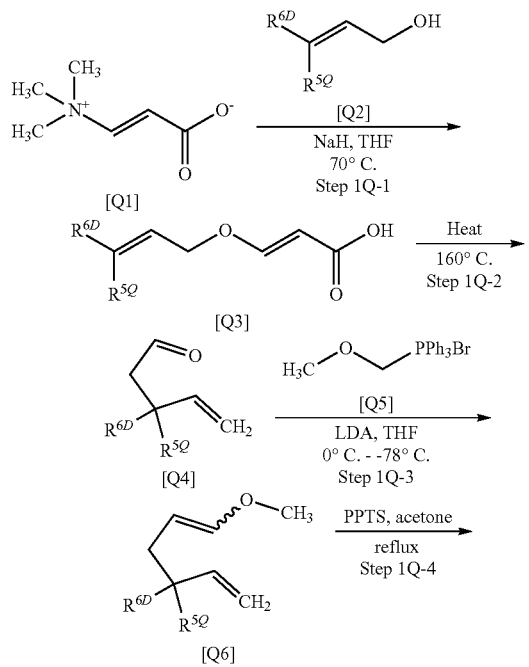

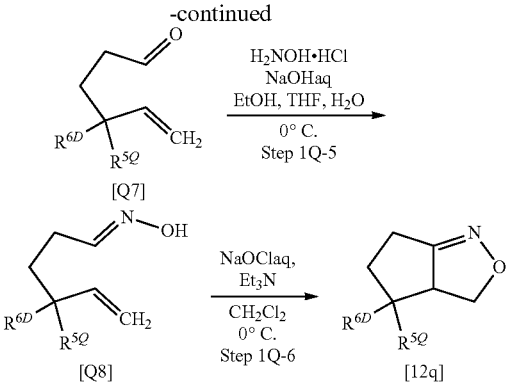

In the scheme, $R^{5Q}$ and $R^{6D}$ are defined as defined above.

[Preparation Method 1R]: Preparation of Compound [I-1R] or a Salt Thereof

Compound [I] wherein $X^2$ is =C($R^4$)—, $R^4$ is hydrogen, $X^4$ is —C($R^7$)($R^8$)—, both of $R^7$ and $R^8$ are hydrogen, $X^5$ is —C($R^9$)($R^{10}$)—, and both of $R^9$ and $R^{10}$ are hydrogen (Compound [I-1R]):

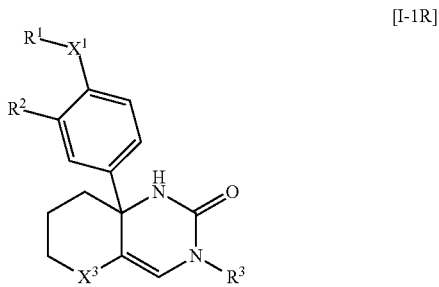

wherein $R^1$, $R^2$, $R^3$, $X^1$, and $X^3$ are defined as defined above, or a salt thereof, may be obtained by, for example, using Compound [12r] or a salt thereof obtained in Preparation method 1R as follows, instead of Compound [12] or a salt thereof in the above Preparation method 1.

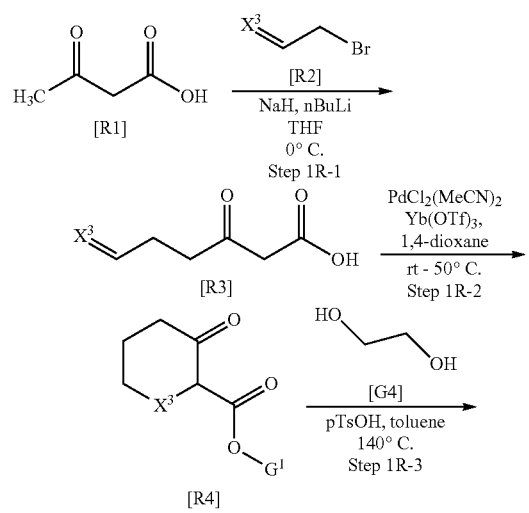

-continued

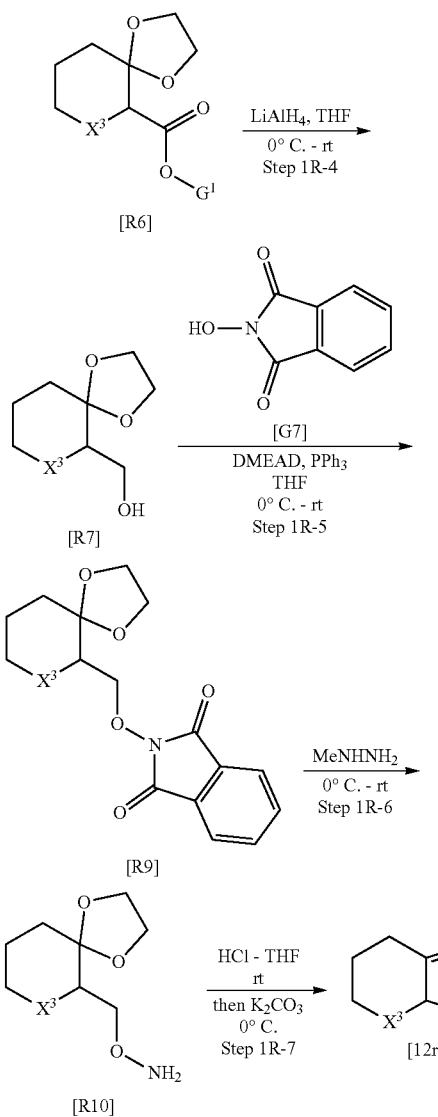

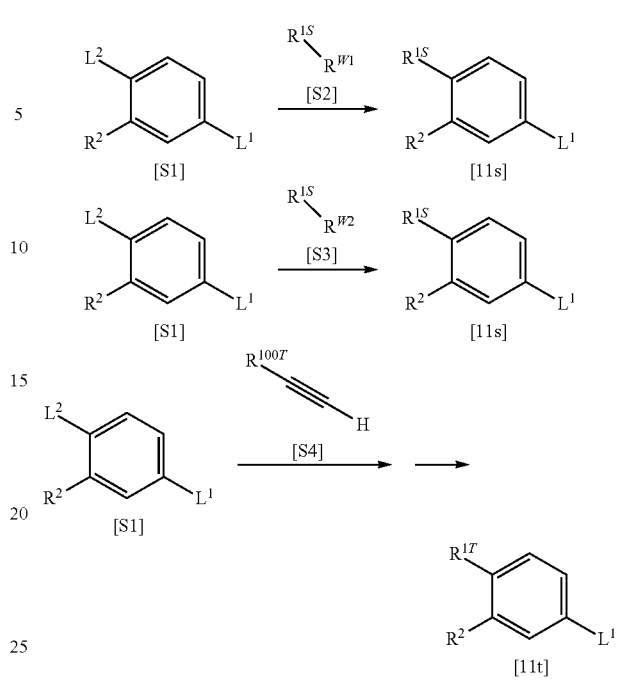

In the scheme, $X^3$ and $G^1$ are defined as defined above.

[Preparation Method 1S]: Preparation of Compound [11] used in Preparation Method 1

Compound [11]:

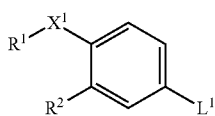

[11]

wherein $R^1$, $R^2$, $X^1$, and $L^1$ are defined as defined above, may be prepared by, for example, cross-coupling reaction of Compound [S1] shown as follows, when $X^1$ is a bond, $R^1$ is $C_{1-8}$ alkyl, optionally substituted $C_{3-8}$ cycloalkyl, or optionally substituted $C_{3-8}$ cycloalkyl-$C_{1-4}$ alkyl (i.e., Compound [11s] or [11t]).

In the scheme, $R^2$ and $L^1$ are defined as defined above,
$L^2$ is halogen (e.g., iodo) or trifluoromethanesulfonyloxy,
$R^{1S}$ is $C_{1-8}$ alkyl, optionally substituted $C_{3-8}$ cycloalkyl, or optionally substituted $C_{3-8}$ cycloalkyl-$C_{1-4}$ alkyl,
$R^{W1}$ is boronic acid, boronic acid ester, or trifluoroborate,
$R^{W2}$ is zinc, or zinc halide,
$R^{1T}$ is $C_{2-8}$ alkyl, or optionally substituted cycloalkyl-$C_{2-4}$ alkyl, and
$R^{100T}$ is trimethylsilyl or a straight- or branched-chain saturated hydrocarbon with 1 to 6 carbon atoms.

Such a cross-coupling reaction includes methods described in literatures such as F. Diederich, P. J. Stang (1908). Metal-catalyzed Cross-coupling Reactions, Weinheim, Germany, Wiley-VCH, which includes Suzuki coupling, Negishi coupling, and Sonogashira coupling.

Compound [S1] is preferably a compound wherein $L^1$ is bromo and $L^2$ is iodo, more preferably a compound shown as follows.

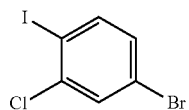

As for Compound [S2], Compound [S3], and Compound [S4], for example, commercially available products such as isobutylboronic acid, 1-hexylboronic acid pinacol ester, potassium (3,3-dimethylbutyl)trifluoroborate, butylzinc bromide, and cyclohexylacetylene may be used, or these compounds may be prepared from corresponding commercially available compounds with chloro, promo, or iodo, such as 1-chloro-3,3-dimethyl-butane and bromomethyl-cyclohexane, according to known methods.

Compound [S2] wherein $R^{W1}$ is boronic acid may be prepared by preparation of a Grignard reagent from commercially available compounds such as $R^1$—Br and magnesium, followed by reaction with, for example, trimethyl borate or triisopropyl borate.

Compound [S2] wherein $R^{W1}$ is boronic acid ester may be prepared by, for example, reaction of a boronic acid compound with pinacol.

Compound [S2] wherein $R^{W1}$ is trifluoroborate may be prepared by, for example, reaction of a boronic acid compound with potassium hydrogen fluoride.

Compound [S3] may be prepared from, for example, commercially available compounds such as $R^1$—I and zinc.

An activating agent for zinc includes iodine, trimethylsilyl chloride, and 1,2-dibromoethane, and these agents can be used alone or in combination with any two or more them. A preferable activating agent is trimethylsilyl chloride or 1,2-dibromoethane.

As for Compound [S4], commercially available products such as 3,3-dimethyl-1-butyne, cyclohexylacetylene, and phenylacetylene may be used.

Compound [11t] may be obtained by catalytic hydrogenation of an alkynylene compound obtained in Sonogashira reaction with a catalyst such as palladium carbon, platinum carbon, and rhodium-alumina to convert into an alkyl compound.

The solvent in each step includes tetrahydrofuran, N,N-dimethylformamide, and N,N-dimethylacetamide. A preferable solvent herein is tetrahydrofuran or N,N-dimethylacetamide.

The reaction temperature in each step includes room temperature to 80° C. A preferable reaction temperature herein is room temperature.

[Preparation Method 1Z]: Preparation of Compound [15] or a Salt Thereof Used in Preparation Method 1

Compound [15] or a salt thereof may be a commercially available product such as ethyl 6-isocyanato-hexanoate, methyl 2-isocyanato-2-methyl-propionate, methyl 3-isocyanato-propionate, ethyl 3-isocyanato-propionate, methyl 4-isocyanato-cyclohexanecarboxylate, and ethyl 4-isocyanatobenzoate, or may also be obtained by, for example, Preparation method 1Z shown as follows.

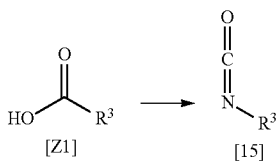

In the scheme, $R^3$ is defined as defined above.

Compound [15] or a salt thereof may be prepared by azidation reaction of Compound [Z1] such as a commercially available product such as 3-(methoxycarbonyl)bicyclo[1.1.1]pentane-1-carboxylic acid, 3-(methoxycarbonyl)bicyclo[2.1.1]pentane-1-carboxylic acid, 1-(2-methoxy-2-oxoethyl)-5-oxopyrrolidine-3-carboxylic acid, and 3-[1-(ethoxycarbonyl)cyclopropyl]propanoic acid, or a salt thereof, in the presence of a base in a solvent, followed by Curtius rearrangement.

Such a solvent includes, for example, benzene, toluene, xylene, tetrahydrofuran, and a mixed solvent of any of them. A preferable solvent herein is toluene.

The azidation agent herein includes, for example, diphenylphosphoryl azide.

Such a base includes, for example, triethylamine and diisopropylethylamine. A preferable base herein is triethylamine.

The reaction temperature herein ranges, for example, from 0° C. to 140° C., preferably from 100° C. to 120° C.

When $R^3$ is —$Y^3$—COO—$R^{30}$ and $R^{30}$ is $C_{1-4}$ alkyl in Compound [15] or a salt thereof obtained from Preparation method 1Z illustrated herein, Compound [I-1] wherein $R^{30}$ is hydrogen may be obtained by preparation of Compound [I-1] wherein $R^{30}$ is $C_{1-4}$ alkyl from the aforementioned Compound [15] or a salt thereof in Preparation method 1, followed by hydrolysis under known methods.

[Preparation Method 2]: Preparation of Compound [I-2A] or a Salt Thereof

Compound [I] wherein $X^2$ is =N—, $X^3$ is —C($R^5$)($R^6$)—, $R^3$ is hydrogen, and $R^5$ is hydrogen (Compound [I-2A]), or a salt thereof, may be obtained by, for example, Preparation method 2 as follows.

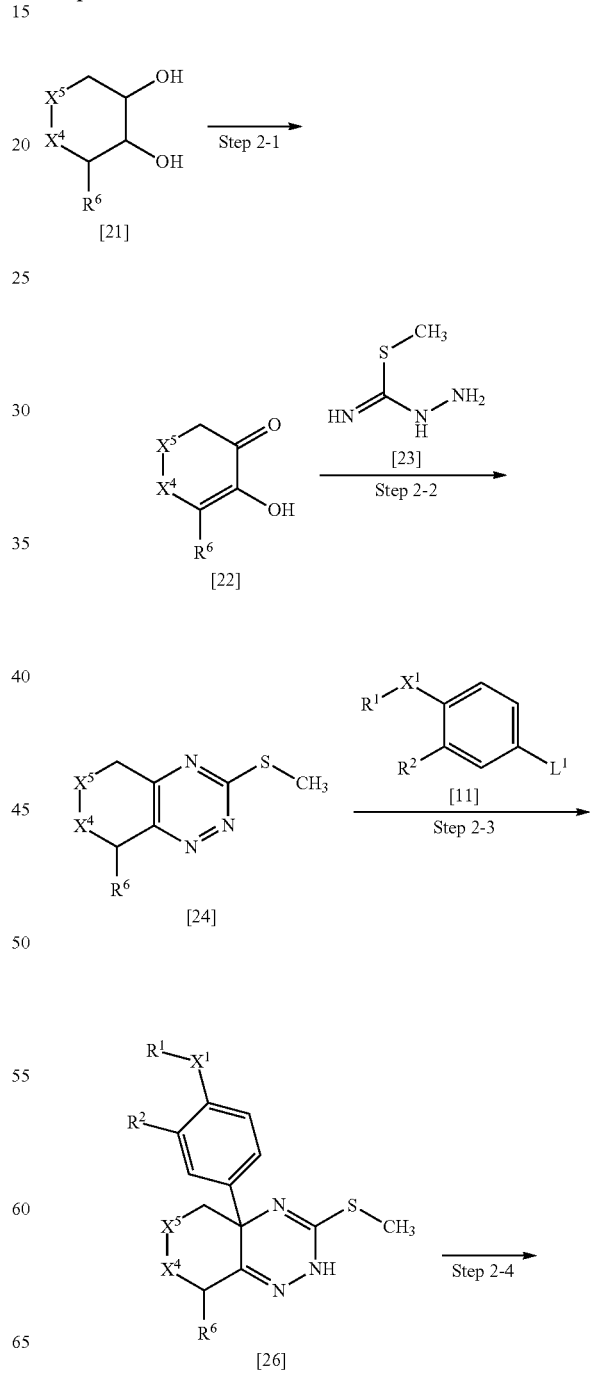

-continued

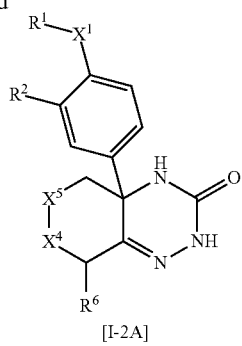

[I-2A]

In the scheme, $R^1$, $R^2$, $R^6$, $X^1$, $X^4$, $X^5$, and $L^1$ are defined as defined above.

(Step 2-1)

Compound [22] or a salt thereof may be prepared by oxidation of Compound [21] or a salt thereof in a solvent.

Such a solvent includes, for example, ether solvents such as tetrahydrofuran; ester solvents such as ethyl acetate; hydrocarbon solvents such as toluene; halogenated solvents such as dichloromethane; nitrile solvents such as acetonitrile; and a mixed solvent of any of them. A preferable solvent herein is dichloromethane.

An oxidizing agent used herein includes, for example, sulfur trioxide-pyridine complex, dimethyl sulfoxide, pyridinium chlorochromate, and Dess-Martin reagent. A preferable oxidizing agent herein is sulfur trioxide-pyridine complex.

The reaction temperature herein ranges, for example, from −60° C. to 60° C., preferably from 0° C. to room temperature.

(Step 2-2)

Compound [24] or a salt thereof may be prepared by reaction of Compound [22] or a salt thereof with Compound [23] or a salt thereof in a solvent in the presence of a base.

Such a solvent includes, for example, alcohol solvents such as ethanol; halogenated solvents such as chloroform; hydrocarbon solvents such as chlorobenzene; and a mixed solvent of any of them. A preferable solvent herein is ethanol or water.

Such a base includes, for example, sodium hydrogen carbonate and triethylamine. A preferable base herein is sodium hydrogen carbonate.

The reaction temperature herein ranges, for example, from −10° C. to 100° C., preferably from 0° C. to room temperature.

(Step 2-3)

Compound [26] or a salt thereof may be prepared by reaction of Compound [24] or a salt thereof with Compound [11] or a salt thereof in a solvent.

Such a solvent includes, for example, ether solvents such as tetrahydrofuran. A preferable solvent herein is tetrahydrofuran or diethyl ether.

A reagent used herein includes, for example, organometallic reagents such as n-butyllithium and Grignard reagents such as magnesium. A preferable reagent herein is n-butyllithium.

The reaction temperature herein ranges from −78° C. to room temperature.

(Step 2-4)

Compound [I-2A] or a salt thereof may be prepared by oxidation of Compound [26] or a salt thereof in a solvent.

Such a solvent includes halogenated solvents such as dichloromethane. A preferable solvent herein is dichloromethane.

An oxidizing agent used herein includes m-chloroperoxybenzoic acid.

The reaction temperature herein is room temperature.

EXAMPLES

The present invention is illustrated in more detail with Examples and Test Examples, but is not intended to be limited thereto.

$^1$H-NMR spectra were measured in $CDCl_3$, $DMSO-D_6$, or $MeOH-D_4$ with tetramethylsilane as an internal standard, and all δ values are shown in ppm. Symbols in spectral data mean as follows.

s: singlet
d: doublet
t: triplet
q: quartet
dd: double doublet
ddd: double double doublet
brs: broad singlet
m: multiplet
J: coupling constant Example 1

(Step 1)

4-Bromo-2-chloro-1-(2,2-dimethyl-propoxy)benzene

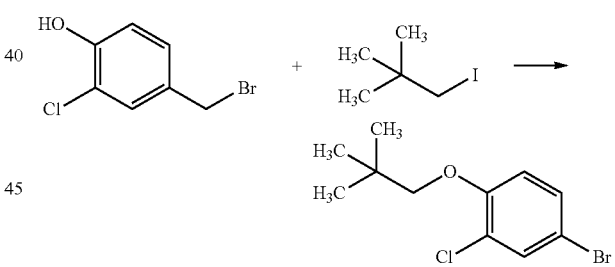

4-Bromo-2-chloro-phenol (100 g) and cesium carbonate (126 g) were mixed in N-dimethylformamide (800 mL) under nitrogen gas, and thereto was added 1-iodo-2,2-dimethyl-propanol (100 mL) at room temperature. The reaction solution was stirred under heating at 100° C. for 2 days. The reaction solution was slowly cooled to room temperature, and then, thereto were added water (500 mL) and n-hexane (500 mL). The solution was separated. The organic layer was washed with 20 w/w % aqueous sodium sulfite solution (100 mL), 2N aqueous sodium hydroxide solution (100 mL), water (100 mL), and saturated aqueous sodium chloride solution (100 mL), and dried over sodium sulfate. Sodium sulfate was removed with a filter, and then the filtrate was concentrated under reduced pressure to give the title compound (138 g).

$^1$H-NMR (400 MHz, $CDCl_3$) 1.07 (s, 9H), 3.61 (s, 2H), 6.76 (d, J=8.8 Hz, 1H), 7.29 (dd, J=8.8, 2.3 Hz, 1H), 7.49 (d, J=2.5 Hz, 1H)

(Step 2)

3-Methylsulfanyl-6,7-dihydro-5H-cyclopenta[1,2,4]triazine

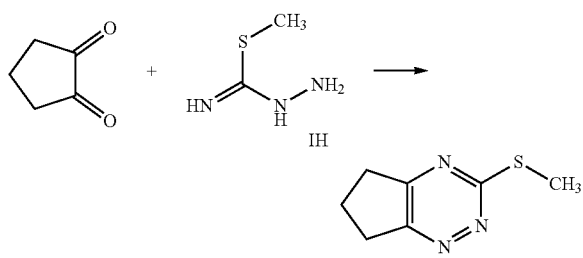

Cyclopentane-1,2-dione (580 mg) was mixed in 1M aqueous sodium hydrogen carbonate solution (6.0 mL) and ethanol (6.0 mL) under nitrogen gas, and then, thereto was added S-methyl isothiosemicarbazide hydroiodide (1.38 g) at room temperature. The reaction solution was stirred at room temperature for 1 day. To the reaction solution were added ethyl acetate and water, and the reaction solution was separated. The organic layer was washed with saturated aqueous sodium chloride solution and dried over sodium sulfate. Sodium sulfate was removed with a filter, and then the filtrate was concentrated under reduced pressure. The resulting residue was purified by silica gel column chromatography (20 g, ethyl acetate/chloroform=1/5) to give the title compound (520 mg).

$^1$H-NMR (400 MHz, CDCl$_3$) 2.17-2.24 (m, 2H), 2.56 (s, 3H), 3.00 (t, J=7.7 Hz, 2H), 3.17 (t, J=7.7 Hz, 2H)

(Step 3)

4a-[3-Chloro-4-(2,2-dihydro-propoxy)phenyl]-3-methylsulfanyl-4a,5,6,7-tetrahydro-2H-cyclopenta[1,2,4]triazine

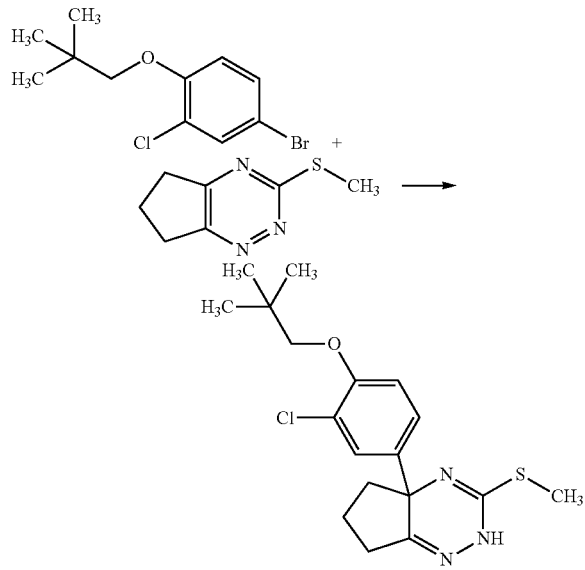

Magnesium (30 mg) and diethyl ether (2.0 mL) were mixed under nitrogen gas, and then thereto was added one drop of a mixed solution of diethyl ether in iodine at room temperature. The reaction solution was stirred at room temperature for 30 minutes. To the reaction solution was added a mixed solution of 4-bromo-2-chloro-1-(2,2-dimethyl-propoxy)benzene (420 mg) in diethyl ether (2.0 mL) at room temperature. The reaction solution was stirred under heating at 60° C. for 4 hours. The reaction solution was slowly cooled to room temperature, and then, to the reaction solution was added a mixed solution of 3-methylsulfanyl-6,7-dihydro-5H-cyclopenta[1,2,4]triazine (100 mg) in tetrahydrofuran (2 mL). The reaction solution was stirred at room temperature for 1 day. To the reaction solution were added aqueous ammonium chloride solution and ethyl acetate under ice cooling, and the reaction solution was separated. The organic layer was washed with saturated aqueous sodium chloride solution and dried over sodium sulfate. The resulting residue was purified by thin-layer silica gel column chromatography (ethyl acetate/chloroform=1/3) to give the title compound (17.4 mg).

$^1$H-NMR (400 MHz, CDCl$_3$) 1.06 (s, 9H), 1.68-1.78 (m, 2H), 2.13-2.20 (m, 1H), 2.39-2.43 (m, 1H), 2.44 (d, J=5.5 Hz, 3H), 2.53-2.62 (m, 1H), 2.67-2.75 (m, 1H), 3.60 (s, 2H), 6.78 (d, J=8.6 Hz, 1H), 7.07 (dd, J=8.6, 2.3 Hz, 1H), 7.30 (d, J=2.1 Hz, 1H), 7.74 (br s, 1H)

(Step 4)

4a-[3-Chloro-4-(2,2-dimethyl-propoxy)phenyl]-2,4,4a,5,6,7-hexahydro-cyclopenta[1,2,4]triazin-3-one

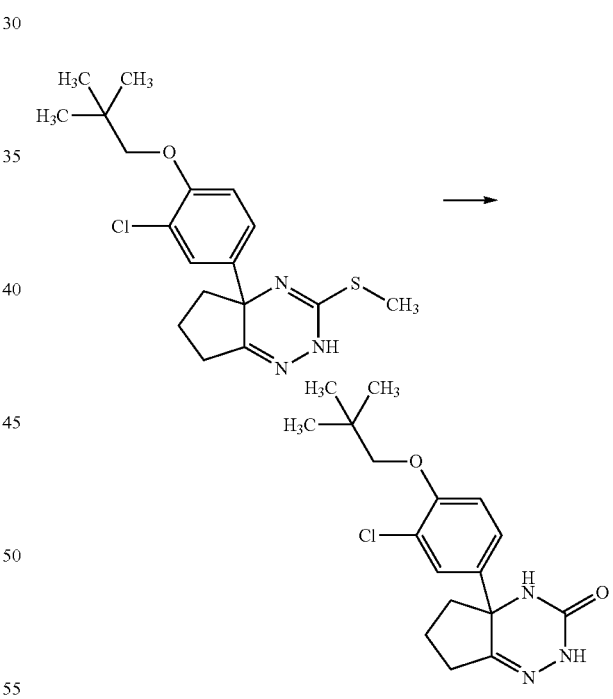

4a-[3-Chloro-4-(2,2-dihydro-propoxy)phenyl]-3-methylsulfanyl-4a,5,6,7-tetrahydro-2H-cyclopenta[1,2,4]triazine (17.4 mg) and dichloromethane (0.5 mL) were mixed under nitrogen gas, and thereto was added meta-chloroperoxybenzoic acid (75 wt % of water inclusive, 26 mg) under ice cooling. The reaction solution was stirred at room temperature for 1 hour. To the reaction solution were added 20 w/w % aqueous sodium sulfite solution (5 mL) and ethyl acetate (10 mL) under ice cooling. The organic layer was washed with saturated aqueous sodium hydrogen carbonate solution (5 mL) and saturated aqueous sodium chloride solution (5 mL) and dried over sodium sulfate. The resulting residue was purified by thin-layer silica gel column chromatography (methanol/chloroform=1/15) to give the title compound (4.2 mg).

Example 3

(Step 1)

Methyl 7,7-dimethyl-1,4-dioxa-spiro[4.4]nonane-6-carboxylate

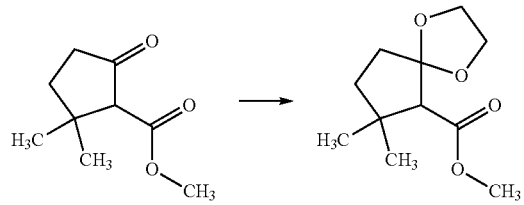

2,2-Dimethyl-5-oxo-cyclopentanecarboxylic acid methyl ester (3.58 g) was mixed in ethylene glycol (1.76 mL) and toluene (40 mL) under nitrogen gas, and thereto was added para-toluenesulfonic acid monohydrate (200 mg) at room temperature. The reaction solution was stirred under heating at 140° C. for 3 hours to remove water. The resultant was slowly cooled to room temperature. Then, to the reaction solution were added 1M aqueous sodium carbonate solution (1.1 mL) and ethyl acetate, and the solution was separated. The organic layer was washed with saturated aqueous sodium chloride solution and dried over sodium sulfate. Sodium sulfate was removed with a filter, and then the filtrate was concentrated under reduced pressure to give a crude product of the title compound (4.24 g).

(Step 2)

(7,7-Dimethyl-1,4-dioxa-spiro[4.4]non-6-yl)methanol

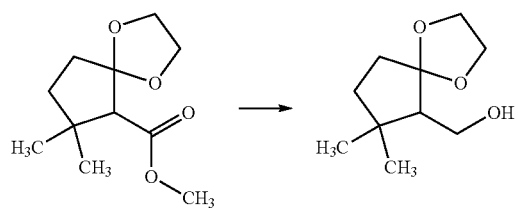

Lithium aluminum hydride (1.6 g) and tetrahydrofuran (30 mL) were mixed under nitrogen gas, and thereto was added a mixed solution of 7,7-dimethyl-1,4-dioxa-spiro[4.4]none-6-carboxylic acid methyl ester (4.24 g) in tetrahydrofuran (10 mL) under ice cooling. The reaction solution was stirred at room temperature for 1 hour. Then, thereto were added sequentially water (1.6 mL), 2N aqueous sodium hydroxide solution (1.6 mL), and water (4.8 mL) under ice cooling. Celite (20 g) and magnesium sulfate (20 g) were added thereto, and the mixture was stirred at room temperature for 1 hour. The reaction solution was diluted with tetrahydrofuran (100 mL), and the resulting solid was removed through Celite. Then, the filtrate was concentrated under reduced pressure to give a crude product of the title compound.

(Step 3)

2-(7,7-Dimethyl-1,4-dioxa-spiro[4.4]non-6-ylmethoxy)isoxazole-1,3-dione

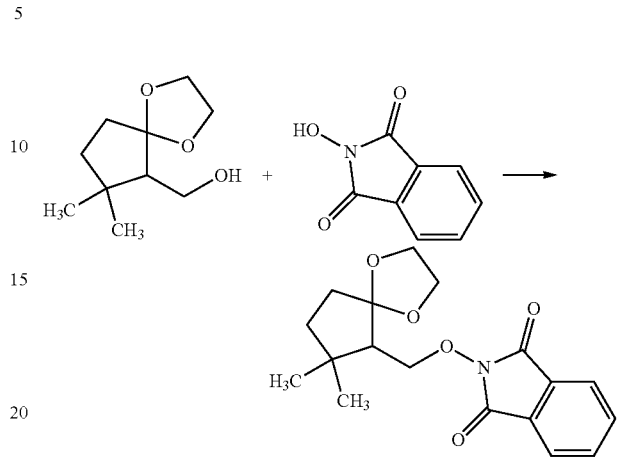

(7,7-Dimethyl-1,4-dioxa-spiro[4.4]non-6-yl)methanol, N-hydroxyphthalimide (5.14 g) and triphenylphosphine (8.26 g) were mixed in tetrahydrofuran (50 mL) under nitrogen gas, and thereto was added di-2-methoxyethyl azodicarboxylate (7.37 g) under ice cooling. The reaction solution was stirred at room temperature for 3 hours. The reaction solution was concentrated under reduced pressure, and thereto were added ethyl acetate and water. The solution was separated. The organic layer was washed with saturated aqueous sodium chloride solution and dried over sodium sulfate. Sodium sulfate was removed with a filter, and then the filtrate was concentrated under reduced pressure. The resulting residue was purified by silica gel column chromatography (200 g, ethyl acetate/n-hexane=1/3) to give the title compound (1.58 g).

$^1$H-NMR (400 MHz, CDCl$_3$) 1.02 (s, 3H), 1.22 (s, 3H), 1.49-1.60 (m, 2H), 1.86-1.91 (m, 2H), 2.29 (t, J=6.6 Hz, 1H), 3.81 (dd, J=5.0, 4.5 Hz, 1H), 3.91 (dt, J=6.9, 2.1 Hz, 1H), 4.03 (dq, J=16.9, 5.1 Hz, 2H), 4.22 (dd, J=8.3, 6.7 Hz, 1H), 4.35 (dd, J=8.2, 6.6 Hz, 1H), 7.73 (d, J=3.0 Hz, 1H), 7.74 (d, J=3.0 Hz, 1H), 7.82 (d, J=3.0 Hz, 1H), 7.83 (d, J=3.0 Hz, 1H)

(Step 4)

O-(7,7-Dimethyl-1,4-dioxa-spiro[4.4]non-6-ylmethyl)-hydroxylamine

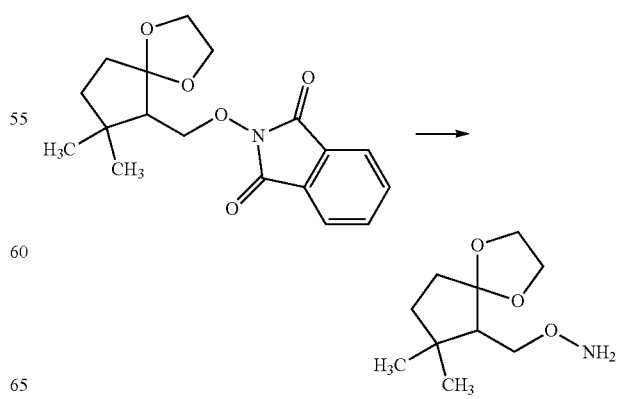

2-(7,7-dimethyl-1,4-dioxa-spiro[1.4]non-6-ylmethoxy) isoxazole-1,3-dione (1.58 g) and chloroform (20 mL) were mixed under nitrogen gas, and thereto was added N-methylhydrazine (0.3 mL) under ice cooling. The reaction solution was stirred at room temperature for 1 hour. The reaction solution was filtered through Celite, and then the filtrate was concentrated under reduced pressure to give a crude product of the title compound (1.61 g).

$^1$H-NMR (400 MHz, CDCl$_3$) 0.90 (s, 3H), 1.10 (s, 3H), 1.43-1.56 (m, 2H), 1.82-1.87 (m, 2H), 2.08 (dd, J=7.4, 6.5 Hz, 1H), 3.68-3.96 (m, 6H), 5.31 (br s, 2H)

(Step 5)

4,4-Dimethyl-3a,4,5,6-tetrahydro-3H-cyclopenta[c] isoxazole

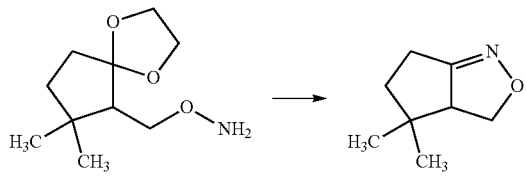

O-(7,7-Dimethyl-1,4-dioxa-spiro[4.4]non-6-ylmethyl)-hydroxylamine (1.61 g) and tetrahydrofuran (10 mL) were mixed under nitrogen gas, and thereto was added 3N hydrochloric acid (5 mL) at room temperature. The reaction solution was stirred at room temperature for 2 hours. To the reaction solution were added potassium carbonate (2.1 g) and diethyl ether, and the solution was separated. The organic layer was washed with saturated aqueous sodium chloride solution and dried over sodium sulfate. Sodium sulfate was removed with a filter, and then the filtrate was concentrated under reduced pressure. The resulting residue was purified by silica gel column chromatography (20 g, diethyl ether/n-hexane=1/1) to give the title compound (573 mg).

$^1$H-NMR (400 MHz, CDCl$_3$) 0.91 (s, 3H), 1.12 (s, 3H), 1.96 (ddd, J=13.0, 7.2, 3.6 Hz, 1H), 2.05-2.13 (m, 1H), 2.43-2.49 (m, 2H), 3.53-3.59 (m, 1H), 3.89 (dd, J=11.9, 8.2 Hz, 1H), 4.33 (dd, J=10.5, 8.2 Hz, 1H)

(Step 6)

6a-[3-Chloro-4-(3,3-dimethyl-butyl)phenyl]-4,4-dimethyl-hexahydro-cyclopenta[c]isoxazole

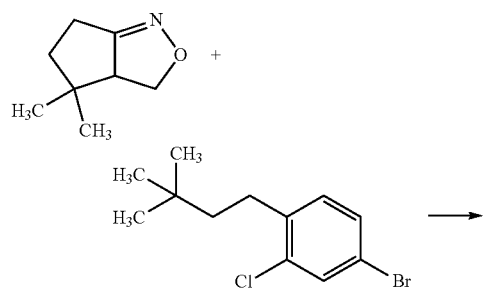

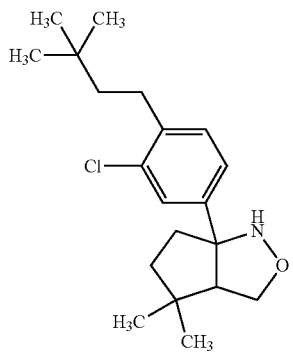

4-Bromo-2-chloro-1-(3,3-dimethyl-butyl)benzene (702 mg) was mixed in toluene (7.0 mL) and tetrahydrofuran (2.8 mL) under argon gas, and thereto was added dropwise 1.6M n-butyllithium/n-hexane solution (1.55 mL) under cooling at −78° C. The reaction solution was stirred under cooling at −78° C. for 1 hour (Reaction solution A). 4,4-Dimethyl-3a,4,5,6-tetrahydro-3H-cyclopenta[c]isoxazole (173 mg) and toluene (10 mL) were mixed, and thereto were added boron trifluoride-diethyl ether complex (0.314 mL) and Reaction solution A under cooling at −78° C. The reaction solution was stirred for 1 hour, and then thereto were added aqueous ammonium chloride solution (5 mL) and ethyl acetate at −78° C. The solution was separated. The organic layer was washed with saturated aqueous sodium chloride solution and dried over sodium sulfate. The resulting residue was purified by silica gel column chromatography (10 g, diethyl ether/n-hexane=1/1) to give the title compound (364 mg).

$^1$H-NMR (400 MHz, CDCl$_3$) 0.98 (s, 9H), 1.10 (s, 6H), 1.12-1.30 (m, 2H), 1.42-1.47 (m, 2H), 1.74-1.82 (m, 1H), 2.15-2.24 (m, 1H), 2.64-2.68 (m, 2H), 2.79 (dd, J=6.7, 5.5 Hz, 1H), 3.80-4.20 (m, 2H), 4.98 (s, 1H), 7.17 (d, J=7.9 Hz, 1H), 7.30 (d, J=7.9 Hz, 1H), 7.47 (s, 1H)

(Step 7)

{2-Amino-2-[3-chloro-4-(3,3-dimethyl-butyl)phenyl]-5,5-dimethyl-cyclopentyl}methanol

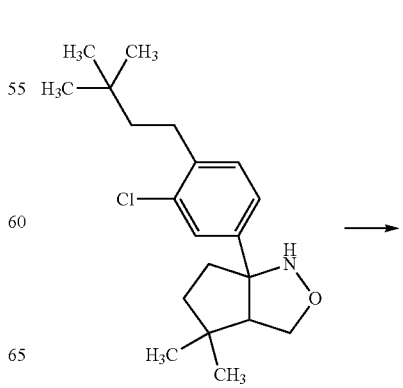

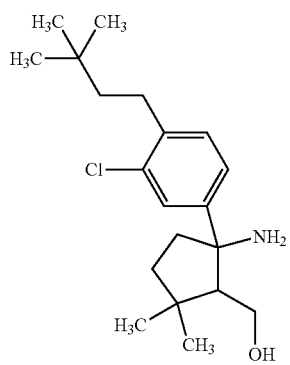

6a-[3-Chloro-4-(3,3-dimethyl-butyl)phenyl]-4,4-dimethyl-hexahydro-cyclopenta[c]isoxazole (320 mg) was mixed in acetic acid (4 mL), tetrahydrofuran (1.5 mL), and water (1.5 mL) under nitrogen gas, and thereto was added zinc powder (640 mg) in two parts under heating at 60° C. The reaction solution was stirred under heating at 60° C. for 1.5 hours. The reaction solution was filtered through Celite at room temperature, and then the filtrate was concentrated under reduced pressure. The resulting residue was mixed with chloroform (30 mL) and 28 w/w % ammonia water (7.5 mL) and separated. The organic layer was washed with saturated aqueous sodium chloride solution and dried over sodium sulfate. Sodium sulfate was removed with a filter, and then the filtrate was concentrated under reduced pressure to give a crude product of the title compound (383 mg).

$^1$H-NMR (400 MHz, CDCl$_3$) 0.98 (s, 9H), 1.11 (s, 3H), 1.16 (s, 3H), 1.41-1.47 (m, 2H), 1.70-1.88 (m, 3H), 2.25-2.34 (m, 4H), 2.63-2.68 (m, 2H), 3.77 (dd, J=7.3, 1.7 Hz, 2H), 7.17 (d, J=8.1 Hz, 1H), 7.33 (dd, J=8.1, 2.1 Hz, 1H), 7.47 (d, J=2.1 Hz, 1H)

(Step 8)

Ethyl 3-(3-{1-[3-Chloro-4-(3,3-dimethyl-butyl)phenyl]-2-hydroxymethyl-3,3-dimethyl-cyclopentyl}ureido)propionate

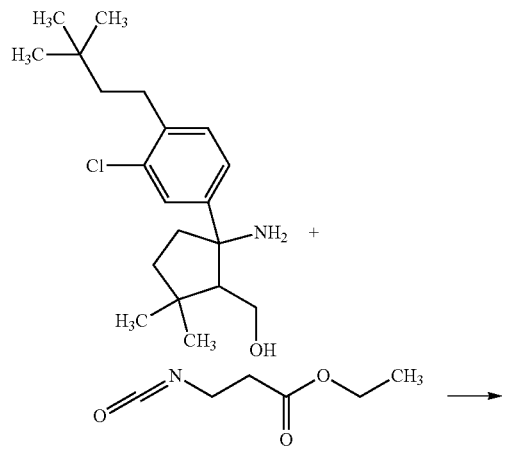

{2-Amino-2-[3-chloro-4-(3,3-dimethyl-butyl)phenyl]-5,5-dimethyl-cyclopentyl}methanol (190 mg) and tetrahydrofuran (2.0 mL) were mixed under nitrogen gas, and thereto was added ethyl 3-isocyanato-propionate (0.076 mL). The reaction solution was stirred at room temperature for 1 hour. The reaction solution was concentrated under reduced pressure, and the resulting residue was purified by silica gel column chromatography (10 g, ethyl acetate/chloroform=2/3) to give the title compound (163 mg).

$^1$H-NMR (400 MHz, CDCl$_3$) 0.98 (s, 9H), 1.12 (s, 3H), 1.13 (s, 3H), 1.27 (t, J=7.2 Hz, 3H), 1.43-1.48 (m, 2H), 1.65-1.78 (m, 2H), 1.98 (dd, J=6.7, 4.2 Hz, 1H), 2.26 (dq, J=27.3, 7.1 Hz, 2H), 2.47 (td, J=5.9, 1.7 Hz, 2H), 2.61-2.66 (m, 2H), 3.40 (ddd, J=12.0, 6.0, 1.2 Hz, 2H), 3.78 (ddd, J=9.9, 5.6, 3.3 Hz, 2H), 4.14 (q, J=7.2 Hz, 2H), 4.87 (t, J=6.1 Hz, 1H), 5.93 (s, 1H), 7.13 (d, J=8.1 Hz, 1H), 7.27 (dd, J=8.1, 2.1 Hz, 1H), 7.38 (d, J=2.1 Hz, 1H)

(Step 9)

Ethyl 3-{7a-[3-chloro-4-(3,3-dimethyl-butyl)phenyl]-5,5-dimethyl-2-oxo-1,2,5,6,7,7a-hexahydro-cyclopentapyrimidin-3-yl}propionate

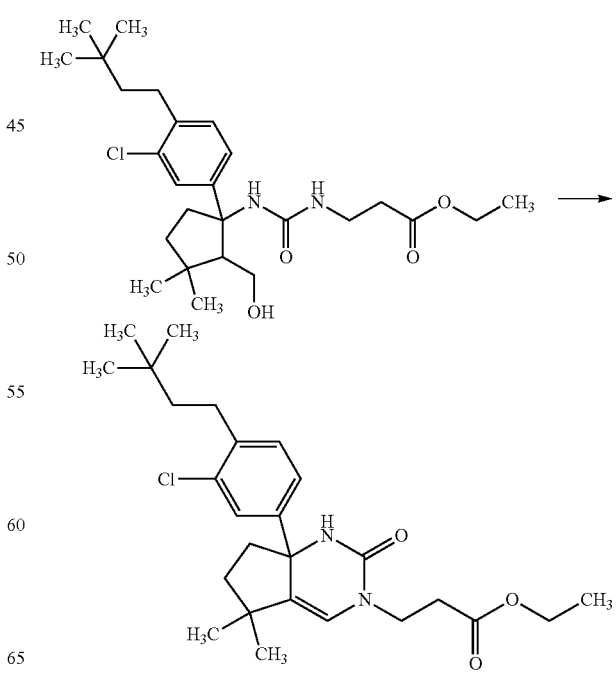

Ethyl 3-(3-{1-[3-chloro-4-(3,3-dimethyl-butyl)phenyl]-2-hydroxymethyl-3,3-dimethyl-cyclopentyl}ureido)propionate and dichloromethane (1.5 mL) were mixed under nitrogen gas, and thereto were added (diacetoxyiodo)benzene (109 mg) and 2,2,6,6-tetramethylpiperidin-1-oxyl radical (2.7 mg) at room temperature. The reaction solution was stirred at room temperature for 16 hours, and then thereto was added trifluoroacetic acid (0.1 mL) at room temperature. The mixture was stirred at room temperature for 4 hours. To the reaction solution were added saturated aqueous sodium hydrogen carbonate solution (2 mL) and ethyl acetate, and the solution was separated. Thereto was added aqueous sodium carbonate solution (30 mL), and the mixture was separated. The organic layer was dried over sodium sulfate. Sodium sulfate was removed with a filter, and then the filtrate was concentrated under reduced pressure. The resulting residue was purified by thin-layer silica gel column chromatography (ethyl acetate/chloroform=1/10) to give a racemate of the title compound. Then, the racemate was purified by preparative chiral column chromatography (IA, isopropanol/n-hexane=7/93, 15 ml/min) to give the title compound (55.1 mg, 94.5% ee).

$^1$H-NMR (400 MHz, CDCl$_3$) 0.98 (s, 9H), 1.10 (s, 3H), 1.24 (s, 3H), 1.26 (t, J=6.2 Hz, 3H), 1.34-1.41 (m, 1H), 1.42-1.47 (m, 2H), 1.59 (ddd, J=9.6, 3.6, 2.8 Hz, 1H), 2.12 (td, J=11.8, 7.2 Hz, 1H), 2.38 (ddd, J=12.3, 6.2, 3.1 Hz, 1H), 2.56 (t, J=6.7 Hz, 2H), 2.62-2.67 (m, 2H), 3.47 (dt, J=14.1, 6.9 Hz, 1H), 3.95 (dt, J=14.0, 6.4 Hz, 1H), 4.15 (ddd, J=14.2, 7.1, 2.3 Hz, 2H), 5.09 (s, 1H), 6.14 (s, 1H), 7.11 (dd, J=7.9, 1.8 Hz, 1H), 7.15 (d, J=7.9 Hz, 1H), 7.27 (s, 1H)

(Step 10)

3-{7a-[3-Chloro-4-(3,3-dimethyl-butyl)phenyl]-5,5-dimethyl-2-oxo-1,2,5,6,7,7a-hexahydro-cyclopentapyrimidin-3-yl}propionate

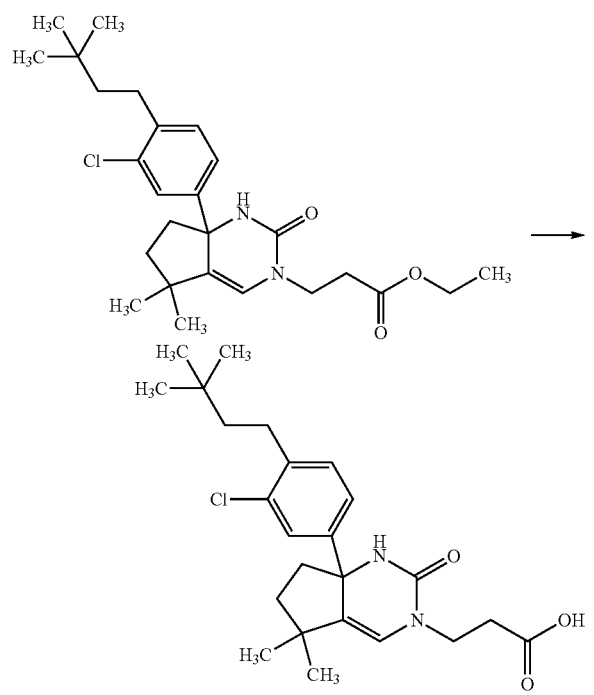

Ethyl 3-{7a-[3-chloro-4-(3,3-dimethyl-butyl)phenyl]-5,5-dimethyl-2-oxo-1,2,5,6,7,7a-hexahydro-cyclopentapyrimidin-3-yl}propionate (55 mg) and methanol (0.5 mL) were mixed under nitrogen gas, and thereto was added 2N aqueous sodium hydroxide solution (0.24 mL) under ice cooling. The reaction solution was stirred at room temperature for 4 hours. To the reaction solution was added 2N hydrochloric acid (0.24 mL) under ice cooling, and the mixture was extracted with ethyl acetate. The organic layer was dried over sodium sulfate. Sodium sulfate was removed with a filter, and then the filtrate was concentrated under reduced pressure to give the title compound (44.0 mg).

Example 7

(Step 1)

Ethyl (1,1-dimethylallyloxy)acetate

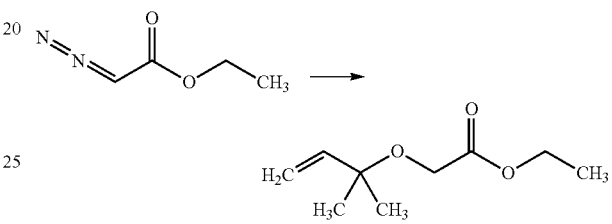

2-Methyl-3-buten-2-ol (4.6 mL) and rhodium (II) acetate (97 mg) were mixed under nitrogen gas, and thereto was added dropwise ethyl diazoacetate (4.6 mL) for 2 hours under water cooling. The mixture was stirred for 1 hour and then concentrated under reduced pressure. The resulting residue was purified by silica gel column chromatography (eluent: ethyl acetate/n-hexane (ethyl acetate/n-hexane=1/5→1/2) to give the title compound (3.65 g).

$^1$H-NMR (400 MHz, CDCl$_3$) 1.27 (t, J=7.1 Hz, 3H), 1.32 (s, 6H), 3.95 (s, 2H), 4.20 (q, J=7.17 Hz, 2H), 5.20-5.15 (m, 2H), 5.83 (dd, J=17.34, 10.87 Hz, 1H)

(Step 2)

(1,1-Dimethylallyloxy)acetaldehyde oxime

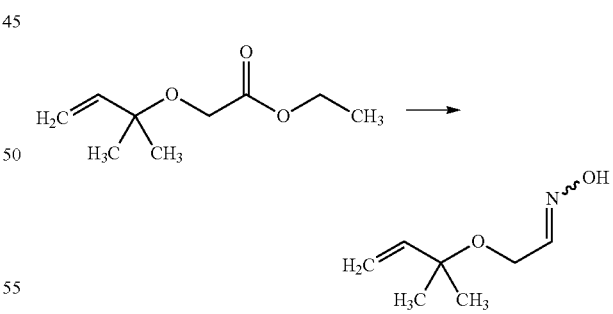

Ethyl (1,1-dimethylallyloxy)acetate (1.65 g) and toluene (1.50 mL) were mixed under nitrogen gas, and thereto was added dropwise 1M diisobutylaluminum hydride/toluene solution (14 mL) under cooling at −78° C. The mixture was stirred for 30 minutes, and then the reaction solution was added to 1N hydrochloric acid (15 mL) under ice cooling. The mixture was stirred for 1 hour and then separated. Hydroxylamine hydrochloride (910 mg) was mixed in ethanol (10 mL) and water (2.5 mL), and thereto was added dropwise 4N aqueous solution of sodium hydroxide (3.35 mL) for 20 minutes under ice cooling. The resulting organic layer was added thereto, and the mixture was stirred at room temperature for 1 hour. The organic layer was washed sequentially with water and saturated aqueous sodium chloride solution and then concentrated under reduced pressure. The resulting residue was purified by silica gel column chromatography (eluent: ethyl acetate/n-hexane (ethyl acetate/n-hexane=1/3→2/3) to give a geometric isomer mixture (1:4) of the title compound (774 mg).

¹H-NMR (400 MHz, CDCl₃) 1.31 (s, 6H), 3.96 (d, J=5.55 Hz, 1.6H), 4.23 (d, J=3.47 Hz, 0.4H), 5.15-5.19 (m, 2H), 5.77-5.86 (m, 1H), 6.87 (t, J=3.47 Hz, 0.2H), 7.42 (br s, 0.8H), 7.46 (t, J=5.55 Hz, 0.8H), 7.69 (br s, 0.2H)

(Step 3)

4,4-Dimethyl-3a,4-dihydro-3H,6H-furan[3,4c]isoxazole

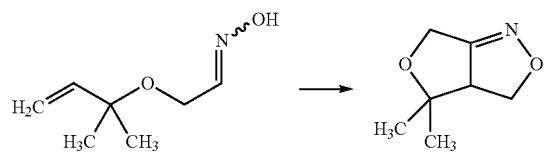

(1,1-Dimethylallyloxy)acetaldehyde oxime (774 mg) and dichloromethane (40 mL) were mixed, and thereto was added triethylamine (65 mL) under ice cooling. Then, thereto was added dropwise antiformin (10 mL) for 15 minutes, and then the mixture was stirred for 30 minutes. Then, thereto was added chloroform. The organic layer was washed sequentially with water and saturated aqueous sodium chloride solution and then concentrated under reduced pressure. The resulting residue was purified by silica gel column chromatography (eluent: ethyl acetate/n-hexane (ethyl acetate/n-hexane=1/2) to give the title compound (771 mg).

¹H-NMR (400 MHz, CDCl₃) 1.20 (s, 3H), 1.41 (s, 3H), 4.01-3.92 (m, 2H), 4.38 (dd, J=13.99, 1.27 Hz, 1H), 4.45-4.50 (m, 2H)

(Step 4)

6a-[3-Chloro-4-(3,3-dimethyl-butyl)phenyl]-4,4-dimethyl-tetrahydro-furan[3,4-c]isoxazole

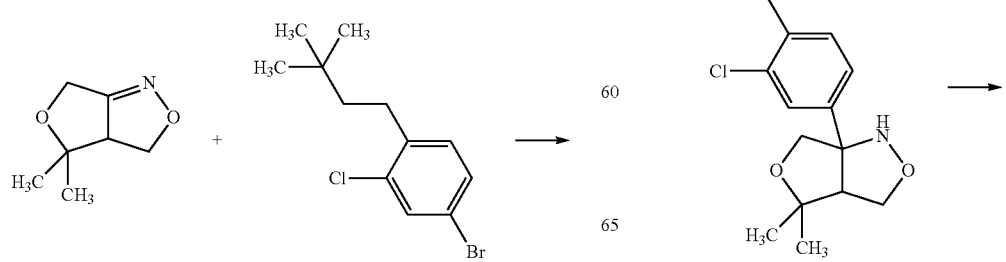

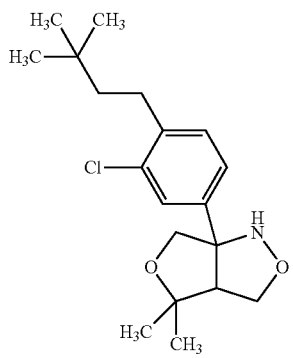

4-Bromo-2-chloro-1-(3,3-dimethyl-butyl)-benzene (1.23 g) was mixed in tetrahydrofuran (5 mL) and toluene (12 mL), and then thereto was added dropwise 1.6M n-butyllithium/n-hexane solution (2.66 mL) under cooling at −78° C. The reaction solution was stirred at −78° C. for 1 hour (Reaction solution A). 4,4-Dimethyl-3a,4-dihydro-3H,6H-furan[3,4-c]isoxazole (300 mg) and toluene (18 mL) were mixed, and thereto was added boron trifluoride-diethyl ether complex (0.537 mL) under cooling at −78° C. The mixture was stirred for 10 minutes. Then, thereto was added dropwise Reaction solution A under cooling at −78° C. The reaction solution was stirred for 1 hour, and then thereto was added an aqueous solution of ammonium chloride (8 mL) under cooling at −78° C. The mixture was extracted with ethyl acetate, and the organic layer was concentrated under reduced pressure. The resulting residue was purified by silica gel column chromatography (eluent: ethyl acetate/n-hexane (ethyl acetate/n-hexane=1/5→1/3) to give the title compound (439 mg).

¹H-NMR (400 MHz, CDCl₃) 0.98 (s, 9H), 1.38 (s, 3H), 1.42 (s, 3H), 1.43-1.47 (m, 2H), 2.65-2.69 (m, 2H), 3.04 (dd, J=6.94, 4.16 Hz, 1H), 3.86-4.22 (m, 4H), 5.20 (br s, 1H), 7.21 (d, J=8.55 Hz, 1H), 7.33-7.28 (m, 1H), 7.52-7.46 (m, 1H)

(Step 5)

{4-Amino-4-[3-chloro-4-(3,3-dimethyl-butyl)phenyl]-2,2-dimethyl-tetrahydro-furan-3-yl}methanol

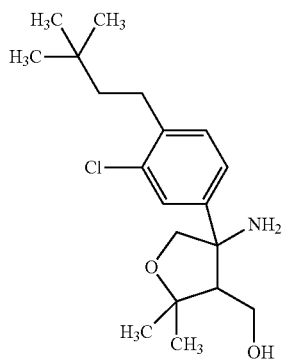

6a-[3-Chloro-4-(3,3-dimethyl-butyl)phenyl]-4,4-dimethyl-tetrahydro-furan[3,4-c]isoxazole (411 mg) was mixed in acetic acid (6 mL), tetrahydrofuran (2 mL), and water (2 mL), and thereto was added zinc powder (800 mg) under heating at 60° C. The mixture was stirred with heating at 60° C. for 3 hours, and then ammonia water (10 mL) was added dropwise to the reaction solution room temperature. The reaction solution was extracted with chloroform (15 mL, three times), and the organic layers were dried over sodium sulfate. Sodium sulfate was removed with a filter, and then the filtrate was concentrated under reduced pressure to give a crude product of the title compound (229 mg).

$^1$H-NMR (400 MHz, CDCl$_3$) 0.98 (s, 9H), 1.36 (s, 3H), 1.41 (s, 3H), 1.43-1.47 (m, 2H), 2.19 (t, J=6.01 Hz, 1H), 2.65-2.69 (m, 2H), 3.68 (d, J=9.25 Hz, 1H), 3.83 (d, J=6.01 Hz, 2H), 4.11 (d, J=9.25 Hz, 1H), 7.20 (d, J=8.09 Hz, 1H), 7.34 (dd, J=8.09, 2.08 Hz, 1H), 7.49 (d, J=2.08 Hz, 1H)

(Step 6)

Ethyl 4-(3-{3-[3-chloro-4-(3,3-dimethyl-butyl)phenyl]-4-hydroxymethyl-5,5-dimethyl-tetrahydro-furan-3-yl}ureido)benzoate

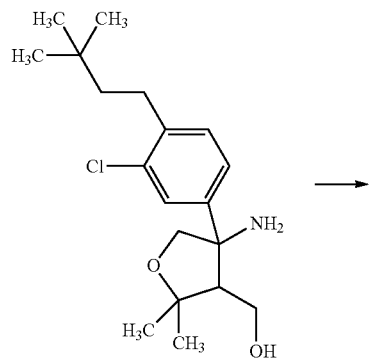

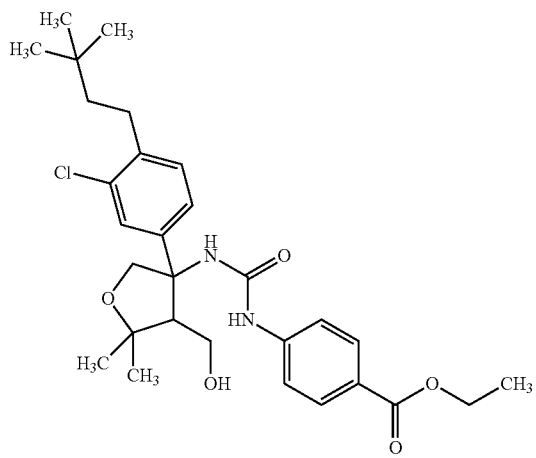

{4-Amino-4-[3-chloro-4-(3,3-dimethyl-butyl)phenyl]-2,2-dimethyl-tetrahydro-furan-3-yl}methanol (125 mg) and tetrahydrofuran (2.5 mL) were mixed, and thereto was added 4-ethoxycarbonylphenyl isocyanate (70 mg) under ice cooling. The mixture was stirred at room temperature for 51 minutes, and then the reaction solution was concentrated under reduced pressure. The resulting residue was purified by silica gel column chromatography (eluent: ethyl acetate/n-hexane (ethyl acetate/n-hexane=1/10→1/6→1/2→1/1) to give the title compound (142 mg).

$^1$H-NMR (400 MHz, CDCl$_3$) 0.96 (s, 9H), 1.28 (s, 3H), 1.37 (t, J=7.00 Hz, 3H), 1.40 (s, 3H), 1.41-1.44 (m, 2H), 2.61-2.65 (m, 2H), 2.85 (dd, J=9.66, 4.35 Hz, 1H), 3.34 (br s, 1H), 3.75-3.87 (m, 2H), 3.90 (d, J=10.14 Hz, 1H), 4.00 (d, J=10.14 Hz, 1H), 4.34 (q, J=7.00 Hz, 2H), 6.34 (br s, 1H), 7.08 (br s, 1H), 7.16 (d, J=8.21 Hz, 1H), 7.32 (d, J=8.69 Hz, 2H), 7.37 (dd, J=8.21, 2.17 Hz, 1H), 7.52 (d, J=2.17 Hz, 1H), 7.94 (d, J=8.69 Hz, 2H)

(Step 7)

Ethyl 4-{(S)-7a-[3-chloro-4-(3,3-dimethyl-butyl)phenyl]-5,5-dimethyl-2-oxo-1,2,7,7a-tetrahydro-5H-furan[3,4-d]pyrimidin-3-yl}benzoate

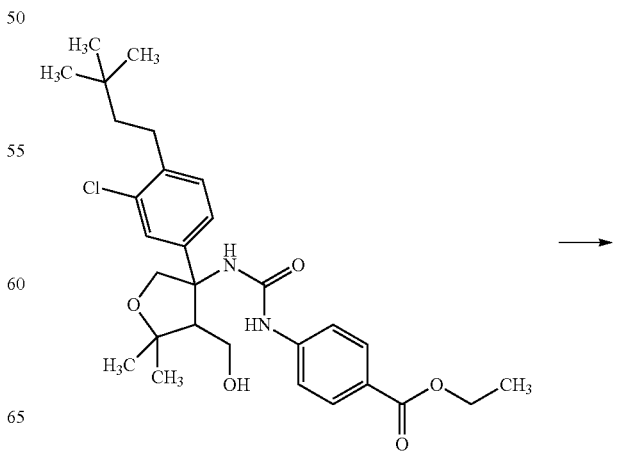

-continued

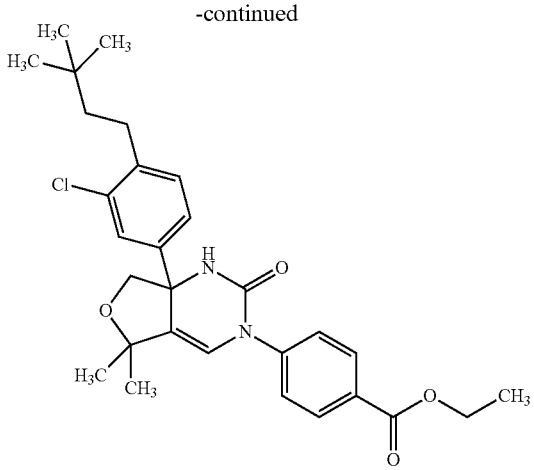

Ethyl 4-(3-{3-[3-chloro-4-(3,3-dimethyl-butyl)phenyl]-4-hydroxymethyl-5,5-dimethyl-tetrahydro-furan-3-yl}ureido)benzoate (124 mg) and chloroform (3 mL) were mixed, and thereto were added (diacetoxyiodo)benzene (75 mg) and 2,2,6,6-tetramethylpiperidin-1-oxyl radical (3.6 mg) at room temperature. The mixture was stirred at room temperature for 7 hours, and then thereto was added an aqueous solution of sodium thiosulfate under ice cooling. The mixture was extracted with chloroform, and the organic layer was dried over magnesium sulfate. Magnesium sulfate was removed with a filter, and then the filtrate was concentrated under reduced pressure. The resulting residue was mixed in cyclopentyl methyl ether (5 mL), and thereto was added 4N hydrogen chloride/cyclopentyl methyl ether solution (0.137 mL) under ice cooling. The mixture was stirred under ice cooling for 2 hours and then stirred at room temperature for 1 hour. The mixture was stirred under heating at 40° C. for 1 hour, and then the reaction solution was concentrated under reduced pressure. The resulting residue was purified by thin-layer silica gel column chromatography (ethyl acetate/n-hexane=1/1) to give a racemate of the title compound (73.2 mg). The racemate was purified with a Recycling Preparative Liquid Chromatograph to give a single enantiomer of the title compound (30.8 mg).

Purification conditions for the preparative chromatography are shown as follows.

Preparative apparatus: Recycling preparative liquid chromatograph LC-92XX NEXT SERIES, Japan Analytical Industry Co., Ltd.

Column: Daicel CHIRALPAK IA 2.0 cmφ×25 cm

Mobile phase: n-hexane:2-propanol=80:20

Flow rate: 10.0 mL/min

Detection: UV (254 nm)

Measurement of the resulting compound with a chiral column showed 6.5 minutes of the retention time for the resulting enantiomer with >99% ee of optical purity. The retention time for the opposite enantiomer on the phenyl group was 8.8 minutes.

Analytical conditions for the chiral column are shown as follows.

Measurement apparatus: HPLC system, Shimadzu Corporation, High-Performance Liquid Chromatograph Prominence Column: Daicel CHIRALPAK IA-3 0.46 cmφ×15 cm Column temperature: 30° C.

Mobile phase: hexane:2-propanol=80:20

Flow rate: 1.0 mL/min

Detection: UV (254 nm)

$^1$H-NMR (400 MHz, CDCl$_3$) 0.98 (s, 9H), 1.33 (s, 3H), 1.40 (t, J=7.12 Hz, 3H), 1.42-1.46 (m, 2H), 1.50 (s, 3H), 2.65-2.69 (m, 2H), 4.09 (d, J=8.69 Hz, 1H), 4.38 (q, J=7.12 Hz, 2H), 4.51 (d, J=8.69 Hz, 1H), 5.35 (s, 1H), 6.34 (s, 1H), 7.22 (d, J=7.97 Hz, 1H), 7.30 (dd, J=7.97, 1.93 Hz, 1H), 7.15 (d, J=9.02 Hz, 2H), 7.49 (d, J=1.93 Hz, 1H), 8.07 (d, J=9.02 Hz, 2H)

(Step 8)

4-{(S)-7a-[3-Chloro-4-(3,3-dimethyl-butyl)phenyl]-5,5-dimethyl-2-oxo-1,2,7,7a-tetrahydro-5H-furan[3,4-d]pyrimidin-3-yl}benzoic acid

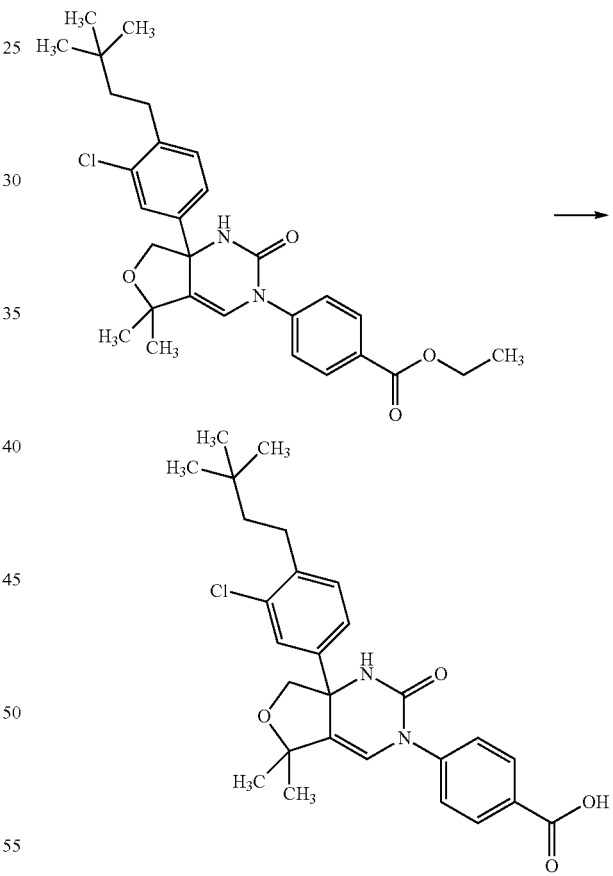

Ethyl 4-{(S)-7a-[3-chloro-4-(3,3-dimethyl-butyl)phenyl]-5,5-dimethyl-2-oxo-1,2,7,7a-tetrahydro-5H-furan[3,4-d]pyrimidin-3-yl}benzoate (28.0 mg) and ethanol (1 mL) were mixed, and thereto was added 2N aqueous solution of sodium hydroxide (0.110 mL) at room temperature. The reaction solution was stirred at room temperature for 4 hours 30 minutes, and then thereto was added 2N hydrochloric acid (0.136 mL). The precipitated solid was collected by filtration to give the title compound (22.1 mg).

Example 10

(Step 1)

Ethyl 4-(3-{1-[3-chloro-4-(3,3-dimethyl-butyl)phenyl]-2-hydroxymethyl-3,3-dimethyl-cyclopentyl}ureido)benzoate

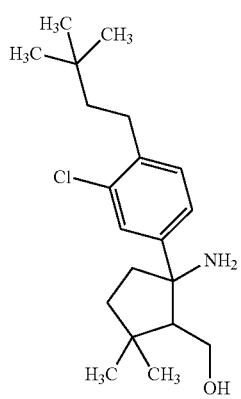

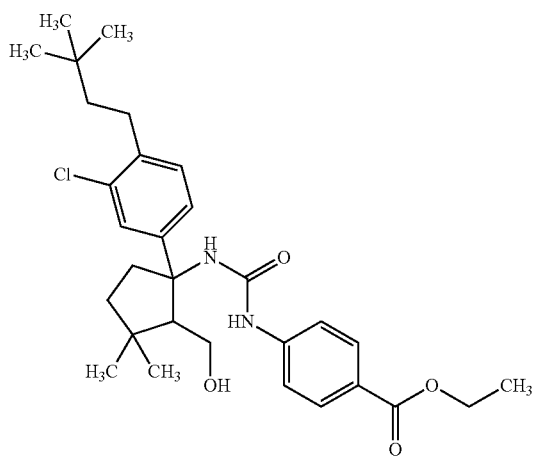

{2-Amino-2-[3-chloro-4-(3,3-dimethyl-butyl)phenyl]-5,5-dimethyl-cyclopentyl}methanol (166 mg) was mixed with tetrahydrofuran (2 mL) under nitrogen gas, and thereto was added ethyl 4-isocyanatobenzoate (94 mg) under ice cooling. The reaction solution was stirred at room temperature for 1 hour. The reaction solution was concentrated, and then purified by silica gel column chromatography (eluent: ethyl acetate/n-hexane (ethyl acetate/n-hexane=25/1→1/1) to give the title compound (141 mg).

$^1$H-NMR (100 MHz, CDCl$_3$) 0.97 (s, 9H), 1.13 (s, 3H), 1.21 (s, 3H), 1.33-1.39 (m, 3H), 1.40-1.46 (m, 2H), 1.69-1.88 (m, 3H), 1.91-1.99 (m, 1H), 2.38-2.48 (m, 1H), 2.53-2.66 (m, 3H), 3.80-3.95 (m, 2H), 4.30-4.37 (m, 2H), 6.45-6.49 (m, 1H), 6.88-6.96 (m, 1H), 7.13-7.17 (m, 1H), 7.26-7.29 (m, 1H), 7.32-7.42 (m, 3H), 7.90-7.96 (m, 2H)

(Step 2)

Ethyl 4-{7a-[3-chloro-4-(3,3-dimethyl-butyl)phenyl]-5,5-dimethyl-2-oxo-1,2,5,6,7,7a-hexahydro-cyclopentapyrimidin-3-yl}benzoate

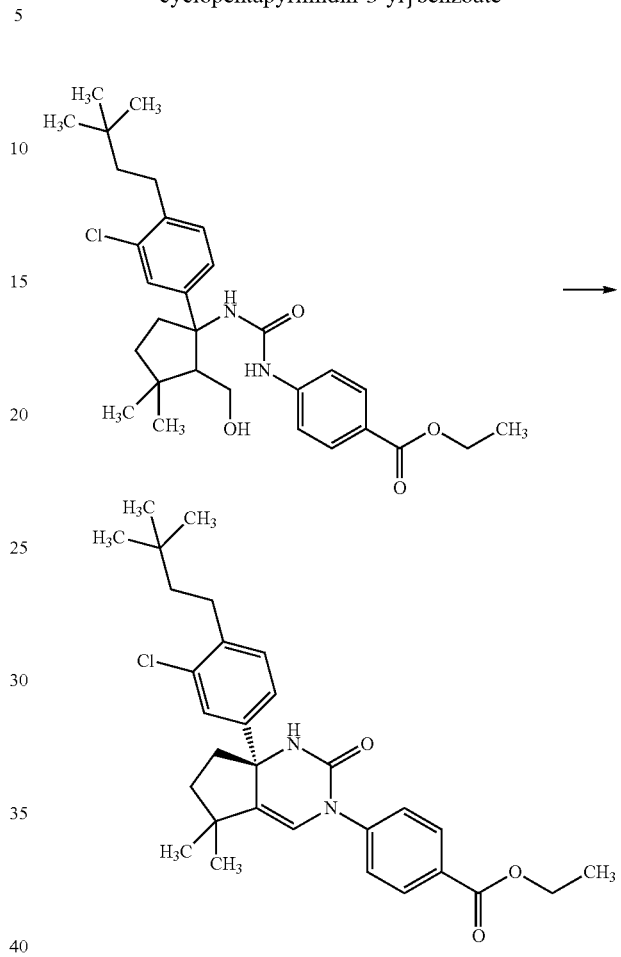

Ethyl 4-(3-{1-[3-chloro-4-(3,3-dimethyl-butyl)phenyl]-2-hydroxymethyl-3,3-dimethyl-cyclopentyl}ureido)benzoate (135 mg) and dichloromethane (5 mL) were mixed under nitrogen gas, and thereto were added (diacetoxyiodo)benzene (82 mg) and 2,2,6,6-tetramethylpiperidin-1-oxyl radical (4 mg) at room temperature. The reaction solution was stirred at room temperature for 3.5 hours, and then thereto was added trifluoroacetic acid (78 μL) at room temperature. The mixture was stirred at room temperature overnight, and then thereto were added aqueous sodium thiosulfate solution and chloroform under ice cooling. The mixture was separated. The organic layer was dried over sodium sulfate. Sodium sulfate was removed with a filter, and then the filtrate was concentrated under reduced pressure. The resulting residue was purified by thin-layer silica gel column chromatography (eluent: ethyl acetate/n-hexane=1/1, Rf=0.5) to give a racemate of the title compound (91 mg). The racemate was purified with a Recycling Preparative Liquid Chromatograph to give single enantiomer of the title compound (23 mg).

Purification conditions for the preparative chromatography are shown as follows.

Preparative apparatus: Recycling preparative liquid chromatograph LC-92XX NEXT SERIES, Japan Analytical Industry Co., Ltd.

Column: Daicel CHIRALPAK IA 2.0 cmφ×25 cm

Mobile phase: n-hexane/2-propanol=80/20

Flow rate: 10.0 mL/min

Detection: UV (254 nm)

Measurement of the resulting compound with a chiral column showed 12.8 minutes of the retention time for the resulting enantiomer with >99% ee of optical purity. The retention time for the opposite enantiomer was 10.6 minutes.

Analytical conditions for the chiral column are shown as follows.

Measurement apparatus: HPLC system, Shimadzu Corporation, High-Performance Liquid Chromatograph Prominence Column: Daicel CHIRALPAK IA-3 0.46 cmφ×15 cm Column temperature: 40° C.

Mobile phase: n-hexane/2-propanol=90/10

Flow rate: 1.0 mL/min

Detection: UV (254 nm)

$^1$H-NMR (400 MHz, CDCl$_3$) 0.98 (s, 9H), 1.17 (s, 3H), 1.30 (s, 3H), 1.36-1.41 (m, 3H), 1.41-1.47 (m, 2H), 1.64-1.71 (m, 1H), 2.18-2.27 (m, 1H), 2.43-2.51 (m, 1H), 2.62-2.69 (m, 2H), 4.33-4.40 (m, 2H), 5.36 (br s, 1H), 6.36 (s, 1H), 7.17-7.24 (m, 2H), 7.37-7.39 (m, 1H), 7.41-7.47 (m, 2H), 8.01-8.06 (m, 2H)

(Step 3)

4-{7a-[3-Chloro-4-(3,3-dimethyl-butyl)phenyl]-5,5-dimethyl-2-oxo-1,2,5,6,7,7a-hexahydro-cyclopentapyrimidin-3-yl}benzoic acid

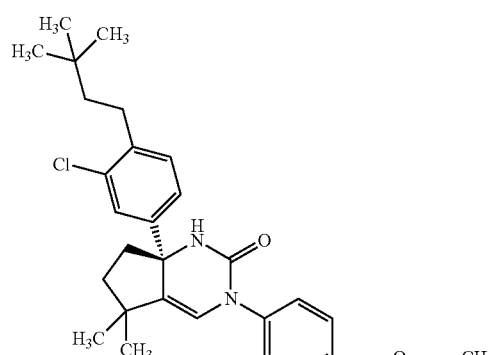

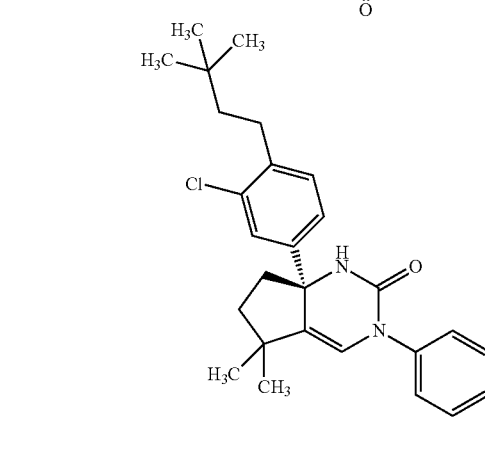

Ethyl 4-{7a-[3-chloro-4-(3,3-dimethyl-butyl)phenyl]-5,5-dimethyl-2-oxo-1,2,5,6,7,7a-hexahydro-cyclopentapyrimidin-3-yl}benzoate (21 mg) and ethanol (1 mL) were mixed under nitrogen gas, and thereto was added 2N aqueous sodium hydroxide solution (82 μL) at room temperature. The reaction solution was stirred under heating at 60° C. for 1 hour, and then concentrated under reduced pressure. To the resulting residue were added 2N hydrochloric acid and water at room temperature, and the resulting slurry was stirred at room temperature. The precipitated solid was collected by filtration to give the title compound (16 mg).

Example 27

(Step 1)

Ethyl 6-(tert-butyl-dimethyl-silanyloxy)-3-vinyl-hexanoate

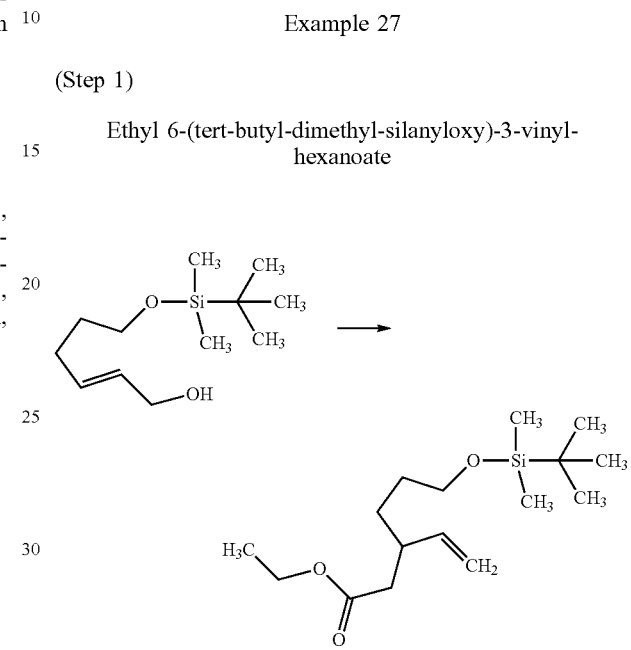

(E)-6-(tert-butyl-dimethyl-silanyloxy)hex-2-en-1-ol (10.1 g) and triethyl orthoformate (102 mL) were mixed, and thereto was added propionate (51 mL). The reaction solution was stirred under heating at 150° C. for 3.5 hours. The reaction solution was concentrated under reduced pressure. The resulting residue was purified by silica gel column chromatography (Biotage flash purification systems, eluent: ethyl acetate/n-hexane, Rf=0.33 (ethyl acetate/n-hexane=5/95)) to give the title compound (13.2 g).

$^1$H-NMR (400 MHz, CDCl$_3$) 0.04 (s, 6H), 0.89 (s, 9H), 1.24 (t, J=6.94 Hz, 3H), 1.29-1.38 (m, 1H), 1.42-1.60 (m, 3H), 2.28 (dd, J=14.57, 8.55 Hz, 1H), 2.36 (dd, J=14.57, 6.24 Hz, 1H), 2.48-2.57 (m, 1H), 3.59 (t, J=6.47 Hz, 2H), 4.11 (q, J=7.17 Hz, 2H), 4.99-5.06 (m, 2H), 5.62 (ddd, J=17.34, 10.40, 8.32 Hz, 1H)

(Step 2)

6-(tert-Butyl-dimethyl-silanyloxy)-3-vinyl-hexan-1-ol

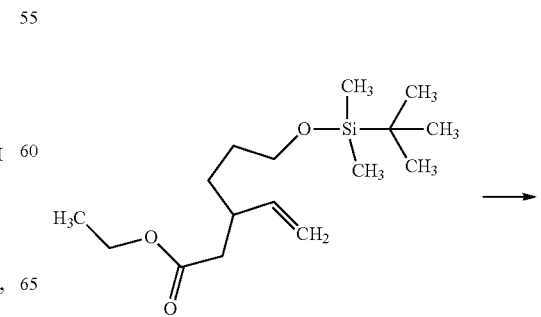

-continued

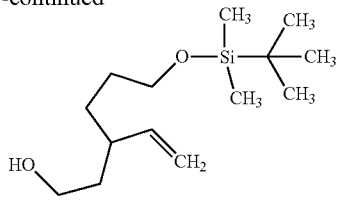

Ethyl 6-(tert-butyl-dimethyl-silanyloxy)-3-vinyl-hexanoate (11.5 g) and tetrahydrofuran (231 mL) were mixed under argon gas, and thereto was added dropwise 1M diisobutylaluminum hydride/toluene solution (92.2 mL) under cooling at −78° C. The reaction solution was stirred under ice cooling for 1 hour. In the reaction solution was added dropwise an aqueous solution of Rochelle salt (231 mL) under ice cooling. The reaction solution was stirred at room temperature for 16 hours. To the reaction solution was added ethyl acetate, and the solution was separated. The aqueous layer was extracted with ethyl acetate. Combined organic layers were washed with brine, and then dried over magnesium sulfate. Magnesium sulfate was removed with a filter, and then concentrated under reduced pressure. The resulting residue was azeotroped with toluene to give a crude product of the title compound (11.3 g).

$^1$H-NMR (400 MHz, CDCl$_3$) 0.04 (s, 6H), 0.89 (s, 9H), 1.24-1.34 (m, 2H), 1.40-1.61 (m, 3H), 1.64-1.72 (m, 1H), 2.10-2.19 (m, 1H), 3.59 (t, J=6.47 Hz, 2H), 3.62-3.72 (m, 2H), 4.99-5.04 (m, 2H), 5.57 (ddd, J=18.73, 9.71, 9.02 Hz, 1H)
(Step 3)

[4-(2-Benzyloxy-ethyl)hex-5-enyloxy]-tert-butyl-dimethyl-silane

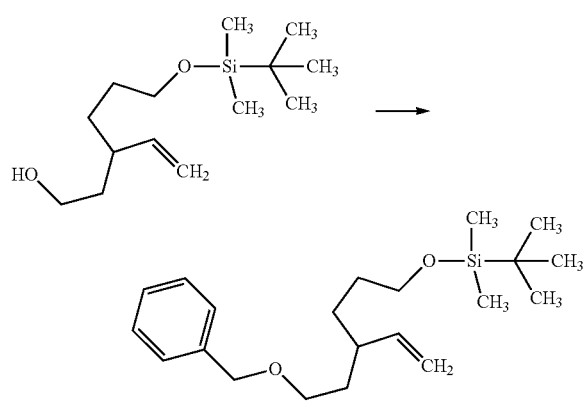

Sodium hydride (2.73 g) and dimethylformamide (125 mL) were mixed under argon gas, and thereto was added dropwise a mixed solution of 6-(tert-butyl-dimethyl-silanyloxy)-3-vinyl-hexan-1-ol (12.6 g) in dimethylformamide (60 mL) under ice cooling. The reaction solution was stirred under ice cooling for 1 hour. To the reaction solution was added dropwise a mixed solution of benzyl bromide (8.41 mL) in dimethylformamide (60 mL) under ice cooling. The reaction solution was stirred at room temperature overnight. To the reaction solution were added aqueous ammonium chloride solution (125 mL), water (60 mL), and ethyl acetate/n-hexane=1/3, and the solution was separated. The aqueous layer was extracted with ethyl acetate/n-hexane=1/3. Combined organic layers were washed with water (three times) and brine, and then dried over magnesium sulfate. Magnesium sulfate was removed with a filter, and then concentrated under reduced pressure. The resulting residue was purified by silica gel column chromatography (Biotage flash purification systems, eluent: ethyl acetate/n-hexane, Rf=0.36 (ethyl acetate/n-hexane=10/90)) to give the title compound (19.5 g).

$^1$H-NMR (400 MHz, CDCl$_3$) 0.04 (s, 6H), 0.89 (s, 9H), 1.21-1.31 (m, 2H), 1.38-1.60 (m, 3H), 1.70-1.78 (m, 1H), 2.10-2.20 (m, 1H), 3.41-3.51 (m, 2H), 3.58 (t, J=6.24 Hz, 2H), 4.46 (d, J=11.79 Hz, 1H), 4.49 (d, J=11.79 Hz, 1H), 4.93-4.99 (m, 2H), 5.52 (ddd, J=17.11, 10.40, 9.02 Hz, 1H), 7.27-7.37 (m, 5H)
(Step 4)

4-(2-Benzyloxy-ethyl)hex-5-en-1-ol

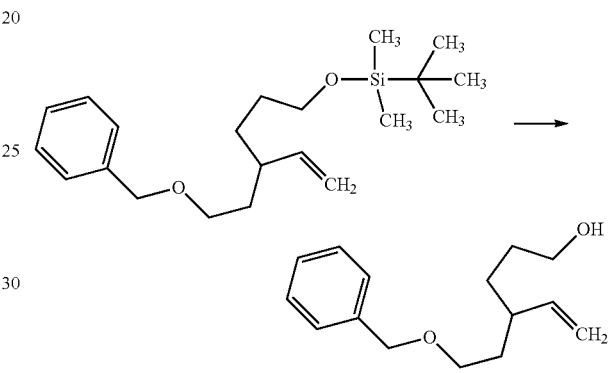

[4-(2-Benzyloxy-ethyl)hex-5-enyloxy]-tert-butyl-dimethyl-silane (12.88 g) and tetrahydrofuran (130 mL) were mixed under argon gas, and thereto was added dropwise 1M tetra-n-butylammonium fluoride/tetrahydrofuran solution (55.4 mL) under ice cooling. The reaction solution was stirred at room temperature for 19.5 hours. To the reaction solution were added water (100 mL) and ethyl acetate, and the solution was separated. The aqueous layer was extracted with ethyl acetate (three times). Combined organic layers were washed with brine, and then dried over magnesium sulfate. Magnesium sulfate was removed with a filter, and then concentrated under reduced pressure. The resulting residue was purified by silica gel column chromatography (Biotage flash purification systems, eluent: ethyl acetate/n-hexane) to give the title compound (8.43 g).

$^1$H-NMR (400 MHz, CDCl$_3$) 1.35-1.21 (m, 2H), 1.42-1.67 (m, 3H), 1.70-1.79 (m, 1H), 2.13-2.22 (m, 1H), 3.42-3.52 (m, 2H), 3.60-3.64 (m, 2H), 4.46 (d, J=12.02 Hz, 1H), 4.49 (d, J=12.02 Hz, 1H), 4.94-5.01 (m, 2H), 5.52 (ddd, J=16.88, 10.17, 8.79 Hz, 1H), 1.27-7.38 (m, 5H)
(Step 5)

4-(2-Benzyloxy-ethyl)hex-5-enal

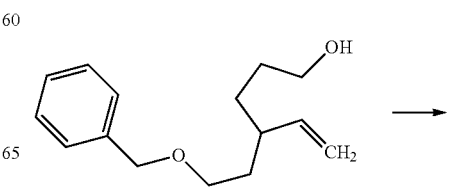

-continued

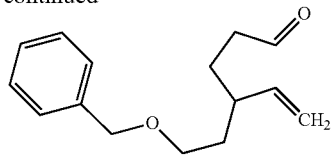

4-(2-Benzyloxy-ethyl)hex-5-en-1-ol (7.14 g) and (diacetoxyiodo)benzene (10.7 g) were mixed in chloroform (72 mL) under nitrogen gas, and thereto was added 2,2,6,6-tetramethylpiperidin-1-oxyl radical (0.477 g) at room temperature. The reaction solution was stirred at room temperature for 22 hours. To the reaction solution were added saturated aqueous sodium hydrogen carbonate solution (20 mL), water (10 mL), sodium thiosulfate (0.723 g), and ethyl acetate, and the solution was separated. The aqueous layer was extracted with ethyl acetate. Combined organic layers were washed with brine, and then dried over magnesium sulfate. Magnesium sulfate was removed with a filter, and then concentrated under reduced pressure. The resulting residue was purified by silica gel column chromatography (Biotage flash purification systems, eluent: ethyl acetate/n-hexane, Rf=0.50 (ethyl acetate/n-hexane=20/80)) to give the title compound (7.24 g).

$^1$H-NMR (400 MHz, CDCl$_3$) 1.50-1.60 (m, 2H), 1.71-1.01 (m, 2H), 2.13-2.23 (m, 1H), 2.35-2.51 (m, 2H), 3.42-3.52 (m, 2H), 4.46 (d, J=11.79 Hz, 1H), 4.49 (d, J=11.79 Hz, 1H), 4.96-5.05 (m, 2H), 5.47 (ddd, J=17.11, 10.17, 9.02 Hz, 1H), 7.27-7.36 (m, 5H), 9.73 (t, J=1.39 Hz, 1H)

(Step 6)

4-(2-Benzyloxy-ethyl)hex-5-enal oxime

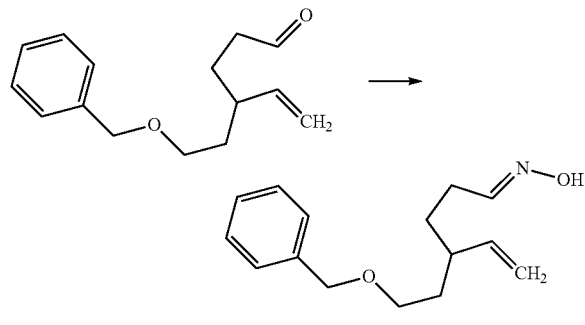

4-(2-Benzyloxy-ethyl)hex-5-enal (5.94 g), ethanol (51.2 mL), and water (25.6 mL) were mixed under nitrogen gas, and thereto were added sodium acetate (15.4 g) and hydroxylamine hydrochloride (7.78 g) at room temperature. The reaction solution was stirred under heating at 60° C. for 21.5 hours. The reaction solution was concentrated under reduced pressure, and thereto was added toluene. The solution was separated. The aqueous layer was extracted with toluene (twice). Combined organic layers were washed with brine (twice), and then dried over sodium sulfate. Sodium sulfate was removed with a filter, and then concentrated under reduced pressure. The resulting residue was purified by silica gel column chromatography (Biotage flash purification systems, eluent: ethyl acetate/n-hexane, Rf=0.27 (ethyl acetate/n-hexane=20/80)) to give the title compound (7.38 g).

$^1$H-NMR (400 MHz, CDCl$_3$) 1.38-1.48 (m, 1H), 1.50-1.64 (m, 2H), 1.70-1.80 (m, 1H), 2.09-2.28 (m, 2H), 2.30-2.44 (m, 1H), 3.41-3.52 (m, 2H), 4.46 (d, J=12.95 Hz, 1H), 4.49 (d, J=12.95 Hz, 1H), 4.97-5.05 (m, 2H), 5.56-5.45 (m, 1H), 6.70 (t, J=5.55 Hz, 0.5H), 7.27-7.36 (m, 5H), 7.41 (t, J=6.01 Hz, 0.5H)

(Step 7)

4-(2-Benzyloxy-ethyl)-3a,4,5,6-tetrahydro-3H-cyclopenta[c]isoxazole

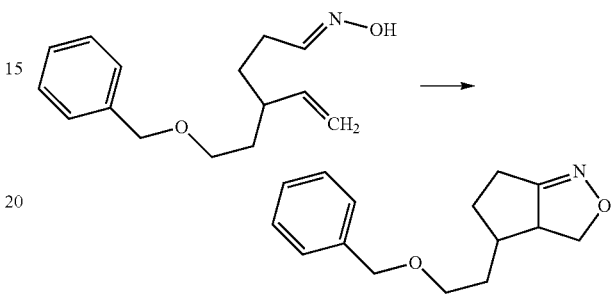

4-(2-Benzyloxy-ethyl)hex-5-enal oxime (5.90 g) and triethylamine (2.04 mL) were mixed in dichloromethane (118 mL), and then thereto was added a mixed aqueous solution of sodium hypochlorite 5-hydrate (3.61 g) in water (53.1 mL) under water cooling. The reaction solution was stirred at room temperature for 3.5 hours. To the reaction solution was added a mixed solution of sodium hypochlorite 5-hydrate (4.95 g) in water (53.1 mL) under water cooling. The reaction solution was stirred at room temperature for 17 hours. To the reaction solution was added ethyl acetate, and the solution was separated. The aqueous layer was extracted with ethyl acetate. Combined organic layers were washed with water (twice) and brine, and then dried over sodium sulfate. Sodium sulfate was removed with a filter, and then concentrated under reduced pressure. The resulting residue was purified by silica gel column chromatography (Biotage flash purification systems, eluent: ethyl acetate/n-hexane, Rf=0.27 (ethyl acetate/n-hexane=30/70)) and (Biotage flash purification systems, eluent: acetone/chloroform) to give the title compound (2.34 g).

$^1$H-NMR (400 MHz, CDCl$_3$) 1.66-1.57 (m, 1H), 1.77-2.06 (m, 3H), 2.33-2.56 (m, 3H), 3.35-3.50 (m, 3H), 3.73 (dd, J=12.26, 8.07 Hz, 1H), 4.41 (dd, J=9.57, 8.07 Hz, 1H), 4.44 (d, J=11.66 Hz, 1H), 4.48 (d, J=11.66 Hz, 1H), 7.28-7.37 (m, 5H)

(Step 8)

4-(2-Benzyloxy-ethyl)-6a-[3-chloro-4-(3,3-dimethylbutyl)phenyl]hexahydro-cyclopenta[c]isoxazole

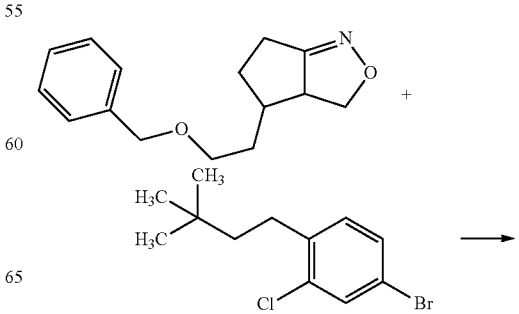

-continued

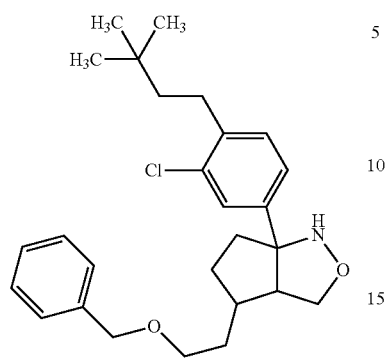

This step was performed according to Example 3 Step 6.

(Step 9)

{2-Amino-5-(2-benzyloxy-ethyl)-2-[3-chloro-4-(3,3-dimethyl-butyl)phenyl]cyclopentyl}methanol

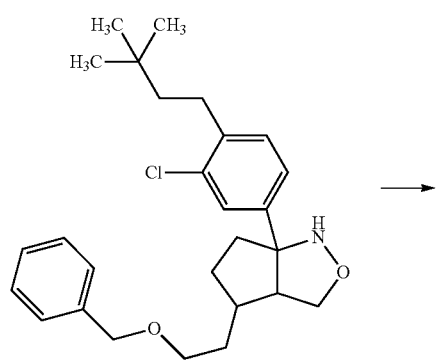

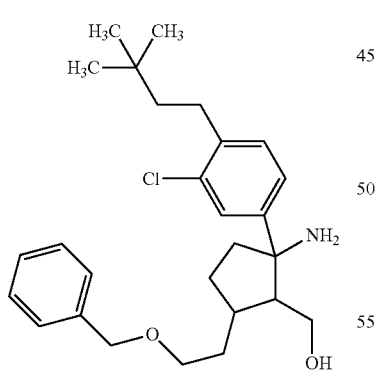

This step was performed according to Example 3 Step 7.
¹H NMR (400 MHz, CDCl₃) 0.98 (s, 9H), 1.42-1.77 (m, 6H), 1.88-1.96 (m, 1H), 2.02-2.12 (m, 1H), 2.25-2.37 (m, 2H), 2.64-2.69 (m, 2H), 3.53-3.59 (m, 2H), 3.64 (dd, J=11.91, 4.97 Hz, 1H), 3.72 (dd, J=11.91, 3.12 Hz, 1H), 3.77-3.82 (m, 2H), 4.49 (d, J=11.79 Hz, 1H), 4.53 (d, J=11.79 Hz, 1H), 7.18 (d, J=8.09 Hz, 1H), 7.28-7.35 (m, 6H), 7.44 (d, J=2.08 Hz, 1H)

(Step 10)

Ethyl 3-(3-{3-(2-benzyloxy-ethyl)-1-[3-chloro-4-(3,3-dimethyl-butyl)phenyl]-2-hydroxymethyl-cyclopentyl}ureido)propionate

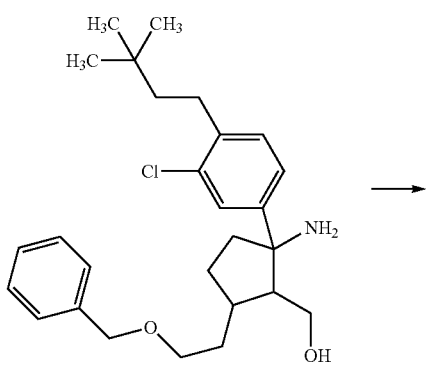

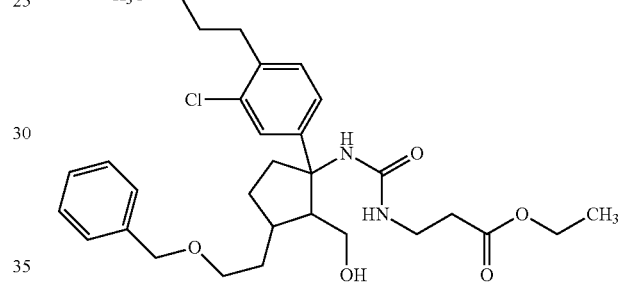

This step was performed according to Example 3 Step 8.
¹H-NMR (400 MHz, CDCl₃) 0.97 (s, 9H), 1.25 (t, J=7.17 Hz, 3H), 1.42-1.68 (m, 6H), 1.77-1.85 (m, 1H), 2.08-2.15 (m, 1H), 2.27-2.41 (m, 2H), 2.45-2.50 (m, 2H), 2.60-2.65 (m, 2H), 3.34-3.42 (m, 2H), 3.52-3.68 (m, 4H), 4.12 (q, J=7.17 Hz, 2H), 4.52 (s, 2H), 4.69 (t, J=5.53 Hz, 1H), 6.52 (s, 1H), 7.13 (d, J=7.92 Hz, 1H), 7.19 (dd, J=7.92, 1.94 Hz, 1H), 7.29-7.38 (m, 6H)

(Step 11)

Ethyl 3-(5-(2-benzyloxy-ethyl)-7a-[3-chloro-4-(3,3-dimethyl-butyl)phenyl]-2-oxo-1,2,5,6,7,7a-hexa-hydro-cyclopentapyrimidin-3-yl)propionate

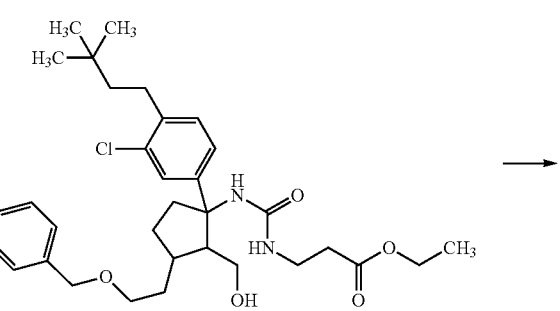

-continued

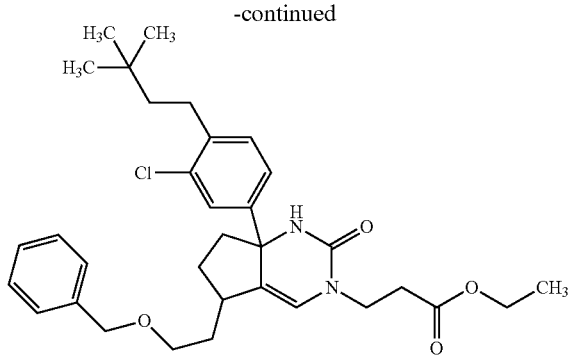

This step was performed according to Example 3 Step 9. (Step 12)

Ethyl 3-{7a-[3-chloro-4-(3,3-dimethyl-butyl)phenyl]-5-(2-hydroxy-ethyl)-2-oxo-1,2,5,6,7,7a-hexahydro-cyclopentapyrimidin-3-yl}propionate

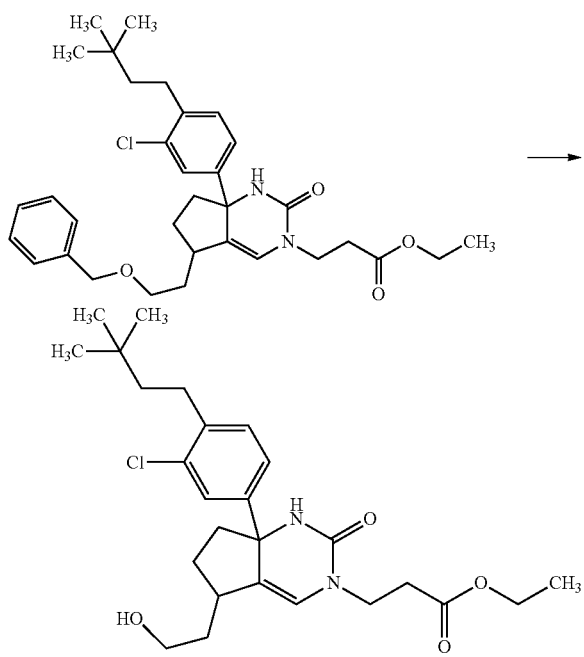

Ethyl 3-{5-(2-benzyloxy-ethyl)-7a-[3-chloro-4-(3,3-dimethyl-butyl)phenyl]-2-oxo-1,2,5,6,7,7a-hexahydro-cyclopentapyrimidin-3-yl}propionate (0.100 g) and dichloromethane (2 mL) were mixed under nitrogen gas, and thereto was added dropwise 1.01M boron tribromide/dichloromethane solution (0.42 mL) under cooling at −78° C. The reaction solution was stirred under cooling at −78° C. for 1 hour. To the reaction solution was added a mixed solution of triethylamine (0.42 mL) in methanol (0.42 mL) under cooling at −78° C. The reaction solution was stirred at room temperature for 10 minutes. To the reaction solution was added dropwise water (0.5 mL). To the reaction solution was added ethyl acetate, and the solution was separated. The aqueous layer was extracted with ethyl acetate. Combined organic layers were washed with brine, and then dried over sodium sulfate. Sodium sulfate was removed with a filter, and then concentrated under reduced pressure. The resulting residue was purified by silica gel column chromatography (Biotage flash purification systems, eluent: ethyl acetate/n-hexane, Rf=0.07 (ethyl acetate/n-hexane=2/3)) and (Biotage flash purification systems, eluent: acetone/chloroform, Rf=0.43 (acetone/chloroform=3/7), followed by purification by thin-layer silica gel column chromatography (acetone/chloroform=1/4) to give the title compound (10.8 mg)

$^1$H-NMR (400 MHz, CDCl$_3$) 0.98 (s, 9H), 1.14-1.08 (m, 1H), 1.18-1.33 (m, 5H), 1.42-1.46 (m, 2H), 1.65-1.73 (m, 1H), 1.97-2.06 (m, 2H), 2.45-2.49 (m, 1H), 2.53-2.61 (m, 2H), 2.62-2.67 (m, 2H), 2.91-2.99 (m, 1H), 3.45-3.53 (m, 1H), 3.64-3.73 (m, 2H), 3.89-3.96 (m, 1H), 4.08-4.19 (m, 2H), 5.11 (s, 1H), 6.25 (d, J=1.85 Hz, 1H), 7.06-7.27 (m, 3H)

(Step 13)

Ethyl 3-{7a-[3-chloro-4-(3,3-dimethyl-butyl)phenyl]-5-(2-methoxy-ethyl)-2-oxo-1,2,5,6,7,7a-hexahydro-cyclopentapyrimidin-3-yl}propionate

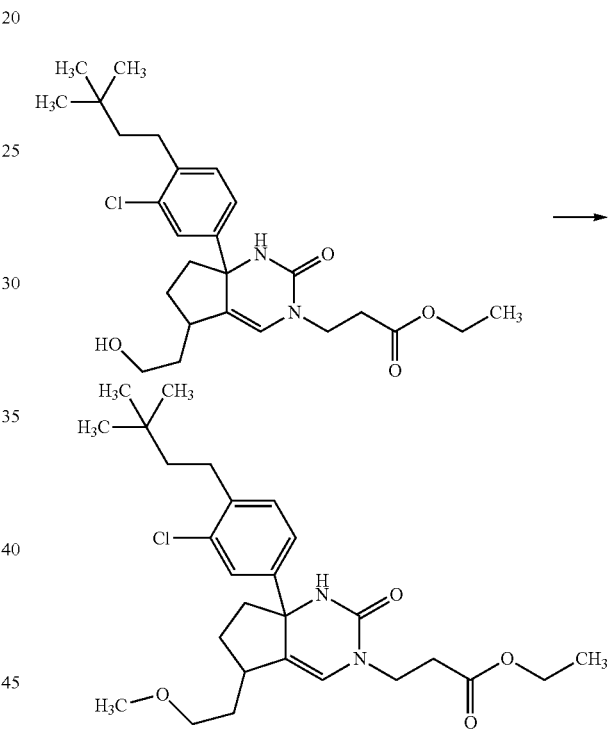

Ethyl 3-{7a-[3-chloro-4-(3,3-dimethyl-butyl)phenyl]-5-(2-hydroxy-ethyl)-2-oxo-1,2,5,6,7,7a-hexahydro-cyclopentapyrimidin-3-yl}propionate (52 mg) and acetonitrile (0.75 mL) were mixed under nitrogen gas, and thereto were added methyl iodide (0.75 mL) and silver (I) oxide (38 mg) at room temperature. The reaction solution was stirred under heating at 80° C. The resulting solid was removed with Celite, and then the filtrate was concentrated under reduced pressure. The resulting residue was purified by thin-layer silica gel column chromatography (ethyl acetate/n-hexane=1/1) and thin-layer silica gel column chromatography (acetone/chloroform=7/93) to give the title compound (15.5 mg).

$^1$H-NMR (400 MHz, CDCl$_3$) 0.98 (s, 9H), 1.04-1.14 (m, 1H), 1.25 (t, J=7.17 Hz, 3H), 1.41-1.46 (m, 2H), 1.50-1.59 (m, 2H), 1.66-1.74 (m, 1H), 1.94-2.06 (m, 2H), 2.42-2.47 (m, 1H), 2.55-2.59 (m, 2H), 2.62-2.66 (m, 2H), 2.83-2.95 (m, 1H), 3.34 (s, 3H), 3.35-3.53 (m, 3H), 3.89-3.95 (m, 1H), 4.12-1.19 (m, 2H), 5.20 (s, 1H), 6.21 (d, J=1.85 Hz, 1H), 7.06-7.24 (m, 3H)

(Step 14)

3-{7a-[3-Chloro-4-(3,3-dimethyl-butyl)phenyl]-5-(2-methoxy-ethyl)-2-oxo-1,2,5,6,7,7a-hexahydro-cyclopentapyrimidin-3-yl}propionate

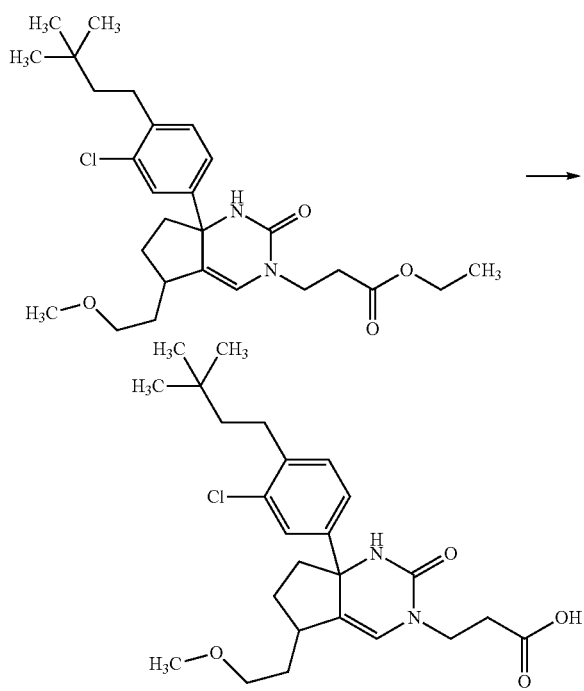

This step was performed according to Example 3 Step 10.

Example 34

(Step 1)

2,2,3-Trimethylpent-4-en-1-ol

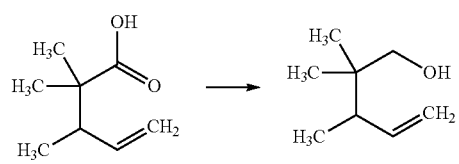

Lithium aluminum hydride (4.0 g) and tetrahydrofuran (210 mL) were mixed under argon gas, and thereto was added a mixed solution of 2,2,3-trimethylpent-4-enoic acid (5.0 g) in tetrahydrofuran (70 mL) under ice cooling. The mixture was stirred under ice cooling for 20 minutes, and then the reaction solution was stirred with being heated to reflux for 2 hours 30 minutes. Then, thereto were added dropwise sequentially water (4 mL), 2N sodium hydroxide (4 mL), and water (12 mL) under ice cooling. The reaction solution was stirred at room temperature for 1 hour. To the reaction solution were added Celite (4 g) and magnesium sulfate (4 g), and Celite was removed with a filter, and then the filtrate was concentrated under reduced pressure to give the title compound (4.2 g).

$^1$H-NMR (400 MHz, CDCl$_3$) 0.84 (s, 3H), 0.87 (s, 3H), 0.97 (d, J=6.94 Hz, 3H), 1.37 (br s, 1H), 2.13-2.21 (m, 1H), 3.37 (s, 2H), 4.97-5.05 (m, 2H), 3.82 (ddd, J=18.15, 9.25, 7.86 Hz, 1H)

(Step 2)

2,2,3-Trimethyl-pent-4-en-1-ol methanesulfonic acid ester

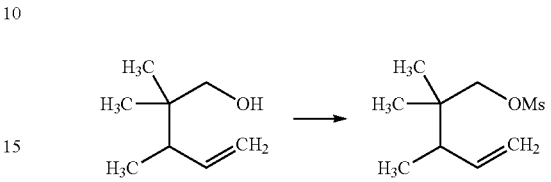

2,2,3-Trimethylpent-4-en-1-ol (4.2 g) and triethylamine (7.2 mL) were mixed in chloroform (50 mL) under argon gas, and thereto was added dropwise a mixed solution of methanesulfonyl chloride (3.8 mL) in chloroform (15 mL) under ice cooling. The reaction solution was stirred under ice cooling for 5 minutes, and then warmed to room temperature. The reaction solution was stirred at room temperature for 3 hours, and then thereto was added water (13 mL). The solution was stirred at room temperature, and then thereto was added ethyl acetate (20 mL). The solution was separated. The aqueous layer was extracted with ethyl acetate (20 mL) once. The organic layer was washed with 1N hydrochloric acid (12 mL), saturated sodium hydrogen carbonate (12 mL), and saturated aqueous sodium chloride solution (12 mL) and dried over magnesium sulfate. Magnesium sulfate was removed with a filter, and then the filtrate was concentrated under reduced pressure to give the title compound (7.1 g).

$^1$H-NMR (400 MHz, CDCl$_3$) 0.92 (s, 3H), 0.96 (s, 3H), 0.99 (d, J=6.88 Hz, 3H), 2.16-2.24 (m, 1H), 3.00 (s, 3H), 3.94 (s, 2H), 5.01-5.08 (m, 2H), 5.67-5.78 (m, 1H)

(Step 3)

5-Iodo-3,4,4-trimethylpent-1-ene

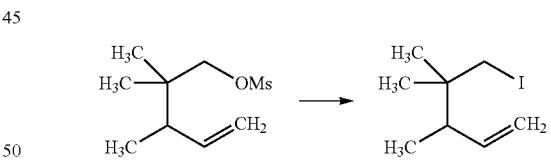

2,2,3-Trimethyl-pent-4-en-1-ol methanesulfonic acid ester (7.1 g) and N-methylpyridone (65 mL) were mixed under nitrogen gas, and thereto was added sodium iodide (24 g) at room temperature. The reaction solution was heated at 140° C. for 4 hours 20 minutes. Then, thereto was added 20 w/w % aqueous sodium thiosulfate solution (31 mL) at room temperature, and the mixture was stirred for 1 hour. The reaction solution was extracted with ethyl acetate/n-hexane=1/2 (50 mL) twice. The organic layer was washed with water (21 mL) twice, 20 w/w % aqueous sodium thiosulfate solution (21 mL), and saturated aqueous sodium chloride solution (21 mL) and dried over magnesium sulfate. Magnesium sulfate was removed with a filter, and then the filtrate was concentrated under reduced pressure to give the title compound (5.4 g).

¹H-NMR (400 MHz, CDCl₃) 0.95-0.99 (m, 9H), 2.20-2.28 (m, 1H), 3.16-3.24 (m, 2H), 5.00-5.11 (m, 2H), 5.70 (ddd, J=18.03, 9.25, 7.86 Hz, 1H)

(Step 4)

3,3,4-Trimethylhex-5-enenitrile

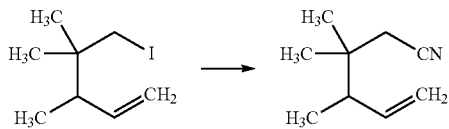

5-Iodo-3,4,1-trimethylpent-1-ene (3.8 g) and dimethyl sulfoxide (42 mL) were mixed under argon gas, and thereto was added tetraethylammonium cyanide (6.8 g) at room temperature. The reaction solution was stirred under heating at 80° C. for 7 hours. To the reaction solution was added water (21 mL) at room temperature, and the aqueous layer was extracted with a mixed solvent of ethyl acetate/n-hexane=1/2 (21 mL, twice). The organic layer was washed with water (12 mL, three times) and saturated aqueous sodium chloride solution (12 mL) and dried over magnesium sulfate. Magnesium sulfate was removed with a filter, and then the filtrate was concentrated under reduced pressure. The resulting residue was combined with a crude product (0.5 g) synthesized separately according to Example 34 Step 4 and purified by silica gel column chromatography (Biotage flash purification systems, eluent: ethyl acetate/n-hexane, 5/95 to 30/70) and then azeotroped with n-hexane to give the compound (2.0 g).

¹H-NMR (400 MHz, CDCl₃) 0.97-1.02 (m, 6H), 1.06 (s, 3H), 2.13-2.22 (m, 1H), 2.24 (s, 2H), 5.04-5.12 (m, 2H), 5.69 (ddd, J=18.15, 9.13, 7.98 Hz, 1H)

(Step 5)

3,3,4-Trimethylhex-5-enal

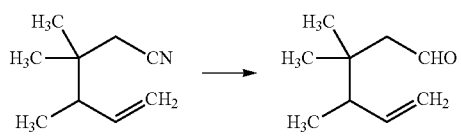

3,3,4-Trimethylhex-5-enenitrile (2.0 g) and dichloromethane (150 mL) were mixed under argon gas, and thereto was added dropwise 1.02M diisobutylaluminum hydride/n-hexane solution (22 mL) under cooling at −78° C. The reaction solution was stirred under cooling at −78° C. for 15 minutes. The reaction solution was gradually warmed to 0° C. and stirred under ice cooling for 2 hours. Then, thereto was added dropwise a saturated aqueous solution of Rochelle salt (150 mL) under ice cooling. The reaction solution was stirred at room temperature for 2 hours. The aqueous layer was extracted with ethyl acetate/n-hexane=1/2 (20 mL, twice). The organic layer was washed with saturated aqueous sodium chloride solution (6 mL) and dried over magnesium sulfate. Magnesium sulfate was removed with a filter, and then the filtrate was concentrated under reduced pressure to give the title compound (1.8 g).

¹H-NMR (400 MHz, CDCl₃) 0.99 (d, J=5.78 Hz, 3H), 1.03 (s, 3H), 1.05 (s, 3H), 2.06-2.15 (m, 1H), 2.27-2.30 (m, 2H), 4.98-5.05 (m, 2H), 5.74 (ddd, J=18.09, 9.19, 7.69 Hz, 1H), 9.86 (t, J=3.12 Hz, 1H)

(Step 6)

3,3,4-Trimethylhex-5-enal oxime

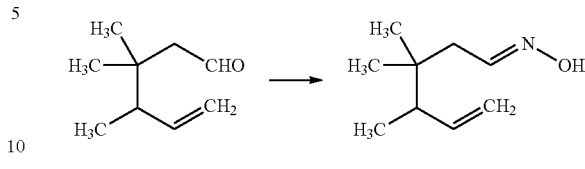

3,3,4-Trimethylhex-5-enal (1.8 g) was mixed in ethanol (30 mL) and water (15 mL) under argon gas, and thereto were added sodium acetate (7.4 g) and hydroxylamine hydrochloride (3.1 g) at room temperature. The reaction solution was stirred under heating at 60° C. for 1 day. The reaction solution was concentrated under reduced pressure, and thereto were added ethyl acetate and water. The solution was separated. The aqueous layer was extracted with ethyl acetate. The organic layer was washed with saturated aqueous sodium chloride solution (twice) and dried over sodium sulfate. Sodium sulfate was removed with a filter, and then the filtrate was concentrated under reduced pressure. The resulting residue was mixed with ethyl acetate, and the resulting solid was filtered with Celite. Then, the filtrate was concentrated under reduced pressure. The resulting residue was purified by silica gel column chromatography (Biotage flash purification systems, eluent: ethyl acetate/n-hexane, 5/95 to 20/80) to give the title compound (1.7 g).

¹H-NMR (400 MHz, CDCl₃) 0.90 (s, 1.5H), 0.91 (s, 1.5H), 0.93 (s, 1.5H), 0.94 (s, 1.5H), 0.97 (d, J=4.39 Hz, 1.5H), 0.99 (d, J=4.39 Hz, 1.5H), 1.98-2.09 (m, 1H), 2.12 (dd, J=6.82, 2.89 Hz, 1H), 2.29 (dd, J=15.67, 5.55 Hz, 0.5H), 2.38 (dd, J=15.67, 5.90 Hz, 0.5H), 4.96-5.03 (m, 2H), 5.72-5.82 (m, 1H), 6.83 (t, J=5.90 Hz, 0.5H), 6.91 (br s, 1H), 7.48 (t, J=6.82 Hz, 0.5H)

(Step 7)

4,5,5-Trimethyl-3a,4,5,6-tetrahydro-3H-cyclopenta[c]isoxazole

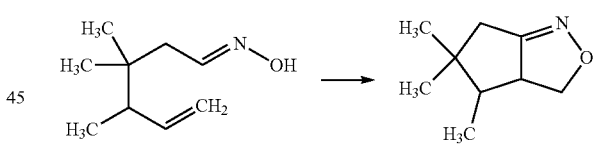

Heptan-6-al oxime (1.7 g) and methanol (34 mL) were mixed under nitrogen gas, and thereto was added trifluoroacetic acid (0.25 mL) under sodium chloride-ice cooling, followed by addition of (diacetoxyiodo)benzene (5.1 g) over 40 minutes. The reaction solution was stirred under ice cooling for 20 minutes and at room temperature for 35 minutes. Then, thereto were added saturated aqueous sodium hydrogen carbonate solution (17 mL) and sodium sulfite (0.75 g) under ice cooling, and the mixture was stirred at room temperature for 30 minutes. The reaction solution was concentrated under reduced pressure. The aqueous layer was extracted with ethyl acetate (10 mL, twice). The organic layer was washed with saturated aqueous sodium chloride solution (5 mL, twice) and dried over sodium sulfate. Sodium sulfate was removed with a filter, and then the filtrate was concentrated under reduced pressure. The resulting residue was purified by silica gel column chromatography (Biotage flash purification systems, eluent: ethyl acetate/n-hexane=5/95 to 30/70), followed by further purification by silica gel column chromatography (Biotage flash purification systems, eluent: acetone/n-hexane=5/95 to 20/80), and then azeotroped with n-hexane to give the title compound (0.87 g).
¹H-NMR (400 MHz, CDCl₃) 0.96 (d, J=6.94 Hz, 3H), 1.02 (s, 3H), 1.12 (s, 3H), 1.35-1.64 (m, 1H), 2.35-2.37 (m, 2H), 3.51-3.62 (m, 1H), 3.78 (dd, J=12.02, 7.86 Hz, 1H), 4.48 (dd, J=9.48, 7.86 Hz, 1H)
(Step 8)

6a-(3-Chloro-4-(3,3-dimethylbutyl)phenyl)-4,5,5-trimethylhexahydro-1H-cyclopenta[c]isoxazole

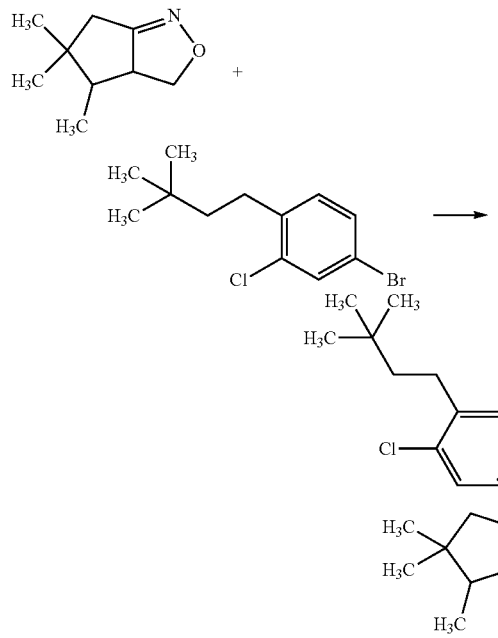

This step was performed according to Example 3 Step 6.
¹H-NMR (400 MHz, CDCl₃) 0.57-0.69 (m, 3H), 0.94-1.01 (m, 15H), 1.42-1.49 (m, 2H), 1.59-1.68 (m, 1H), 1.93-1.99 (m, 1H), 2.33-2.41 (m, 1H), 2.64-2.68 (m, 2H), 2.85-2.91 (m, 1H), 3.73-3.79 (m, 1H), 4.00-4.04 (m, 1H), 7.18 (d, J=8.09 Hz, 1H), 7.26-7.30 (m, 1H), 7.42-7.44 (m, 1H)
(Step 9)

(2-Amino-2-(3-chloro-4-(3,3-dimethylbutyl)phenyl)-4,4,5-trimethylcyclopentyl)methanol

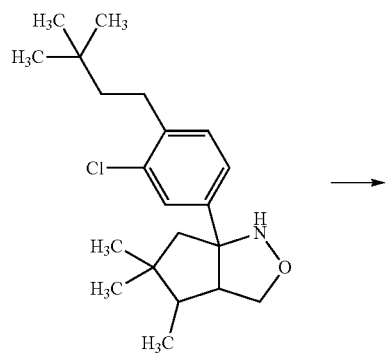

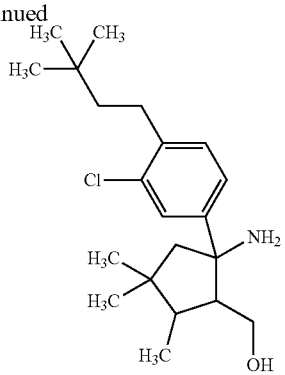

This step was performed according to Example 3 Step 7.
¹H-NMR (400 MHz, CDCl₃) 0.85 (s, 3H), 0.94 (d, J=6.70 Hz, 3H), 0.97 (s, 9H), 1.14 (s, 3H), 1.42-1.48 (m, 2H), 1.52-1.57 (m, 1H), 1.79-1.85 (m, 1H), 2.07-2.16 (m, 1H), 2.30 (d, J=14.10 Hz, 1H), 2.63-2.69 (m, 2H), 3.23 (s, 3H), 3.66 (dd, J=12.02, 4.62 Hz, 1H), 3.77-3.83 (m, 2H), 7.17 (d, J=7.86 Hz, 1H), 7.25-7.28 (m, 1H), 7.42 (d, J=2.08 Hz, 1H)
(Step 10)

Methyl 3-(3-{1-[3-chloro-4-(3,3-dimethyl-butyl)phenyl]-2-(hydroxymethyl)-3,4,4-trimethylcyclopentyl}ureido)bicyclo[1.1.1]pentane-1-carboxylate

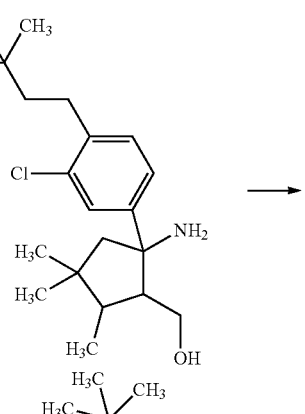

This step was performed according to Example 54 Step 8.
¹H-NMR (400 MHz, CDCl₃) 0.85 (s, 3H), 0.92 (d, J=6.70 Hz, 3H), 0.97 (s, 10H), 0.99 (s, 3H), 1.14 (s, 3H), 1.41-1.46 (m, 3H), 1.57-1.63 (m, 1H), 2.13-2.18 (m, 1H), 2.22-2.26

(m, 1H), 2.33 (s, 6H), 2.57-2.65 (m, 3H), 3.66-3.69 (m, 5H), 4.63-4.67 (m, 1H), 6.67-6.70 (m, 1H), 7.10-7.18 (m, 2H)
(Step 11)

Methyl 3-{(S)-7a-[3-chloro-4-(3,3-dimethyl-butyl)phenyl]-5,6,6-trimethyl-2-oxo-1,2,5,6,7,7a-hexahydro-3H-cyclopenta[d]pyrimidin-3-yl}bicyclo[1.1.1]pentane-1-carboxylate

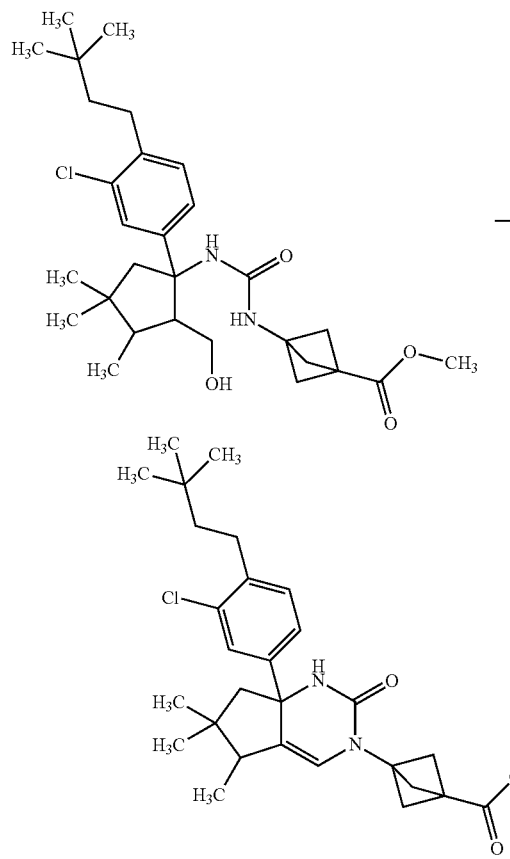

This step was performed according to Example 54 Step 9.

Purification was performed with a chiral preparative column. Purification conditions for the preparative column are shown as follows.
- Preparative apparatus: Recycling Preparative Liquid Chromatograph LC-92XX NEXT SERIES, Japan Analytical Industry Co., Ltd.
- Column: Daicel CHIRALPAK IA 2.0 cmφ×25 cmL
- Mobile phase: n-hexane/2-propanol=92/8
- Flow rate: 10.0 mL/min
- Detection: UV (254 nm)

Measurement with a chiral column showed 6.0 minutes of the retention time for the resulting title compound (8.5 minutes of the retention time for the enantiomer of the title compound) with >99% ee purity. Analytical conditions for the chiral column are shown as follows.
- Measurement apparatus: HPLC system, Shimadzu Corporation, High-Performance Liquid Chromatograph Prominence
- Column: Daicel CHIRALPAK IA-3 0.46 cmφ×15 cmL
- Column temperature: 30° C.
- Mobile phase: n-hexane/2-propanol=90/10
- Flow rate: 1.0 mL/min
- Detection: UV (254 nm)

$^1$H-NMR (400 MHz, CDCl$_3$) 0.76 (s, 3H), 0.90 (d, J=7.34 Hz, 3H), 0.97 (s, 9H), 1.13 (s, 3H), 1.41-2.47 (m, 2H), 2.01 (d, J=13.33 Hz, 1H), 2.30 (d, J=13.33 Hz, 1H), 2.37-2.46 (m, 7H), 2.60-2.67 (m, 2H), 3.69 (s, 3H), 4.91 (s, 1H), 6.23 (d, J=0.73 Hz, 1H), 7.05 (dd, J=7.83, 1.96 Hz, 1H), 7.14 (d, J=7.83 Hz, 1H), 7.20 (d, J=1.96 Hz, 1H)
(Step 12)

3-{(S)-7a-[3-Chloro-4-(3,3-dimethyl-butyl)phenyl]-5,6,6-trimethyl-2-oxo-1,2,5,6,7,7a-hexahydro-3H-cyclopenta[d]pyrimidin-3-yl}bicyclo[1.1.1]pentane-1-carboxylic acid

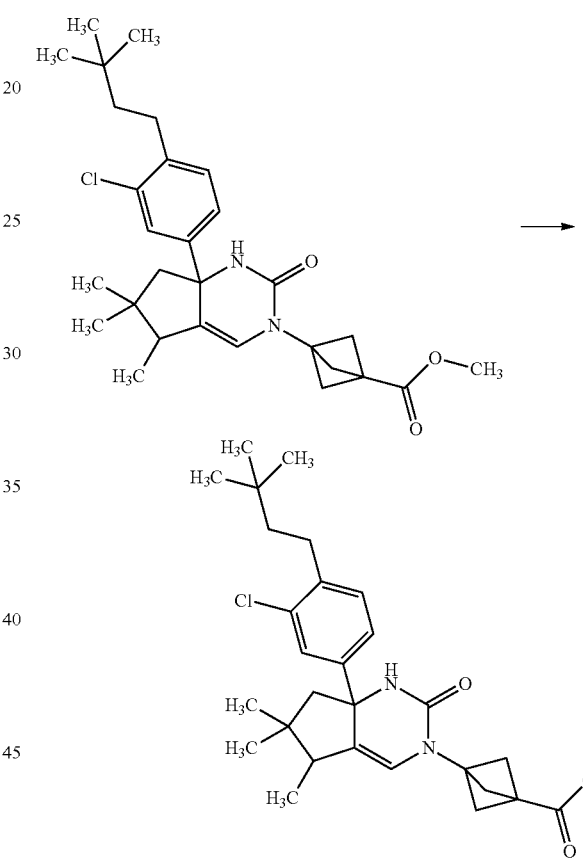

This step was performed according to Example 54 Step 10.

Example 54

(Step 1)

Hept-6-enal

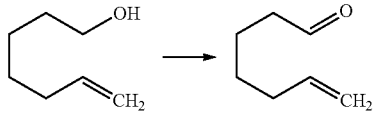

Hept-6-en-1-ol (150 g) and (diacetoxyiodo)benzene (508 g) were mixed in chloroform (1500 mL) under nitrogen gas, and thereto was added a mixed solution of 2,2,6,6-tetramethylpiperidin-1-oxyl radical (20.5 g) in chloroform (20.0 mL) at room temperature. The reaction solution was stirred at room temperature for 3 days. Then, thereto was added an aqueous solution (1500 mL) of sodium carbonate (278 g) and sodium thiosulfate (208 g) under water cooling, and the mixture was stirred at room temperature for 1 hour, and then separated. The aqueous layer was extracted with chloroform (1000 mL). Combined organic layers were washed with saturated aqueous sodium chloride solution and dried over sodium sulfate. Sodium sulfate was removed with a filter, and then the filtrate was concentrated under reduced pressure. The resulting residue was distilled under reduced pressure (85° C., 70 mmHg) to give a crude product of the title compound (21.4 g, 46.4 w % of iodobenzene inclusive).

$^1$H-NMR (400 MHz, CDCl$_3$) 1.40-1.47 (m, 2H), 1.62-1.69 (m, 2H), 2.03-2.11 (m, 2H), 2.44 (td, J=7.40, 1.62 Hz, 2H), 4.95-5.04 (m, 2H), 5.74-5.84 (m, 1H), 9.77 (t, J=1.62 Hz, 1H)

(Step 2)

Hept-6-enal oxime

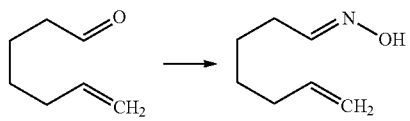

Hept-6-enal (214 g, 46.4 w % of iodobenzene inclusive) was mixed in water (1149 mL) and ethanol (2298 mL) under nitrogen gas, and then thereto were added sodium acetate (151 g) and hydroxylamine hydrochloride (107 g) at room temperature. The reaction solution was stirred at room temperature for 2 days. The reaction solution was concentrated under reduced pressure, and thereto were added ethyl acetate and water. The solution was separated. The aqueous layer was extracted with ethyl acetate (twice). The organic layer was washed with saturated aqueous sodium chloride solution and concentrated under reduced pressure. The resulting residue was mixed with ethyl acetate, and the resulting solid was filtered with Celite. The filtrate was concentrated under reduced pressure to give a crude product of the title compound (203 g, 24.5 w % of ethyl acetate, 2.5 w % of ethanol, and 9.2 w % of iodobenzene inclusive) (geometric isomer mixture).

$^1$H-NMR (400 MHz, CDCl$_3$) 1.40-1.56 (m, 4H), 2.05-2.10 (m, 2H), 2.18-2.24 (m, 1H), 2.38-2.43 (m, 1H), 4.94-5.04 (m, 2H), 5.74-5.85 (m, 1H), 6.72 (t, J=5.32 Hz, 0.55H), 7.43 (t, J=6.01 Hz, 0.45H)

(Step 3)

3,3a,4,5,6,7-Hexahydro-benzo[c]isoxazole

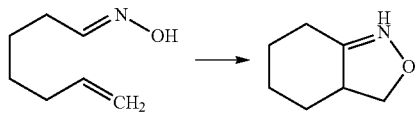

Hept-6-enal oxime (203 g, 24.5 w % of ethyl acetate, 2.5 w % of ethanol, and 9.2 w % of iodobenzene inclusive) and methanol (2333 mL) were mixed under nitrogen gas, and thereto was added trifluoroacetic acid (17.5 mL) under salt-ice cooling, followed by addition of (diacetoxyiodo)benzene (384 g) over 1 hour. The reaction solution was stirred at room temperature for 3 hours. Then, thereto was added an aqueous solution (1000 mL) of sodium carbonate (194 g) and sodium sulfite (57.8 g) under ice cooling, and the solution was stirred at room temperature for 1 hour. The reaction solution was concentrated under reduced pressure, and thereto was added water (2500 mL). The aqueous layer was extracted with ethyl acetate (1200 mL, twice). The organic layer was washed with saturated aqueous sodium chloride solution (twice) and concentrated under reduced pressure. The resulting residue was combined with a crude product (45.0 g) synthesized separately according to Example 54 Steps 1 to 2 and purified by silica gel column chromatography (Yamazen Corporation, automated refining apparatus, eluent: ethyl acetate/n-hexane, Rf=0.25 (ethyl acetate/n-hexane=1/4)), and then azeotroped with n-hexane to give the title compound (92.2 g, 2.5 w % of n-hexane inclusive).

$^1$H-NMR (400 MHz, CDCl$_3$) 1.24-1.45 (m, 3H), 1.84-1.90 (m, 1H), 1.96-2.20 (m, 3H), 2.77-2.82 (m, 1H), 3.10-3.20 (m, 1H), 3.77 (dd, J=9.48, 7.86 Hz, 1H), 4.49 (dd, J=9.48, 7.86 Hz, 1H)

(Step 4)

7a-[3-Chloro-4-(3,3-dimethyl-butyl)phenyl]octahydro-benzo[c]isoxazole

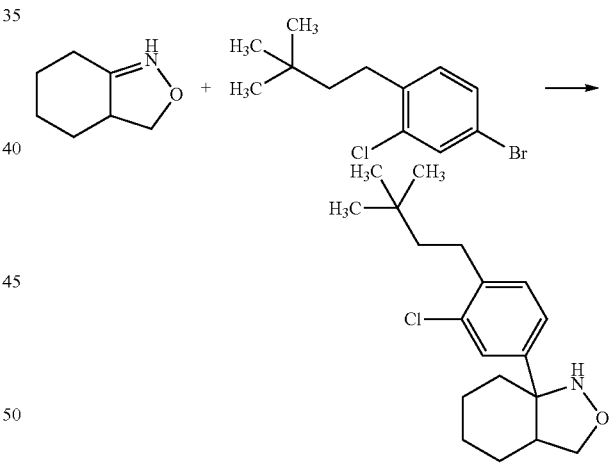

4-Bromo-2-chloro-1-(3,3-dimethyl-butyl)benzene (119 g) and tetrahydrofuran (210 mL) were mixed under argon gas, and thereto was added 2.69M n-butyllithium/n-hexane solution (100 mL) under cooling at −78° C. The reaction solution was stirred under cooling at −78° C. for 2.5 hours (Reaction solution A). 3,3a,4,5,6,7-Hexahydro-benzo[c]isoxazole (33.4 g) was mixed in toluene (900 mL) and tetrahydrofuran (180 mL), and thereto were added boron trifluoride-diethyl ether complex (37.7 mL) and Reaction solution A under cooling at −78° C. The reaction solution was stirred for 2 hours, and then thereto was added 2N aqueous sodium hydroxide solution (240 mL) under cooing at −78° C. The mixture was stirred at room temperature, and then thereto were added toluene (300 mL) and water (240 mL). The mixture was separated. The organic layer was washed with 13 w/w % aqueous sodium chloride solution (400 mL) and saturated. aqueous sodium chloride solution and dried over sodium sulfate. Sodium sulfate was removed with a filter, and then the filtrate was concentrated under reduced pressure to give a crude product of the title compound (107 g).

¹H-MMR (400 MHz, CDCl₃) 0.98 (s, 9H), 1.43-1.86 (m, 7H), 1.86-1.98 (m, 3H), 2.64-2.77 (m, 3H), 3.37-4.20 (brm, 2H), 5.82 (brs, 1H), 7.18 (d, J=7.83 Hz, 1H), 7.37 (d, J=6.60 Hz, 1H), 7.52 (s, 1H)

(Step 5)

{2-Amine-2-[3-chloro-4-(3,3-dimethyl-butyl)phenyl]cyclohexyl}methanol

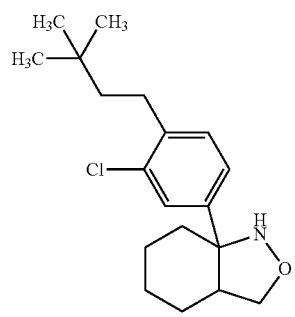

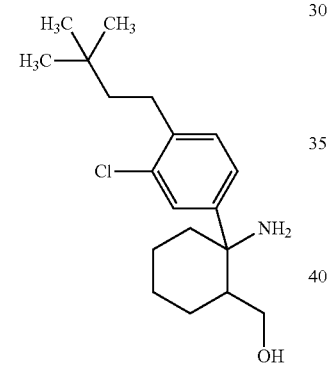

7a-[3-Chloro-4-(3,3-dimethyl-butyl)phenyl]octahydro-benzo[c]isoxazole (107 g) was mixed in acetic acid (600 mL), tetrahydrofuran (180 mL), and water (180 mL) under nitrogen gas, and thereto was added zinc powder (24.4 g) in 5 parts under heating at 80° C. The reaction solution was stirred under heating at 80° C. for 30 minutes. The reaction solution was filtered with Celite at room temperature, and then the filtrate was concentrated under reduced pressure. The resulting residue was mixed in ethyl acetate (1000 mL) and 28 w/w % ammonia water (140 mL), and the mixture was separated. The organic layer was washed with 20 w/w % aqueous sodium carbonate solution (200 mL) and saturated aqueous sodium chloride solution and dried over sodium sulfate. Sodium sulfate was removed with a filter, and then the filtrate was concentrated under reduced pressure to give a crude product of the title compound (99.6 g).

¹H-NMR (400 MHz, CDCl₃) 0.98 (s, 9H), 1.39-1.50 (m, 4H), 1.53-1.66 (m, 2H), 1.70-1.93 (m, 4H), 2.02 (td, J=13.20, 2.93 Hz, 1H), 2.65-2.69 (m, 2H), 3.26 (dd, J=11.25, 2.93 Hz, 1H), 3.44 (dd, J=11.25, 2.93 Hz, 1H), 7.19 (d, J=8.07 Hz, 1H), 7.33 (dd, J=8.07, 1.96 Hz, 1H), 7.48 (d, J=1.96 Hz, 1H)

(Step 6)

{(R)-2-Amino-2-[3-chloro-4-(3,3-dimethyl-butyl)phenyl]cyclohexyl}methanol (2S,3S)-2,3-bis-benzoyloxy-succinate

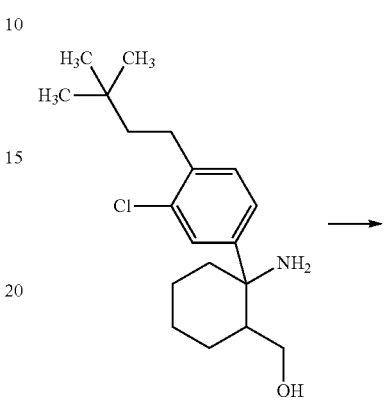

{2-Amino-2-[3-chloro-4-(3,3-dimethyl-butyl)phenyl]cyclohexyl}methanol (99.6 g) and tetrahydrofuran (245 mL) were mixed under nitrogen gas, and thereto was added a mixed solution of (2S,3S)-2,3-bis-benzoyloxy-succinic acid (94.0 g) in tetrahydrofuran (345 mL) under heating at 85° C. The reaction solution was stirred under heating at 85° C. for 5.5 hours. The solution was stirred for 13.5 hours with being slowly cooled to room temperature, and then the precipitated solid was collected by filtration to give the title compound (62.2 g).

¹H-NMR (400 MHz, DMSO-D₆) 0.96 (s, 9H), 1.38-1.65 (m, 4H), 1.78-1.70 (m, 2H), 1.86-1.94 (m, 1H), 1.99-2.06 (m, 1H), 2.62-2.67 (m, 2H), 3.09 (dd, J=10.76, 5.62 Hz, 1H), 3.19 (dd, J=10.76, 2.45 Hz, 1H), 5.64 (s, 2H), 7.36-7.42 (m, 2H), 7.45-7.49 (m, 4H), 7.58-7.63 (m, 3H), 7.89-7.91 (m, 4H)

(Step 7)

{(R)-2-Amino-2-[3-chloro-4-(3,3-dimethyl-butyl)phenyl]cyclohexyl}methanol

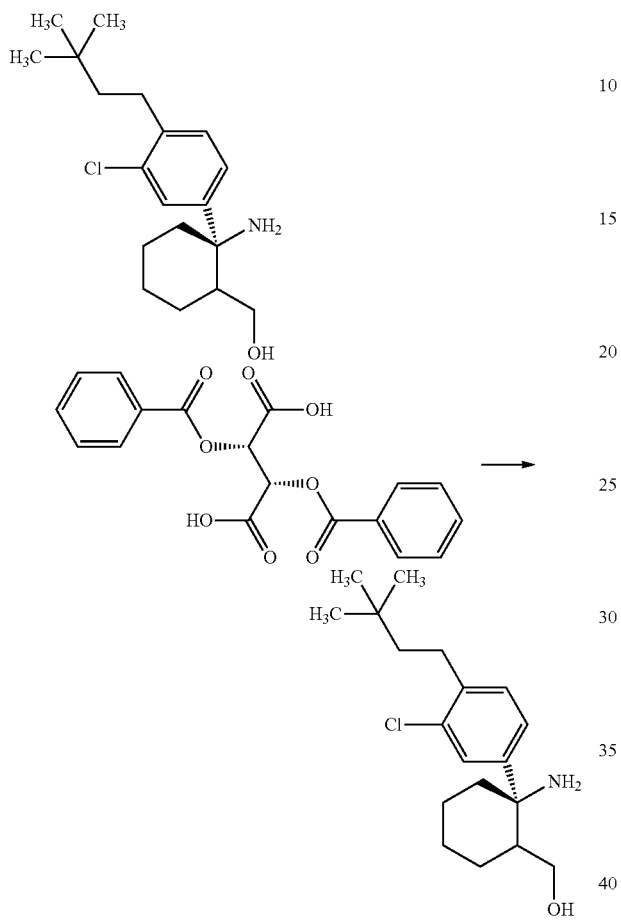

{(R)-2-Amino-2-[3-chloro-4-(3,3-dimethyl-butyl)phenyl]cyclohexyl}methanol (2S,3S)-2,3-bis-benzoyloxy-succinate (62.2 g) and tetrahydrofuran (290 mL) were mixed under nitrogen gas. The reaction solution was stirred under heating at 85° C. for 6 hours. The solution was stirred for 13.5 hours with being slowly cooled to room temperature, and then the precipitated solid was collected by filtration to give {2-amino-2-[3-chloro-4-(3,3-dimethyl-butyl)phenyl]cyclohexyl}methanol (2S,3S)-2,3-bis-benzoyloxy-succinate (59.5 g). The resulting {2-amine-2-[3-chloro-4-(3,3-dimethyl-butyl)phenyl]cyclohexyl}methanol (2S,3S)-2,3-bis-benzoyloxy-succinate was mixed in ethyl acetate (600 mL) and methanol (60 mL), and thereto was added 1N aqueous sodium hydroxide solution (150 mL) under ice cooling. The mixture was separated at room temperature. The organic layer was washed with 20 w/w % aqueous sodium carbonate solution (135 mL for the first round and 50 mL for the second round), 13 w/w % aqueous sodium chloride solution (130 mL), and saturated aqueous sodium chloride solution and dried over sodium sulfate. Sodium sulfate was removed with a filter, and then the filtrate was concentrated under reduced pressure to give the title compound (25.5 g).

$^1$H-NMR (400 MHz, CDCl$_3$) 0.98 (s, 9H), 1.39-1.50 (m, 4H), 1.53-1.66 (m, 2H), 1.70-1.93 (m, 4H), 2.02 (td, J=13.20, 2.93 Hz, 1H), 2.65-2.69 (m, 2H), 3.26 (dd, J=11.25, 2.93 Hz, 1H), 3.44 (dd, J=11.25, 2.93 Hz, 1H), 7.19 (d, J=8.07 Hz, 1H), 7.33 (dd, J=8.07, 1.96 Hz, 1H), 7.48 (d, J=1.96 Hz, 1H)

(Step 8)

Methyl 3-(3-{(R)-1-[3-chloro-4-(3,3-dimethyl-butyl)phenyl]-2-hydroxymethyl-cyclohexyl}ureido)bicyclo[1.1.1]pentane-1-carboxylate

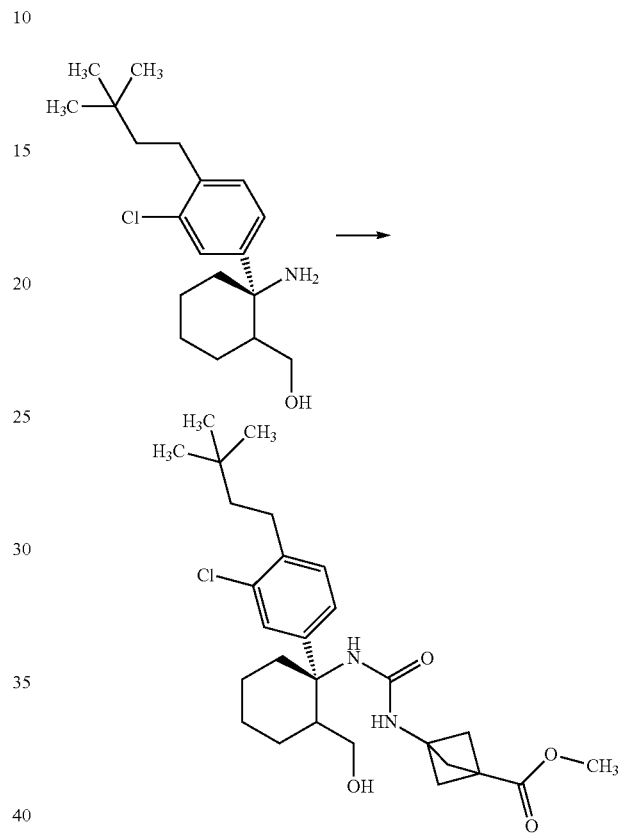

3-(Methoxycarbonyl)bicyclo[1.1.1]pentane-1-carboxylic acid (14.7 g) and toluene (135 mL) were mixed under nitrogen gas, and thereto were added diphenylphosphoryl azide (20.3 mL) and triethylamine (13.1 mL) at room temperature. The reaction solution was stirred under heating at 100° C. for 1 hour. The reaction solution was added dropwise to a mixed solution of {(R)-2-amino-2-[3-chloro-4-(3,3-dimethyl-butyl)phenyl]cyclohexyl}methanol (25.5 g) in tetrahydrofuran (135 mL) over 35 minutes under ice cooling. The reaction solution was stirred at room temperature for 26 hours, and then the precipitated solid was collected by filtration to give the title compound (21.3 g). To the filtrate were added ethyl acetate (400 mL) and saturated aqueous sodium hydrogen carbonate solution (150 mL), and the mixture was separated. The organic layer was washed with saturated aqueous sodium hydrogen carbonate solution (150 mL), water (100 mL), and saturated aqueous sodium chloride solution and dried over sodium sulfate. Sodium sulfate was removed with a filter, and then the filtrate was concentrated under reduced pressure. The resulting residue was mixed with ethyl acetate (50 mL) and stirred under heating at 70° C. for 1.5 hours. The reaction solution was stirred at room temperature for 2 hours, and then the precipitated solid was collected by filtration to give the title compound (13.9 g).

Measurement with a chiral column showed 9.4 minutes of the retention time for the resulting title compound (12.3 minutes of the retention time for the enantiomer of the title compound) with >99% ee purity. Conditions for the chiral column are shown as follows.

Measurement apparatus: HPLC system, Shimadzu Corporation, High-Performance Liquid Chromatograph Prominence
Column: Daicel CHIRALPAK OZ-3R 0.46 cmφ×15 cmL
Column temperature: 40° C.
Mobile phase: 0.1 v/v % aqueous formic acid solution/0.1 v/v % formic acid-acetonitrile solution=45/55
Flow rate: 1.0 mL/min
Detection: UV (254 nm)

$^1$H-NMR (400 MHz, CDCl$_3$) 0.97 (s, 9H), 1.42-1.43 (m, 3H), 1.70-1.52 (m, 4H), 1.72-1.79 (m, 1H), 1.88-1.98 (m, 2H), 2.37 (s, 6H), 2.61-2.66 (m, 2H), 2.98-3.04 (m, 1H), 3.37-3.41 (m, 1H), 3.45-3.49 (m, 1H), 3.69 (s, 3H), 4.71 (s, 1H), 6.27 (s, 1H), 7.15-7.18 (m, 1H), 7.26-7.27 (m, 2H)

(Step 9)

Methyl 3-{(S)-8a-[3-chloro-4-(3,3-dimethyl-butyl)phenyl]-2-oxo-1,5,6,7,8,8a-hexahydro-2H-quinazolin-3-yl}bicyclo[1.1.1]pentane-1-carboxylate

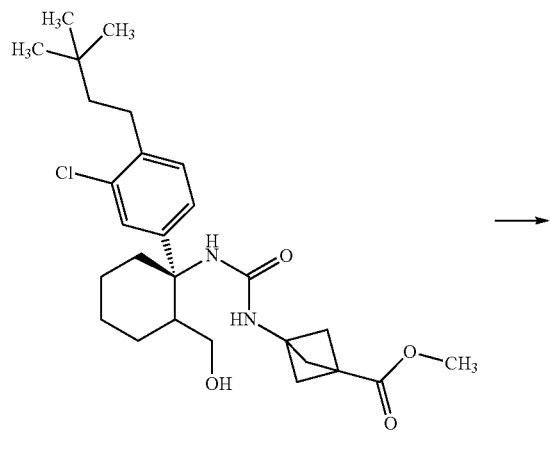

Methyl 3-(3-{(R)-1-[3-chloro-4-(3,3-dimethyl-butyl)phenyl]-2-hydroxymethyl-cyclohexyl}ureido)bicyclo[1.1.1]pentane-1-carboxylate (16.7 g) and chloroform (495 mL) were mixed under nitrogen gas, and thereto were added at room temperature (diacetoxyiodo)benzene (11.9 g) and 2,2,6,6-tetramethylpiperidin-1-oxyl radical (0.527 g). The reaction solution was stirred at room temperature for 21.5 hours, and then thereto was added 2,2,6,6-tetramethylpiperidin-1-oxyl radical (0.527 g) at room temperature. The mixture was stirred at room temperature for 4 hours, and then thereto were added (diacetoxyiodo)benzene (1.20 g) and 2,2,6,6-tetramethylpiperidin-1-oxyl radical (0.527 g) at room temperature. The mixture was stirred at room temperature for 17 hours, and then thereto were added 20 w/w % aqueous sodium sulfite solution (200 mL) and 20 w/w % aqueous sodium carbonate solution (30 mL) at room temperature. The mixture was separated. The organic layer was dried over sodium sulfate. Sodium sulfate was removed with a filter, and then the filtrated was concentrated under reduced pressure. The resulting residue was mixed with toluene (300 mL), and thereto was added pentafluoroaniline trifluoromethanesulfonate (0.561 g) at room temperature. The reaction solution was stirred for 2 hours with being heated to 100° C., and then thereto was added trifluoroacetic acid (10 mL) at room temperature. The reaction solution was stirred at room temperature for 15 hours, and then concentrated under reduced pressure. The resulting residue was combined with a crude product (48.2 g) synthesized separately according to Example 54 Steps 1 to 8 and purified by silica gel column chromatography (ethyl acetate/n-hexane=1/4→1/2→1/1) to give the title compound (35.3 g).

$^1$H-NMR (400 MHz, CDCl$_3$) 0.98 (s, 9H), 1.26-1.42 (m, 2H), 1.43-1.47 (m, 2H), 1.68-1.73 (m, 2H), 1.88-1.97 (m, 2H), 2.13-2.17 (m, 1H), 2.44 (s, 6H), 2.48-2.53 (m, 1H), 2.64-2.69 (m, 2H), 3.70 (s, 3H), 4.54 (s, 1H), 5.96 (d, J=1.47 Hz, 1H), 7.15 (dd, J=8.07, 1.96 Hz, 1H), 7.21 (d, J=8.07 Hz, 1H), 7.28 (d, J=1.96 Hz, 1H)

(Step 10)

3-{(S)-8a-[3-Chloro-4-(3,3-dimethyl-butyl)phenyl]-2-oxo-1,5,6,7,8,8a-hexahydro-2H-quinazolin-3-yl}bicyclo[1.1.1]pentane-1-carboxylic acid

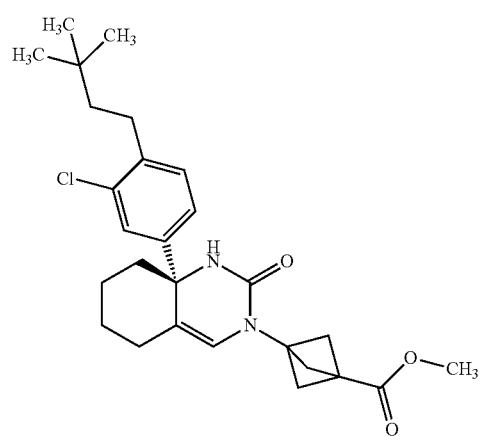

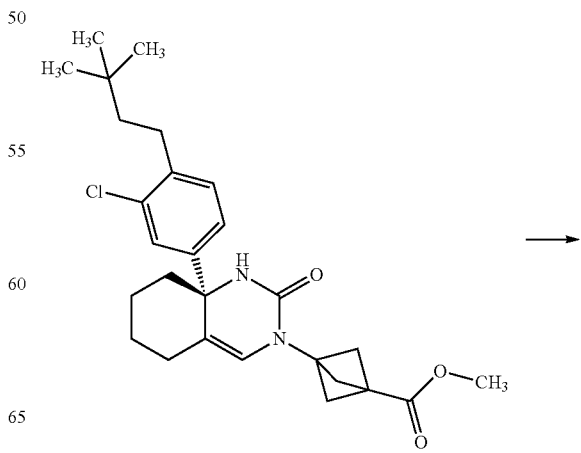

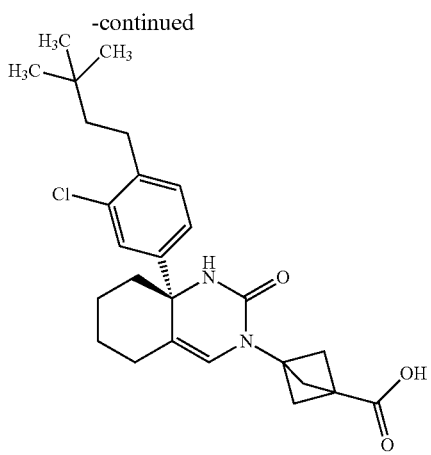

Methyl 3-{(S)-8a-[3-chloro-4-(3,3-dimethyl-butyl)phenyl]-2-oxo-1,5,6,7,8,8a-hexahydro-2H-quinazolin-3-yl}bicyclo[1.1.1]pentane-1-carboxylate (35.3 g) was mixed in tetrahydrofuran (150 mL) and methanol (600 mL) under nitrogen gas, and thereto was added 2N aqueous sodium hydroxide solution (72 mL) under ice cooling. The reaction solution was stirred at room temperature for 17.5 hours, and then thereto was added water (300 mL). The reaction solution was concentrated under reduced pressure. To the resulting residue was added 2N hydrochloric acid (90 mL) under ice cooling, and the mixture was extracted with ethyl acetate/methanol=100/1 (1010 mL). The organic layer was washed with 1.3 w/w % aqueous sodium chloride solution (200 mL, twice) and saturated aqueous sodium chloride solution (twice) and dried over sodium sulfate. Sodium sulfate was removed with a filter, and then the filtrate was concentrated under reduced pressure. The resulting residue was mixed in ethyl acetate (55 mL) and n-hexane (220 mL) and stirred under heating at 55° C. for 9 hours. The reaction solution was stirred for 9 hours with being slowly cooled to room temperature, and then the precipitated solid was collected by filtration to give the title compound (22.8 g).

Absolute configuration of the asymmetric carbon of the title compound was determined by single-crystal X-ray structural analysis.

(Intermediate Step 1)

4-Bromo-2-chloro-1-(3,3-dimethyl-but-1-ynyl)benzene

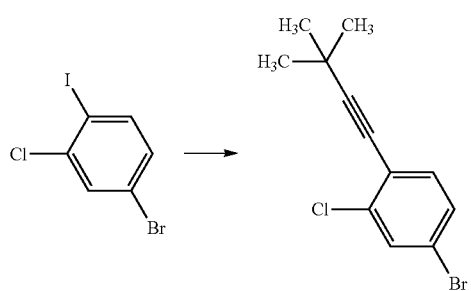

4-Bromo-2-chloro-1-iodo-benzene (325 g), 3,3-dimethyl-but-1-yne (97 g), bis(triphenylphosphino)palladium (II) dichloride (14.3 g), copper (I) iodide (7.80 g), triphenylphosphine (10.7 g), and diisopropylamine (2.17 L) were mixed under argon gas and stirred under heating at 100° C. for 15 hours. Then, thereto was added n-hexane (2.20 L) at room temperature, and the precipitated solid was filtered with Celite. Then, the filtrate was concentrated under reduced pressure. The resulting residue was mixed with n-hexane (2.00 L) and silica gel (327 g) and stirred at room temperature for 17 hours. The resulting solid was removed with a filter, and then the filtrate was concentrated under reduced pressure to give a crude product of the title compound (316 g).

$^1$H-NMR (400 MHz, CDCl$_3$) 1.33 (s, 9H), 7.26 (d, J=8.31 Hz, 1H), 7.30 (dd, J=8.31, 1.71 Hz, 1H), 7.54 (d, J=1.96 Hz, 1H)

(Intermediate Step 2)

4-Bromo-2-chloro-1-(3,3-dimethyl-butyl)benzene

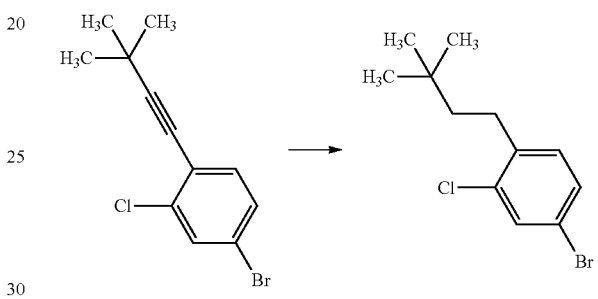

4-Bromo-2-chloro-1-(3,3-dimethyl-but-1-ynyl)benzene (66.0 g) was mixed with ethanol (330 mL), and thereto was added 5 w/w % platinum/activated carbon (13.2 g). The reaction solution was stirred under ordinary pressure and hydrogen gas for 6 hours, and then the gas in the reaction vessel was replaced with nitrogen gas. Celite was added to the reaction solution and removed with a filter, and then the filtrate was concentrated under reduced pressure. The resulting residue was mixed with ethanol (330 mL), and thereto was added 5 w/w % platinum/activated carbon (13.6 g). The reaction solution was stirred under 0.1 MPa hydrogen gas for 55 hours, and then the gas in the reaction vessel was replaced with nitrogen gas. Celite was added to the reaction solution and removed with a filter, and then the filtrate was concentrated under reduced pressure. The resulting residue was mixed with n-hexane (200 mL), and the mixture was separated. The organic layer was washed with water. All aqueous layers were extracted with n-hexane (20 mL). The organic layer was washed with water and saturated aqueous sodium chloride solution and dried over magnesium sulfate. Magnesium sulfate was removed with a filter, and then the filtrate was concentrated under reduced pressure to glue Crude product A (61.0 g).

4-Bromo-2-chloro-1-(3,3-dimethyl-but-1-ynyl)benzene (10.0 g) was mixed with ethanol (50.0 mL), and thereto was added 5 w/w % platinum/activated carbon (2.03 g). The reaction solution was stirred under ordinary pressure and hydrogen gas for 18 hours, and then the gas in the reaction vessel was replaced with nitrogen gas. Celite was added to the reaction solution and removed with a filter, and then the filtrate was concentrated under reduced pressure to give Crude product B (9.81 g).

4-Bromo-2-chloro-1-(3,3-dimethyl-but-1-ynyl)benzene (82.1 g) was mixed with ethanol (411 mL), and thereto was added 5 w/w % platinum/activated carbon (16.7 g). The reaction solution was stirred under ordinary pressure and hydrogen gas for 26 hours, and then the gas in the reaction vessel was replaced with nitrogen gas. Celite was added to the reaction solution and removed with a filter, and then the filtrate was concentrated under reduced pressure. The resulting residue was mixed with n-hexane (250 mL) and water (20 mL) and separated. The organic layer was washed with water. All aqueous layers were extracted with n-hexane (50 mL). The organic layer was washed with water and saturated aqueous sodium chloride solution and dried over magnesium sulfate. Magnesium sulfate was removed with a filter, and then the filtrate was concentrated under reduced pressure to give Crude product C (78.4 g).

4-Bromo-2-chloro-1-(3,3-dimethyl-but-1-ynyl)benzene (82.1 g) was mixed with ethanol (411 mL), and thereto was added 5 w/w % platinum/activated carbon (16.7 g). The reaction solution was stirred under ordinary pressure and hydrogen gas for 26 hours, and then the gas in the reaction vessel was replaced with nitrogen gas. Celite was added to the reaction solution and removed with a filter, and then the filtrate was concentrated under reduced pressure. The resulting residue was mixed with n-hexane (250 mL) and water (20 mL), and the mixture was separated. The organic layer was washed with water. All aqueous layers were extracted with n-hexane (50 mL). The organic layer was washed with water and saturated aqueous sodium chloride solution and dried over magnesium sulfate. Magnesium sulfate was removed with a filter, and then the filtrate was concentrated under reduced pressure to give Crude product D (74.9 g).

4-Bromo-2-chloro-1-(3,3-dimethyl-but-1-ynyl)benzene (82.1 g) was mixed with ethanol (410 mL), and thereto was added 5 w/w % platinum/activated carbon (16.4 g). The reaction solution was stirred under ordinary pressure and hydrogen gas for 27 hours, and then the gas in the reaction vessel was replaced with nitrogen gas. Celite was added to the reaction solution and removed with a filter, and then the filtrate was concentrated under reduced pressure. The resulting residue was mixed with n-hexane (250 mL) and water (20 mL), and the mixture was separated. The organic layer was washed with water. All aqueous layers were extracted with n-hexane (50 mL). The organic layers were washed with water and saturated aqueous sodium chloride solution and dried over magnesium sulfate. Magnesium sulfate was removed with a filter, and then the filtrate was concentrated under reduced pressure to give Crude product E (74.4 g).

The title compound (298.51 g) of Crude products A, B, C, D, and E was mixed with n-hexane (2.00 L) and silica gel (150 g) and stirred at room temperature for 3 hours. The resulting solid was removed with as filter, and then the filtrate was concentrated under reduced pressure. The resulting residue was azeotroped with toluene (300 mL) to give a crude product of the title compound (304 g).

$^1$H-NMR (400 MHz, CDCl$_3$) 0.97 (s, 9H), 1.40-1.45 (m, 2H), 2.61-2.66 (m, 2H), 7.08 (d, J=8.07 Hz, 1H), 7.29 (dd, J=8.07, 1.96 Hz, 1H), 7.48 (d, J=1.96 Hz, 1H)

Example 63

(Step 1)

Ethyl 8,8-difluoro-1,4-dioxa-spiro[4.5]decane-6-carboxylate

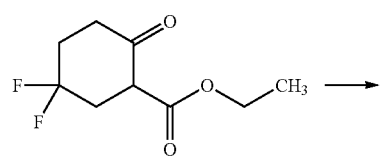

-continued

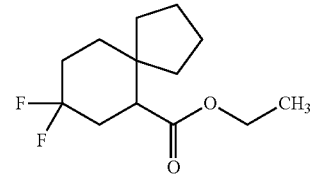

Ethyl 5,5-difluoro-2-oxo-cyclohexanecarboxylate (4.45 g) and toluene (53 mL) were mixed under nitrogen gas, and thereto were added ethylene glycol (1.45 mL) and p-toluenesulfonic acid monohydrate (205 mg) at room temperature. The reaction solution was stirred under heating at 140° C. with dehydration for 1 day. Then, thereto was added a mixed aqueous solution of sodium carbonate (114 mg) in water (18 mL) under ice cooling, and the mixture was separated. The aqueous layer was extracted with ethyl acetate (twice). The organic layer was washed with water (three times) and saturated aqueous sodium chloride solution and dried over magnesium sulfate. Magnesium sulfate was removed with a filter, and then the filtrate was concentrated under reduced pressure. The resulting residue was purified by silica gel column chromatography (Biotage flash purification systems, eluent: ethyl acetate/n-hexane, Rf=0.38 (ethyl acetate/n-hexane=1/4)) to give a crude product of the title compound (3.46 g, 15 wt % of ethyl acetate inclusive).

$^1$H-NMR (400 MHz, CDCl$_3$) 1.28 (t, J=7.1 Hz, 3H), 1.78-1.91 (m, 2H), 2.06-2.16 (m, 2H), 2.23-2.31 (m, 1H), 2.38-2.53 (m, 1H), 2.99 (ddd, J=12.4, 4.6, 1.6 Hz, 1H), 3.90-4.01 (m, 4H), 4.17 (q, J=7.1 Hz, 2H)

(Step 2)

(8,8-Difluoro-1,4-dioxa-spiro[4.5]dec-6-yl)methanol

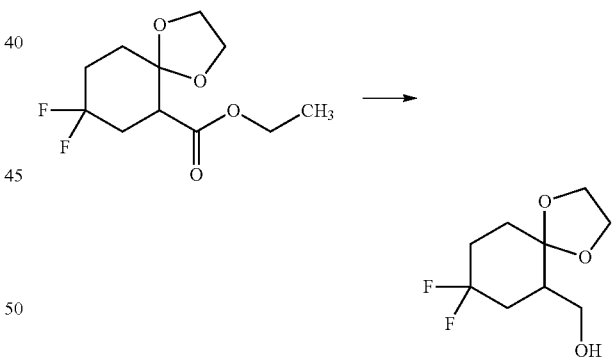

Lithium aluminum hydride (886 mg) and tetrahydrofuran (12 mL) were mixed under argon gas, and thereto was added dropwise a mixed solution in tetrahydrofuran (18 mL) of ethyl 8,8-difluoro-1,4-dioxa-spiro[4.5]decane-6-carboxylate (2.92 g) azeotroped with toluene over 1 hour under ice cooling. The reaction solution was stirred under ice cooling for 20 minutes and stirred at room temperature for 4 hours. To the reaction solution were added slowly water (0.886 mL), 2N aqueous solution of sodium hydroxide (0.886 mL), and water (2.66 mL) under ice cooling. The reaction solution was stirred at room temperature for 30 minutes. To the reaction solution were added Celite (1 g), magnesium sulfate (1 g), and ethyl acetate (30 mL), and the mixture was stirred for 30 minutes. Solids were removed with Celite, and then the filtrate was concentrated under reduced pressure to give a crude product of the title compound (3.06 g, 22 w % of ethyl acetate inclusive).

¹H-NMR (400 MHz, CDCl₃) 1.67-1.75 (m, 1H), 1.83-1.90 (m, 1H), 1.91-2.10 (m, 4H), 2.18-2.26 (m, 1H), 2.56 (dd, J=6.5, 5.3 Hz, 1H), 3.62-3.76 (m, 2H), 3.98-4.08 (m, 4H)

(Step 3)

2-(8,8-Difluoro-1,4-dioxa-spiro[4.5]dec-6-yl-methoxy)-isoindole-1,3-dione

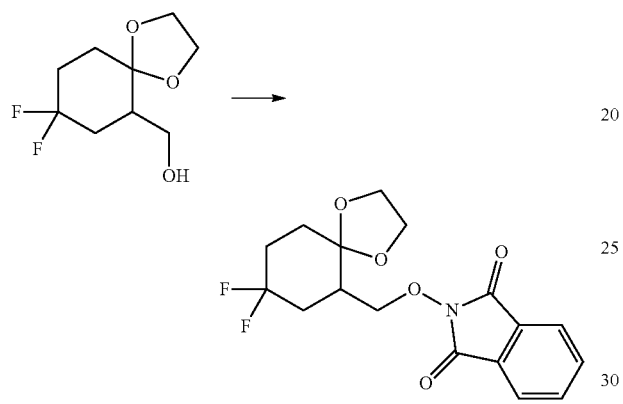

(8,8-Difluoro-1,4-dioxa-spiro[4.5]dec-6-yl)methanol (2.38 g) and tetrahydrofuran (36 mL) were mixed, and thereto were added N-hydroxyphthalimide (2.79 g) and triphenylphosphine (4.49 g) under ice cooling. To the mixed solution was added bis(2-methoxyethyl)azodicarboxylate (4.01 g) in 8 parts over 40 minutes under ice cooling. The reaction solution was stirred at room temperature for 15 hours. The reaction solution was concentrated under reduced pressure, and the resulting residue was purified by silica gel column chromatography (Biotage flash purification systems, eluent: ethyl acetate/n-hexane, Rf=0.46 (ethyl acetate=2/3)) to give a crude product of the title compound (3.44 g).

¹H-NMR (400 MHz, CDCl₃) 1.71-1.85 (m, 2H), 1.96-2.20 (m, 3H), 2.51-2.59 (m, 1H), 2.65-2.75 (m, 1H), 3.93-4.10 (m, 5H), 4.41 (ddd, J=9.1, 4.0, 2.0 Hz, 1H), 7.74 (d, J=3.0 Hz, 1H), 7.76 (d, J=3.0 Hz, 1H), 7.83 (d, J=3.0 Hz, 1H), 7.84 (d, J=3.0 Hz, 1H)

(Step 4)

O-((8,8-Difluoro-1,4-dioxaspiro[4.5]decan-6-yl)methyl)hydroxylamine

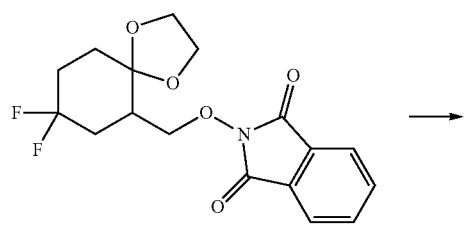

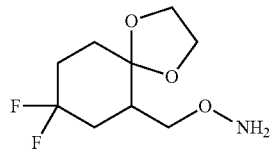

2-(8,8-Difluoro-1,4-dioxa-spiro[4.5]dec-6-ylmethoxy)-isoindole-1,3-dione (3.44 g) and chloroform (34 mL) were mixed, and thereto was added a mixed solution of methylhydrazine (0.619 mL) in chloroform (2 mL) over 5 minutes under ice cooling. The reaction solution was stirred at room temperature for 2 hours. Solids were removed with Celite, and then the filtrate was concentrated under reduced pressure to give a crude product of the title compound (3.49 g, 38 w % of chloroform inclusive).

¹H-NMR (400 MHz, CDCl₃) 1.71-2.10 (m, 5H), 2.23-2.32 (m, 1H), 2.39-2.47 (m, 1H), 3.52 (dd, J=9.9, 8.3 Hz, 1H), 3.88 (ddd, J=10.1, 4.3, 2.2 Hz, 1H), 3.91-4.02 (m, 4H), 5.40 (s, 2H)

(Step 5)

5,5-Difluoro-3,3a,4,5,6,7-hexahydrobenzo[c]isoxazole

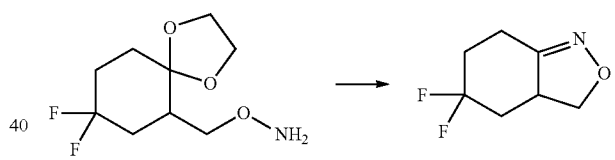

O-(8,8-Difluoro-1,4-dioxa-spiro[4.5]dec-6-ylmethyl)-hydroxylamine (2.17 g, 38 w % of chloroform inclusive) and tetrahydrofuran (19.5 mL) were mixed, and then thereto was added slowly 6N hydrochloric acid (4.87 mL) under ice cooling. The reaction solution was stirred at room temperature for 1 hour, and then thereto was added tetrahydrofuran (20 mL). The mixture was stirred further for 4 hours. To the reaction solution was added water (5 mL), and the mixture was stirred under heating at 60° C. for 6 hours. Then, thereto was added potassium carbonate (4.04 g) under ice cooling, and the mixture was concentrated under reduced pressure and then extracted with ethyl acetate (twice). The organic layers were washed with saturated aqueous sodium chloride solution (twice) and dried over sodium sulfate. Sodium sulfate was removed with a filter, and then the filtrate was concentrated under reduced pressure. The resulting residue was purified by silica gel column chromatography (Biotage flash purification systems, eluent: ethyl acetate/n-hexane, Rf=0.19 (ethyl acetate/n-hexane=2/3)) to give the title compound (1.11 g).

¹H-NMR (400 MHz, CDCl₃) 1.76-2.02 (m, 2H), 2.33-2.42 (m, 1H), 2.44-2.60 (m, 2H), 2.89 (ddt, J=14.6, 5.8, 2.1 Hz, 1H), 3.49-3.59 (m, 1H), 3.91 (dd, J=9.8, 8.4 Hz, 1H), 4.57 (ddd, J=10.4, 8.3, 1.5 Hz, 1H)

(Step 6)

7a-[3-Chloro-1-(3,3-dimethyl-butyl)phenyl]-5,5-difluoro-octahydro-benzo[c]isoxazole

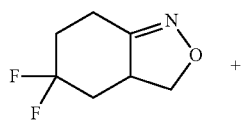

+

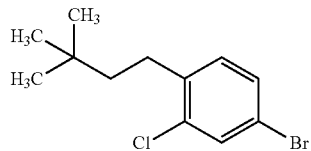

→

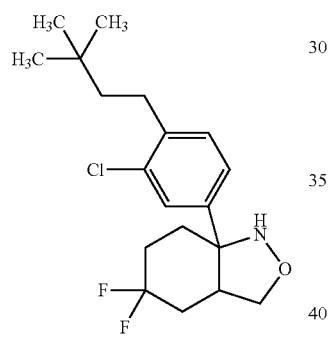

4-Bromo-2-chloro-1-(3,3-dimethyl-butyl)-benzene (1.26 g) and tetrahydrofuran (5 mL) were mixed under argon gas, and thereto was added dropwise 1.54M n-butyllithium/n-hexane solution (2.42 mL) under cooling at −78° C. The reaction solution was stirred for 1 hour under cooling at −78° C. (Reaction solution A), 5,5-Difluoro-3,3a,4,5,6,7-hexahydro-benzo[c]isoxazole (500 mg) and toluene (12.5 mL) were mixed, and thereto were added boron trifluoride-diethyl ether complex (0.464 mL) and Reaction solution A under cooling at −78° C. The reaction solution was stirred at −78° C. for 3 hours, and then thereto was added saturated aqueous sodium chloride solution (16 mL). The aqueous layer was extracted with ethyl acetate (twice) at room temperature. The organic layers were washed with saturated aqueous sodium chloride solution (twice) and dried over sodium sulfate. Sodium sulfate was removed with a filter, and then the filtrate was concentrated under reduced pressure. The resulting residue was purified by silica gel column chromatography (Biotage flash purification systems, eluent: ethyl acetate/n-hexane, Rf=0.43 (ethyl acetate/n-hexane=1/4)) to give a crude product of the title compound (1.09 g, 8 w % of ethyl acetate inclusive).

$^1$H-NMR (400 MHz, CDCl$_3$) 0.98 (s, 9H), 1.43-1.47 (m, 2H), 1.88-2.32 (m, 6H), 2.65-2.70 (m, 2H), 3.02 (qd, J=7.0, 3.8 Hz, 1H), 3.79-3.88 (m, 2H) 5.67 (s, 1H), 7.21 (d, J=7.9 Hz, 1H), 7.34 (dd, J=8.0, 2.0 Hz, 1H), 7.52 (d, J=1.4 Hz, 1H)

(Step 7)

{2-Amino-2-[3-chloro-4-(3,3-dimethyl-butyl)phenyl]-5,5-difluoro-cyclohexyl}methanol

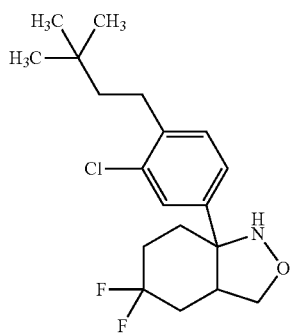

→

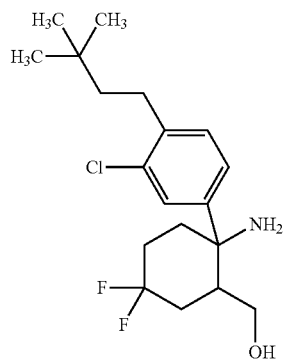

7a-[3-Chloro-4-(3,3-dimethyl-butyl)phenyl]-5,5-difluoro-octahydro-benzo[c]isoxazole (1.00 g), acetic acid (15 mL), tetrahydrofuran (10 mL), and water (5 mL) were mixed under nitrogen gas, and thereto was added zinc powder (1.83 g) in 5 parts under heating at 60° C. The reaction solution was stirred under heating at 60° C. for 4 hours. Then, thereto was added 28 w/w % ammonia water (25 mL) under ice cooling, and the mixture was extracted with cyclopentyl methyl ether (three times). The organic layers were washed with saturated aqueous sodium chloride solution and dried over sodium sulfate. Sodium sulfate was removed with a filter, and then the filtrate was concentrated under reduced pressure to give a crude product of the title compound (1.41 g, 31 w % of cyclopentyl methyl ether inclusive).

$^1$H-NMR (400 MHz, CDCl$_3$) 0.99 (s, 9H), 1.43-1.48 (m, 2H), 1.50-1.75 (m, 7H), 2.04-2.44 (m, 3H), 2.66-2.70 (m, 2H), 3.30 (dd, J=11.7, 3.4 Hz, 1H), 3.44 (dt, J=11.6, 2.9 Hz, 1H), 7.22 (d, J=8.1 Hz, 1H), 7.29 (dd, J=8.1, 2.1 Hz, 1H), 7.47 (d, J=2.1 Hz, 1H)

121

(Step 8)

Ethyl 3-(3-(1-[3-chloro-4-(3,3-dimethyl-butyl)phenyl]-4,4-difluoro-2-hydroxymethyl-cyclohexyl)ureido)propionate

122

(Step 9)

Ethyl 3-{8a-[3-chloro-4-(3,3-dimethyl-butyl)phenyl]-6,6-difluoro-2-oxo-1,5,6,7,8,8a-hexahydro-2H-quinazolin-3-yl}propionate

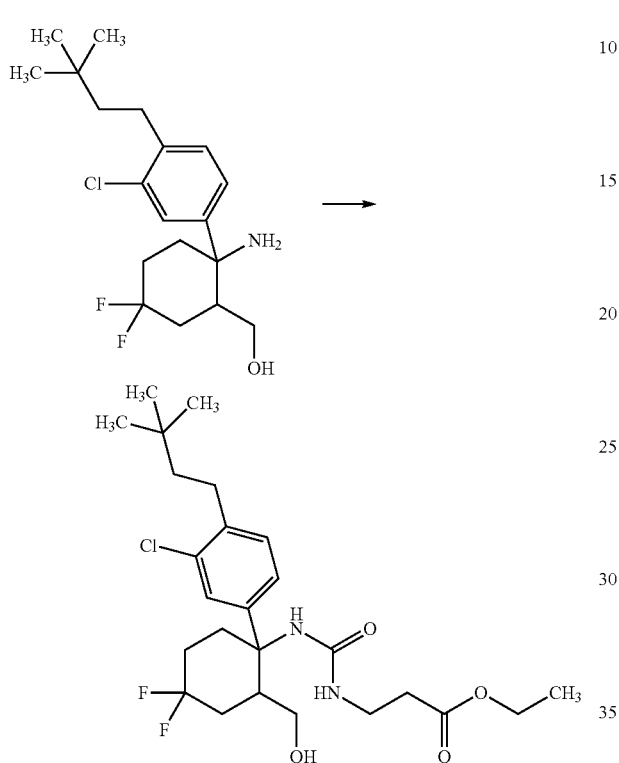

{2-Amino-2-[3-chloro-4-(3,3-dimethyl-butyl)phenyl]-5,5-difluoro-cyclohexyl}methanol (300 mg, 31 w % of cyclopentyl methyl ether inclusive) and tetrahydrofuran (3 mL) were mixed under argon gas, and thereto was added ethyl 3-isocyanato-propionate (0.122 mL) under ice cooling. The reaction solution was stirred at room temperature for 24 hours. Then, thereto was added N,N,N'-trimethylethylenediamine, and the mixture was stirred at room temperature for 10 minutes. The organic layer was concentrated under reduced pressure. Then, thereto was added ethyl acetate, and the mixture was washed with 10 w/w % aqueous citric acid solution, 10 w/w % aqueous sodium chloride solution, and saturated aqueous sodium chloride solution. The organic layer was dried over magnesium sulfate. Magnesium sulfate was removed with a filter, and then the filtrate was concentrated under reduced pressure. The resulting residue was purified by silica gel column chromatography (Biotage flash purification systems, eluent: ethyl acetate/n-hexane, Rf=0.41 (ethyl acetate/n-hexane=1/2)) to give a crude product of the title compound (496 mg, 21 w % of ethyl acetate inclusive).

$^1$H-NMR (400 MHz, CDCl$_3$) 0.97 (s, 9H), 1.29 (t, J=7.2 Hz, 3H), 1.41-1.46 (m, 2H), 1.81-1.89 (m, 2H), 1.96-2.11 (m, 5H), 2.54 (dd, J=6.7, 5.2 Hz, 2H), 2.61-2.67 (m, 2H), 3.20 (d, J=9.3 Hz, 1H), 3.38-3.52 (m, 4H), 4.18 (q, J=7.2 Hz, 2H), 4.91 (t, J=6.1 Hz, 1H), 6.44 (s, 1H), 7.12 (dd, J=8.1, 1.8 Hz, 1H), 7.17 (d, J=7.8 Hz, 1H), 7.26 (d, J=1.8 Hz, 1H)

Ethyl 3-(3-{1-[3-chloro-4-(3,3-dimethyl-butyl)phenyl]-4,4-difluoro-2-hydroxymethyl-cyclohexyl}ureido)propionate (366 mg) and chloroform (3.7 mL) were mixed, and thereto were added (diacetoxyiodo)benzene (266 mg) and 2,2,6,6-tetramethylpiperidin-1-oxyl radical (11 mg) at room temperature. The reaction solution was stirred at room temperature for 24 hours, and then thereto were added 20 w/w % aqueous sodium sulfite solution and saturated aqueous sodium hydrogen carbonate solution at room temperature. The mixture was stirred at room temperature for 30 minutes. The aqueous layer was extracted with ethyl acetate (twice) and washed with saturated aqueous sodium chloride solution. The organic layers were dried over magnesium sulfate. Magnesium sulfate was removed with a filter, and then the filtrate was concentrated under reduced pressure. The resulting residue and toluene (7.3 mL) were mixed, and thereto was added pentafluoroaniline trifluoromethanesulfonate (12.1 mg) at room temperature. The reaction solution was stirred under heating at 120° C. for 6 hours, and then the reaction solution was concentrated under reduced pressure. To the resulting residue was added saturated aqueous sodium hydrogen carbonate solution at room temperature, and the aqueous layer was extracted with ethyl acetate (twice). The organic layers were washed with saturated aqueous sodium chloride solution and dried over magnesium sulfate. Magnesium sulfate was removed with a filter, and then the filtrate was concentrated under reduced pressure. The resulting residue was purified by silica gel column chromatography (Biotage flash purification systems, eluent: ethyl acetate/n-hexane, Rf=0.37 (ethyl acetate/n-hexane=2/

3)) to give a crude product of the title compound (330 mg, 18 w % of ethyl acetate inclusive).

¹H-NMR (400 MHz, CDCl₃) 0.98 (d, J=4.9 Hz, 9H), 1.28 (t, J=7.1 Hz, 3H), 1.42-1.47 (m, 2H), 1.61-1.77 (m, 1H), 2.13 (s, 1H), 2.21-2.38 (m, 2H), 2.53-2.73 (m, 6H), 3.58-3.65 (m, 1H), 3.83 (dt, J=14.1, 6.1 Hz, 1H), 4.19 (q, J=7.2 Hz, 2H), 4.78 (s, 1H), 6.22 (d, J=1.8 Hz, 1H), 7.16 (dd, J=8.0, 2.0 Hz, 1H), 7.24 (d, J=8.1 Hz, 1H), 7.30 (d, J=2.1 Hz, 1H)

(Step 10)

3-{8a-[3-Chloro-4-(3,3-dimethyl-butyl)phenyl]-6,6-difluoro-2-oxo-1,5,6,7,8,8a-hexahydro-2H-quinazolin-3-yl}propionic acid

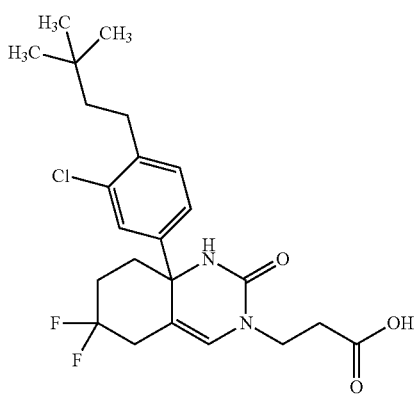

Ethyl 3-{8a-[3-chloro-4-(3,3-dimethyl-butyl)phenyl]-6,6-difluoro-2-oxo-1,5,6,7,8,8a-hexahydro-2H-quinazolin-3-yl}propionate (25 mg) was mixed in tetrahydrofuran (0.25 mL) and methanol (0.25 mL), and thereto was added 2N aqueous solution of sodium hydroxide (0.518 mL) at room temperature. The reaction solution was stirred at room temperature for 16 hours, and then the reaction solution was concentrated under reduced pressure. To the resulting residue were added water and 2N hydrochloric acid (0.518 mL) under ice cooling, and the precipitated solid was collected by filtration to give the title compound (23.6 mg).

Example 68

(Step 1)

7a-[3-Chloro-4-(3,3-dimethyl-butyl)phenyl]-5-methoxy-octahydro-benzo[c]isoxazole

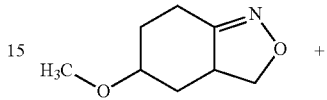

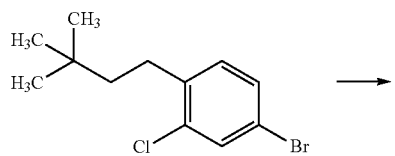

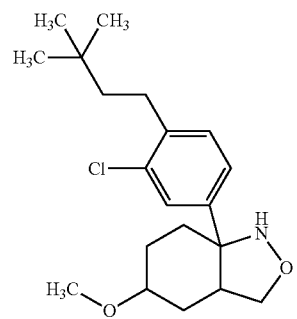

4-Bromo-2-chloro-1-(3,3-dimethyl-butyl)-benzene (1.3 g) was mixed in toluene (11 mL) and tetrahydrofuran (4.4 mL) under argon gas, and thereto was added dropwise 2.66M n-butyllithium/n-hexane solution (1.45 mL) under cooling at −78° C. The reaction solution was stirred under cooling at −78° C. for 1 hour (Reaction solution A). 5-methoxy-3,3a,4,5,6,7-hexahydrobenzo[c]isoxazole (0.5 g) and toluene (32 mL) were mixed, and thereto were added boron trifluoride-diethyl ether complex (0.49 mL) and Reaction solution A under cooling at −78° C. The reaction solution was stirred under cooling at −78° C. for 2 hours, and then thereto was added a saturated aqueous solution of ammonium chloride. The mixture was stirred at room temperature, and then thereto were added ethyl acetate and water. The mixture was separated. The aqueous layer was extracted with chloroform. The organic layer was concentrated under reduced pressure, and the crude product was purified by silica gel column chromatography (ethyl acetate/n-hexane=1/9→2/3) to give the title compound (0.68 g).

¹H-NMR (400 MHz, CDCl₃) 0.97 (s, 9H), 1.40-1.48 (m, 2H), 1.49-1.61 (m, 4H), 1.79-2.19 (m, 4H), 2.63-2.69 (m, 2H), 2.86-2.98 (m, 1H), 3.39 (s, 3H), 3.49-3.61 (m, 1H), 3.65-3.81 (m, 1H), 7.13-7.20 (m, 1H), 7.34-7.42 (m, 1H), 7.52-7.58 (m, 1H)

(Step 2)

{2-Amino-2-[3-chloro-4-(3,3-dimethyl-butyl)phenyl]-5-methoxy-cyclohexyl}methanol

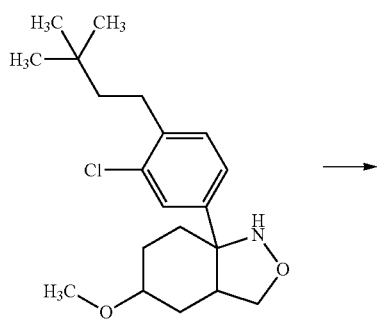

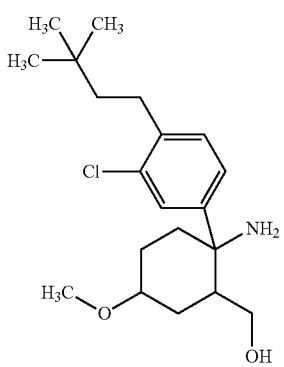

7a-[3-Chloro-4-(3,3-dimethyl-butyl)phenyl]-5-methoxy-octahydro-benzo[c]isoxazole (0.66 g) was mixed in acetic acid (10 mL), tetrahydrofuran (3.3 mL), and water (3.3 mL) under nitrogen gas, and thereto was added zinc powder (1.24 g) in parts at room temperature. The reaction solution was stirred under heating at 60° C. for 1 hour 30 minutes. Then, thereto was added 28 w/w % ammonia water (15 mL) under ice cooling, and the mixture was stirred at room temperature. To the reaction solution were added chloroform, methanol, and water, and the mixture was separated. The organic layer was dried over magnesium sulfate. Magnesium sulfate was removed with a filter, and then the filtrate was concentrated under reduced pressure. The crude product was purified by silica gel column chromatography (methanol/ethyl acetate=0/1→1/99) to give the title compound (0.75 g).

$^1$H-NMR (400 MHz, CDCl$_3$) 0.96 (s, 9H), 1.11-1.28 (m, 1H), 1.40-1.48 (m, 2H), 1.48-1.65 (m, 3H), 1.67-1.78 (m, 1H), 1.89-2.05 (m, 5H), 2.29-2.43 (m, 1H), 2.62-2.69 (m, 2H), 3.18-3.25 (m, 1H), 3.36 (s, 3H), 3.43-3.48 (m, 1H), 3.64-3.69 (m, 1H), 7.15-7.19 (m, 1H), 7.31-7.35 (m, 1H), 7.47-7.50 (m, 1H)

(Step 3)

Ethyl 3-(3-{1-[3-chloro-4-(3,3-dimethyl-butyl)phenyl]-2-hydroxymethyl-4-methoxy-cyclohexyl}ureido)propionate

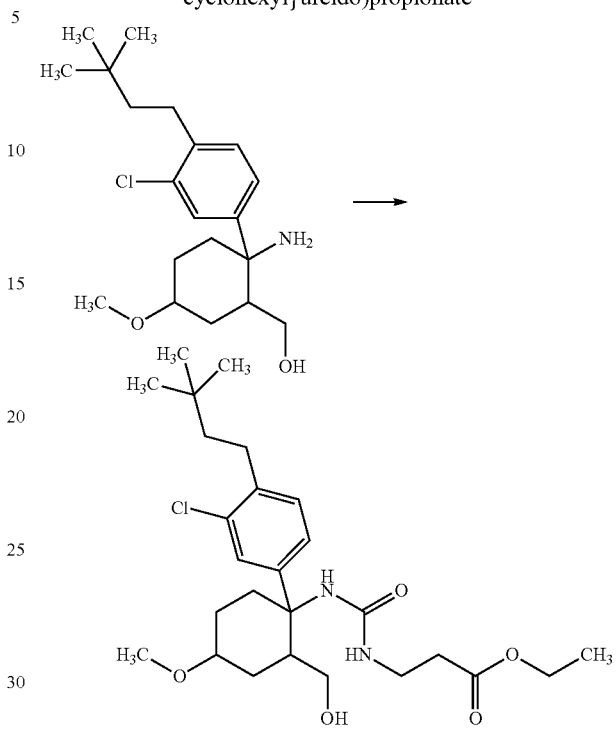

{2-Amino-2-[3-chloro-4-(3,3-dimethyl-butyl)phenyl]-5-methoxy-cyclohexyl}methanol (0.18 g) and tetrahydrofuran (3 mL) were mixed, and thereto was added ethyl 3-isocyanato-propionate (74 μL) under ice cooling. The reaction solution was stirred at room temperature for 40 minutes and then concentrated under reduced pressure. The resulting residue was purified by silica gel column chromatography (methanol/ethyl acetate=0/1→1/99) to give the title compound (0.26 g).

$^1$H-NMR (400 MHz, CDCl$_3$) 0.97 (s, 9H), 1.22-1.33 (m, 3H), 1.40-1.49 (m, 2H), 1.64-1.72 (m, 2H), 1.72-1.86 (m, 2H), 1.86-2.00 (m, 2H), 2.05-2.21 (m, 2H), 2.49-2.57 (m, 2H), 2.59-2.68 (m, 2H), 2.68-2.81 (m, 1H), 3.29-3.40 (m, 3H), 3.40-3.53 (m, 3H), 3.62-3.66 (m, 1H), 4.09-4.22 (m, 2H), 4.30 (br s, 1H), 6.35 (br s, 1H), 7.12-7.21 (m, 2H), 7.29-7.34 (m, 1H)

(Step 4)

Ethyl 3-{8a-[3-chloro-4-(3,3-dimethyl-butyl)phenyl]-6-methoxy-2-oxo-1,5,6,7,8,8a-hexahydro-2H-quinazolin-3-yl}propionate

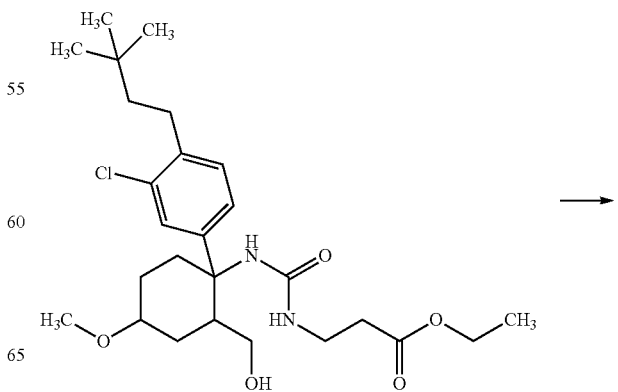

127

-continued

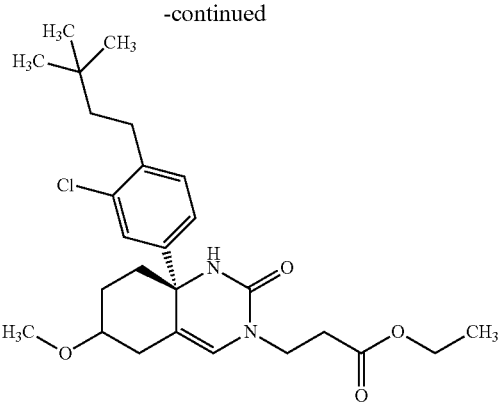

Ethyl 3-(3-{1-[3-chloro-4-(3,3-dimethyl-butyl)phenyl]-2-hydroxymethyl-4-methoxy-cyclohexyl}ureido)propionate (0.257 g) and dichloromethane (3 mL) were mixed under nitrogen gas, and thereto were added (diacetoxyiodo)benzene (0.18 g) and 2,2,6,6-tetramethylpiperidin-1-oxyl radical (8 mg) under ice cooling. The reaction solution was stirred at room temperature for 3 hours, and then thereto were added ethyl acetate, an aqueous solution of sodium thiosulfate, and an aqueous solution of sodium hydrogen carbonate at room temperature. The mixture was separated. The organic layer was washed with water and then dried over sodium sulfate. Sodium sulfate was removed with a filter, and then the filtrate was concentrated under reduced pressure. The resulting residue and toluene (4 mL) were mixed, and thereto was added pentafluoroaniline trifluoromethanesulfonate (8 mg) at room temperature. The reaction solution was stirred under heating at 120° C. for 1 hour 30 minutes and then concentrated under reduced pressure. The resulting residue was purified by silica gel column chromatography (ethyl acetate/n-hexane=1/4→1/2→1/1) to give a diastereomeric mixture of the title compound (0.19 g). The diastereomeric mixture was purified with a Recycling Preparative Liquid Chromatograph to give a single enantiomer of the title compound (40 mg).

Purification conditions for the preparative chromatography are shown as follows.

Preparative apparatus: Recycling preparative liquid chromatograph LC-92XX NEXT SERIES, Japan Analytical Industry Co., Ltd.
Column: Daicel CHIRALPAK IA 2.0 cmφ×25 cm
Mobile phase: n-hexane:2-propanol=85:15
Flow rate: 10.0 mL/min
Detection: UV (254 nm)

Measurement of the resulting compound with a chiral column showed 7.8 minutes of the retention time for the resulting enantiomer with >99% ee of optical purity. The retention time for the opposite enantiomer was 5.2 minutes.

Analytical conditions for the chiral column are shown as follows.

Measurement apparatus: HPLC system, Shimadzu Corporation, High-Performance Liquid Chromatograph Prominence
Column: Daicel CHIRALPAK IA-3 0.46 cmφ×15 cm
Column temperature: 40° C.
Mobile phase: n-hexane:2-propanol=85:15
Flow rate: 1.0 mL/min
Detection: UV (254 nm)

128

$^1$H-NMR (400 MHz, CDCl$_3$) 0.96 (s, 9H), 1.15-1.23 (m, 1H), 1.23-1.29 (m, 3H), 1.37-1.45 (m, 2H), 1.74-1.84 (m, 1H), 1.87-1.98 (m, 1H), 1.98-2.06 (m, 1H), 2.47-2.56 (m, 2H), 2.57-2.70 (m, 4H), 3.17-3.27 (m, 1H), 3.29 (s, 3H), 3.53-3.63 (m, 1H), 3.75-3.85 (m, 1H), 4.13-4.21 (m, 2H), 4.65 (br s, 1H), 6.09-6.13 (m, 1H), 7.09-7.15 (m, 1H), 7.15-7.21 (m, 1H), 7.25-7.28 (m, 1H)

(Step 5)

3-{(S)-8a-[3-Chloro-4-(3,3-dimethyl-butyl)phenyl]-6-methoxy-2-oxo-1,5,6,7,8,8a-hexahydro-2H-quinazolin-3-yl}propionic acid

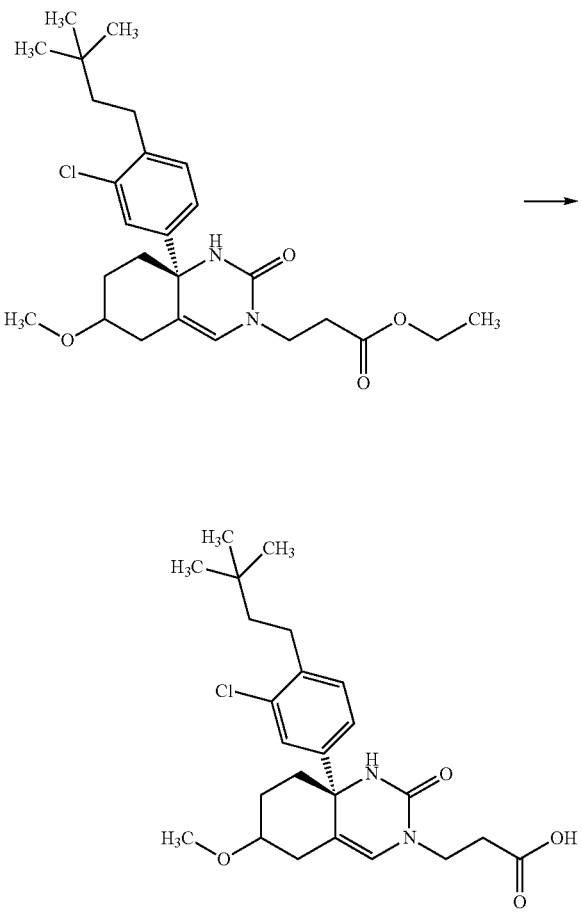

Ethyl 3-{8a-[3-chloro-4-(3,3-dimethyl-butyl)phenyl]-6-methoxy-2-oxo-1,5,6,7,8,8a-hexahydro-2H-quinazolin-3-yl}propionate (36 mg) and ethanol (1 mL) were mixed, and thereto was added 2N aqueous solution of sodium hydroxide (0.11 mL) at room temperature. The reaction solution was stirred at room temperature for 1 hour 30 minutes and then concentrated under reduced pressure. To the resulting residue were added at room temperature 1N hydrochloric acid (0.23 mL) and water, and then the precipitated solid was collected by filtration to give the title compound (27.4 mg).

Example 77

(Step 1)

Methyl 3-(3-{1-[3-chloro-4-(3,3-dimethyl-butyl)phenyl]-2-hydroxymethyl-4-methoxy-cyclohexyl}ureido)bicyclo[1.1.1]pentane-1-carboxylate

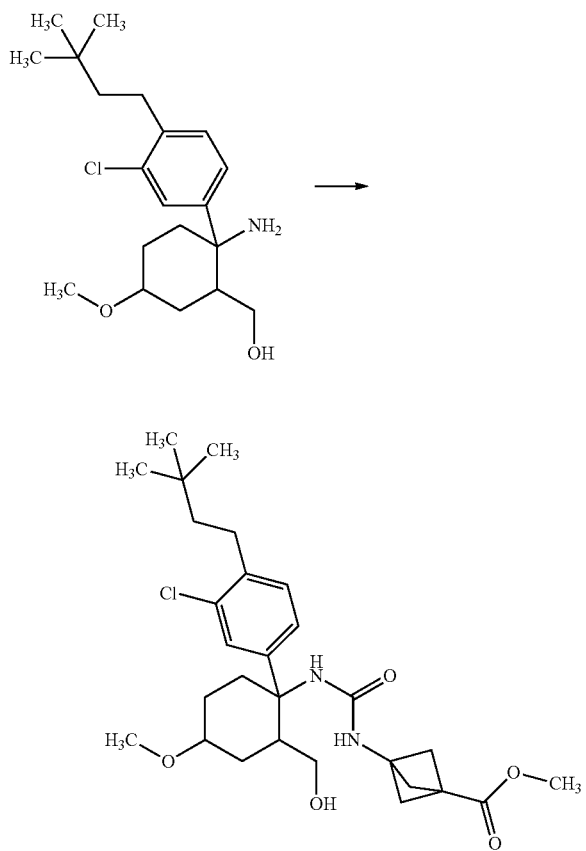

3-(Methoxycarbonyl)bicyclo[1.1.1]pentane-1-carboxylic acid (96 mg) and toluene (2 mL) were mixed under argon gas, and thereto were added diphenylphosphoryl azide (0.13 mL) and triethylamine (0.037 mL) at room temperature. The reaction solution was stirred under heating at 120° C. for hour. The reaction solution was added dropwise to a mixed solution of {2-amino-2-[3-chloro-4-(3,3-dimethyl-butyl)phenyl]-5-methoxy-cyclohexyl}methanol (200 mg) in tetrahydrofuran (3 mL) under ice cooling. The reaction solution was stirred at room temperature for 2 hours and then concentrated under reduced pressure. The resulting residue was purified by silica gel column chromatography (methanol/ethyl acetate=0/1→1/99) to give the title compound (0.29 g).

$^1$H-NMR (400 MHz, CDCl$_3$) 0.97 (s, 9H), 1.40-1.47 (m, 2H), 1.61-1.72 (m, 1H), 1.75-1.84 (m, 1H), 1.88-1.99 (m, 2H), 2.05-2.17 (m, 2H), 2.36 (s, 6H), 2.60-2.67 (m, 2H), 2.76-2.88 (m, 1H), 3.31-3.37 (m, 1H), 3.38 (s, 3H), 3.45-3.53 (m, 1H), 3.61-3.67 (m, 1H), 3.69 (s, 4H), 4.80-4.87 (m, 1H), 6.41 (br s, 1H), 7.13-7.16 (br m, 2H), 7.29 (br s, 1H)

(Step 2)

Methyl 3-{8a-[3-chloro-4-(3,3-dimethyl-butyl)phenyl]-6-methoxy-2-oxo-1,5,6,7,8,8a-hexahydro-2H-quinazolin-3-yl}bicyclo[1.1.11]pentane-1-carboxylate

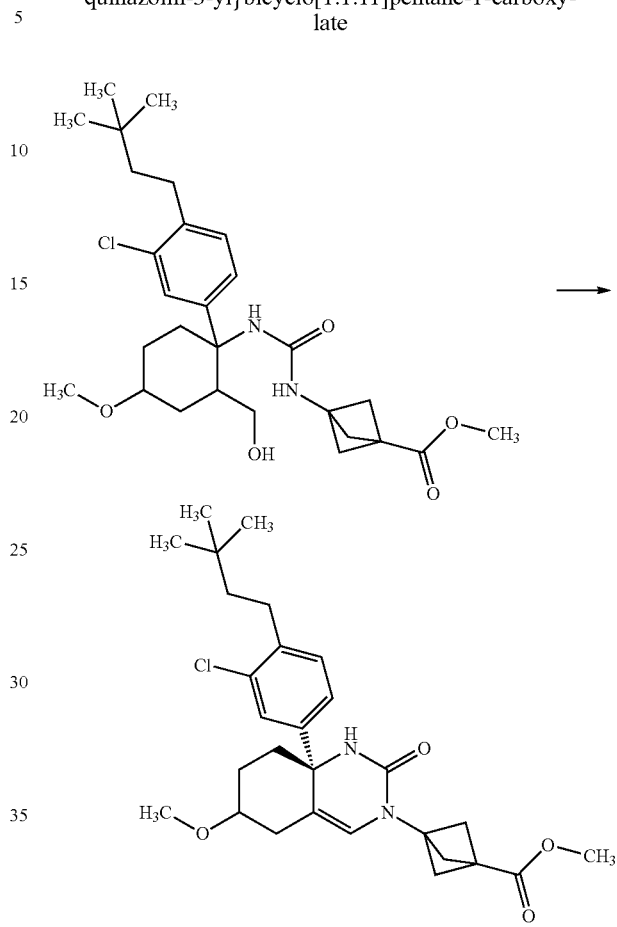

Methyl 3-(3-{1-[3-chloro-4-(3,3-dimethyl-butyl)phenyl]-2-hydroxymethyl-4-methoxy-cyclohexyl}ureido)bicyclo[1.1.1]pentane-1-carboxylate (0.287 g) and dichloromethane (7 mL) were mixed, and thereto were added (diacetoxyiodo)benzene (0.195 g) and 2,2,6,6-tetramethylpiperidin-1-oxyl radical (9 mg) under ice cooling. The reaction solution was stirred at room temperature for 14 hours 30 minutes, and then thereto were added ethyl acetate, an aqueous solution of sodium thiosulfate, and saturated aqueous sodium hydrogen carbonate solution at room temperature. The mixture was separated and dried over magnesium sulfate. Magnesium sulfate was removed with a filter, and then the filtrate was concentrated under reduced pressure. The resulting residue and toluene (3 mL) were mixed, and then thereto was added pentafluoroaniline trifluoromethanesulfonate (9 mg) at room temperature. The reaction solution was stirred under beating at 120° C. for 1 hour and then concentrated under reduced pressure. The resulting residue was purified by silica gel column chromatography (ethyl acetate/n-hexane=1/4→1/2→1/1) to give a diastereomeric mixture of the title compound (0.20 g). The diastereomeric mixture was purified with a Recycling Preparative Liquid Chromatograph to give a single enantiomer of the title compound (78 mg).

Purification conditions for the preparative chromatography are shown as follows.

Preparative apparatus: Recycling preparative liquid chromatograph LC-92XX NEXT SERIES, Japan Analytical Industry Co., Ltd.

Column: Daicel CHIRALPAK IA 2.0 cmφ×25 cm
Mobile phase: n-hexane:2-propanol=85:15
Flow rate: 10.0 mL/min
Detection: UV (254 nm)

Measurement of the resulting compound with a chiral column showed 6.5 minutes of the retention time for the resulting enantiomer with >99% ee of optical purity. The retention time for the opposite enantiomer was 4.0 minutes.

Analytical conditions for the chiral column are shown as follows.

Measurement apparatus: HPLC system, Shimadzu Corporation, High-Performance Liquid Chromatograph Prominence
Column: Daicel CHIRALPAK IA-3 0.46 cmφ×15 cm
Column temperature: 40° C.
Mobile phase: n-hexane:2-propanol=85:15
Flow rate: 1.0 mL/min
Detection: UV (254 nm)

$^1$H-NMR (400 MHz, CDCl$_3$) 0.99 (s, 9H), 1.16-1.28 (m, 1H), 1.39-1.47 (m, 2H), 1.80-1.89 (m, 1H), 1.89-2.00 (m, 1H), 2.00-2.08 (m, 1H), 2.45 (s, 6H), 2.51-2.59 (m, 2H), 2.62-2.69 (m, 2H), 3.20-3.29 (m, 1H), 3.31 (s, 3H), 3.70 (s, 3H), 4.67-4.70 (m, 1H), 6.01-6.04 (m, 1H), 7.10-7.16 (m, 1H), 7.16-7.23 (m, 1H), 7.24-7.29 (m, 1H)

(Step 3)

3-{(S)-8a-[3-Chloro-4-(3,3-dimethyl-butyl)phenyl]-6-methoxy-2-oxo-1,5,6,7,8,8a-hexahydro-2H-quinazolin-3-yl}bicyclo[1.1.1]pentane-1-carboxylic acid

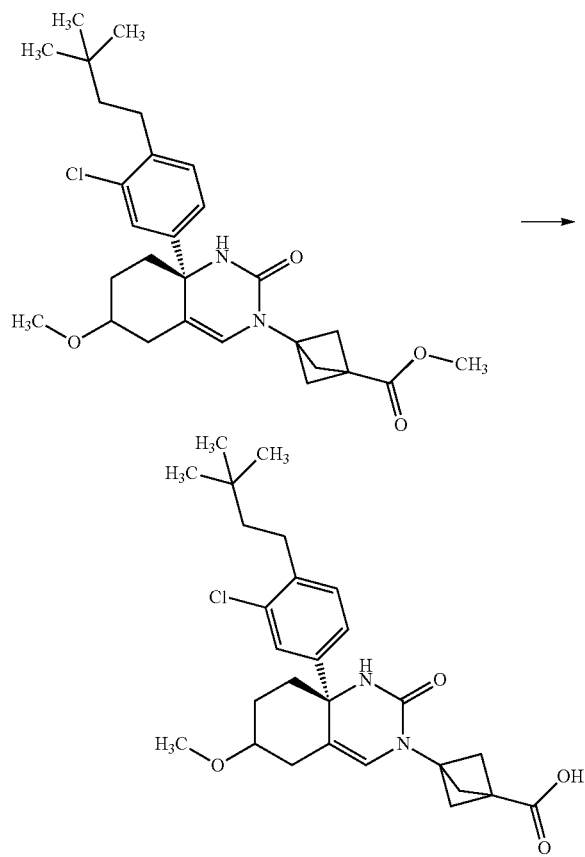

Methyl 3-{(S)-8a-[3-chloro-4-(3,3-dimethyl-butyl)phenyl]-6-methoxy-2-oxo-1,5,6,7,8,8a-hexahydro-2H-quinazolin-3-yl}bicyclo[1.1.1]pentane-1-carboxylate (69 mg) and methanol (2 mL) were mixed, and thereto was added 2N aqueous solution of sodium hydroxide (0.21 mL) at room temperature. The reaction solution was stirred at room temperature for 2 hours and then concentrated under reduced pressure. To the resulting residue were added 2N hydrochloric acid (0.3 mL), chloroform, and methanol at room temperature, and the mixture was separated. The organic layer was dried over sodium sulfate. Sodium sulfate was removed with a filter, and then the filtrate was concentrated under reduced pressure to give the title compound (60 mg).

Example 87

(Step 1)

Methyl 3-(3-{1-[3-chloro-4-(3,3-dimethyl-butyl)phenyl]-4,4-difluoro-2-hydroxymethyl-cyclohexyl}ureido)bicyclo[1.1.1]pentane-1-carboxylate

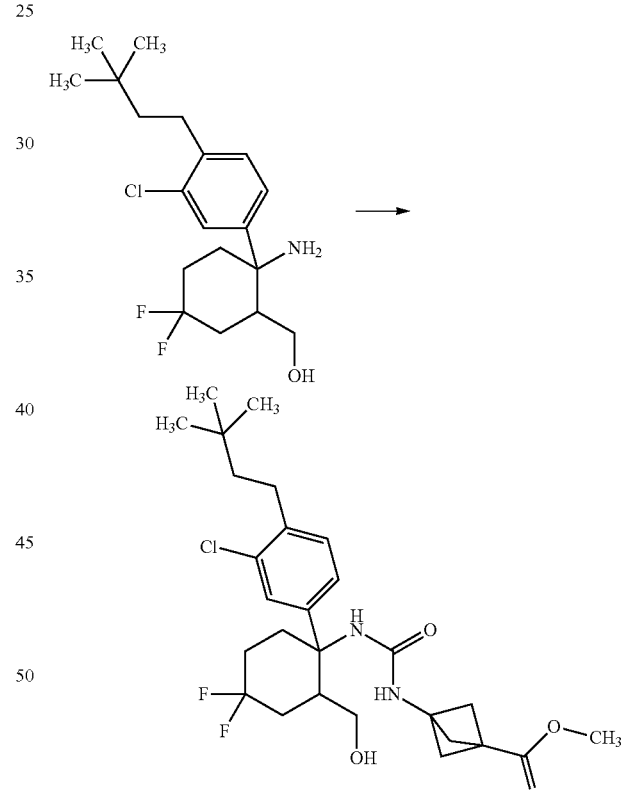

3-(Methoxycarbonyl)bicyclo[1.1.1]pentane-1-carboxylic acid (319 mg) and toluene (4 mL) were mixed under argon gas, and thereto were added diphenylphosphoryl aside (0.445 mL) and triethylamine (0.288 mL) at room temperature. The reaction solution was stirred under heating at 120° C. for 1 hour 30 minutes. To the reaction solution was added tetrahydrofuran (2 mL), and the mixture was added dropwise to a mixed solution of {2-amine-2-[3-chloro-4-(3,3-dimethyl-butyl)phenyl]-5,5-difluoro-cyclohexyl}methanol (979 mg, 31 w % of cyclopentyl methyl ether inclusive) in tetrahydrofuran (6.5 mL) over 10 minutes under ice cooling.

The reaction solution was stirred at room temperature for 1 hour 30 minutes and then concentrated under reduced pressure. The resulting residue was purified by silica gel column chromatography (Biotage flash purification systems, eluent: ethyl acetate/n-hexane, Rf=0.62 (ethyl acetate/n-hexane=1/2)) to give the title compound (493 mg).

$^1$H-NMR (400 MHz, CDCl$_3$) 0.97 (s, 9H), 1.42-1.46 (m, 2H), 1.88-1.93 (m, 1H), 2.06-2.51 (m, 12H), 2.62-2.67 (m, 2H), 3.21-3.25 (m, 1H), 3.42 (d, J=10.4 Hz, 1H), 3.50 (d, J=10.9 Hz, 1H), 3.69 (s, 3H), 4.84 (d, J=2.8 Hz, 1H), 6.45 (s, 1H), 7.11 (dd, J=8.2, 2.0 Hz, 1H), 7.18 (d, J=8.2 Hz, 1H), 7.25 (d, J=2.0 Hz, 1H)

(Step 2)

Methyl 3-{8a-[3-chloro-4-(3,3-dimethyl-butyl)phenyl]-6,6-difluoro-2-oxo-1,5,6,7,8,8a-hexahydro-2H-quinazolin-3-yl}bicyclo[1.1.1]pentane-1-carboxylate

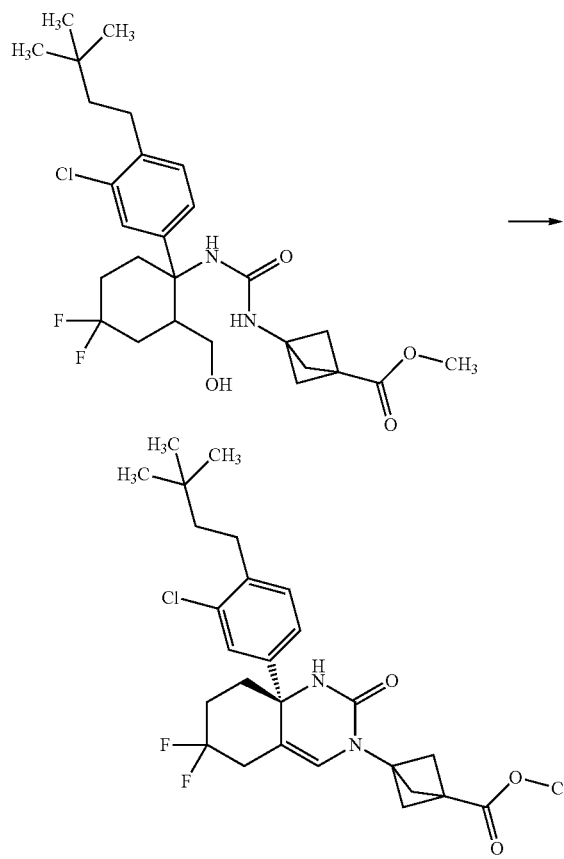

Methyl 3-(3-{1-[3-chloro-4-(3,3-dimethyl-butyl)phenyl]-4,4-difluoro-2-hydroxymethyl-cyclohexyl}ureido)bicyclo[1.1.1]pentane-1-carboxylate (493 mg) and chloroform (16 mL) were mixed, and thereto were added (diacetoxyiodo)benzene (332 mg) and 2,2,6,6-tetramethylpiperidin-1-oxyl radical (15 mg) at room temperature. The reaction solution was stirred at room temperature for 16 hours, and then thereto were added an aqueous solution of sodium thiosulfate and saturated aqueous sodium hydrogen carbonate solution at room temperature. The aqueous layer was extracted with chloroform (twice). The organic layers were dried over magnesium sulfate. Magnesium sulfate was removed with a filter, and then the filtrate was concentrated under reduced pressure. The resulting residue and toluene (20 mL) were mixed, and thereto was added pentafluoroaniline trifluoromethanesulfonate (16 mg) at room temperature. The reaction solution was stirred under heating at 120° C. for 2 hours and then concentrated under reduced pressure. The resulting residue was purified by silica gel column chromatography (Biotage flash purification systems, eluent: ethyl, acetate/n-hexane, Rf=0.46 (ethyl acetate/n-hexane=1/2)) to give a crude product of a racemate of the title compound (326 mg). The racemate was purified with a Recycling Preparative Liquid Chromatograph to give a single enantiomer of the title compound (112 mg).

Purification conditions for the preparative chromatography are shown as follows.

Preparative apparatus: Recycling preparative liquid chromatograph LC-92XX NEXT SERIES, Japan Analytical Industry Co., Ltd.
Column: Daicel CHIRALPAK IA 2.0 cmφ×25 cm
Mobile phase: n-hexane:2-propanol=85:15
Flow rate: 10.0 mL/min
Detection: UV (254 nm)

Measurement of the resulting compound with a chiral column showed 5.2 minutes of the retention time for the resulting enantiomer with >99% ee of optical purity. The retention time for the opposite enantiomer was 3.1 minutes.

Analytical conditions for the chiral column are shown as follows.

Measurement apparatus: HPLC system, Shimadzu Corporation, High-Performance Liquid Chromatograph Prominence
Column: Daicel CHIRALPAK IA-3 0.46 cmφ×15 cm
Column temperature: 40° C.
Mobile phase: n-hexane:2-propanol=80:20
Flow rate: 1.0 mL/min
Detection: UV (254 nm)

$^1$H-NMR (400 MHz, CDCl$_3$) (s, 9H), 1.43-1.47 (m, 2H), 1.61-1.77 (m, 1H), 2.09-2.15 (m, 1H), 2.21-2.42 (m, 2H), 2.45 (s, 6H), 2.53-2.64 (m, 2H), 2.66-2.70 (m, 2H), 3.71 (s, 3H), 4.84 (s, 1H), 6.10 (d, J=1.8 Hz, 1H), 7.15 (dd, 1.9 Hz, 1H), 7.25 (d, J=8.1 Hz, 1H), 7.29 (d, J=2.1 Hz, 1H)

(Step 3)

3-{(S)-8a-[3-Chloro-4-(3,3-dimethyl-butyl)phenyl]-6,6-difluoro-2-oxo-1,5,6,7,8,8a-hexahydro-2H-quinazolin-3-yl}bicyclo[1.1.1]pentane-1-carboxylic acid

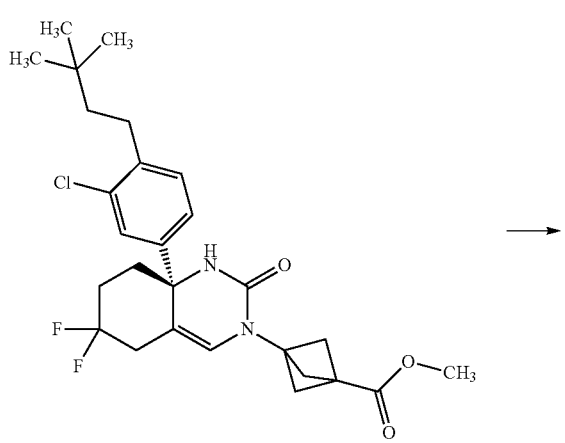

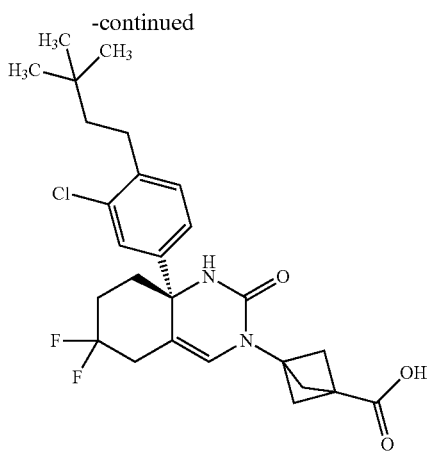

Methyl 3-{(S)-8a-[3-chloro-4-(3,3-dimethyl-butyl)phenyl]-6,6-difluoro-2-oxo-1,5,6,7,8,8a-hexahydro-2H-quinazolin-3-yl}bicyclo[1.1.1]pentane-1-carboxylate (94 mg) and methanol (2 mL) were mixed, and thereto was added 2N aqueous solution of sodium hydroxide (0.28 mL) at room temperature. The reaction solution was stirred at room temperature for 26 hours and then concentrated under reduced pressure. To the resulting residue were added 2N hydrochloric acid (0.28 mL) and water under ice cooling, and the mixture was extracted with a mixed solution of chloroform and methanol. The organic layer was dried over sodium sulfate. Sodium sulfate was removed with a filter, and then the filtrate was concentrated under reduced pressure to give the title compound (73.0 mg).

Example 109

(Step 1)

4-(2,2-Diethoxy-ethoxy)-3,4-dimethyl-pent-1-ene

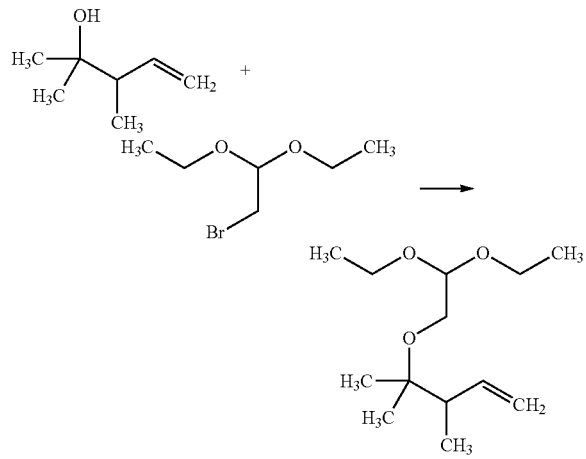

60 w % Sodium hydride (5.17 g) and tetrahydrofuran (66 mL) were mixed under argon gas, and thereto was added slowly a mixed solution of 2,3-dimethyl-pent-4-en-2-ol (5.0 g) in tetrahydrofuran (11 mL) under ice cooling. The reaction solution was stirred under ice cooling for 1 hour, and then thereto was added bromoacetaldehyde diethyl acetal (20.4 mL) under ice cooling. The reaction solution was stirred under heating at 80° C. for 18 hours. To the reaction solution was added water (20 mL) under ice cooling, and the mixture was stirred at room temperature for 1 hour. Then, the aqueous layer was extracted with ethyl acetate (twice). The organic layers were washed with saturated aqueous sodium chloride solution and dried over sodium sulfate. Sodium sulfate was removed with a filter, and then the filtrate was concentrated under reduced pressure. The resulting residue was purified by silica gel column chromatography (Biotage flash purification systems, eluent: ethyl acetate/nhexane, Rf=0.24 (ethyl acetate/n-hexane=1/19)). Evaporation of bromoacetaldehyde diethyl acetal included in the resulting crude product under reduced pressure gave a crude product of the title compound (2.80 g, 50 w % of bromoacetaldehyde diethyl acetal inclusive).

$^1$H-NMR (400 MHz, CDCl$_3$) 1.00 (d, J=6.9 Hz, 3H), 1.09 (s, 3H), 1.11 (s, 3H), 1.22 (t, J=7.1 Hz, 6H), 2.33 (dt, J=14.6, 6.9 Hz, 1H), 3.40 (dd, J=5.2, 2.7 Hz, 2H), 3.54-3.62 (m, 2H), 3.67-3.75 (m, 2H), 4.54 (t, J=5.3 Hz, 1H), 4.97-5.03 (m, 2H), 5.83 (ddd, J=17.7, 9.8, 7.3 Hz, 1H)

(Step 2)

(1,1,2-Trimethyl-but-3-enyloxy)acetaldehyde

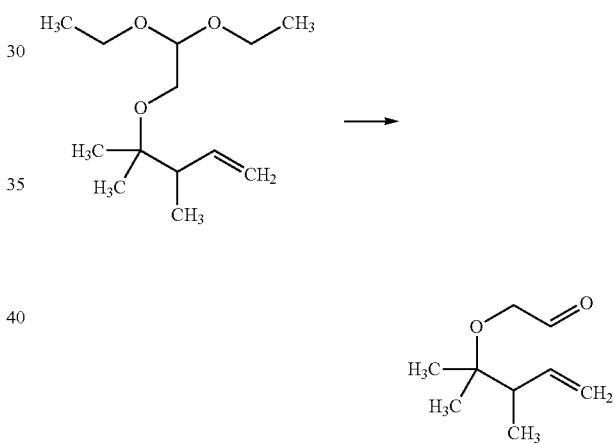

4-(2,2-Diethoxy-ethoxy)-3,4-dimethyl-pent-1-ene (2.80 g, 50 w % of bromoacetaldehyde diethyl acetal inclusive) and tetrahydrofuran (12.2 mL) were mixed, and thereto was added 2N hydrochloric acid (6.1 mL) under ice cooling. The reaction solution was stirred under heating at 60° C. for 4 hours. To the reaction solution was added potassium carbonate (0.84 g) under ice cooling. The reaction solution was concentrated under reduced pressure, and thereto was added saturated aqueous sodium chloride solution (10 mL). The aqueous layer was extracted with diethyl ether (twice). The organic layer was washed with saturated aqueous sodium chloride solution and dried over magnesium sulfate. Magnesium sulfate was removed with a filter, and then the filtrate was concentrated under reduced pressure to give a crude product of the title compound (2.03 g, 44 w % of tetrahydrofuran inclusive).

$^1$H-NMR (400 MHz, CDCl$_3$) 1.04 (d, J=6.9 Hz, 3H), 1.14 (s, 3H), 1.15 (s, 3H), 2.36 (t, J=7.4 Hz, 1H), 3.96 (t, J=1.3 Hz, 2H), 5.02-5.08 (m, 2H), 5.84 (ddd, J=17.9, 9.9, 7.4 Hz, 1H), 9.72 (t, J=1.3 Hz, 1H)

(Step 3)

(1,1,2-Trimethyl-but-3-enyloxy)acetaldehyde oxime

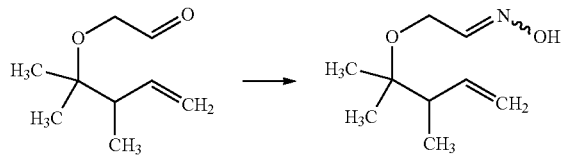

(1,1,2-Trimethyl-but-3-enyloxy)acetaldehyde (2.03 g, 44 w % of tetrahydrofuran inclusive) was mixed in ethanol (16.1 mL) and water (8.1 mL) under argon gas, and thereto were added sodium acetate (4.62 g) and hydroxylamine hydrochloride (2.24 g) at room temperature. The reaction solution was stirred under heating at 60° C. for 20 hours. The reaction solution was concentrated under reduced pressure, and thereto was added saturated aqueous sodium chloride solution (10 mL). The aqueous layer was extracted with ethyl acetate (twice). The organic layers were washed with saturated aqueous sodium chloride solution (twice) and dried over sodium sulfate. Sodium sulfate was removed with a filter, and then the filtrate was concentrated under reduced pressure. The resulting residue was purified by silica gel column chromatography (Biotage flash purification systems, eluent: ethyl acetate/n-hexane, Rf=0.38 (ethyl acetate/n-hexane=1/4)) to give a crude product of the title compound (1.00 g, 32 w % of ethyl acetate inclusive).

$^1$H-NMR (400 MHz, CDCl$_3$) 1.00 (d, J=6.7 Hz, 1.38H), 1.01 (d, J=6.7 Hz, 1.62H), 1.12 (s, 3H), 1.15 (s, 1.62H), 1.16 (s, 1.38H), 2.33-2.40 (m, 1H), 2.95 (s, 1H), 4.03 (dd, J=5.5, 2.1 Hz, 0.92H), 4.29 (d, J=3.2 Hz, 1.08H), 5.00-5.06 (m, 2H), 5.77-5.86 (m, 1H), 6.87 (t, J=3.6 Hz, 0.54H), 7.47 (t, J=5.4 Hz, 0.46H)

(Step 1)

4,5,5-Trimethyl-3,3a,4,5-tetrahydro-7H-pyrano[3,4-c]isoxazole

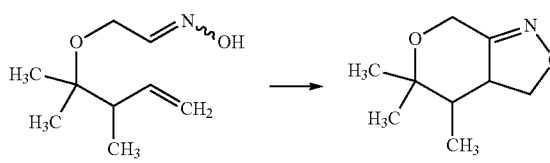

(1,1,2-Trimethyl-but-3-enyloxy)acetaldehyde oxime (1.00 g, 32 w % of ethyl acetate inclusive) and methanol (13.5 mL) were mixed, and thereto was added slowly trifluoroacetic acid (0.101 mL) under ice cooling. To the reaction solution was added (diacetoxyiodo)benzene (1.70 g) over 1 hour under ice cooling. The reaction solution was stirred under ice cooling for 20 minutes and stirred at room temperature for 1 hour. To the reaction solution were added saturated aqueous sodium hydrogen carbonate solution (7 mL) and sodium sulfite (248 mg), and then the mixture was stirred at room temperature for 30 minutes. The reaction solution was concentrated under reduced pressure, and the residue was extracted with ethyl acetate (twice). The organic layers were washed with saturated aqueous sodium chloride solution (twice) and dried over sodium sulfate. Sodium sulfate was removed with a filter, and then the filtrate was concentrated under reduced pressure. The resulting residue was purified by silica gel column chromatography (Biotage flash purification systems, eluent: ethyl acetate/n-hexane, Rf=0.24 (ethyl acetate/n-hexane=1/4)) to give the title compound (495 mg).

$^1$H-NMR (400 MHz, CDCl$_3$) 0.94 (d, J=6.9 Hz, 1.95H), 0.94 (d, J=7.2 Hz, 1.05H), 1.22 (s, 1.95H), 1.23 (s, 1.05H), 1.26 (s, 1.95H), 1.42 (s, 1.05H), 1.64-1.72 (m, 0.65H), 1.84 (dt, J=13.7, 6.1 Hz, 0.35H), 3.16 (q, J=11.0 Hz, 0.65H), 3.77 (dd, J=11.5, 7.9 Hz, 0.65H), 3.86-3.93 (m, 0.35H), 4.14 (t, J=8.5 Hz, 0.35H), 4.34 (ddd, J=15.3, 13.8, 1.1 Hz, 1H), 4.38 (dd, J=7.6, 4.0 Hz, 0.35H), 4.49 (d, J=9.6 Hz, 0.65H), 1.53 (d, J=9.3 Hz, 0.35H), 4.60 (dd, J=10.2, 7.8 Hz, 0.65H)

(Step 5)

7a-[3-Chloro-4-(3,3-dimethyl-butyl)phenyl]-4,5,5-trimethyl-hexahydro-pyrano[3,4-c]isoxazole

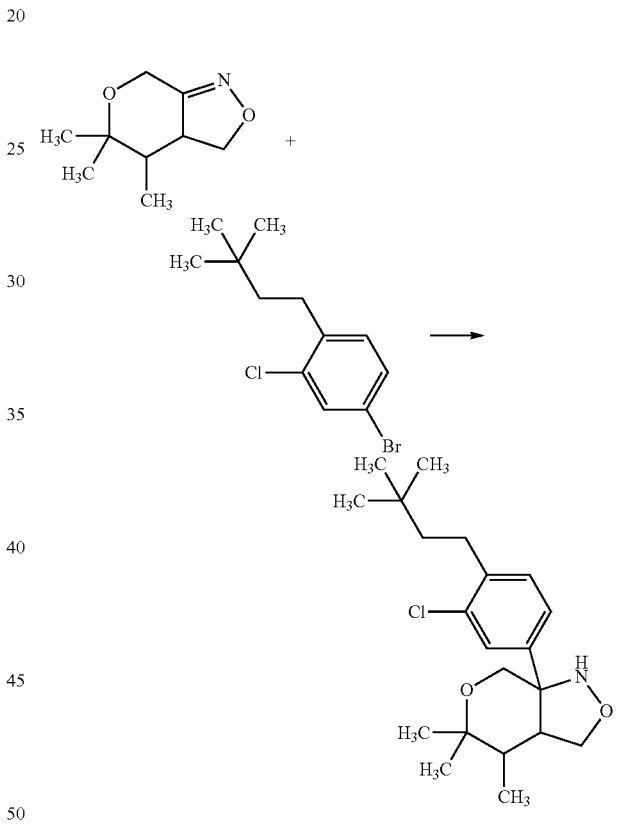

4-Bromo-2-chloro-1-(3,3-dimethyl-butyl)-benzene (0.553 g) was mixed in tetrahydrofuran (2.2 mL) and toluene (5.53 mL) under argon gas, and then thereto was added dropwise 1.54M n-butyllithium/n-hexane solution (1.25 mL) under cooling at −78° C. The reaction solution was stirred under cooling at −78° C. for 1 hour (Reaction solution A). 4,5,5-Trimethyl-3,3a,4,5-tetrahydro-7H-pyrano [3,4-c]isoxazole (250 mg) and toluene (15 mL) were mixed, and thereto was added boron trifluoride-diethyl ether complex (0.241 mL) under cooling at −78° C. The mixture was stirred for 10 minutes. Then, thereto was added dropwise slowly Reaction solution A over 25 minutes under cooling at −78° C. The reaction solution was stirred for 3 hours, and then thereto was added a saturated aqueous solution of ammonium chloride (0 mL) under cooling at −78° C. The mixture was stirred at room temperature for 30 minutes. The aqueous layer was extracted with ethyl acetate (twice). The organic layers were washed with saturated aqueous sodium chloride solution (twice) and dried over sodium sulfate. Sodium sulfate was removed with a filter, and then the filtrate was concentrated under reduced pressure. The resulting residue was purified by silica gel column chromatography (Biotage flash purification systems, eluent: ethyl acetate/n-hexane, Rf=0.48 (ethyl acetate/n-hexane=1/4)) to give a crude product the title compound (511 mg, 23 w % of ethyl acetate inclusive).

$^1$H-NMR (400 MHz, CDCl$_3$) 0.96 (d, J=6.7 Hz, 1.95H), 0.98 (s, 9H), 1.05 (d, J=7.4 Hz, 1.05H), 1.28 (s, 1.05H), 1.29 (s, 1.95H), 1.30 (s, 1.05H), 1.32 (s, 1.95H), 1.41-1.47 (m, 2H), 1.63 (dt, J=18.0, 6.9 Hz, 0.65H), 2.19 (t, J=7.1 Hz, 0.35H), 2.43 (dd, J=11.0, 5.0 Hz, 0.65H), 2.64-2.68 (m, 2H), 2.91 (td, J=9.2, 5.6 Hz, 0.35H), 3.55 (dd, J=7.4, 5.1 Hz, 0.65H), 3.64 (d, J=13.2 Hz, 0.65H), 3.74 (d, J=13.2 Hz, 0.35H), 3.82 (d, J=7.6 Hz, 0.35H), 3.85 (d, J=13.2 Hz, 1H), 3.89-4.20 (m, 1H), 5.73 (s, 0.35H), 6.24 (s, 0.65H), 7.18 (d, J=8.3 Hz, 0.35H), 7.19 (d, J=8.1 Hz, 0.65H), 7.36 (dd, J=8.2, 2.0 Hz, 0.35H), 7.42 (dd, J=8.0, 2.2 Hz, 0.65H), 7.52 (d, J=1.8 Hz, 0.35H), 7.57 (d, J=1.8 Hz, 0.65H)

(Step 6)

{5-Amino-5-[3-chloro-4-(3,3-dimethyl-butyl)phenyl]-2,2,3-trimethyl-tetrahydro-pyran-4-yl}methanol

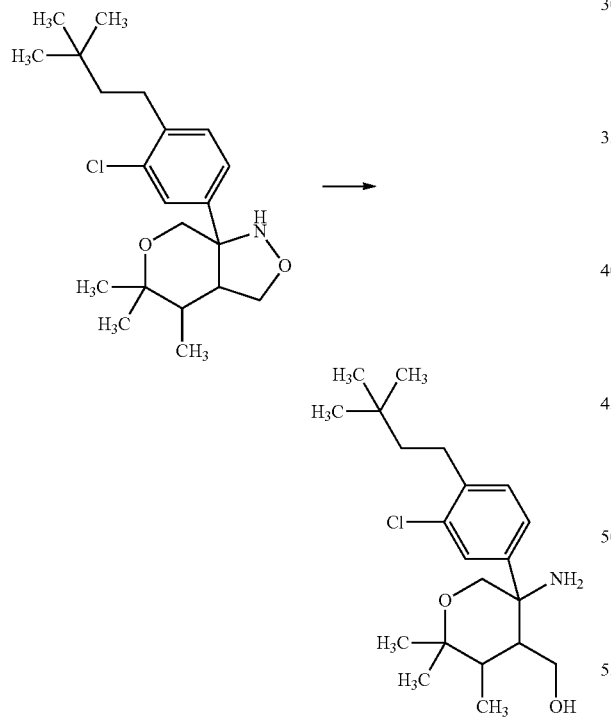

7a-[3-Chloro-4-(3,3-dimethyl-butyl)phenyl]-4,5,5-trimethyl-hexahydropyrano[3,4-c]isoxazole (392 mg) was mixed in acetic acid (5.9 mL), tetrahydrofuran (2 mL), and water (2 mL), and thereto was added zinc powder (700 mg) in parts over 25 minutes under heating at 60° C. The reaction solution was stirred under heating at 60° C. for 3 hours. To the reaction solution was added 28 w/w % ammonia water (10 mL) under ice cooling, and the aqueous layer was extracted with cyclopentyl methyl ether (three times). The organic layers were washed with saturated aqueous sodium chloride solution and dried over sodium sulfate. Sodium sulfate was removed with a filter, and then the filtrate was concentrated under reduced pressure to give a crude product of the title compound (467 mg, 21 w % of cyclopentyl methyl ether inclusive).

$^1$H-NMR (400 MHz, CDCl$_3$) 0.97 (d, J=6.7 Hz, 1.95H), 0.99 (s, 9H), 1.14 (d, J=8.6 Hz, 1.05H), 1.20 (s, 1.05H), 1.28 (s, 1.95H), 1.32 (s, 1.05H), 1.38 (s, 1.95H), 1.44-1.49 (m, 2H), 1.50-1.76 (m, 4H), 2.13-2.21 (m, 0.65H), 2.26-2.30 (m, 0.35H), 2.66-2.71 (m, 2H), 3.03 (d, J=12.5 Hz, 0.65H), 3.41 (dd, J=12.5, 1.4 Hz, 0.35H), 3.42 (dd, J=12.0, 1.4 Hz, 0.65H), 3.53 (dd, J=11.9, 3.1 Hz, 0.65H), 3.72 (d, J=5.1 Hz, 0.70H), 4.04 (d, J=12.0 Hz, 0.35H), 4.10 (d, J=12.0 Hz, 0.65H), 7.21 (d, J=7.9 Hz, 0.35H), 7.23 (d J=7.6 Hz, 0.65H), 7.27 (dd, J=8.0, 2.2 Hz, 0.65H), 7.40 (d, J=2.1 Hz, 0.65H), 7.42 (dd, J=7.7, 2.0 Hz, 0.35H), 7.57 (d, J=1.8 Hz, 0.35H)

(Step 7)

Methyl 3-(3-{3-[3-chloro-4-(3,3-dimethyl-butyl)phenyl]-4-hydroxymethyl-5,6,6-trimethyl-tetrahydro-pyran-3-yl}ureido)bicyclo[1.1.1]pentane-1-carboxylate

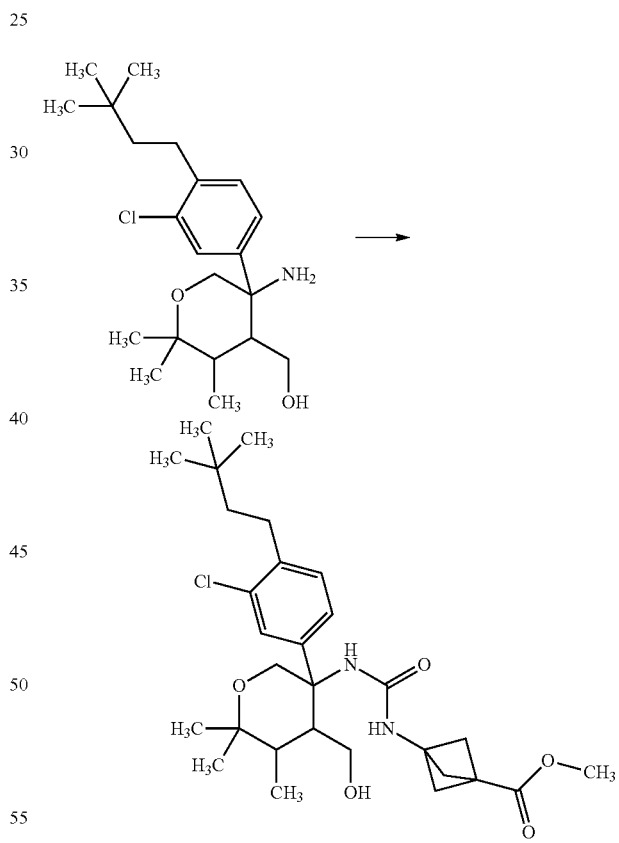

3-(Methoxycarbonyl)bicyclo[1.1.1]pentane-1-carboxylic acid (197 mg) and toluene (4 mL) were mixed under argon gas, and thereto were added diphenylphosphoryl azide (0.270 mL) and triethylamine (0.174 mL) at room temperature. The reaction solution was stirred under heating at 120° C. for 1 hour. To the reaction solution was added tetrahydrofuran (4 mL), and the mixture was added dropwise to a mixed solution of {5-amino-5-[3-chloro-4-(3,3-dimethyl-butyl)phenyl]-2,2,3-trimethyl-tetrahydro-pyran-4-yl}methanol (467 mg, 21 w % of cyclopentyl methyl ether inclusive) in tetrahydrofuran (4 mL) over 10 minutes under ice cooling. The reaction solution was stirred at room temperature for 13 hours, and then thereto was added N,N,N'-trimethylethylenediamine (0.0195 mL). The reaction solution was concentrated under reduced pressure. The resulting residue was purified by silica gel column chromatography (Biotage flash purification systems, eluent: acetone/n-hexane, Rf=0.50 (acetone/n-hexane=2/3)) to give a crude product of the title compound (511 mg, 5 w % of ethyl acetate inclusive).

$^1$H-NMR (400 MHz, CDCl$_3$) 0.90-0.99 (m, 3H), 0.97 (s, 9H), 1.10 (s, 1.05H), 1.21 (s, 1.95H), 1.32 (s, 1.95H), 1.42-1.49 (m, 2H), 1.43 (s, 1.05H), 1.50-1.73 (m, 1H), 1.98-2.41 (m, 2H), 2.29 (s, 2.1H), 2.38 (s, 3.9H), 2.61-2.67 (m, 2H), 3.58-3.76 (m, 23), 3.67 (s, 1.05H), 3.69 (s, 1.95H), 3.79-3.87 (m, 1.30H), 4.01-4.09 (m, 0.70H), 4.68 (s, 0.35H), 4.97 (s, 0.65H), 5.94 (s, 0.65H), 6.21 (s, 0.35H), 7.12-7.17 (m, 1.65H), 7.25-7.27 (m, 0.65H), 7.45 (d, J=8.1 Hz, 0.35H), 7.51 (d, J=1.8 Hz, 0.35H)

(Step 8)

Methyl 3-{8a-[3-chloro-4-(3,3-dimethyl-butyl)phenyl]-5,6,6-trimethyl-2-oxo-1,2,5,6,8,8a-hexahydropyrano[3,4-d]pyrimidin-3-yl}bicyclo[1.1.1]pentane-1-carboxylate

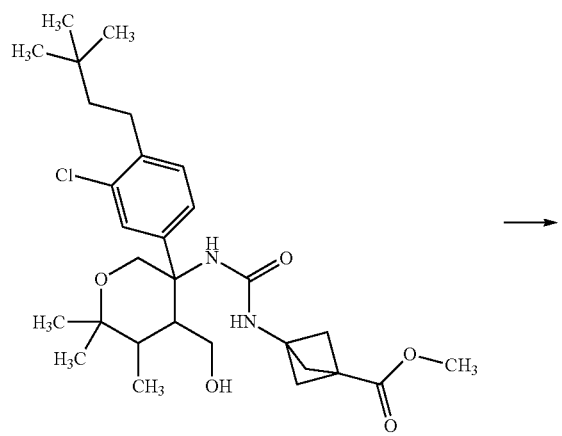

→

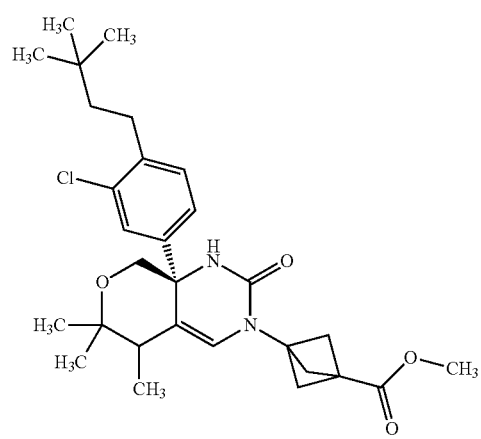

Methyl 3-(3-{3-[3-chloro-4-(3,3-dimethyl-butyl)phenyl]-4-hydroxymethyl-5,6,6-trimethyl-tetrahydro-pyran-3-yl}ureido)bicyclo[1.1.1]pentane-1-carboxylate (511 mg, 5 w % of ethyl acetate inclusive) and chloroform (4.8 mL) were mixed, and thereto were added (diacetoxyiodo)benzene (330 mg) and 2,2,6,6-tetramethylpiperidin-1-oxyl radical (14.1 mg) at room temperature. The reaction solution was stirred at room temperature for 19 hours, and then thereto were added 20 w/w % aqueous sodium sulfite solution and saturated aqueous sodium hydrogen carbonate solution at room temperature. The mixture was stirred at room temperature 30 minutes. The aqueous layer was extracted with ethyl acetate (twice). The organic layers were washed with saturated aqueous sodium chloride solution and dried over magnesium sulfate. Magnesium sulfate was removed with a filter, and then the filtrate was concentrated under reduced pressure. The resulting residue and toluene (9.7 mL) were mixed, and thereto was added pentafluoroaniline trifluoromethanesulfonate (15 mg) at room temperature. The reaction solution was stirred under heating at 120° C. for 1 hour 30 minutes and then concentrated under reduced pressure. The resulting residue was purified by silica gel column chromatography (Biotage flash purification systems, eluent: ethyl acetate/n-hexane, Rf=0.40 (ethyl acetate/n-hexane=2/3)) to give a diastereomeric mixture of the title compound (434 mg). The diastereomeric mixture was purified with a Recycling Preparative Liquid Chromatograph to give a single enantiomer of the title compound (39.8 mg).

Purification conditions for the preparative chromatography are shown as follows.

Preparative apparatus: Recycling preparative liquid chromatograph LC-92 XX NEXT SERIES, Japan Analytical Industry Co., Ltd.

Column: Daicel CHIRALPAK IA 2.0 cmφ×25 cm

Mobile phase: n-hexane:2-propanol=85:15

Flow rate: 10.0 mL/min

Detection: UV (254 nm)

Measurement of the resulting compound with a chiral column showed 7.6 minutes of the retention time for the resulting enantiomer with >99% ee of optical purity. The retention time for a diastereomer on the methyl group was 9.8 minutes, and the retention time for a diastereomer on the phenyl group as well as the opposite enantiomer was 3.9 minutes.

Analytical conditions for the chiral column are shown as follows.

Measurement apparatus: HPLC system, Shimadzu Corporation, High-Performance Liquid Chromatograph Prominence Column: Daicel CHIRALPAK IA-3 0.46 cmφ×15 cm Column temperature: 30° C.

Mobile phase: n-hexane:2-propanol=85:15

Flow rate: 1.0 mL/min

Detection: UV (254 nm)

$^1$H-NMR (400 MHz, CDCl$_3$) 0.88 (d, J=6.9 Hz, 3H), 0.98 (s, 9H), 1.14 (s, 3H), 1.21 (s, 3H), 1.42-1.47 (m, 2H), 2.09 (ddd, J=13.8, 7.1, 2.4 Hz, 1H), 2.49 (s, 6H), 2.64-2.69 (m, 2H), 3.71 (s, 3H), 3.90 (d, J=11.6 Hz, 1H), 4.08 (d, J=11.6 Hz, 1H), 4.45 (s, 1H), 5.74 (d, J=1.8 Hz, 1H), 7.19 (d, J=8.1 Hz, 1H), 7.33 (dd, J=8.0, 2.0 Hz, 1H), 7.50 (d, J=2.1 Hz, 1H)

(Step 9)

3-{(S)-8a-[3-Chloro-4-(3,3-dimethyl-butyl)phenyl]-5,6,6-trimethyl-2-oxo-1,2,5,6,8,8a-hexahydro-pyrano[3,4-d]pyrimidin-3-yl}bicyclo[1.1.1]pentane-1-carboxylic acid

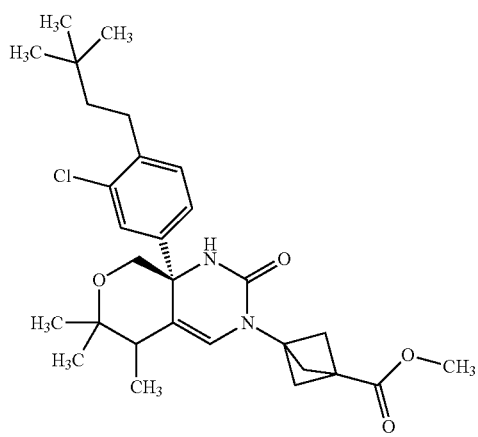

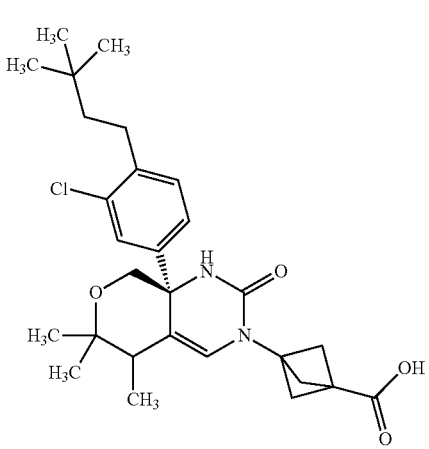

Methyl 3-{(S)-8a-[3-chloro-4-(3,3-dimethyl-butyl)phenyl]-5,6,6-trimethyl-2-oxo-1,2,5,6,8,8a-hexahydro-pyrano[3,4-d]pyrimidin-3-yl}bicyclo[1.1.1]pentane-1-carboxylate (39.8 mg) was mixed in tetrahydrofuran (0.398 mL) and methanol (0.398 mL) under nitrogen gas, and thereto was added 2N aqueous solution of sodium hydroxide (0.0791 mL) at room temperature. The reaction solution was stirred at room temperature for 16 hours and then concentrated under reduced pressure. To the resulting residue was added water (1 mL), and then thereto was added 2N hydrochloric acid (0.0791 mL) under ice cooling. The precipitated solid was collected by filtration to give the title compound (19.7 mg).

Example 114

(Step 1)

Methyl 3-(3-{(3R,4S)-1-[4-(3-tert-butyl-2,2-difluoro-cyclopropyl)-3-chloro-phenyl]-2-hydroxymethyl-3,4-dimethyl-cyclohexyl}ureido)bicyclo[1.1.1]pentane-1-carboxylate

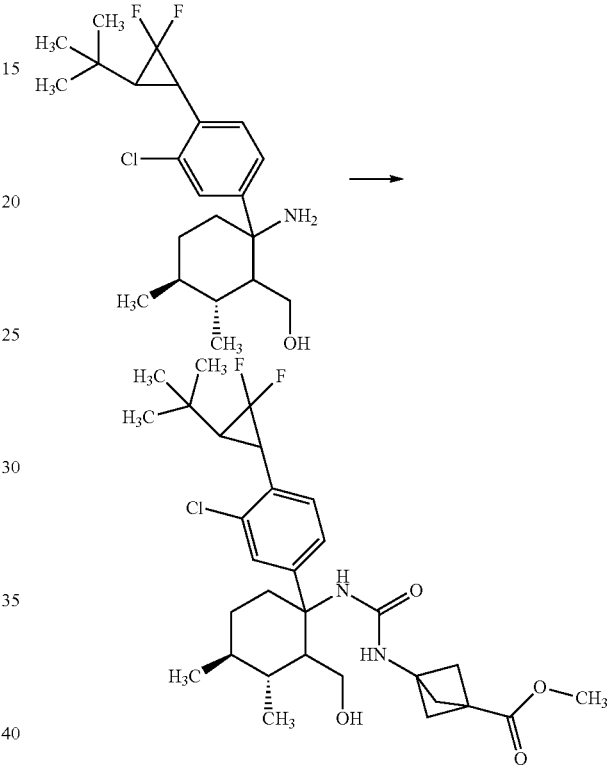

3-(Methoxycarbonyl)bicyclo[1.1.1]pentane-1-carboxylic acid (97.9 mg) was mixed in toluene (2 mL) and tetrahydrofuran (2 mL) under arson gas, and thereto were added triethylamine (0.866 mL) and diphenylphosphoryl azide (0.134 mL) at room temperature. The reaction solution was stirred under heating at 120° C. for 1 hour. The reaction solution was added dropwise to a mixed solution of {(5S, 6R)-2-amino-2-[4-(3-tert-butyl-2,2-difluoro-cyclopropyl)-3-chloro-phenyl]-5,6-dimethyl-cyclohexyl}methanol (200 mg) in tetrahydrofuran (4 mL) under ice cooling. The reaction solution was stirred at room temperature for 13 hours, and then thereto was added trimethylethylenediamine (0.129 mL). The reaction solution was concentrated under reduced pressure, and then the resulting residue was purified by silica gel column chromatography (Biotage flash purification systems, eluent: acetone/n-hexane) to give the title compound (328 mg).

$^1$H-NMR (400 MHz, CDCl$_3$) 1.02-1.05 (m, 6H), 1.11-1.11 (m, 9H), 1.30-1.34 (m, 1H), 1.37-1.42 (m, 1H), 1.46-1.48 (m, 1H), 1.61-1.73 (m, 2H), 1.78-1.85 (m, 1H), 2.39-2.35 (m, 7H), 2.73-2.80 (m, 1H), 3.04 (d, J=13.64 Hz, 1H), 3.32 (d, J=11.79 Hz, 1H), 3.69 (s, 3H), 3.74 (d, J=11.33 Hz, 1H), 4.73 (s, 1H), 6.37 (s, 1H), 7.13-7.15 (m, 2H), 7.32 (d, J=14.57 Hz, 1H)

(Step 2)

Methyl 3-{(5R,6S)-8a-[4-(3-tert-butyl-2,2-difluoro-cyclopropyl)-3-chloro-phenyl]-5,6-dimethyl-2-oxo-1,5,6,7,8,8a-hexahydro-2H-quinazolin-3-yl}bicyclo[1.1.1]pentane-1-carboxylate

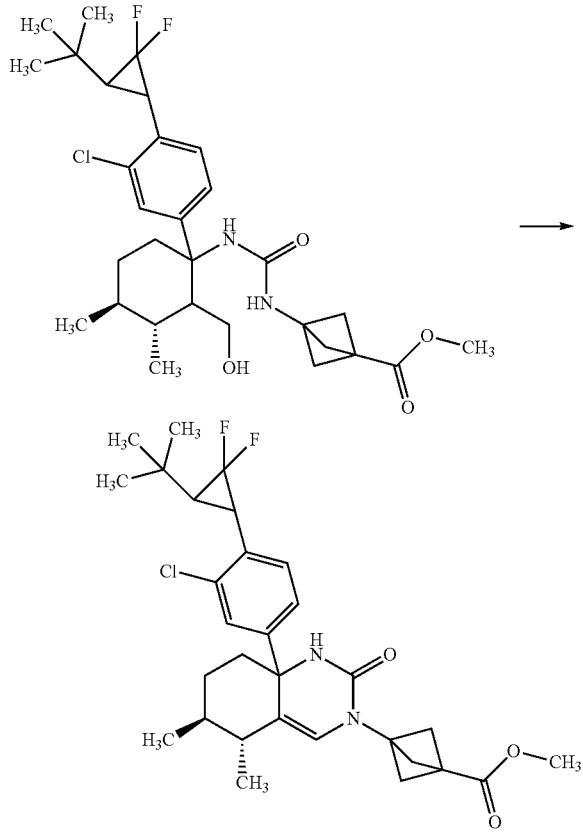

Methyl 3-(3-{(3R,4S)-1-[4-(3-tert-butyl-2,2-difluoro-cyclopropyl)-3-chloro-phenyl]-2-hydroxymethyl-3,4-dimethyl-cyclohexyl}ureido)bicyclo[1.1.1]pentane-1-carboxylate (216 mg) and chloroform (2.2 mL) were mixed, and thereto were added (diacetoxyiodo)benzene (139 mg) and 2,2,6,6-tetramethylpiperidin-1-oxyl radical (6.0 mg) at room temperature. The reaction solution was stirred at room temperature for 14 hours, and then thereto were added 20 w/w % aqueous sodium sulfite solution and 5 w/w % aqueous solution of sodium hydrogen carbonate at room temperature. The mixture was stirred at room temperature for 30 minutes and then extracted with ethyl acetate (twice). The organic layer was washed with saturated aqueous sodium chloride solution and dried over magnesium sulfate. Magnesium sulfate was removed with a filter, and then the filtrate was concentrated under reduced pressure. The resulting residue and toluene (4.3 mL) were mixed, and then thereto was added pentafluoroaniline trifluoromethanesulfonate (6.3 mg) at room temperature. The reaction solution was stirred under heating at 120° C. for 3 hours 30 minutes, and then stirred under microwave radiation (100 W, 120° C.) for 30 minutes. The reaction solution was concentrated under reduced pressure, and then the resulting residue was purified by silica gel column chromatography (Biotage flash Purification systems, eluent: ethyl acetate/n-hexane) to give a diastereomeric mixture of the title compound (61.2 mg). The diastereomeric mixture was purified with a Recycling Preparative Liquid Chromatograph to give a single enantiomer of the title compound (18.0 mg).

Purification conditions for the preparative chromatography are shown as follows.

Preparative apparatus: Recycling preparative liquid chromatograph LC-92XX NEXT SERIES, Japan Analytical Industry Co., Ltd.

Column: Daicel CHIRALPAK IA 2.0 cmφ×25 cm

Mobile phase: n-hexane:2-propanol=88:12

Flow rate: 10.0 mL/min

Detection: UV (254 nm)

Measurement of the resulting compound with a chiral column showed 8.0 minutes of the retention time for the resulting enantiomer with >99% ee of optical purity. The retention time for the opposite enantiomer on the phenyl group was 4.8 minutes.

Analytical conditions for the chiral column are shown as follows.

Measurement apparatus: HPLC system, Shimadzu Corporation, High-Performance Liquid Chromatograph Prominence Column: Daicel CHIRALPAK IA-3 0.46 cmφ×15 cm Column temperature: 30° C.

Mobile phase: n-hexane:2-propanol=85:15

Flow rate: 1.0 mL/min

Detection: UV (254 nm)

$^1$H-NMR (400 MHz, CDCl$_3$) 0.65 (d, J=7.40 Hz, 3H), 1.03 (d, J=6.94 Hz, 3H), 1.12 (s, 9H), 1.36-1.42 (m, 1H), 1.62-1.74 (m, 2H), 1.71-1.86 (m, 1H), 2.05-2.09 (m, 15H), 2.11-2.16 (m, 1H), 2.31-2.25 (m, 1H), 2.48 (s, 6H), 2.19 (dd, J=14.33, 9.48 Hz, 1H), 3.71 (s, 3H), 1.44 (s, 1H), 6.01 (s, 1H), 7.17 (d, J=8.09 Hz, 1H), 7.24 (dd, J=8.32, 2.08 Hz, 1H), 7.39 (d, J=2.08 Hz, 1H)

(Step 3)

3-{(5R,6S)-8a-[4-(3-tert-Butyl-2,2-difluoro-cyclopropyl)-3-chloro-phenyl]-5,6-dimethyl-2-oxo-1,5,6,7,8,8a-hexahydro-2H-quinazolin-3-yl}bicyclo[1.1.1]pentane-1-carboxylic acid

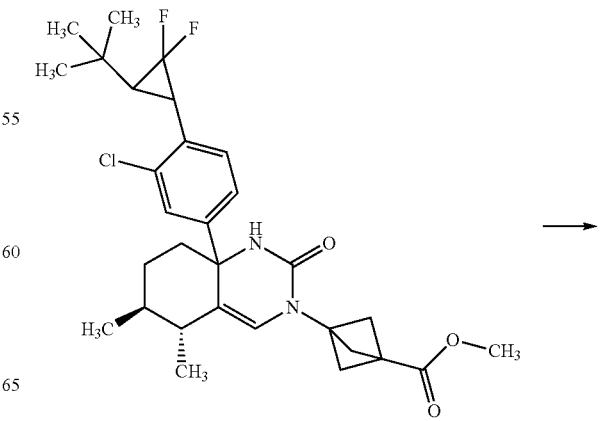

-continued

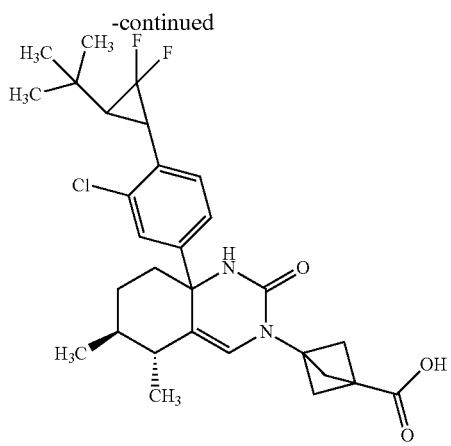

Methyl 3-{(5R,6S)-8a-[4-(3-tert-butyl-2,2-difluoro-cyclopropyl)-3-chloro-phenyl]-5,6-dimethyl-2-oxo-1,5,6,7,8,8a-hexahydro-2H-quinazolin-3-yl}bicyclo[1.1.1]pentane-1-carboxylate (18.0 mg) was mixed in tetrahydrofuran (0.18 mL) and methanol (0.18 mL), and then thereto was added 2N aqueous solution of sodium hydroxide (0.0329 mL) at room temperature. The reaction solution was stirred at room temperature for 7 hours 30 minutes and then concentrated under reduced pressure. To the resulting residue was added water (1 mL), and then thereto was added 2N hydrochloric acid (0.0329 mL) under ice cooling. The precipitated solid was collected by filtration to give the title compound (14.7 mg).

Example 115

(Step 1)

(2R,3S)-2,3-Dimethyl-pent-4-enoic acid methoxy-methyl-amide

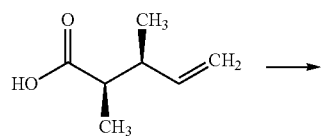

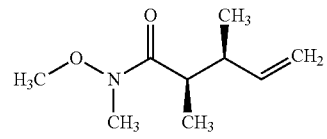

(2R,3S)-2,3-Dimethyl-pent-4-enoic acid (3.5 g), N,O-dimethylhydroxylamine hydrochloride (4.0 g) and 1-hydroxybenzotriazole monohydrate (6.3 g) were mixed in dimethylformamide (20 mL) under nitrogen gas, and thereto were added triethylamine (7.6 mL) and 1-ethyl-3-(3-dimethylaminopropyl)carbodiimide hydrochloride (7.9 g) under ice cooling. The reaction solution was stirred at room temperature overnight. Then, thereto was added water (175 mL), and the aqueous layer was extracted with ethyl acetate/n-hexane=1/1. The organic layer was washed with saturated aqueous sodium hydrogen. carbonate solution, 1N hydrochloric acid, and saturated aqueous sodium chloride solution and dried over magnesium sulfate. Magnesium sulfate was removed with a filter, and then the filtrate was concentrated under reduced pressure. The resulting residue was purified by silica gel column chromatography (Biotage flash purification systems, eluent: ethyl acetate/n-hexane, Rf=0.25 (ethyl acetate/n-hexane=1/4)) to give the title compound (4.4 g).

$^1$H-NMR (400 MHz, CDCl$_3$) 0.99-1.03 (m, 3H), 1.06-1.11 (m, 3H), 2.40-2.49 (m, 1H), 2.74-2.87 (m, 1H), 3.15 (s, 3H), 3.66 (s, 3H), 4.89-5.03 (m 2H), 5.59-5.83 (m, 1H)

(Step 2)

(2R,3S)-2,3-Dimethyl-pent-4-enal

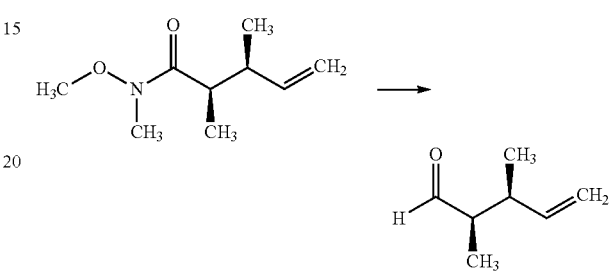

(2R,3S)-2,3-Dimethyl-pent-4-enoic acid methoxy-methyl-amide (4.4 g) and tetrahydrofuran (44 mL) were mixed under nitrogen gas, and thereto was added dropwise 1.02M diisobutylaluminum hydride/n-hexane solution (30 mL) under cooling at −78° C. The mixture was stirred under cooling at −78° C. for 2.5 hours, and then thereto was added dropwise 1.5M aqueous sulfuric acid solution (41 mL). The mixture was stirred for 2 hours under ice cooling, and then the aqueous layer was extracted with methyl tert-butyl ether. The organic layer was washed with 1.0M sulfuric acid and saturated aqueous sodium chloride solution and dried over magnesium sulfate. Magnesium sulfate was removed with a filter, and then the filtrate was concentrated under reduced pressure to give a crude product of the title compound (3.7 g, 39 w % of tetrahydrofuran inclusive).

$^1$H-NMR (400 MHz, CDCl$_3$) 0.99-1.05 (m, 6H), 2.30-2.41 (m, 1H), 2.55-2.66 (m, 1H), 4.97-5.09 (m, 2H), 5.72-5.85 (m, 1H), 9.63-9.68 (m, 1H)

(Step 3)

Ethyl (E)-(4S,5S)-4,5-dimethyl-hepta-2,6-dienoate

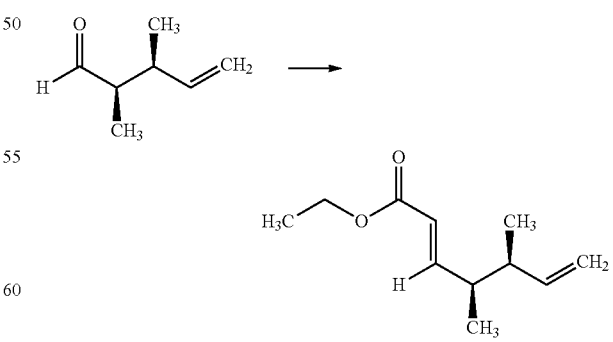

Sodium hydride (960 mg) and tetrahydrofuran (34 mL) were mixed under nitrogen gas, and thereto was added dropwise ethyl diphenylphosphonoacetate (5.2 mL) under ice cooling. The mixture was stirred at room temperature for 30 minutes, and then thereto was added dropwise a mixed solution of (2R,3S)-2,3-dimethyl-pent-4-enal (2.24 g) in tetrahydrofuran (22 mL) under ice cooling. The reaction solution was stirred at room temperature overnight. Then, thereto were added saturated aqueous ammonium chloride solution and water at room temperature, and the organic solvent was evaporated under reduced pressure. The aqueous layer was extracted with ethyl acetate, and the organic layer was washed with saturated aqueous sodium chloride solution and dried over magnesium sulfate. Magnesium sulfate was removed with a filter, and then the filtrate was concentrated under reduced pressure. The resulting residue was purified by silica gel column chromatography (Biotage flash purification systems, eluent: ethyl acetate/n-hexane) to give the title compound (3.2 g).

(Step 4)

Ethyl (4S,5S)-4,5-dimethyl-hept-6-enoate

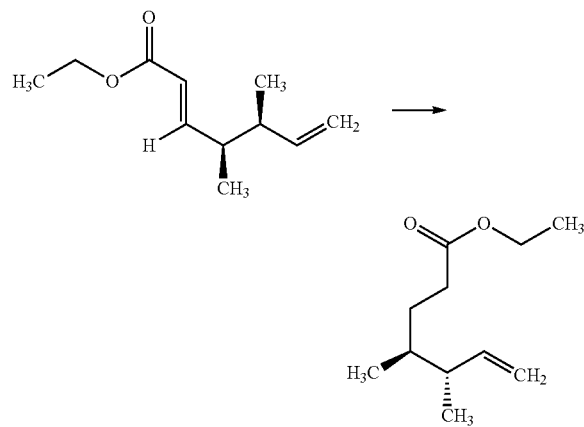

(E)-(4S,5S)-4,5-Dimethyl-hepta-2,6-dienoic acidethyl ester (3.2 g) was mixed in tetrahydrofuran (45 mL) and methanol (26 mL) under nitrogen gas, and thereto was added copper (I) chloride. Then, thereto was added sodium borohydride (4.7 g) under ice cooling. The reaction solution was stirred for 5 hours under ice cooling. To the reaction solution was added 1N hydrochloric acid (33 mL). Insoluble substances were removed with a filter, and the filtrate was concentrated under reduced pressure. To the resulting residue was added ethyl acetate, and the mixture was separated. The organic layer was washed with 1N hydrochloric acid and saturated aqueous sodium chloride solution. The resultant was dried over magnesium sulfate, and then magnesium sulfate was removed with a filter. The filtrate was concentrated under reduced pressure. The resulting residue was purified by silica gel column chromatography (eluent: ethyl acetate/n-hexane=1/1), and then azeotroped with n-hexane to give the title compound (2.8 g, 6 w % of ethyl (E)-(4S, 5S)-4,5-dimethyl-hepta-2,6-dienoate inclusive).

$^1$H-NMR (400 MHz, CDCl$_3$) 0.79-0.84 (m, 3H), 0.92-0.96 (m, 3H), 1.21-1.28 (m, 3H), 1.34-1.47 (m, 2H), 1.70-1.80 (m, 1H), 2.02-2.12 (m, 1H), 2.15-2.39 (m, 2H), 4.05-4.15 (m, 2H), 4.90-4.98 (m, 2H), 5.64-5.79 (m, 1H)

(Step 5)

(4S,5S)-4,5-Dimethyl-hept-6-enal

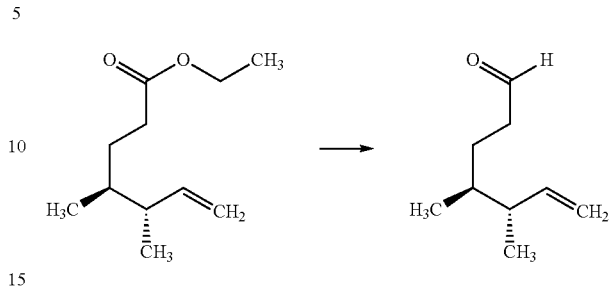

Ethyl (4S,5S)-4,5-dimethyl-hept-6-enoate (2.8 g) and dichloromethane (150 mL) were mixed under nitrogen gas, and thereto was added dropwise diisobutylaluminum hydride/n-hexane solution (19 mL) under cooling at −78° C. The mixture was stirred under cooling at −78° C. for 30 minutes, and then thereto was added dropwise methanol (7.6 mL). Then, thereto was added a saturated aqueous solution of Rochelle salt (76 mL) under ice cooling. Then, the mixture was stirred at room temperature for 2 hours, and thereto was added diethyl ether. The mixture was separated, and the organic layer was washed with saturated aqueous sodium chloride solution. The solution was dried over magnesium sulfate, and her magnesium sulfate was removed with a filter. The filtrate was concentrated under reduced pressure to give a crude product of the title compound (2.6 g).

$^1$H-NMR (400 MHz, CDCl$_3$) 0.81-0.85 (m, 3H), 0.93-0.97 (m, 3H), 1.34-1.45 (m, 25H), 1.70-1.80 (m, 1H), 2.04-2.11 (m, 1H), 2.30-2.50 (m, 2H), 4.90-4.97 (m, 2H), 5.66-5.77 (m, 1H), 9.74-9.76 (m, 1H)

(Step 6)

(4S,5S)-4,5-Dimethyl-hept-6-enal-oxime

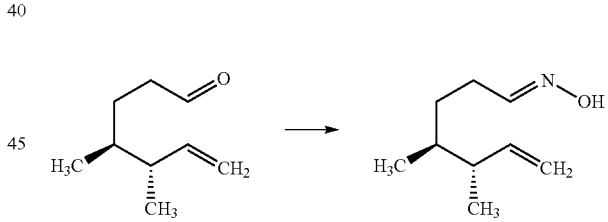

(4S,5S)-4,5-Dimethyl-hept-6-enal (2.1 g) was mixed in water (15 mL) and ethanol (30 mL) under nitrogen gas, and thereto were added sodium acetate (8.7 g) and hydroxylamine hydrochloride (4.2 g) at room temperature. The reaction solution was stirred under heating at 60° C. overnight. The reaction solution was concentrated under reduced pressure, and thereto were added ethyl acetate and water. The solution was separated. The aqueous layer was extracted with ethyl acetate (twice). The organic layer was washed with saturated aqueous sodium chloride solution and concentrated under reduced pressure. The resulting residue was purified by silica gel column chromatography (eluent: ethyl acetate/n-hexane, Rf=0.1 (ethyl acetate/n-hexane=1/10)) to give the title compound (2.0 g).

$^1$H-NMR (400 MHz, CDCl$_3$) 0.83-0.90 (m, 3H), 0.92-0.97 (m, 3H), 1.21-1.67 (m, 3H), 2.04-2.44 (m, 3H), 4.93-5.01 (m, 2H), 5.66-5.80 (m, 1H), 6.67-6.72 (m, 0.5H), 7.38-7.46 (m, 0.5H)

(Step 7)

(4R,5S)-4,5-Dimethyl-3,3a,4,5,6,7-hexahydro-benzo[c]isoxazole

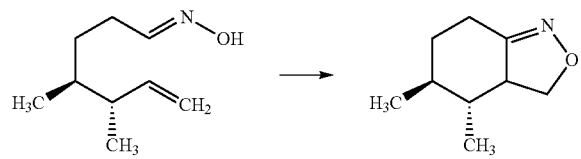

(4S,5S)-4,5-Dimethyl-hept-6-enal-oxime (2.0 g) and methanol (40 mL) were mixed under nitrogen gas, and thereto were added trifluoroacetic acid (0.3 mL) and (diacetoxyiodo)benzene (5.5 g) under sodium chloride-ice cooling. The reaction solution was stirred under ice cooling for 20 minutes and stirred at room temperature for 1 hour. Then, thereto were added saturated aqueous sodium hydrogen carbonate solution (20 ml) and sodium sulfite (0.8 g) under ice cooling, and the mixture was stirred at room temperature for 30 minutes. The reaction solution was concentrated under reduced pressure, and the aqueous layer was extracted with ethyl acetate (twice). The organic layer was washed with saturated aqueous sodium chloride solution (twice) and dried over sodium sulfate. Then, sodium sulfate was removed with a filter, and the filtrate was concentrated under reduced pressure. The resulting residue was purified by silica gel column chromatography (Biotage flash purification systems, eluent: ethyl acetate/n-hexane, Rf=0.1 (ethyl acetate/n-hexane=1/20)) to give the title compound (1.4 g).

$^1$H-NMR (400 MHz, CDCl$_3$) 0.93-0.98 (m, 6H), 1.08-1.34 (m, 2H), 1.77-1.99 (m, 2H), 2.09-2.21 (m, 1H), 2.69-2.78 (m, 2H), 2.78-2.89 (m, 1H), 3.76-3.85 (m, 1H), 4.45-4.52 (m, 1H)

(Step 8)

(4R,5S)-7a-[4-(3-tert-Butyl-2,2-difluoro-cyclopropyl)-3-chloro-phenyl]-4,5-dimethyl-octahydro-benzo[c]isoxazole

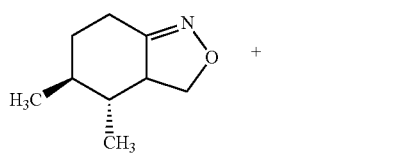

+

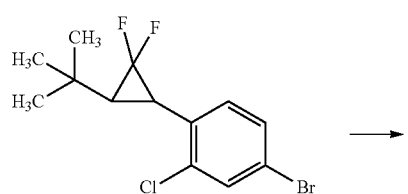

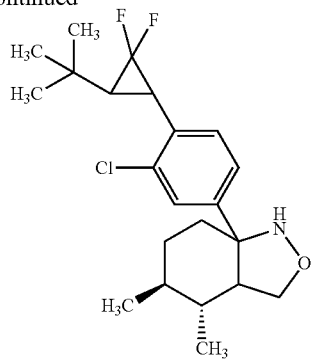

4-Bromo-1-(3-tert-butyl-2,2-difluoro-cyclopropyl)-2-chlorobenzene (648 mg) and tetrahydrofuran (2.6 mL) were mixed under argon gas, and thereto was added dropwise 1.5M n-butyllithium/n-hexane solution (13 mL) under cooling at −78° C. The reaction solution was stirred under cooling at −78° C. for 1 hour (Reaction solution A). To a mixed solution of (4R,5S)-4,5-dimethyl-3,3a,4,5,6,7-hexahydro-benzo[c]isoxazole (245 mg) in toluene (6.5 mL) were added boron trifluoride-diethyl ether complex and Reaction solution A under cooling at −78° C. The reaction solution was stirred for 2 hours, and then thereto was added saturated aqueous ammonium chloride solution (8 mL) under cooling at −78° C. The mixture was stirred at room temperature, and then thereto was added ethyl acetate. The mixture was separated. The organic layer was washed with saturated aqueous sodium chloride solution and dried over sodium sulfate. Sodium sulfate was removed with a filter, and then the filtrate was concentrated under reduced pressure. The resulting residue was purified by silica gel column chromatography (Biotage flash purification systems, eluent: ethyl acetate/n-hexane, Rf=0.30 (ethyl acetate/n-hexane=1/10)) to give the title compound (357 mg, 13 w % of ethyl acetate inclusive).

$^1$H-NMR (400 MHz, CDCl$_3$) 0.97-1.01 (m, 6H), 1.03-1.20 (m, 11H), 1.27-1.37 (m, 1H), 1.59-1.78 (m, 2H), 1.83-1.99 (m, 2H), 2.16-2.28 (m, 1H), 2.71-2.83 (m, 1H), 3.43-3.51 (m, 1H), 3.76-3.82 (m, 1H), 5.83 (br s, 1H), 7.11-7.17 (m, 1H), 7.42-7.49 (m, 1H), 7.58-7.67 (m, 1H)

(Step 9)

{(5S,6R)-2-Amino-2-[4-(3-tert-butyl-2,2-difluoro-cyclopropyl)-3-chloro-phenyl]-5,6-dimethyl-cyclohexyl}methanol

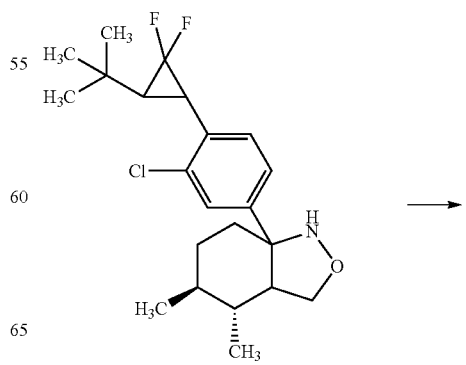

153
-continued

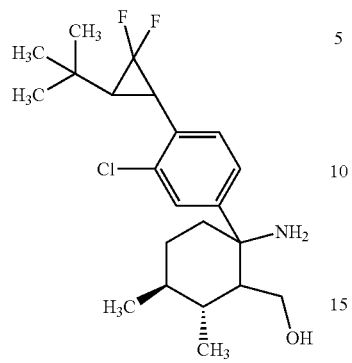

(4R,5S)-7a-[4-(3-tert-Butyl-2,2-difluoro-cyclopropyl)-3-chloro-phenyl]-4,5-dimethyl-octahydro-benzo[c]isoxazole (311 mg) was mixed in acetic acid (4.7 mL), tetrahydrofuran (1.6 mL), and water (1.6 mL) under nitrogen gas, and thereto was added powder (510 mg) in several parts under heating at 60° C. The reaction solution was stirred under heating at 60° C. for 2 hours 20 minutes. To the reaction solution was added dropwise ammonia water (8 mL) under ice cooling. The aqueous layer was extracted with cyclopentyl methyl ether (three times), and then washed with saturated aqueous sodium chloride solution and dried over sodium sulfate. Sodium sulfate was removed with a filter, and then the filtrate was concentrated under reduced pressure to give a crude product of the title compound (492 mg).

$^1$H-NMR (400 MHz, CDCl$_3$) 1.03-1.06 (m, 6H), 1.11 (s, 9H), 1.18-1.33 (m, 2H), 1.34-1.42 (m, 1H), 1.44-1.77 (m, 5H), 2.01-2.14 (m, 1H), 2.73-2.83 (m, 1H), 3.21-3.25 (m, 1H), 3.50-3.58 (m, 1H), 3.75-3.32 (m, 2H), 7.13-7.21 (m, 1H), 7.30-7.39 (m, 1H), 7.44-7.56 (m, 1H)

(Step 10)

Methyl 4-(3-{(3R,4S)-1-[4-(3-tert-butyl-2,2-difluoro-cyclopropyl)-3-chloro-phenyl]-2-hydroxymethyl-3,4-dimethyl-cyclohexyl}ureido)bicyclo[2.1.1]hexane-1-carboxylate

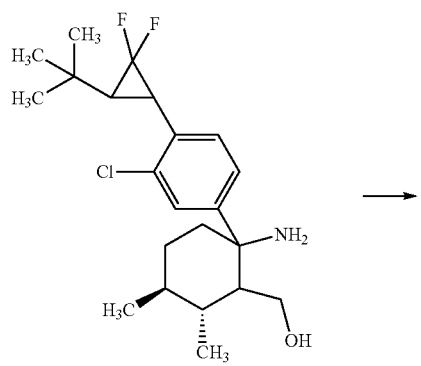

154
-continued

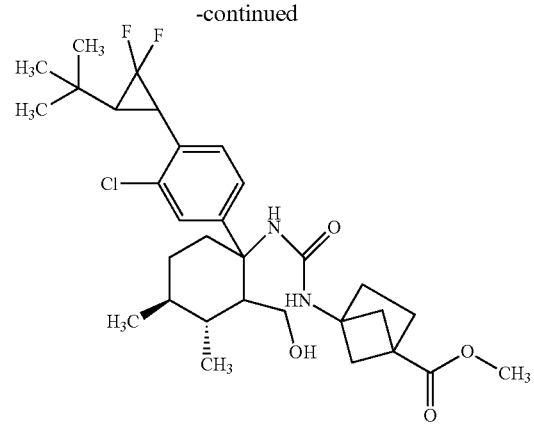

3-(Methoxycarbonyl)bicyclo[2.1.1]pentane-1-carboxylic acid (59 mg) and toluene (1.2 mL) were mixed under nitrogen gas, and thereto were added diphenylphosphoryl azide (75 µL) and triethylamine (49 µL) at room temperature. The reaction solution was stirred under heating at 120° C. for 1 hour. The reaction solution was added dropwise to a mixed solution of {(5S,6R)-2-amino-2-[4-(3-tert-butyl-2,2-difluoro-cyclopropyl)-3-chloro-phenyl]-5,6-dimethyl-cyclohexyl}methanol (112 mg) in tetrahydrofuran (2.3 mL) under ice cooling. The reaction solution was stirred at room temperature for 13 hours, and then thereto was added N,N,N'-trimethyl-ethane-1,2-diamine (7.2 µL). The mixture was concentrated under reduced pressure. The resulting residue was purified by silica gel column chromatography (Biotage flash purification systems, eluent: acetone/n-hexane, Rf=0.40 (acetone/n-hexane=1/4)) to give the title compound (201 mg, 31 w % of ethyl acetate inclusive).

$^1$H-NMR (400 MHz, CDCl$_3$) 0.93-1.06 (m, 8H), 1.10 (s, 9H), 1.54-1.83 (m, 5H), 1.89-1.93 (m, 5H), 1.98-2.02 (m, 1H), 2.12-2.29 (m, 4H), 2.70-2.81 (m, 1H), 2.99-3.09 (m, 1H), 3.29-3.35 (m, 1H), 3.67 (s, 3H), 3.70-3.75 (m, 1H), 4.81 (br s, 1H), 6.28 (br s, 1H), 0.09-7.23 (m, 23), 7.26-7.36 (m, 1H)

(Step 11)

Methyl 4-{(5R,6S)-8a-[4-(3-tert-butyl-2,2-difluoro-cyclopropyl)-3-chloro-phenyl]-5,6-dimethyl-2-oxo-1,5,6,7,8,8a-hexahydro-2H-quinazolin-3-yl}bicyclo[2.1.1]hexane-1-carboxylate

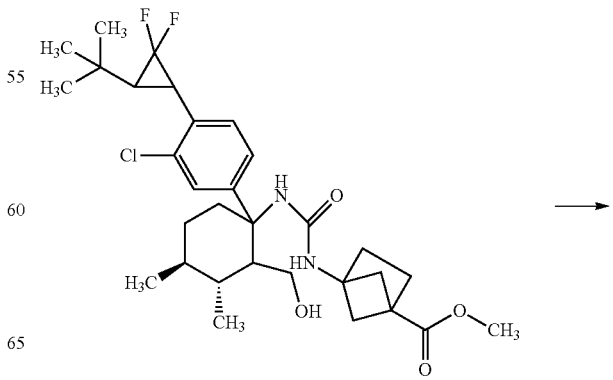

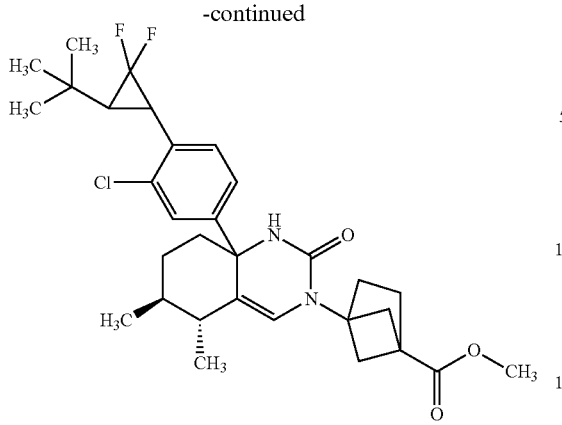

Methyl 4-(3-{(3R,4S)-1-[4-(3-tert-butyl-2,2-difluoro-cyclopropyl)-3-chloro-phenyl]-2-hydroxymethyl-3,4-dimethyl-cyclohexyl}ureido)bicyclo[2.1.1]hexane-1-carboxylate (110 mg) and chloroform (1.4 mL) were mixed under nitrogen gas, and thereto were added (diacetoxyiodo)benzene (88 mg) and 2,2,6,6-tetramethylpiperidin-1-oxyl radical (3.8 mg) at room temperature. The reaction solution was stirred at room temperature for 14 hours, and then thereto were added saturated aqueous sodium hydrogen carbonate solution and sodium sulfite at room temperature. The mixture was stirred at room temperature for 30 minutes, and then extracted with ethyl acetate. The organic layer was washed with saturated aqueous sodium chloride solution, and then dried over magnesium sulfate. Magnesium sulfate was removed with a filter, and then the filtrate was concentrated under reduced pressure. The resulting residue was mixed with toluene (2.8 mL), and thereto was added pentafluoroaniline trifluoromethanesulfonate (4 mg) at room temperature. The reaction solution was stirred for 7 hours under heating at 120° C., and then the reaction solution was concentrated under reduced pressure. The resulting residue was purified by silica gel column chromatography (Biotage flash purification systems, eluent: ethyl acetate/n-hexane, Rf=0.25 (ethyl acetate/n-hexane=3/7)) to give the title compound (36 mg).

This racemate was purified with Recycling Preparative Liquid Chromatograph to give a single enantiomer of the title compound (9 mg).

Purification conditions for the preparative chromatography are shown as follows.

Preparative apparatus: Recycling Preparative Liquid Chromatograph LC-92XX NEXT SERIES, Japan Analytical Industry Co., Ltd.

Column: Daicel CHIRALPAK IA 2.0 cmφ×25 cm

Mobile phase: n-hexane/2-propanol=85/15

Flow rate: 10.0 mL/min

Detection: UV (254 nm)

Measurement of the resulting compound with a chiral column showed 6.9 minutes of the retention time for the resulting enantiomer with >99% ee of optical purity. The retention time for the opposite enantiomer was 10.3 minutes.

Analytical conditions for the chiral column are shown as follows.

Measurement apparatus: HPLC system, Shimadzu Corporation, High-Performance Liquid Chromatograph Prominence Column: Daicel CHIRALPAK IA-3 0.46 cmφ×15 cm Column temperature: 40° C.

Mobile phase: n-hexane/2-propanol=85/15

Flow rate: 1.0 mL/min

Detection: UV (2.54 nm)

$^1$H-NMR (400 MHz, CDCl$_3$) 0.62-0.67 (m, 3H), 0.99-1.05 (m, 5H), 1.12 (s, 9H), 1.33-1.47 (m, 2H), 1.56-1.84 (m, 3H), 1.93-2.13 (m, 9H), 2.22-2.31 (m, 1H), 2.70-2.83 (m, 1H), 3.70 (s, 3H), 4.44 (br s, 1H), 5.96 (br s, 1H), 7.13-7.20 (m, 1H), 7.21-7.23 (m, 1H), 7.38-7.40 (m, 1H)

(Step 12)

4-{(5R,6S)-8a-[4-(3-tert-Butyl-2,2-difluoro-cyclopropyl)-3-chloro-phenyl]-5,6-dimethyl-2-oxo-1,5,6,7,8,8a-hexahydro-2H-quinazolin-3-yl}bicyclo[2.1.1]hexane-1-carboxylic acid

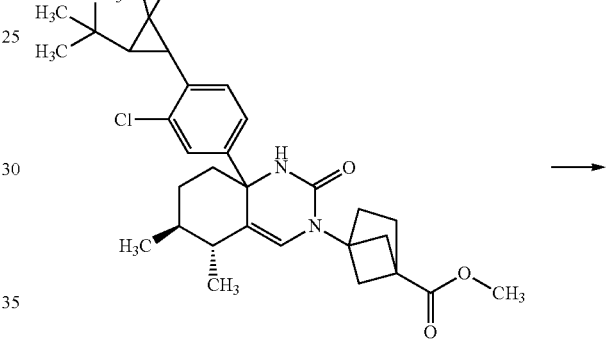

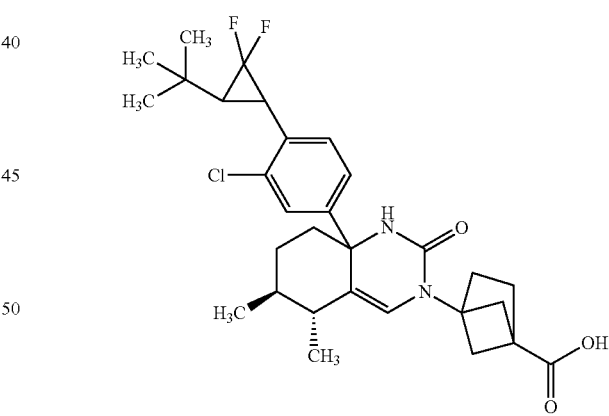

Methyl 3-{8a-[3-chloro-4-(3,3-dimethyl-butyl)phenyl]-2-oxo-1,5,6,7,8,8a-hexahydro-2H-quinazolin-3-yl}bicyclo[1.1.1]pentane-1-carboxylate (8.7 mg) was mixed in tetrahydrofuran (87 μL) and methanol (136 μL) under nitrogen gas, and thereto was added 2N aqueous sodium hydroxide solution (16 μL) at room temperature. The reaction solution was stirred at room temperature for 8 hours, and then thereto was added water (1 mL), followed by addition of 2N hydrochloric acid under ice cooling. Then, the mixture was stirred under ice cooling, and the precipitated solid was collected by filtration to give the title compound (7 mg).

(Intermediate Step 1)

1-(4-Bromo-2-chloro-phenyl)-3,3-dimethyl-butan-1-ol

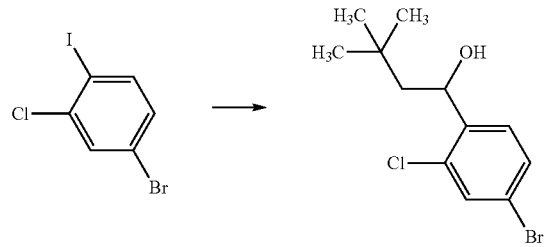

4-Bromo-2-chloro-1-iodo-benzene (10 g) and tetrahydrofuran (100 mL) were mixed under argon gas, and thereto was added dropwise 2.0M isopropylmagnesium chloride/tetrahydrofuran solution (17 mL) under cooling at −40° C. The mixture was stirred under cooling at −40° C. for 1.5 hours, and then thereto was added dropwise 3,3-dimethylbutyraldehyde (4.8 mL). The mixture was stirred under cooling at −40° C. for 1 hour 20 minutes, and then thereto was added 2N hydrochloric acid (17 mL) under ice cooling. Then, thereto was added ethyl acetate, and the mixture was separated. The organic layer was washed with saturated aqueous sodium chloride solution and dried over magnesium sulfate. Then, magnesium sulfate was removed with a filter, and the filtrate was concentrated under reduced pressure and azeotroped with toluene to give the title compound (9.8 g, 9.0 w % of toluene inclusive).

$^1$H-NMR (400 MHz, CDCl$_3$) 1.03 (s, 9H), 1.53-1.55 (m, 2H), 1.75-1.77 (m, 1H), 5.19-5.24 (m, 1H), 7.37-7.48 (m, 3H)

(Intermediate Step 2)

4-Bromo-2-chloro-1-((E)-3,3-dimethyl-but-1-enyl)benzene

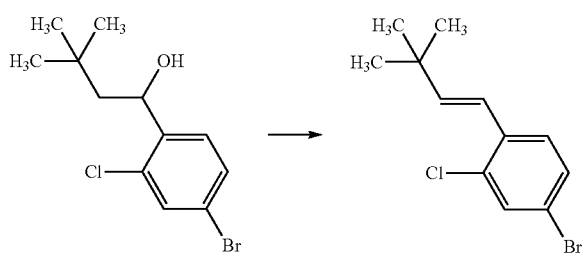

1-(4-Bromo-2-chloro-phenyl)-3,3-dimethyl-butan-1-ol (800 mg) and toluene (12 mL) were mixed, and thereto was added pentafluoroanilinium trifluoromethanesulfonate (494 mg) at room temperature. The mixture was stirred under heating at 120° C. for 3 hours, and then the reaction solution was concentrated under reduced pressure. The resulting residue was purified by silica gel column chromatography (eluent: ethyl acetate/n-hexane, Rf=0.8 (ethyl acetate/n-hexane=5/95)) to give the title compound (9.5 g, 16 w % of ethyl acetate inclusive).

$^1$H-NMR (400 MHz, CDCl$_3$) 1.12 (s, 9H), 6.16-6.24 (m, 1H), 6.53-6.62 (m, 1H), 7.27-7.38 (m, 2H), 7.47-7.50 (m, 1H)

(Intermediate Step 3)

4-Bromo-1-(3-tert-butyl-2,2-difluoro-cyclopropyl)-2-chlorobenzene

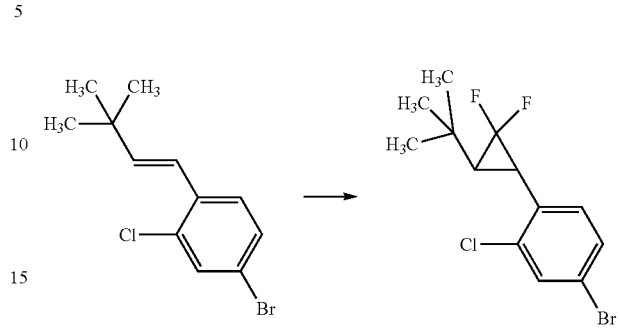

To 4-bromo-2-chloro-1-((E)-3,3-dimethyl-but-1-enyl)benzene (800 mg) were added tetra-n-butylammonium bromide (43 mg) and (bromodifluoromethyl)trimethylsilane (0.69 mL) at room temperature under argon gas. The mixture was stirred under heating at 110° C. overnight, and then thereto were added tetra-n-butylammonium bromide (48 mg) and (bromodifluoromethyl)trimethylsilane (0.69 mL). The mixture was stirred under heating at 120° C. for 8 hours. Then, thereto was added water (12 mL) and ethyl acetate at room temperature, and the mixture was separated. The organic layer was washed with saturated aqueous sodium chloride solution and dried over magnesium sulfate. Then, magnesium sulfate was removed with a filter, and the resulting residue was purified by silica column chromatography (eluent: ethyl acetate/n-hexane, Rf=0.75 (ethyl acetate/n-hexane=5/95)) to give the title compound (697 mg, 7 w % of toluene inclusive).

$^1$H-NMR (400 MHz, CDCl$_3$) 1.10 (s, 9H), 1.60-1.73 (m, 1H), 2.66-2.78 (m, 1H), 7.01-7.08 (m, 1H), 7.31-7.37 (m, 1H), 7.54-7.58 (m, 1H)

Example 118

(Step 1)

Ethyl (E)-4,4,5-trimethylhepta-2,6-dienoate

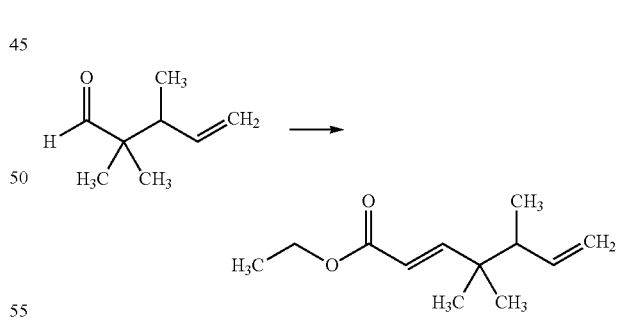

60 wt % Sodium hydride (1.1 g) and tetrahydrofuran (28 mL) were mixed under ice cooling and argon gas, and thereto was added dropwise triethyl phosphonoacetate (6.4 g). The reaction solution was stirred at room temperature for 30 minutes. Then, thereto was added dropwise a mixed solution of 2,2,3-trimethylpent-4-enal in tetrahydrofuran (28 mL) under ice cooling. The reaction solution was stirred under cooling for 10 minutes, and then stirred at room temperature for 12.5 hours. To the reaction solution were added saturated aqueous ammonium chloride solution (22 mL) and water (6 mL), and the mixture was concentrated under reduced pressure. The resultant aqueous layer was extracted with ethyl acetate (20 mL, twice). The organic layer was washed with saturated aqueous sodium chloride solution (10 twice) and dried over magnesium sulfate. Magnesium sulfate was removed with a filter, and then the filtrate was concentrated under reduced pressure to give a crude product of the title compound (3.2 g).

$^1$H-NMR (400 MHz, CDCl$_3$) 0.94 (d, J=6.94 Hz, 3H), 1.01 (s, 3H), 1.02 (s, 3H), 1.30 (t, J=7.17 Hz, 3H), 2.05-2.14 (m, 1H), 4.19 (q, J=7.17 Hz, 2H), 4.97-5.03 (m, 2H), 5.65-5.75 (m, 2H), 6.95 (d, J=15.95 Hz, 1H)
(Step 2)

Ethyl 4,4,5-trimethylhept-6-enoate

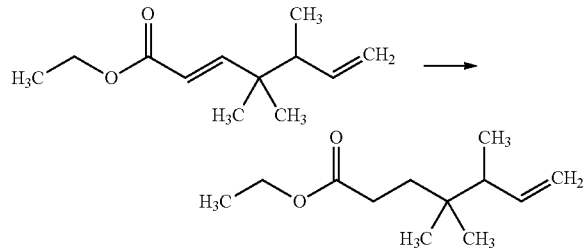

Ethyl (E)-4,4,5-trimethylhepta-2,6-dienoate (3.2 g) and copper (I) chloride (1.6 g) were mixed in tetrahydrofuran (44 mL) and methanol (25 mL) under argon gas, and thereto was added sodium borohydride over 1 hour under ice cooling. The reaction solution was stirred under ice cooling for 2 hours, and then thereto was added 1N hydrochloric acid (32 mL). Solid substances were removed with a filter, and then the resultant was washed with ethyl acetate and water. The filtrate was concentrated under reduced pressure. The resulting aqueous layer was extracted with ethyl acetate (10 mL) twice. The organic layer was washed with 1N hydrochloric acid (9 mL) and saturated aqueous sodium chloride solution (9 mL) and dried over magnesium sulfate. Magnesium sulfate was removed with a filter, and then the filtrate was concentrated under reduced pressure. To The resulting residue were added silica gel (15 g), ethyl acetate (16 mL), and n-hexane (16 mL), and the mixture was stirred for 30 minutes. Silica gel was removed with a filter, and then the filtrate was washed with a mixed solvent of ethyl acetate/ n-hexane=1/1 (64 mL). The filtrate was concentrated under reduced pressure to give a crude product of the title compound (3.4 g).

$^1$H-NMR (400 MHz, CDCl$_3$) 0.83 (s, 3H), 0.83 (s, 3H), 0.95 (d, J=6.94 Hz, 3H), 1.25 (t, J=7.13 Hz, 3H), 1.54-1.61 (m, 2H), 1.94-2.02 (m, 1H), 2.22-2.29 (m, 2H), 4.12 (q, J=7.13 Hz, 2H), 4.94-5.02 (m, 3H), 5.68-5.82 (m, 2H)
(Step 3)

4,4,5-Trimethylhept-6-enal

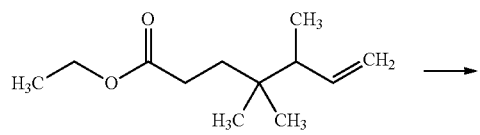

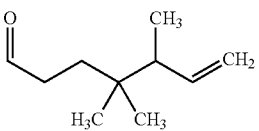

Ethyl 4,4,5-trimethylhept-6-enoate (3.4 g) and dichloromethane (170 mL) were mixed under argon gas, and thereto was added dropwise 1.02M diisobutylaluminum hydride/n-hexane solution (25 mL) under cooling at −78° C. The reaction solution was stirred under cooling at −78° C. for 2 hours. To the reaction solution was added methanol (10 mL) under cooling at −78° C. The reaction solution was warmed to 0° C., and thereto was added a saturated aqueous solution of Rochelle salt (85 mL). The reaction solution was stirred at room temperature for 3 hours. The aqueous layer was extracted with diethyl ether (40 mL, twice). The organic layer was washed with saturated aqueous sodium chloride solution (10 mL, twice) and dried over magnesium sulfate. Magnesium sulfate was removed with a filter, and then the filtrate was concentrated under reduced pressure to give a crude product of the title compound (2.5 g).

$^1$H-NMR (400 MHz, CDCl$_3$) 0.92-0.84 (m, 6H), 0.95-0.97 (m 3H), 1.54-1.58 (m, 2H), 1.96-2.04 (m, 1H), 2.35-2.43 (m, 2H), 4.93-4.99 (m, 3H), 5.71-5.81 (m, 1H), 9.77 (t, J=1.97 Hz, 1H)
(Step 4)

4,4,5-Trimethylhept-6-enal oxime

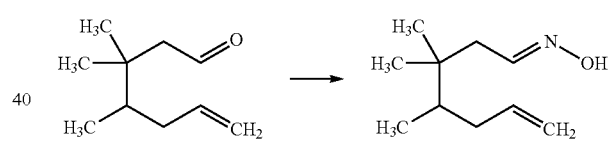

4,4,5-Trimethylhept-6-enal (1.9 g) was mixed in ethanol (25 mL) and water (12 mL) under argon gas, and thereto were added sodium acetate (7.0 g) and hydroxylamine hydrochloride (3.4 g) at room temperature. The reaction solution was stirred under heating at 60° C. for 14.5 hours. The reaction solution was concentrated under reduced pressure, and thereto were added ethyl acetone and water. The mixture was separated. The aqueous layer was extracted with ethyl acetate. The organic layer was washed with saturated aqueous sodium chloride solution (twice) and dried over sodium sulfate. Sodium sulfate was removed with a filter, and then the filtrate was concentrated under reduced pressure. The resulting residue was purified by silica gel column chromatography (Biotage flash purification systems, eluent: ethyl acetate/n-hexane, 5/95 to 20/80) to give the title compound (1.3 g).

$^1$H-NMR (400 MHz, CDCl$_3$) 0.83-0.98 (m, 9H), 1.37-1.43 (m, 2H), 1.97-2.08 (m, 1H), 2.13-2.20 (m, 1H), 2.31-2.37 (m, 1H), 4.93-5.00 (m, 3H), 5.51-5.81 (m, 2H), 6.67-6.73 (m, 1H), 7.00 (t, J=1.27 Hz, 0.5H), 7.41 (t, J=6.13 Hz, 0.5H)

(Step 5)

4,5,5-Trimethyl-3,3a,4,5,6,7-hexahydrobenzo[c]isoxazole

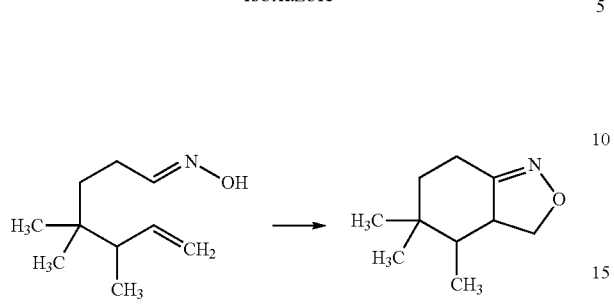

4,4,5-Trimethylhept-6-enal oxime (1.8 g) and methanol (36 mL) were mixed under nitrogen gas, and thereto was added trifluoroacetic acid (0.27 mL) under sodium chloride-ice cooling, followed by addition of (diacetoxyiodo)benzene (4.5 g) over 1 hour. The reaction solution was stirred under ice cooling for 20 minutes and at room temperature for 1.5 hours. Then, thereto were added saturated aqueous sodium hydrogen carbonate solution (18 mL) and sodium sulfite (0.66 g) under ice cooling, and the mixture was stirred at room temperature for 30 minutes. The reaction solution was concentrated under reduced pressure. The aqueous layer was extracted with ethyl acetate (10 mL, twice). The organic layer was washed with saturated aqueous sodium chloride solution (5 mL, twice) and dried over sodium sulfate. Sodium sulfate was removed with a filter, and then the filtrate was concentrated under reduced pressure. The resulting residue was purified by silica gel column chromatography (Biotage flash purification systems, eluent: ethyl acetate/n-hexane=5/95 to 30/70), and then purified further by silica gel column chromatography (Biotage flash purification systems, eluent: acetone/n-hexane=5/95 to 20/80) and azeotroped with n-hexane to give the title compound (0.42 g).

$^1$H-NMR (400 MHz, CDCl$_3$) 0.80-0.98 (m, 9H), 1.25-1.45 (m, 2H), 1.63-1.70 (m, 1H), 3.76 (dd, J=10.87, 7.86 Hz, 1H), 4.10-4.15 (m, 1H), 4.51 (dd, J=10.40, 7.86 Hz, 1H)

(Step 6)

7a-(3-Chloro-4-(3,3-dimethylbutyl)phenyl)-4,5,5-trimethyloctahydrobenzo[c]isoxazole

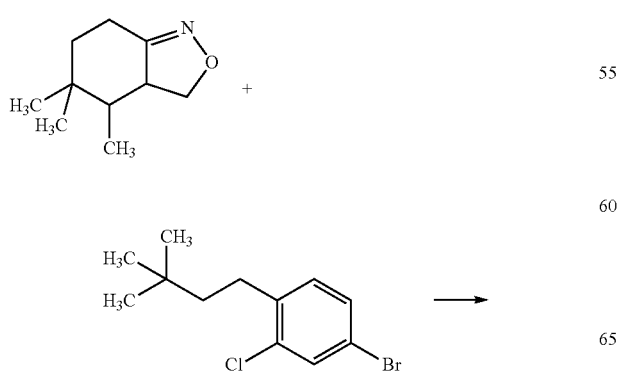

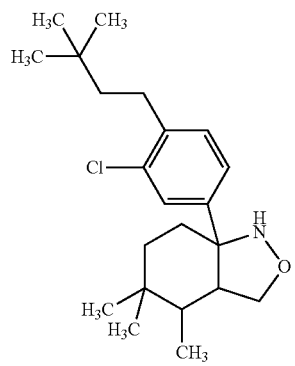

This step was performed according to Example 3 Step 6.

$^1$H-NMR (400 MHz, CDCl$_3$) 0.93 (d, J=6.70 Hz, 3H), 0.98 (s, 9H), 0.99 (s, 3H), 1.01 (s, 3H), 1.27-1.34 (m, 1H), 1.36-1.41 (m, 2H), 1.42-1.48 (m, 2H), 1.79-1.86 (m, 1H), 1.93-2.00 (m, 1H), 2.28-2.35 (m, 1H), 2.62-2.69 (m, 2H), 3.52 (dd, J=7.40, 5.55 Hz, 1H), 3.81 (d, J=7.40 Hz, 1H), 5.88 (s, 1H), 7.16 (d, J=8.04 Hz, 1H), 7.41 (dd, J=8.04, 1.91 Hz, 1H), 7.56 (d, J=1.91 Hz, 1H)

(Step 7)

(2-Amino-2-(3-chloro-4-(3,3-dimethylbutyl)phenyl)-5,5,6-trimethylcyclohexyl)methanol

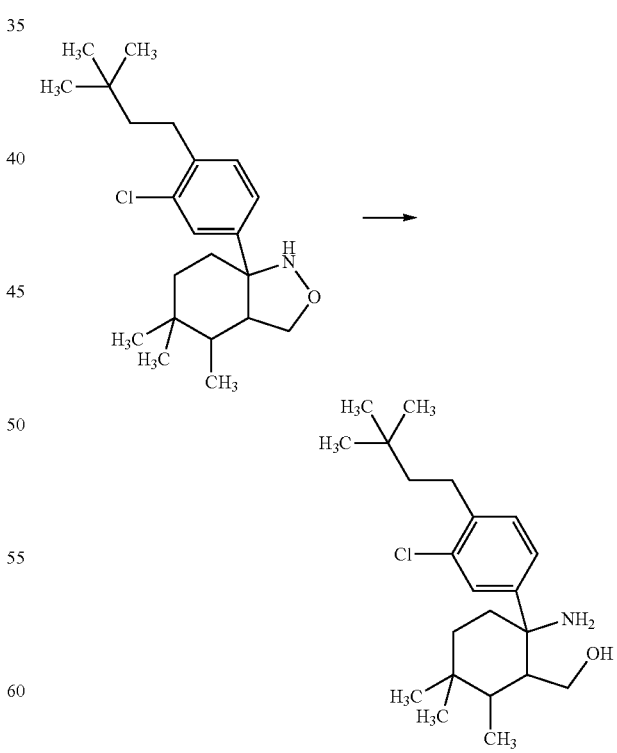

This step was performed according to Example 3 Step 7.

$^1$H-NMR (400 MHz, CDCl$_3$) 0.94 (s, 3H), 0.95-0.99 (m, 12H), 1.05 (s, 3H), 1.18-1.23 (m, 1H), 1.36-1.87 (m, 4H), 2.22-2.31 (m, 1H), 2.65-2.70 (m, 2H), 3.28-3.32 (m, 1H), 3.45-3.49 (m, 1H), 3.77-3.83 (m, 1H), 7.19 (d, J=8.09 Hz, 1H), 7.30 (dd, J=8.09, 2.08 Hz, 1H), 7.45 (d, J=2.08 Hz, 1H)

(Step 8)

Methyl 3-(3-{1-[3-chloro-4-(3,3-dimethyl-butyl)phenyl]-2-(hydroxymethyl)-3,4,4-trimethylcyclohexyl}ureido)bicyclo[1.1.1]pentane-1-carboxylate

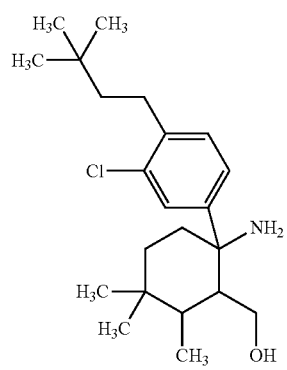

This step was performed according to Example 54 Step 8.

¹H-NMR (400 MHz, CDCl₃) 0.94 (s, 6H), 0.97 (s, 9H), 1.03 (s, 3H), 1.29-1.68 (m, 5H), 1.86-2.00 (m, 2H), 2.36 (s, 6H), 2.59-2.67 (m, 2H), 2.86-2.92 (m, 1H), 3.34-3.40 (m, 1H), 3.62-3.69 (m, 4H), 4.71 (br s, 1H), 6.42 (s, 1H), 7.10-7.17 (m, 2H), 7.22-7.27 (m, 3H)

(Step 9)

Methyl 3-{8a-[3-chloro-4-(3,3-dimethyl-butyl)phenyl]-5,6,6-trimethyl-2-oxo-1,3,6,7,8,0a-hexahydroquinazolin-3(2H)-yl}bicyclo[1.1.1]pentane-1-carboxylate

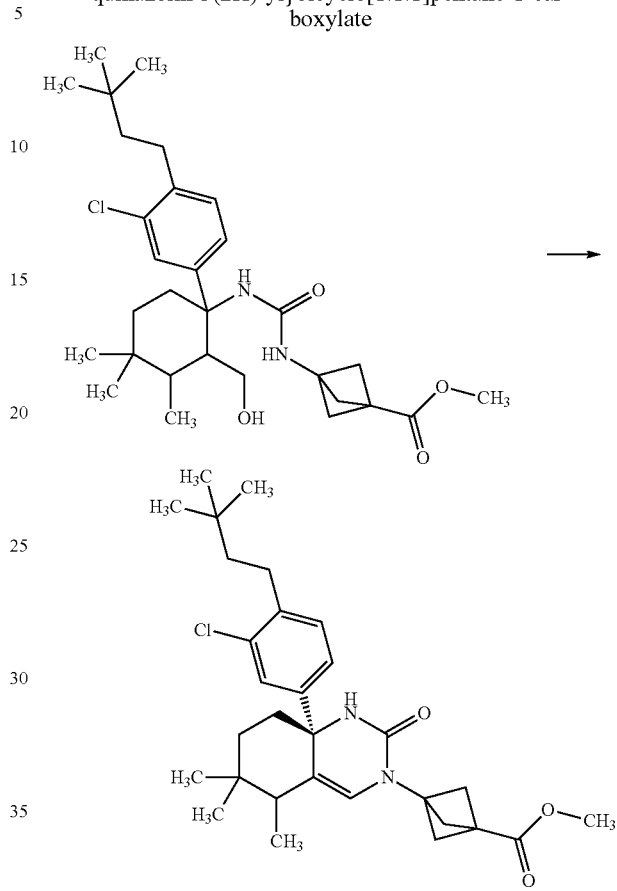

This step was performed according to Example 54 Step 9. The product was purified with a chiral preparative column. Purification conditions for the preparative column are shown as follows.

Preparative apparatus: Recycling Preparative Liquid Chromatograph LC-92XX NEXT SERIES, Japan Analytical Industry Co., Ltd.
Column: Daicel CHIRALPAK IA 2.0 cmφ×25 cmL
Mobile phase: n-hexane/2-propanol=90/10
Flow rate: 10.0 mL/min
Detection: UV (254 nm)

Measurement with a chiral column showed 11.2 minutes of the retention time for the resulting title compound (4.2 minutes of the retention time for the enantiomer of the title compound) with >99% ee purity. Analytical conditions for the chiral column are shown as follows.

Measurement apparatus: HPLC system, Shimadzu Corporation, High-Performance Liquid Chromatograph Prominence
Column: Daicel CHIRALPAK IA-3 0.46 cmφ×15 cmL
Column temperature: 30° C.
Mobile phase: n-hexane/2-propanol=90/10
Flow rate: 1.0 mL/min
Detection: UV (254 nm)

¹H-NMR (400 MHz, CDCl₃) 0.47 (d, J=7.40 Hz, 3H), 0.82 (s, 3H), 0.98 (s, 9H), 1.04 (s, 3H), 1.18-1.32 (m, 2H), 1.40-1.48 (m, 2H), 1.96-2.11 (m, 2H), 2.35-2.41 (m, 1H), 2.48 (s, 6H), 2.63-2.68 (m, 2H), 3.71 (s, 3H), 4.46 (br s, 1H), 5.96-5.98 (m, 1H), 7.16-7.18 (m, 2H), 7.30-7.32 (m, 1H)

(Step 10)

3-{7a-[3-Chloro-4-(3,3-dimethyl-butyl)phenyl]-5,6,6-trimethyl-2-oxo-1,2,5,6,7,7a-hexahydro-3H-cyclopenta[d]pyrimidin-3-yl}bicyclo[1.1.1]pentane-1-carboxylic acid

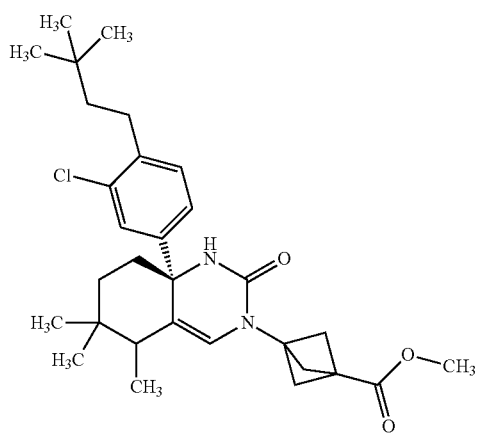

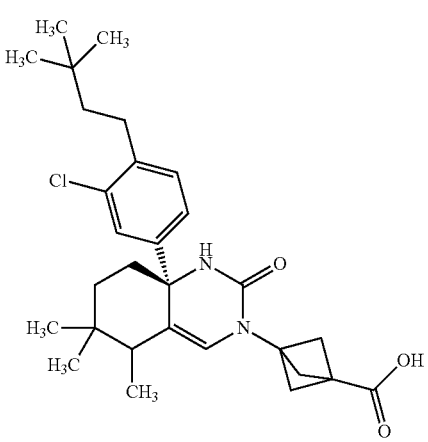

This step was performed according to Example 54 Step 10.

Example 120

(Step 1)

Methyl 4-(3-{3-[3-chloro-4-(3,3-dimethyl-butyl)phenyl]-4-hydroxymethyl-5,6,6-trimethyl-tetrahydro-pyran-3-yl}ureido)bicyclo[2.1.1]hexane-1-carboxylate

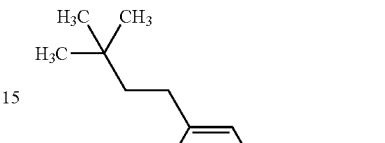

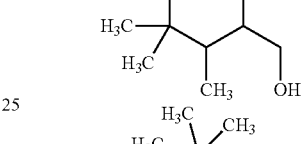

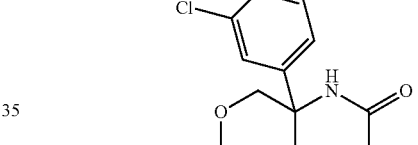

Methyl bicyclo[2.1.1]hexane-1,4-dicarboxylate (144 mg) and toluene (2.89 mL) were mixed under argon gas, and thereto were added diphenylphosphoryl azide (0.183 mL) and triethylamine (0.118 mL) at room temperature. The reaction solution was stirred under heating at 120° C. for 1 hour. To the reaction solution was added tetrahydrofuran (2.89 mL), and the mixture was added dropwise to a mixed solution of {5-amino-5-[3-chloro-4-(3,3-dimethyl-butyl)phenyl]-2,2,3-trimethyl-tetrahydro-pyran-4-yl}methanol (251 mg, 21 w % of cyclopentyl methyl ether inclusive) in tetrahydrofuran (5.02 pat) over 10 minutes under ice cooling. The reaction solution was stirred at room temperature for 13 hours, and then thereto was added N,N,N'-trimethylethylenediamine (0.0176 mL). The reaction solution was concentrated under reduced pressure, and the resulting residue was purified by silica gel column chromatography (Biotage flash purification systems, eluent: acetone/n-hexane, Rf=0.29 (acetone/n-hexane=1/2)) to give a crude product of the title compound (906 mg, 67 w % of ethyl acetate inclusive).

$^1$H-NMR (400 MHz, CDCl$_3$) 0.94 (d, J=7.2 Hz, 3H), 0.96 (s, 9H), 1.08 (s, 1.05H), 1.20 (s, 1.95H), 1.31 (s, 1.95H), 1.40-1.48 (m, 2H), 1.42 (s, 1.05H), 1.66-2.34 (m, 7H), 1.91 (s, 1.40H), 2.03 (s, 2.60H), 2.60-2.66 (m, 2H), 3.55-3.69 (m, 2H), 3.66 (s, 1.95H), 3.69 (s, 1.05H), 3.81-3.87 (m, 1.30H), 4.02-4.00 (m, 0.70H), 4.69 (s, 0.35H), 5.03 (s, 0.65H), 5.80 (s, 0.65H), 6.19 (s, 0.35H), 7.12-7.17 (m, 1.65H), 7.25 (d, J=1.8 Hz, 0.65H), 7.46 (d, J=8.3 Hz, 0.35H), 7.53 (d, J=1.8 Hz, 0.35H)

(Step 2)

Methyl 4-{8a-[3-chloro-4-(3,3-dimethyl-butyl)phenyl]-5,6,6-trimethyl-2-oxo-1,2,5,6,8,8a-hexahydro-pyrano[3,4-d]pyrimidin-3-yl}bicyclo[2.1.1]hexane-1-carboxylate

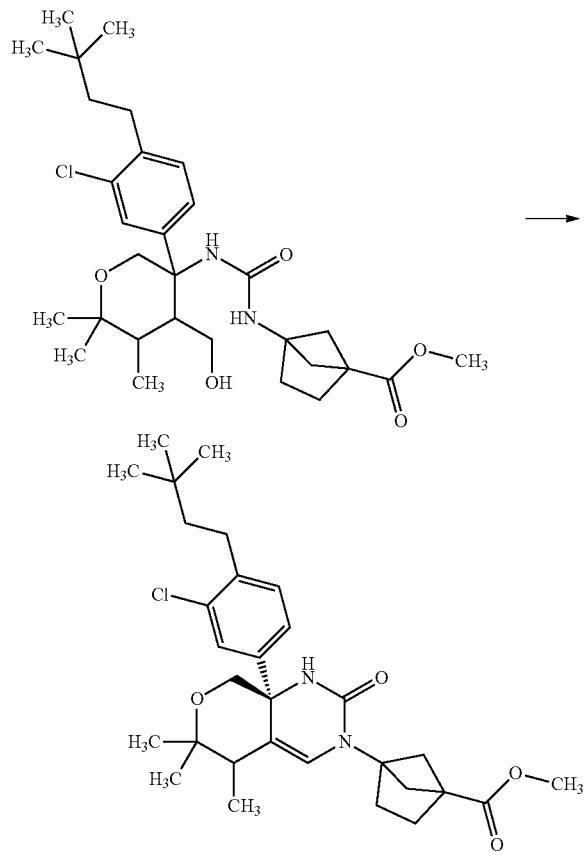

Methyl 4-(3-{3-[3-chloro-4-(3,3-dimethyl-butyl)phenyl]-4-hydroxymethyl-5,6,6-trimethyl-tetrahydro-pyran-3-yl}ureido)bicyclo[2.1.1]hexane-1-carboxylate (906 mg, 67 w % of ethyl acetate inclusive) and chloroform (3.0 mL) were mixed, and then thereto were added (diacetoxyiodo)benzene (202 mg) and 2,2,6,6-tetramethylpiperidin-1-oxyl radical (8.6 mg) at room temperature. The reaction solution was stirred at room temperature for 14 hours, and then thereto were added 20 w/w % aqueous sodium sulfite solution (2 mL) and saturated aqueous sodium hydrogen carbonate solution (2 mL) at room temperature. The mixture was stirred at room temperature for 30 minutes. The aqueous layer was extracted with ethyl acetate (twice). The organic layers were washed with saturated aqueous sodium chloride solution and dried over magnesium sulfate. Magnesium sulfate was removed with a filter, and then the filtrate was concentrated under reduced pressure. The resulting residue and toluene (6.1 mL) were mixed, and then thereto were added pentafluoroaniline trifluoromethanesulfonate (9.1 mg) at room temperature. The reaction solution was stirred under heating at 120° C. for 2 hours and then concentrated under reduced pressure. The resulting residue was purified by silica gel column chromatography (Biotage flash purification systems, eluent: ethyl acetate/n-hexane, Rf=0.42 (ethyl acetate/n-hexane=2/3)) to give a diastereomeric mixture of the title compound (245 mg). The diastereomeric mixture was purified with a Recycling Preparative Liquid Chromatograph to give a single enantiomer of the title compound (50.3 mg).

Purification conditions for the preparative chromatography are shown as follows.

Preparative apparatus: Recycling preparative liquid chromatograph LC-92XX NEXT SERIES, Japan Analytical Industry Co., Ltd.
Column: Daicel CHIRALPAK IA 2.0 cmφ×25 cm
Mobile phase: n-hexane:2-propanol=85:15
Flow rate 10.0 mL/min
Detection: UV (254 nm)

Measurement of the resulting compound with a chiral column showed 12.9 minutes of the retention time for the resulting enantiomer with >99% ee of optical purity. The retention time for a diastereomer on the methyl group was 10.6 minutes, and the retention time for a diastereomer on the phenyl group as well as the opposite enantiomer was 6.6 or 7.5 minutes.

Analytical conditions for the chiral column are shown as follows.

Measurement apparatus: HPLC system, Shimadzu Corporation, High-Performance Liquid Chromatograph Prominence
Column: Daicel CHIRALPAK IA-3 0.46 cmφ×15 cm
Column temperature: 30° C.
Mobile phase: n-hexane:2-propanol=85:15
Flow rate: 1.0 mL/min
Detection: UV (254 nm)

$^1$H-NMR (400 MHz, CDCl$_3$) 0.54 (d, J=7.2 Hz, 3H), 0.98 (s, 9H), 1.12 (s, 3H), 1.34 (s, 3H), 1.41-1.46 (m, 2H), 2.00-2.10 (m, 9H), 2.64-2.69 (m, 2H), 3.73 (s, 3H), 3.90 (d, J=12.0 Hz, 1H), 4.22 (d, J=11.8 Hz, 1H), 4.38 (s, 1H), 5.91 (s, 1H), 7.17 (d, J=8.1 Hz, 1H), 7.31 (dd, J=8.0, 2.0 Hz, 1H), 7.47 (d, J=2.1 Hz, 1H)

(Step 3)

4-{(S)-8a-[3-Chloro-4-(3,3-dimethyl-butyl)phenyl]-5,6,6-trimethyl-2-oxo-1,2,5,6,8,8a-hexahydro-pyrano[3,4-d]pyrimidin-3-yl}bicyclo[2.1.1]hexane-1-carboxylic acid

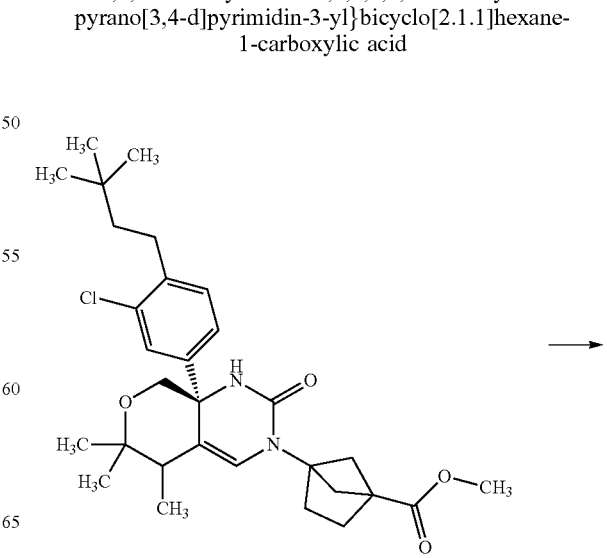

-continued

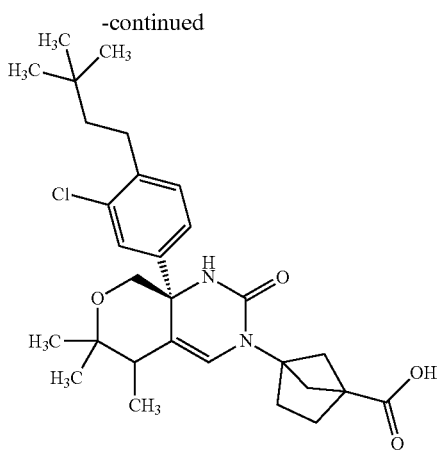

Methyl 4-{(S)-8a-[3-chloro-4-(3,3-dimethyl-butyl)phenyl]-5,6,6-trimethyl-2-oxo-1,2,5,6,8,8a-hexahydro-pyrano[3,4-d]pyrimidin-3-yl}bicyclo[2.1.1]hexane-1-carboxylate (50.3 mg) was mixed in tetrahydrofuran (0.553 mL) and methanol (0.553 mL), and then thereto was added 2N aqueous solution of sodium hydroxide (0.0951 mL) at room temperature. The reaction solution was stirred at room temperature for 16 hours and then concentrated under reduced pressure. To the resulting residue was added water (1 mL), and thereto was added 2N hydrochloric acid (0.0951 mL) under ice cooling. The precipitated solid was collected by filtration to give the title compound (42.4 mg).

The following tables show structures, structural information, and physical property data for the above Example compounds and Example compounds prepared according to any of the above methods of Examples.

In the tables, "chiral column IA-3" means CHIRALPAK IA-3 analytical column (Product code: 80524; internal diameter: 4.6 mm, length: 150 mm, particle size: 3 μm; Daicel Corporation).

"Chiral column AS-3R" means CHIRALPAK AS-3R analytical column (Product code: 20824; internal diameter: 4.6 mm, length: 150 mm, particle size: 3 μm; Daicel Corporation).

Each absolute configuration of the enantiomer shown in the structure of each example compound was estimated according to the following regularities:
1) a certain regularity in the retention time of chiral column. for a methyl or ethyl ester derivative of example compound; and
2) a certain regularity in the degree of inhibitory activity against RORγ transcription of each enantiomer of example compound (see Test Example 1);

provided that the absolute configuration of Example 54 compound was determined by single-crystal X-ray structural analysis.

Tn the following table, the term "methyl ester derivative" or "ethyl ester derivative" described in the structural information means a methyl-ester derivative or ethyl-ester derivative corresponding to each example compound, respectively.

| Example | Structure | Structural Information |
|---|---|---|
| 1 | 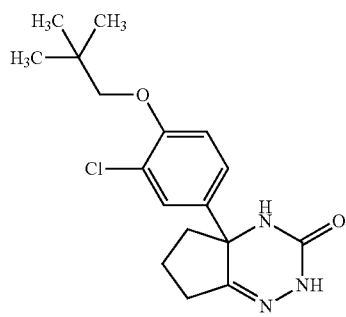 [SMILES: CC(C)(C)COc1ccc(C23CCCC2=NNC(=O)N3)cc1Cl] | Racemate |
| 2 | 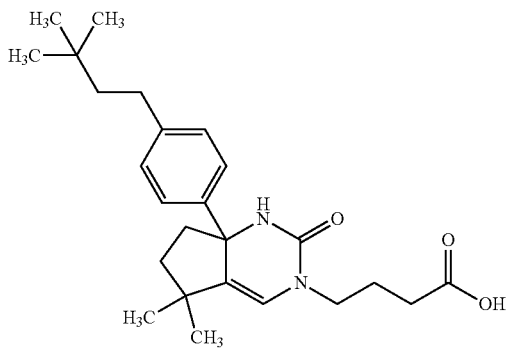 [SMILES: CC(C)(C)CCc1ccc(C23CCC(C)(C)C2=CN(CCCC(=O)O)C(=O)N3)cc1] | Racemate |

-continued

| Example | Structure | Structural Information |
|---|---|---|
| 3 | 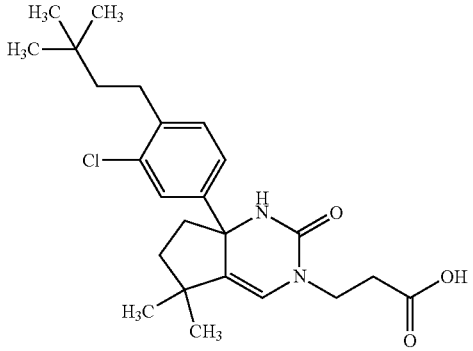 | Enantiomer of Example 4 (Absolute configuration was not determined.) Analytical conditions for corresponding ethyl ester derivative: chiral column IA-3, Hexane/IPA = 93/7, flow 1 ml/min Retention time: 7.4 min |
| 4 | 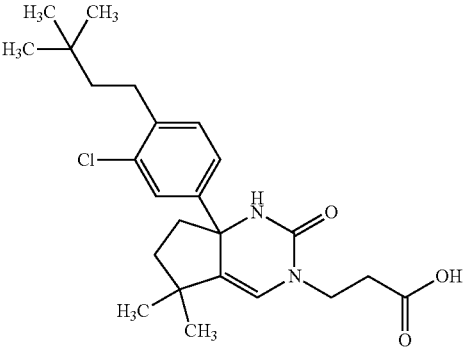 [SMILES: CC(C)(C)CCc1ccc(C23CCC(C)(C)C2=CN(CCC(=O)O)C(=O)N3)cc1Cl] | Enantiomer of Example 3 (Absolute configuration was not determined.) Analytical conditions for corresponding ethyl ester derivative: chiral column IA-3, Hexane/IPA = 93/7, flow 1 ml/min Retention time: B.7 min |
| 5 | 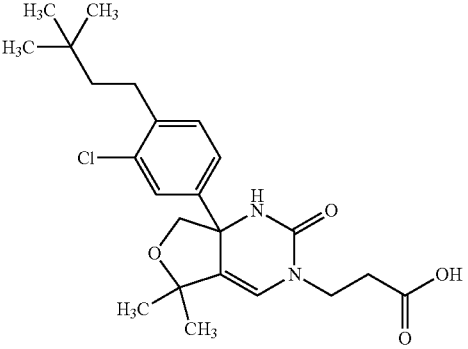 | Enantiomer of Example 6 (Absolute configuration. was not determined.) Analytical conditions for corresponding ethyl ester derivative: chiral column IA-3, Hexane/IPA = 90/10, flow 1 ml/min Retention time: 6.6 min |
| 6 | 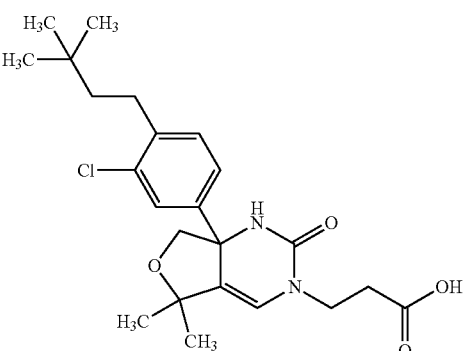 | Enantiomer of Example 5 (Absolute configuration was not determined.) Analytical conditions for corresponding ethyl ester derivative: chiral column IA-3, Hexane/IPA = 90/10, flow 1 ml/min Retention time: 6.9 min |

-continued

| Example | Structure | Structural Information |
|---|---|---|
| 7 | 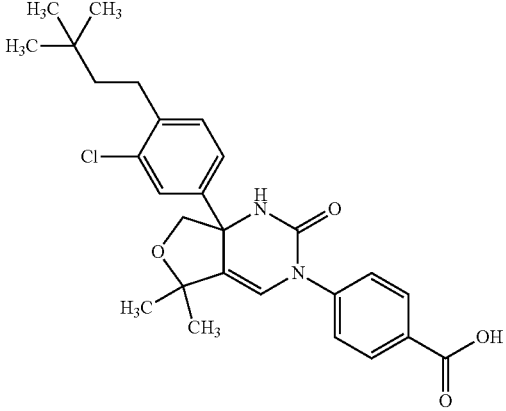 [SMILES: CC(C)(C)CCc1ccc(C23COC(C)(C)C2=CN(c2ccc(C(=O)O)cc2)C(=O)N3)cc1Cl] | Enantiomer of Example 8 (Absolute configuration was not determined.) Analytical conditions for corresponding ethyl ester derivative: chiral column IA-3, Hexane/IPA = 80/20, flow 1 ml/min Retention time: 6.5 min |
| 8 | 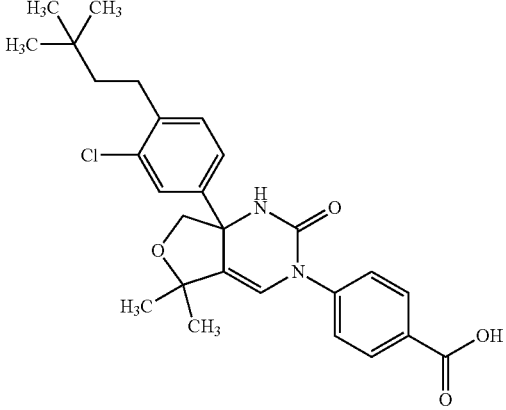 [SMILES: CC(C)(C)CCc1ccc(C23COC(C)(C)C2=CN(c2ccc(C(=O)O)cc2)C(=O)N3)cc1Cl] | Enantiomer of Example 7 (Absolute configuration was not determined.) Analytical conditions for corresponding ethyl ester derivative chiral column IA-3, Hexane/IPA = 80/20, flow 1 ml/min Retention time: 8.8 min |
| 9 | 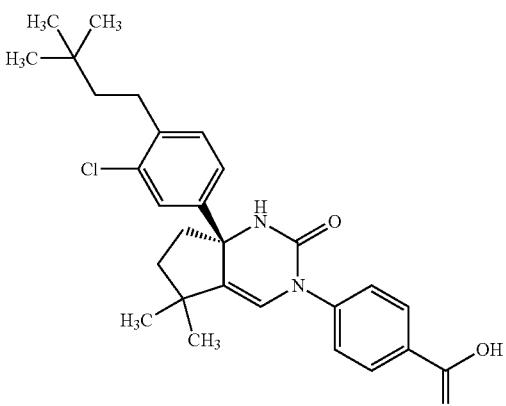 | Enantiomer of Example 10 (Absolute configuration was not determined.) Analytical conditions for corresponding ethyl ester derivative: chiral column IA-3, Hexane/IPA = 90/10, flow 1 ml/min Retention time: 10.6 min |

-continued

| Example | Structure | Structural Information |
|---|---|---|
| 10 | 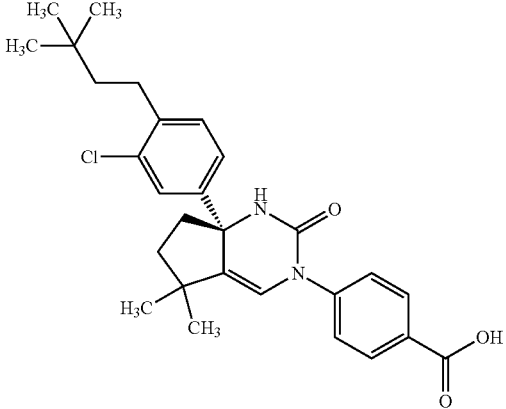 [SMILES: CC(C)(C)CCc1ccc([C@@]23CCC(C)(C)C2=CN(c2ccc(C(=O)O)cc2)C(=O)N3)cc1Cl] | Enantiomer of Example 9 (Absolute configuration was not determined.) Analytical conditions for corresponding ethyl ester derivative: chiral column IA-3, Hexane/IPA = 90/10, flow 1 ml/min Retention time: 12.8 min |
| 11 | 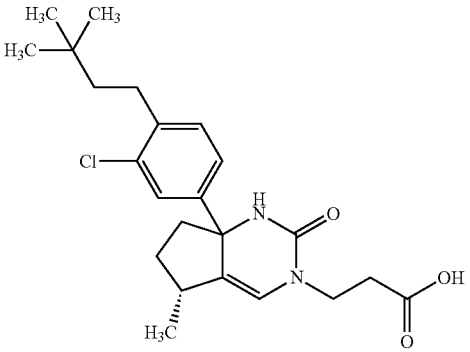 [SMILES: C[C@@H]1CCC2(c3ccc(CCC(C)(C)C)c(Cl)c3)NC(=O)N(CCC(=O)O)C=C12] | Optically active. Optical purity was not determined. (Absolute configuration was not determined.) Single diastereomer. Configuration of methyl group on the cyclopentane ring was estimated to be R derived from a starting material. Analytical conditions for corresponding methyl ester derivative:<br><br>chiral column IA-3,<br><br>Hexane/IPA = 90/10, flow 1 ml/min Retention time: 5.3 min |
| 12 | 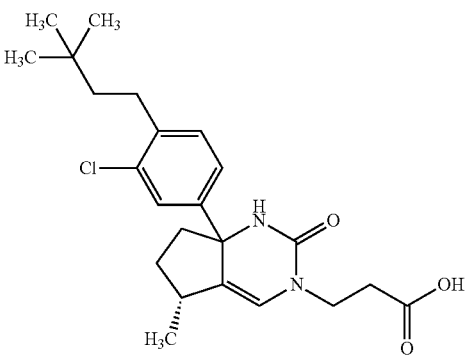 [SMILES: C[C@@H]1CCC2(c3ccc(CCC(C)(C)C)c(Cl)c3)NC(=O)N(CCC(=O)O)C=C12] | Optically active. Optical purity was not determined. (Absolute configuration was not determined.) Single diastereomer. Configuration of methyl group on the cyclopontane ring was estimated to be R derived from a starting material. Analytical conditions for corresponding methyl ester derivative:<br><br>chiral column IA-3, Hexane/IPA = 90/10, flow 1 ml/min Retention time: 6.2 min |

-continued

| Example | Structure | Structural Information |
|---|---|---|
| 13 | 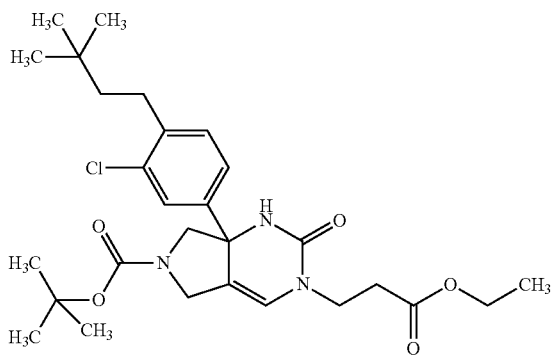 [SMILES: CCOC(=O)CCN1C=C2CN(C(=O)OC(C)(C)C)CC2(c2ccc(CCC(C)(C)C)c(Cl)c2)NC1=O] | Racemate.<br>Estimated structure. |
| 14 | 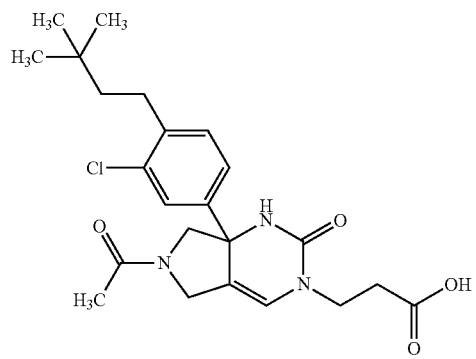 [SMILES: CC(=O)N1CC2=CN(CCC(=O)O)C(=O)NC2(c2ccc(CCC(C)(C)C)c(Cl)c2)C1] | Racemate.<br>Estimated structure. |
| 15 | 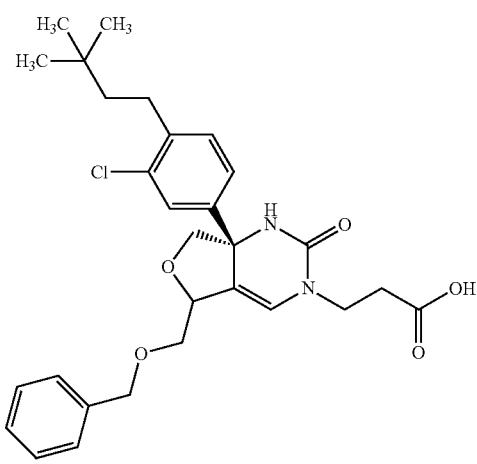 | Enantiomer of Example 16 (Absolute configuration was not determined.) Analytical conditions for corresponding ethyl ester derivative: chiral column IA-3, Hex./IPA = 85/15, flow rate = 1.0 ml/min, Retention time: 6.4 min Relative configuration of 3-chloro-4-(3,3-dimethylbutyl)phenyl and benzyloxymethyl was estimated to be trans |

| Example | Structure | Structural Information |
|---|---|---|
| 16 | 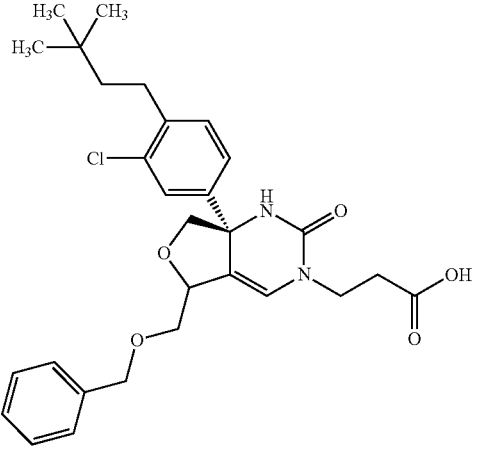 | Enantiomer of Example 15 (Absolute configuration was not determined.) Analytical conditions for corresponding ethyl ester derivative: chiral column Hex./IPA = 85/15, flow rate = 1.0 ml/min, Retention time: 8.8 min Relative configuration of 3-chloro-4-(3,3-dimethylbutyl)phenyl and benzyloxymethyl was estimated to be trans |
| 17 | 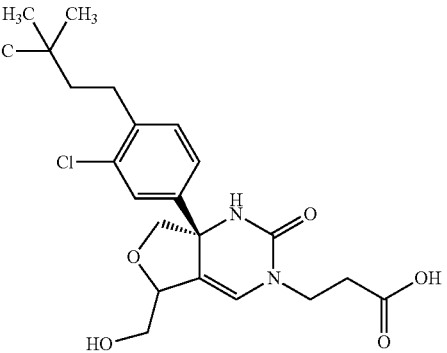 | Enantiomer of Example 18 (Absolute configuration was not determined.) Analytical conditions for corresponding ethyl ester derivative: chiral column IA-3, Hex./IPA = 80/20, flow rate = 1.0 ml/min, Retention time: 6.3 min Relative configuration of 3-chloro-4-(3,3-dimethylbutyl)phenyl and hydroxymethyl was estimated to be trans |
| 18 | 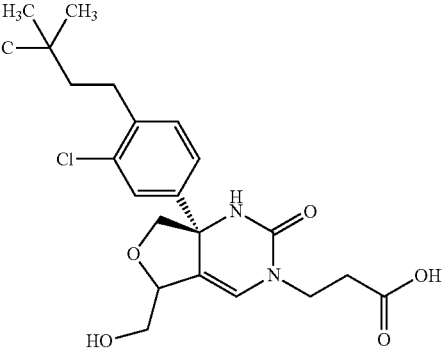 | Enantiomer of Example 17 (Absolute configuration was not determined.) Analytical conditions for corresponding-ethyl ester derivative: chiral column IA-3, Hex./IPA = 80/20, flow rate = 1.0 ml/min, Retention time: 7.6 min Relative configuration 3-chloro-4-(3,3-dimethylbutyl)phenyl and hydroxymethyl was estimated to be trans |
| 19 | 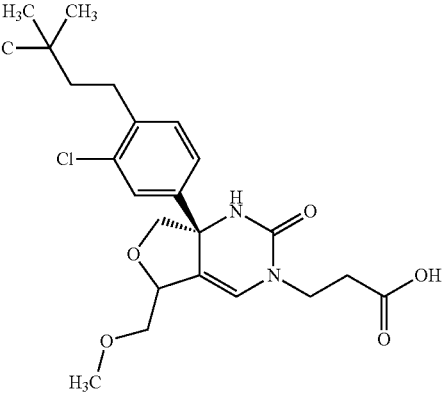 | Enantiomer of Example 20 (Absolute configuration was not determined.) Analytical conditions for corresponding ethyl ester derivative: chiral column IA-3, Hex./IPA = 90/10, flow rate = 1.0 ml/min, Retention time: 8.7 min Relative configuration of 3-chloro-4-(3,3-dimethylbutyl)phenyl and methoxymethyl was estimated to be trans |

-continued

| Example | Structure | Structural Information |
|---|---|---|
| 20 | (structure) | Enantiomer of Example 19 (Absolute configuration was not determined, >98% ee) Analytical conditions for corresponding ethyl ester derivative: chiral column IA-3, Hex./IPA = 90/10, flow rate = 1.0 ml /min, Retention time: 9.8 min Relative configuration of 3-chloro-4-(3,3-dimethylbutyl)phenyl and methoxymethyl was estimated to be trans |
| 21 | (structure) | Enantiomer of Example 22 (Absolute configuration was not determined.) Analytical conditions for corresponding ethyl ester derivative: chiral column IA-3, Hex./IPA - 90/10, flow rate = 1.0 ml/min, Retention time: 7.5 min, Optical purity was not determined Relative configuration. of 3-chloro-4-(3,3-dimethylbutyl)phenyl and butoxymethyl was estimated to be trans |
| 22 | (structure) | Enantiomer of Example 21 (Absolute configuration was not determined.) Analytical conditions for corresponding ethyl ester derivative: chiral column IA-3, Hex./IPA = 90/10, flow rate = 1.0 ml /min, Retention time: 8.3 min, Optical purity was not determined Relative configuration of 3-chloro-4-(3,3-dimethylbutyl)phenyl and butoxymethyl was estimated to be trans |
| 23 | (structure) | Racemate |

-continued

| Example | Structure | Structural Information |
|---|---|---|
| 24 | 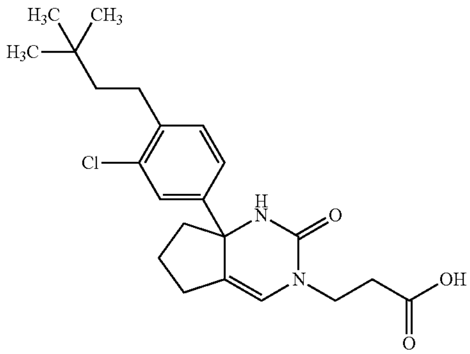 [SMILES: CC(C)(C)CCc1ccc(C23CCCC2=CN(CCC(=O)O)C(=O)N3)cc1Cl] | Racemate |
| 25 | 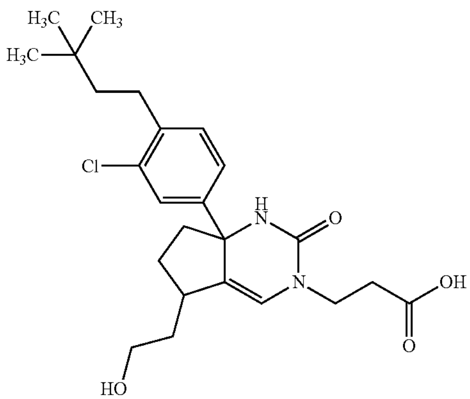 [SMILES: CC(C)(C)CCc1ccc(C23CCC(CCO)C2=CN(CCC(=O)O)C(=O)N3)cc1Cl] | Racemate<br>Configuration of hydroxyethyl and 3-chloro-4-(3,3-dimethylbutyl)phenyl was estimated to be trans<br>Single diastereomer |
| 26 | 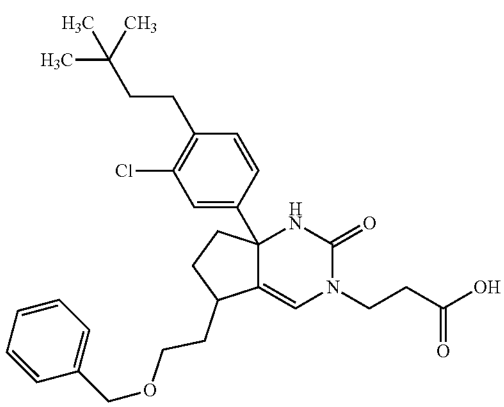 [SMILES: CC(C)(C)CCc1ccc(C23CCC(CCOCc4ccccc4)C2=CN(CCC(=O)O)C(=O)N3)cc1Cl] | Racemate<br>Configuration of benzyloxyethyl and 3-chloro-4-(3,3-dimethylbutyl)phenyl was estimated to be trans<br>Single diastereomer |
| 27 | 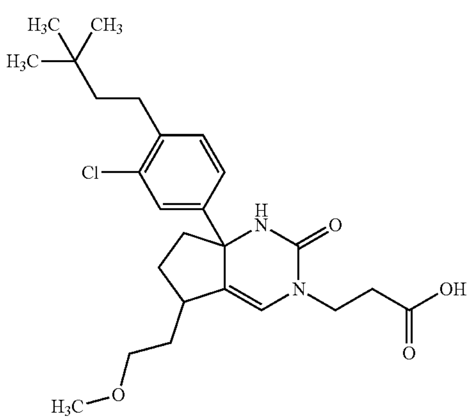 [SMILES: COCCC1CCC2(c3ccc(CCC(C)(C)C)c(Cl)c3)NC(=O)N(CCC(=O)O)C=C12] | Racemate<br>Configuration of methoxyethyl and 3-chloro-4-(3,3-dimethylbutyl)phenyl was estimated to be trans<br>Single diastereomer |

-continued

| Example | Structure | Structural Information |
|---|---|---|
| 28 | 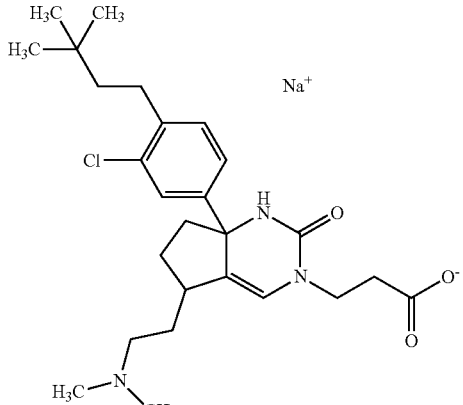 | Racemate<br>The number of sodium salt was estimated.<br>Configuration of dimethylaminoethyl and 3-chloro-4-(3,3-dimethylbutyl)phenyl was estimated to be trans<br>Single diastereomer |
| 29 | 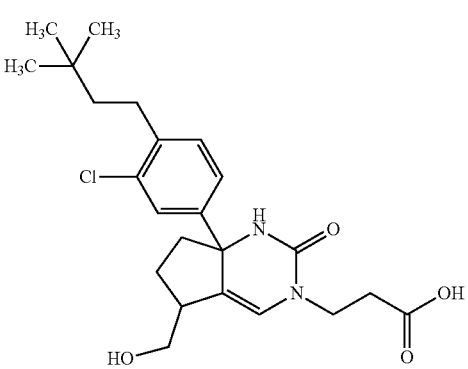 [SMILES: CC(C)(C)CCc1ccc(C23CCC(CO)C2=CN(CCC(=O)O)C(=O)N3)cc1Cl] | Racemate<br>Configuration of hydroxymethyl and 3-chloro-4-(3,3-dimethylbutyl)phenyl was estimated to be trans<br>Single diastereomer |
| 30 | 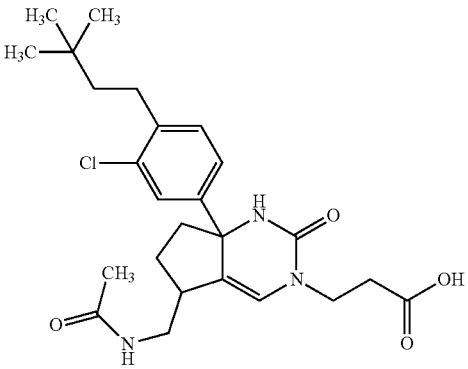 [SMILES: CC(=O)NCC1CCC2(c3ccc(CCC(C)(C)C)c(Cl)c3)NC(=O)N(CCC(=O)O)C=C12] | Racemate<br>Configuration of methylacetamide and 3-chloro-4-(3,3-dimethylbutyl)phenyl was estimated to be trans from the synthetic method<br>Single diastoreomer |
| 31 | 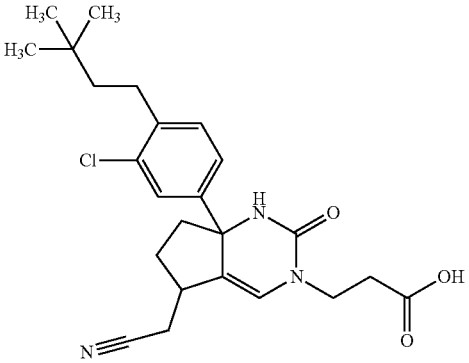 [SMILES: CC(C)(C)CCc1ccc(C23CCC(CC#N)C2=CN(CCC(=O)O)C(=O)N3)cc1Cl] | Racemate<br>Configuration of nitrilemethyl and 3-chloro-4-(3,3-dimethylbutyl)phenyl was estimated to be trans |

-continued

| Example | Structure | Structural Information |
|---|---|---|
| 32 | 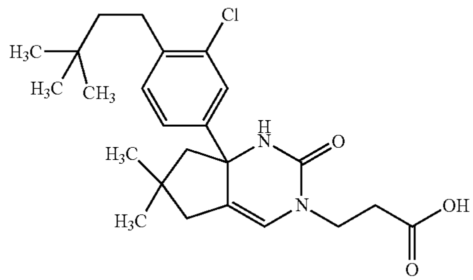 [SMILES: CC(C)(C)CCc1ccc(C23CC(C)(C)CC2=CN(CCC(=O)O)C(=O)N3)cc1Cl] | Enantiomer of Example 33 (Absolute nonfiguration was not determined.) Analytical conditions for corresponding ethyl ester derivative: chiral column IA-3, Hexane/IPA = 90/10, flow 1 ml/min Retention time: 5.9 min |
| 33 | 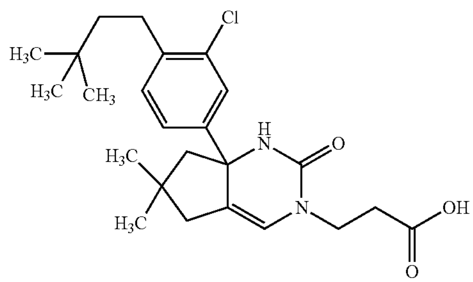 [SMILES: CC(C)(C)CCc1ccc(C23CC(C)(C)CC2=CN(CCC(=O)O)C(=O)N3)cc1Cl] | Enantiomer of Example 32 (Absolute configuration was not determined.) Analytical conditions for corresponding ethyl ester derivative: chiral column IA-3, Hexane/IPA = 90/10, flow 1 ml/min Retention time: 6.9 min |
| 34 | 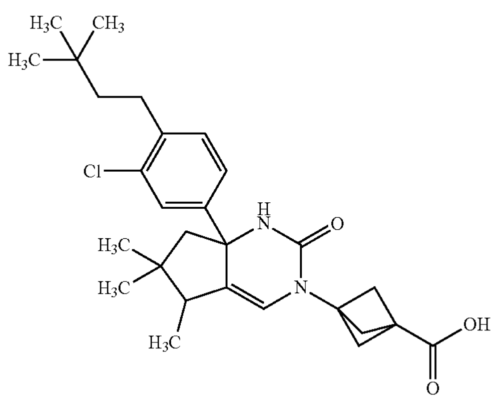 [SMILES: CC1C2=CN(C34CC(C(=O)O)(C3)C4)C(=O)NC2(c2ccc(CCC(C)(C)C)c(Cl)c2)CC1(C)C] | Enantiomer of Example 35 (Absolute configuration was not determined.) (>99% ee for corresponding methyl ester derivative chiral column IA-3, Hexane/IPA = 90/10, flow 1 ml/min Retention time: 6.0 min) Single stereoisomer, Relative configuration of methyl and 3-chloro-4-(3,3-dimethylbutyl)phenyl was uncertain |
| 35 | 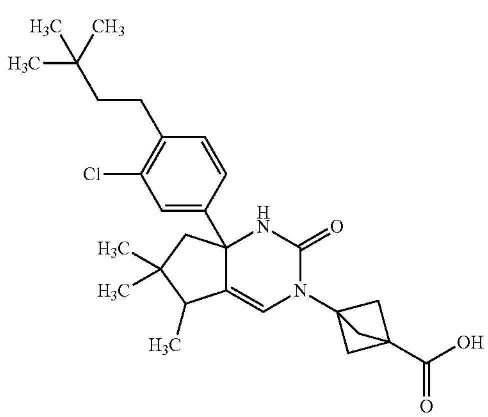 [SMILES: CC1C2=CN(C34CC(C(=O)O)(C3)C4)C(=O)NC2(c2ccc(CCC(C)(C)C)c(Cl)c2)CC1(C)C] | Enantiomer of Example 34 (Absolute configuration was not determined.) (>99% ee for corresponding methyl ester derivative chiral column IA-3, Hexane/IPA = 90/10, flow 1 ml/min Retention time: 8.5 min) Single stereoisomer, Relative configuration of three methyl groups on the cyclopentane ring and 3-chloro-4-(3,3-dimethylbutyl)phenyl was uncertain |

-continued

| Example | Structure | Structural Information |
|---|---|---|
| 36 | 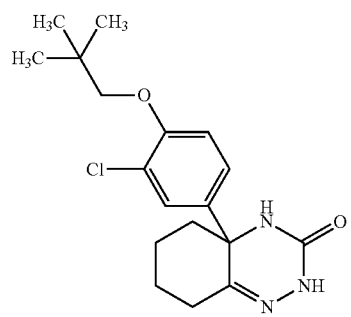 [SMILES: CC(C)(C)COc1ccc(C23CCCCC2=NNC(=O)N3)cc1Cl] | Racemate |
| 37 | 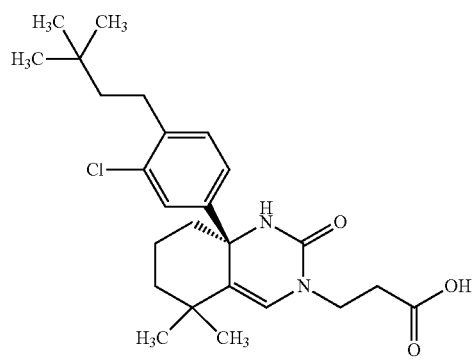 [SMILES: CC(C)(C)CCc1ccc([C@]23CCCC(C)(C)C2=CN(CCC(=O)O)C(=O)N3)cc1Cl] | Enantiomer of Example 38 (Absolute configuration was not determined.) Analytical conditions for corresponding ethyl ester derivative: chiral column IA-3, Hexane/IPA = 90/10, flow 1 ml/min Retention time: 4.9 min |
| 38 | 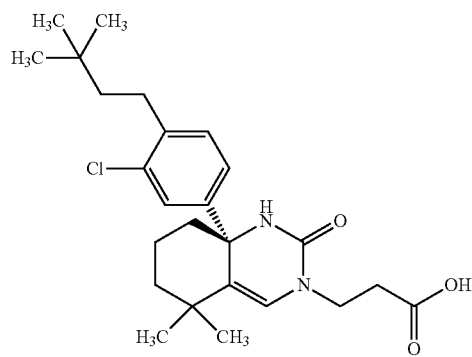 [SMILES: CC(C)(C)CCc1ccc([C@@]23CCCC(C)(C)C2=CN(CCC(=O)O)C(=O)N3)cc1Cl] | Enantiomer of Example 37 (Absolute configuration was not determined.) Analytical conditions for corresponding ethyl ester derivative: chiral column IA-3, Hexane/IPA = 90/10, flow 1 ml/min Retention time: 8.5 min |
| 39 | 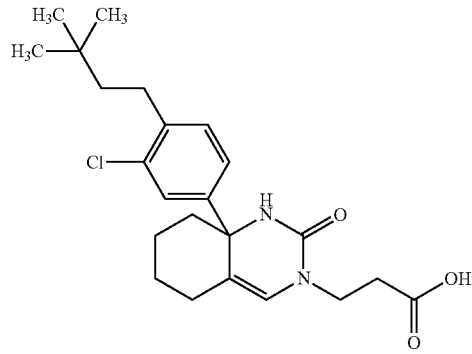 | Racemate |

-continued

| Example | Structure | Structural Information |
|---|---|---|
| 40 | 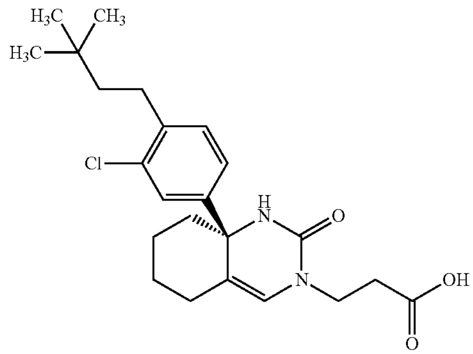 [SMILES: CC(C)(C)CCc1ccc([C@]23CCCCC2=CN(CCC(=O)O)C(=O)N3)cc1Cl] | Optically active (Absolute configuration was not determined.) (>99% ee, IA-3 IPA/Hex. = 7%, flow rate = 1 ml/min, R.T. = 7.3 min) Enantiomer of Example 41 |
| 41 | 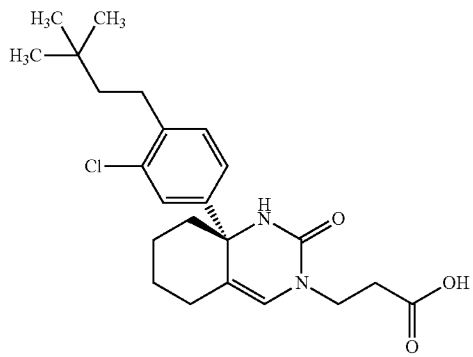 [SMILES: CC(C)(C)CCc1ccc([C@@]23CCCCC2=CN(CCC(=O)O)C(=O)N3)cc1Cl] | Optically active (Absolute configuration was not determined.) (>99% ee, IA-3 IPA/Hex. = 7%, flow rate = 1 ml/min, R.T. = 12.4 min) Enantiomer of Example 40 |
| 42 | 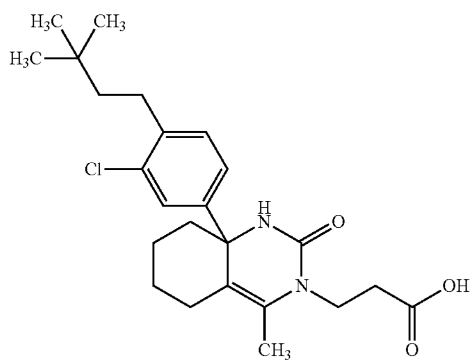 [SMILES: CC1=C2CCCCC2(c2ccc(CCC(C)(C)C)c(Cl)c2)NC(=O)N1CCC(=O)O] | Estimated structure Racemate |
| 43 | 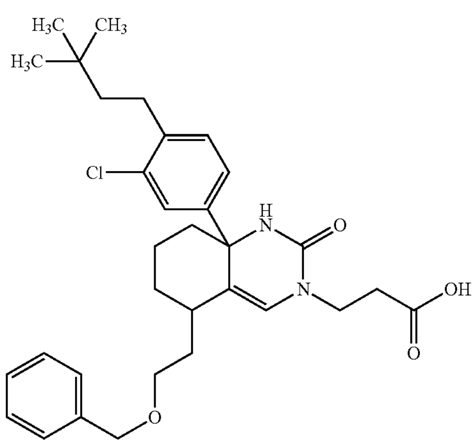 [SMILES: CC(C)(C)CCc1ccc(C23CCCC(CCOCc4ccccc4)C2=CN(CCC(=O)O)C(=O)N3)cc1Cl] | Racemate Configuration of benzyloxyethyl and 3-chloro-4-(3,3-dimethylbutyl)pheny was estimated to be trans |

| Example | Structure | Structural Information |
|---|---|---|
| 44 | 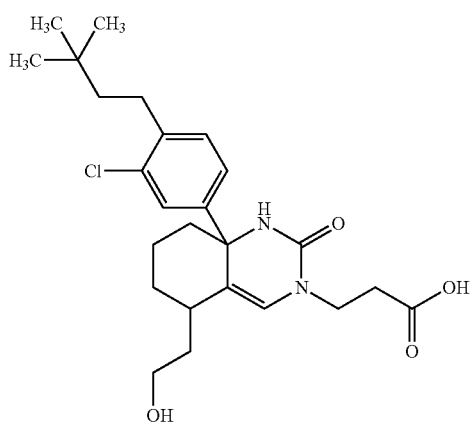 [SMILES: CC(C)(C)CCc1ccc(C23CCCC(CCO)C2=CN(CCC(=O)O)C(=O)N3)cc1Cl] | Racemate Configuration of hydroxyethyl and 3-chloro-4-(3,3-dimethylbutyl)phenyl was estimated to be trans |
| 45 | 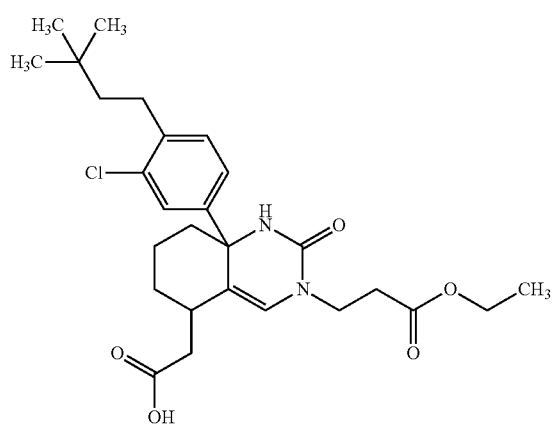 [SMILES: CCOC(=O)CCN1C=C2C(CC(=O)O)CCCC2(c2ccc(CCC(C)(C)C)c(Cl)c2)NC1=O] | Racemate Configuration of carboxymethyl and 3-chloro-4-(3,3-dimethylbutyl)phenyl was estimated to be trans |
| 46 | 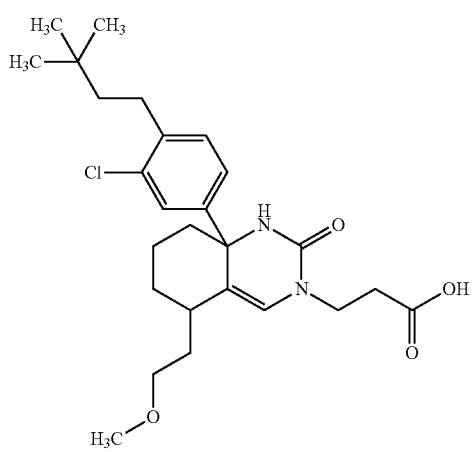 [SMILES: COCCC1CCCC2(c3ccc(CCC(C)(C)C)c(Cl)c3)NC(=O)N(CCC(=O)O)C=C12] | Racemate Configuration of methoxyethyl and 3-chloro-4-(3,3-dimethylbutyl)-phenyl was estimated to be trans |

-continued

| Example | Structure | Structural Information |
|---|---|---|
| 47 | 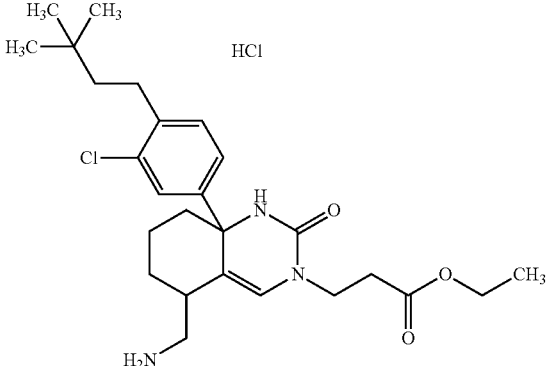 | Racemate<br>Configuration of aminomethyl and 3-chloro-4-(3,3-dimethylbutyl)phenyl was estimated to be trans |
| 48 | 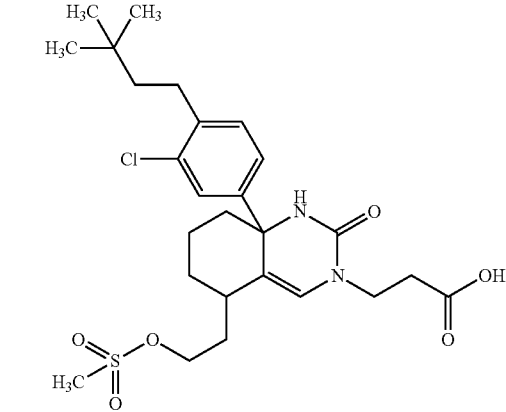 [SMILES: CC(C)(C)CCc1ccc(C23CCCC(CCOS(C)(=O)=O)C2=CN(CCC(=O)O)C(=O)N3)cc1Cl] | Racemate<br>Configuration of mesyloxyethyl and 3-chloro-4-(3,3-dimethylbutyl)phenyl was estimated to be trans |
| 49 | 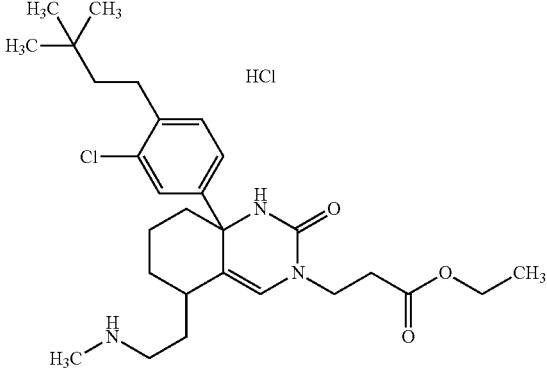 [SMILES: CCOC(=O)CCN1C=C2C(CCNC)CCCC2(c2ccc(CCC(C)(C)C)c(Cl)c2)NC1=O ; Cl] | Racemate<br>Configuration of methylaminoethyl and 3-chloro-4-(3,3-dimethylbutyl)phenyl was estimated to be trans<br>The number of hydrochloride salt was estimated |
| 50 | 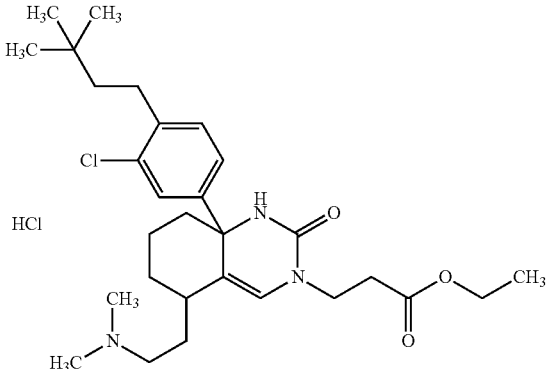 | Racemate<br>Configuration of dimethylaminoethyl and 3-chloro-4-(3,3-dimethylbutyl)phenyl was estimated to be trans<br>The number of hydrochloride salt was estimated |

-continued

| Example | Structure | Structural Information |
|---|---|---|
| 51 | 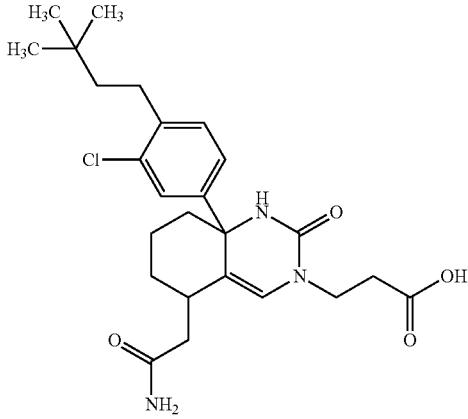 [SMILES: CC(C)(C)CCc1ccc(C23CCCC(CC(N)=O)C2=CN(CCC(=O)O)C(=O)N3)cc1Cl] | Racemate<br>Configuration of carboxamidemethyl and 3-chloro-4-(3,3-dimethylbutyl)phenyl was estimated to be trans |
| 52 | 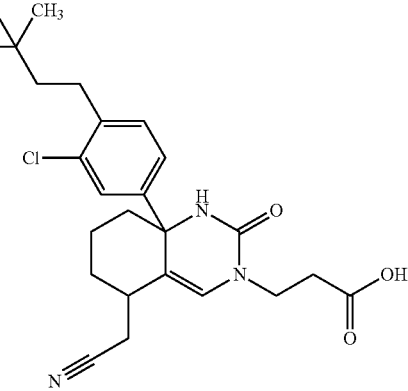 | Racemate<br>Configuration of nitrilemethyl and 3-chloro- 4-(3,3-dimethylbutyl)phenyl was estimated to be trans |
| 53 | 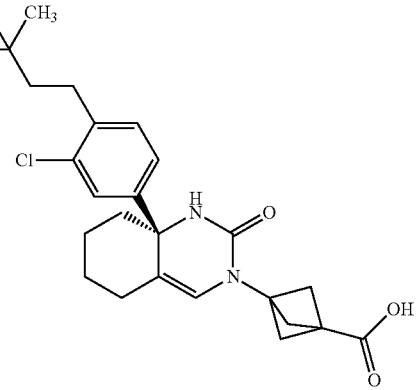 | Optically active<br>Enantiomer of Example 54 (>99% ee for corresponding methyl ester derivative<br>chiral column IA-3, Hexane/IPA = 90/10, flow 1 ml/min<br>Retention time: 5.3 min) |
| 54 | 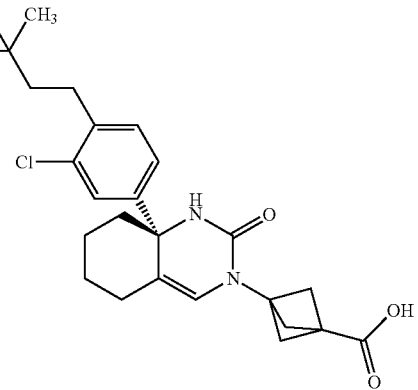 | Optically active<br>Enantiomer of Example 53 (>99% ee for corresponding methyl ester derivative, the product of Example 54 Step 9)<br>chiral column IA-3, Hexan/IPA = 90/10, flow 1 ml /min<br>Retention time: 8.5 min) |

-continued

| Example | Structure | Structural Information |
|---|---|---|
| 55 | 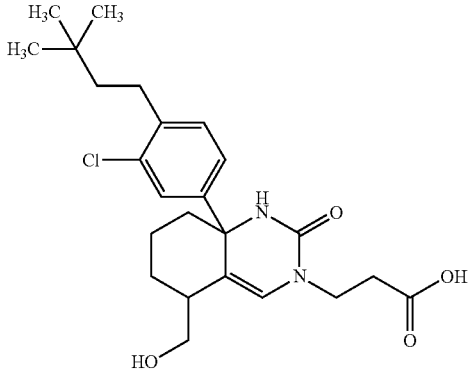 [SMILES: CC(C)(C)CCc1ccc(C23CCCC(CO)C2=CN(CCC(=O)O)C(=O)N3)cc1Cl] | Racemate<br>Configuration of hydroxymethyl and 3-chloro-4-(3,3-dimethylbutyl)phenyl was estimated to be trans |
| 56 | 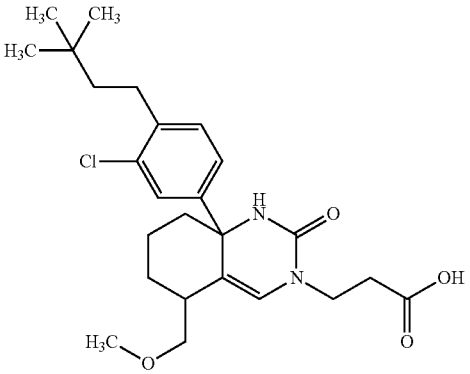 [SMILES: COCC1CCCC2(c3ccc(CCC(C)(C)C)c(Cl)c3)NC(=O)N(CCC(=O)O)C=C12] | Racemate<br>Configuration of methoxymethyl and 3-chloro-4-(3,3-dimethylbutyl)phenyl was estimated to be trans |
| 57 | 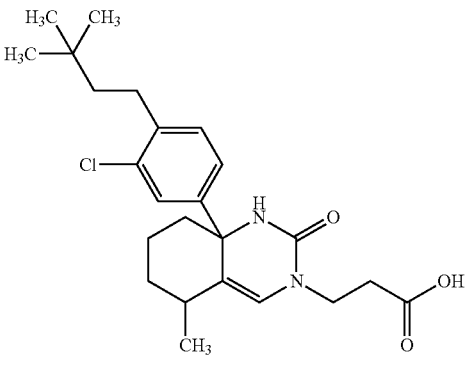 [SMILES: CC1CCCC2(c3ccc(CCC(C)(C)C)c(Cl)c3)NC(=O)N(CCC(=O)O)C=C12] | Racemate<br>Configuration of 3-chloro-4-(3,3-dimethylbutyl)phenyl and methyl group on the cyclohexane ring was estiamted to be cis from NOE |
| 58 | 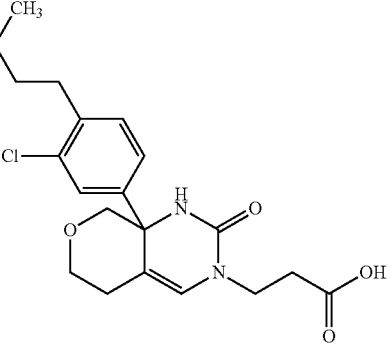 | Racemate |

-continued
| Example | Structure | Structural Information |
|---|---|---|
| 59 | 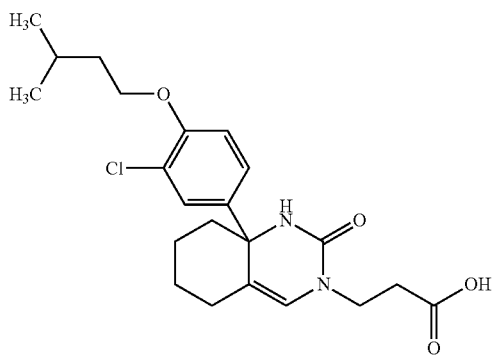 [SMILES: CC(C)CCOc1ccc(C23CCCCC2=CN(CCC(=O)O)C(=O)N3)cc1Cl] | Racemate |
| 60 | 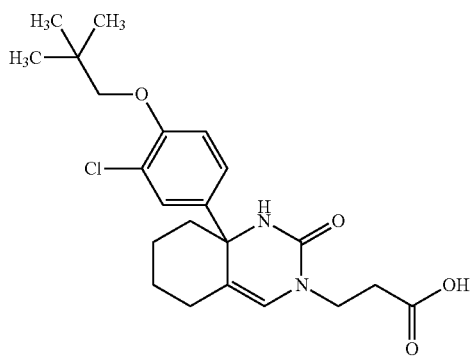 [SMILES: CC(C)(C)COc1ccc(C23CCCCC2=CN(CCC(=O)O)C(=O)N3)cc1Cl] | Racemate |
| 61 | 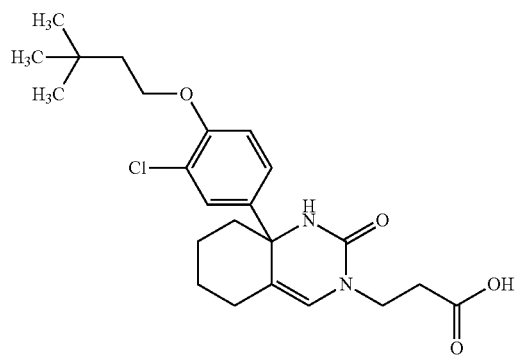 [SMILES: CC(C)(C)CCOc1ccc(C23CCCCC2=CN(CCC(=O)O)C(=O)N3)cc1Cl] | Racemate |
| 62 | 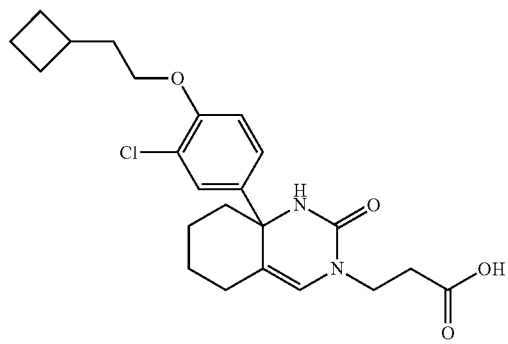 [SMILES: O=C(O)CCN1C=C2CCCCC2(c2ccc(OCCC3CCC3)c(Cl)c2)NC1=O] | Racemate |

-continued
| Example | Structure | Structural Information |
|---|---|---|
| 63 | 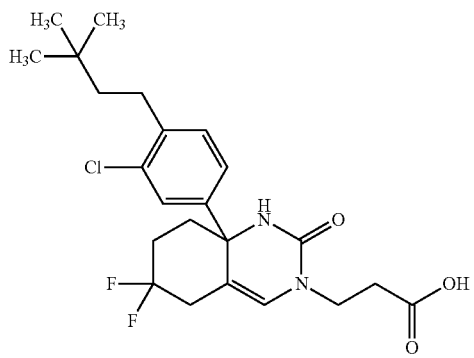 [SMILES: CC(C)(C)CCc1ccc(C23CCC(F)(F)CC2=CN(CCC(=O)O)C(=O)N3)cc1Cl] | Racemate |
| 64 | 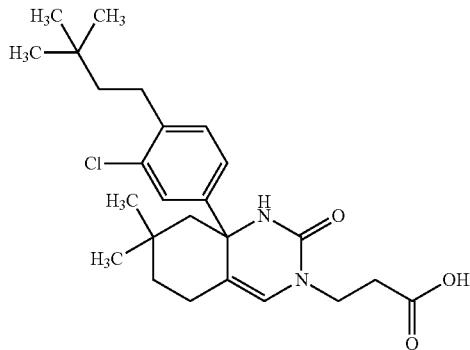 [SMILES: CC(C)(C)CCc1ccc(C23CC(C)(C)CCC2=CN(CCC(=O)O)C(=O)N3)cc1Cl] | Racemate. Estimated structure. |
| 65 | 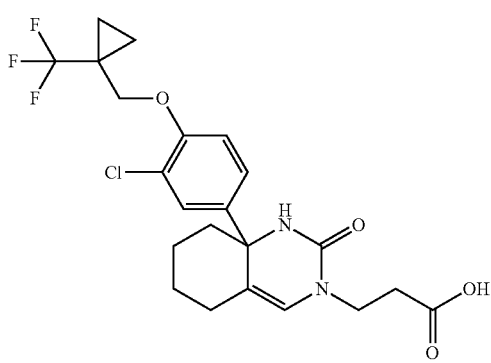 [SMILES: O=C(O)CCN1C=C2CCCCC2(c2ccc(OCC3(C(F)(F)F)CC3)c(Cl)c2)NC1=O] | Racemate |
| 66 | 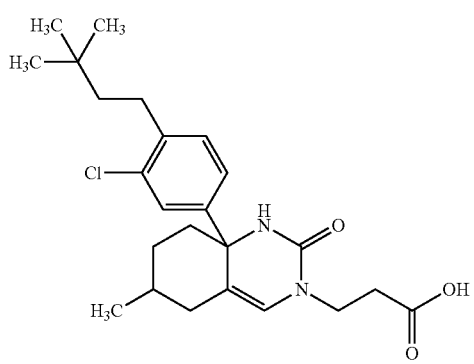 [SMILES: CC1CCC2(c3ccc(CCC(C)(C)C)c(Cl)c3)NC(=O)N(CCC(=O)O)C=C2C1] | Racemate Single diastereomer Relative configuration of 3-chloro-4-(3,3-dimethylbutyl)phenyl and methyl group on the cyclohexane ring was uncertain |

-continued

| Example | Structure | Structural Information |
|---|---|---|
| 67 | 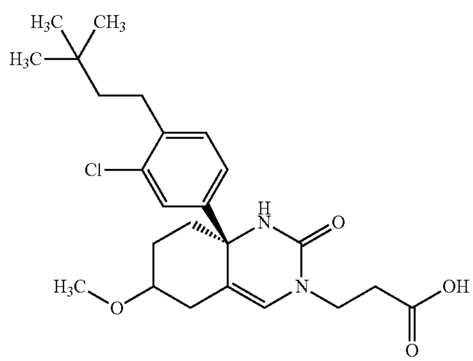 | Enantiomer of Example 68 (Absolute and relative configurations were not determined.) Analytical conditions for corresponding ethyl ester derivative: chiral column IA-3, Hexane/IPA = 85/15, flow 1 ml/min Retention time: 5.2 min |
| 68 | 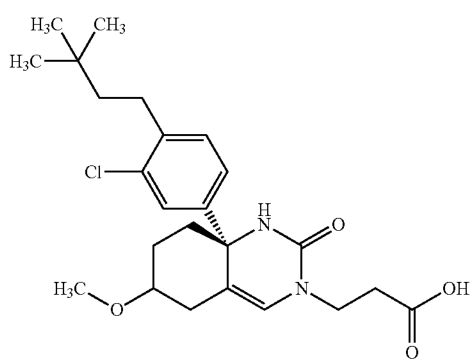 | Enantiomer of Example 67 (Absolute and relative configurations were not determined,) Analytical conditions for corresponding ethyl ester derivative: chiral column IA-3, Hexane/IPA = 85/15, flow 1 ml/min Retention time: 7.8 min |
| 69 | 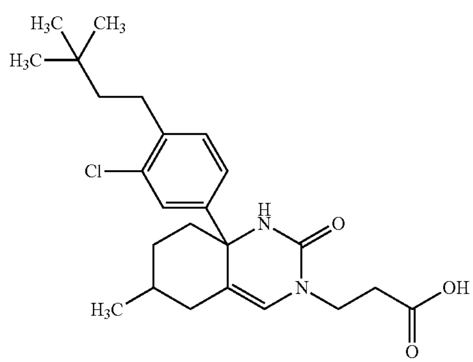 | Racemate Single diastereomer Relative configuration of 3-chloro-4-(3,3-dimethylbutyl)phenyl and methyl group on the cyclohexane ring was uncertain Diastereomer of Example 66 |
| 70 | 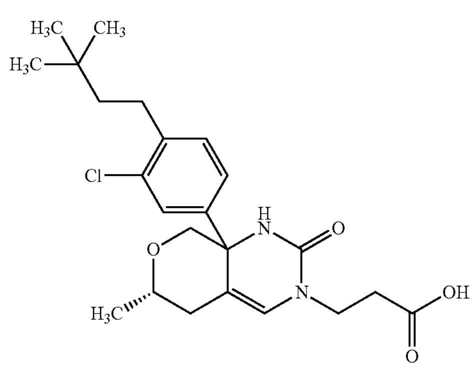 [SMILES: CC1CCC2(c3ccc(CCC(C)(C)C)c(Cl)c3)NC(=O)N(CCC(=O)O)C=C2C1] | Optically active (Absolute configuration was not determined.) (Optical purity was not determined) Single diastereomer Relative configuration of 3-chloro-4-(3,3-dimethylbutyl)phenyl and methyl group on the tetrahydropyrane ring was uncertain Enantiomer of Example 71 |

-continued

| Example | Structure | Structural Information |
|---|---|---|
| 71 | 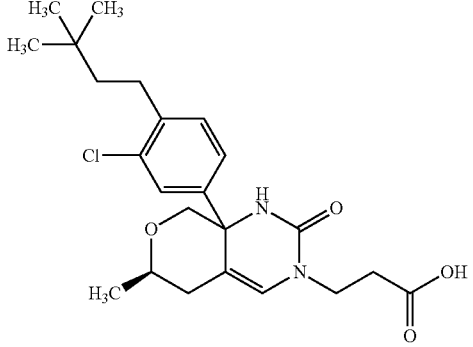 [SMILES: C[C@@H]1CC2=CN(CCC(=O)O)C(=O)NC2(c2ccc(CCC(C)(C)C)c(Cl)c2)CO1] | Optically active (Absolute configuration was not determined.) (Optical purity was not determined) Single diastereomer Relative configuration 3-chloro-4-(3,3-dimethylbutyl)phenyl and methyl group on the tetrahydropyrane ring was uncertain Enantiomer of Example 70 |
| 72 | 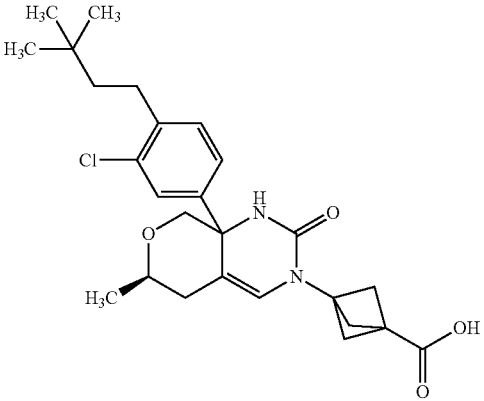 [SMILES: C[C@@H]1CC2=CN(C34CC(C(=O)O)(C3)C4)C(=O)NC2(c2ccc(CCC(C)(C)C)c(Cl)c2)CO1] | Optically active (Absolute configuration was not determined.) (Optical purity was not determined) Single diastereomer Relative configuration of 3-chloro-4-(3,3-dimethylbutyl)phenyl and methyl group on the tetrahydropyrane was uncertain |
| 73 | 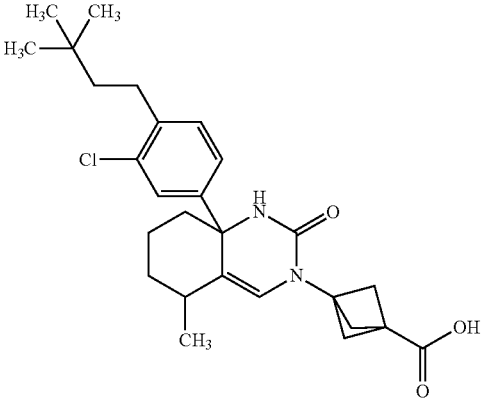 [SMILES: CC1CCCC2(c3ccc(CCC(C)(C)C)c(Cl)c3)NC(=O)N(C34CC(C(=O)O)(C3)C4)C=C12] | Racemate Configuration of 3-chloro-4-(3,3-dimethylbutyl)phenyl and methyl group on the cyclohexane ring was estimated to be cis |
| 74 | 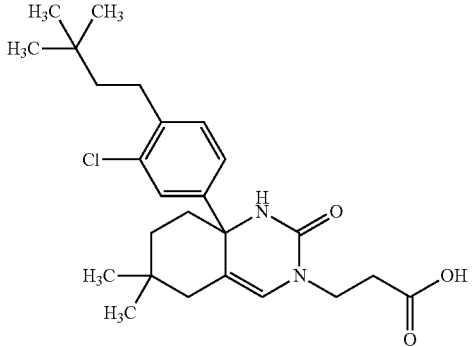 [SMILES: CC(C)(C)CCc1ccc(C23CCC(C)(C)CC2=CN(CCC(=O)O)C(=O)N3)cc1Cl] | Racemate |

-continued

| Example | Structure | Structural Information |
|---|---|---|
| 75 | 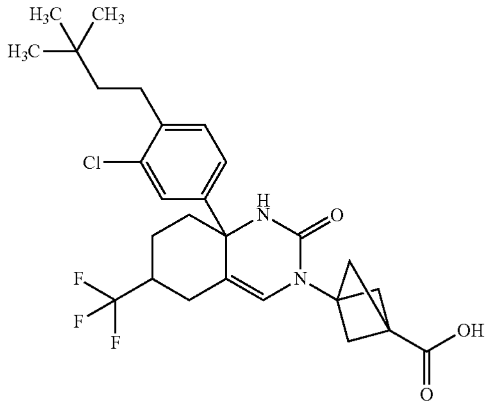 [SMILES: CC(C)(C)CCc1ccc(C23CCC(C(F)(F)F)CC2=CN(C24CC(C(=O)O)(C2)C4)C(=O)N3)cc1Cl] | Estmated to be optically active. (Absolute and relative configurations were not determined.) Estimated structure. |
| 76 | 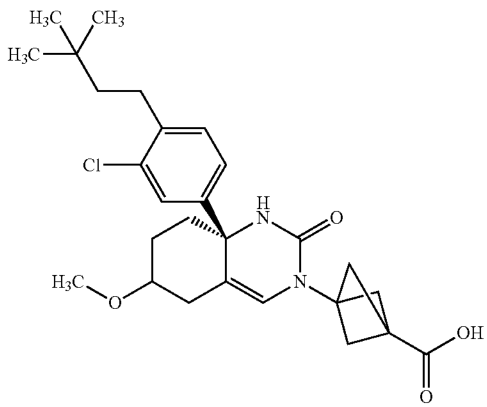 | Enantiomer of Example 77 (Absolute and relative configurations were not determined.) Analytical conditions for corresponding methyl ester derivative: chiral column IA-3, Hexane/IPA = 85/15, flow 1 ml/min Retention time: 4.0 min |
| 77 | 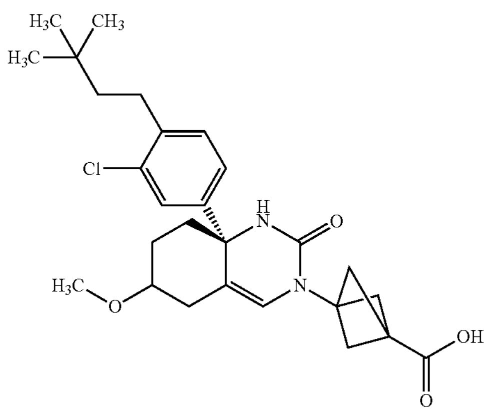 | Enantiomer of Example 76 (Absolute and relative configurations were not determined.) Analytical conditions for corresponding methyl ester derivative: chiral column IA-3, Hexane/IPA = 85/15, flow 1 ml/min Retention time: 6.5 min |
| 78 | 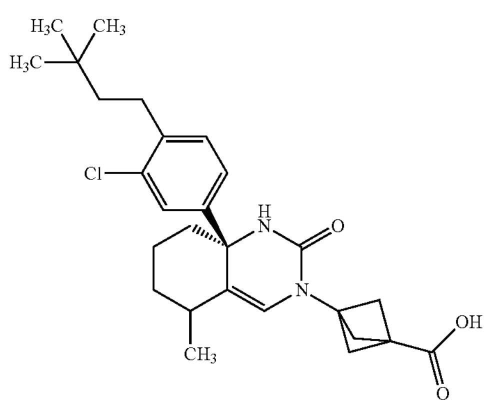 | Optically active compound of Example 73 (Absolute and relative configurations were not determined.) Enantiomer of Example 79 (>99% ee for corresponding methyl ester derivative chiral column IA-3, Hexane/IPA = 85/15, flow 1 ml/min Retention time: 4.2 min) |

-continued

| Example | Structure | Structural Information |
|---------|-----------|------------------------|
| 79 | 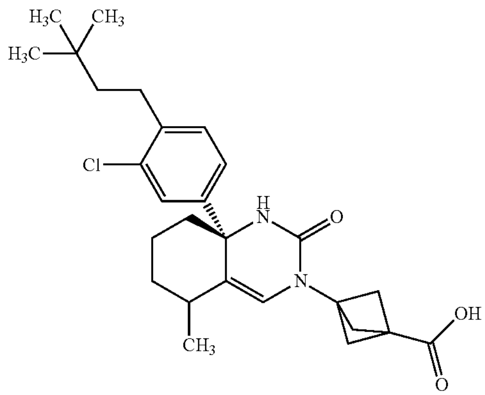 | Optically active compound of Example 73 (Absolute and relative configurations were not determined.) Enantiomer of Example 78 (>99% ee for corresponding methyl ester derivative chiral column IA-3, Hexane/IPA = 85/15, flow 1 ml/min Retention time: 7.2 min) |
| 80 | 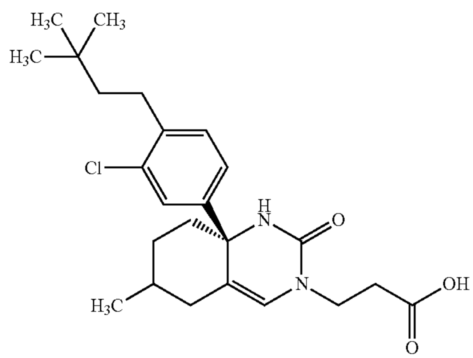 | Optically active compound of Example 69 (Absolute configuration was not determined.) Enantiomer of Example 81 (>99% ee for corresponding ethyl ester derivative chiral column Hexane/IPA = 90/10, flow 1 ml/min Retention time: 5.8 min) Relative configuration of 3-chloro-4-(3,3-dimethylbutyl)phenyl and methyl group on the cyclonexane ring was uncertain. |
| 81 | 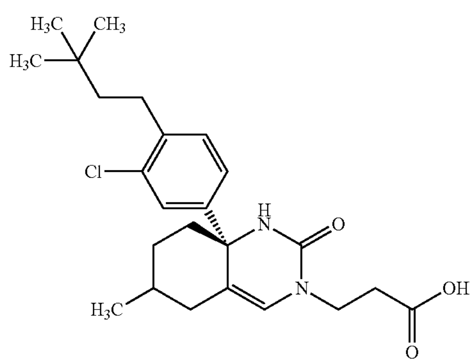 | Optically active compound of Example 69 (Absolute configuration was not determined.) Enantiomer of Example 80 (>99% ee for corresponding ethyl ester derivative (chiral column IA-3, Hexane/IPA = 90/10), flow 1 ml/min Retention time: 8.6 min) Relative configuration of 3-chloro-4-(3,3-dimethylbutyl)phenyl and methyl group on the cyclohexane ring was uncertain |
| 82 | 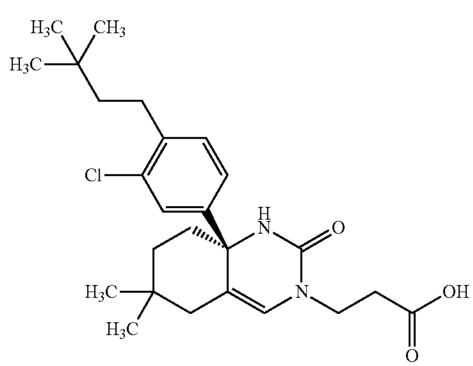 [SMILES: CC(C)(C)CCc1ccc([C@]23CCC(C)(C)CC2=CN(CCC(=O)O)C(=O)N3)cc1Cl] | Optically active compound. of Example 74 (Absolute configuration was not determined.) Enantiomer of Example 83 (>99% ee for corresponding ethyl ester derivative chiral column IA-3, Hexane/IPA = 90/10, flow 1 ml/min Retention time: 5.2 min) |

US 11,834,421 B2

-continued

| Example | Structure | Structural Information |
|---|---|---|
| 83 | 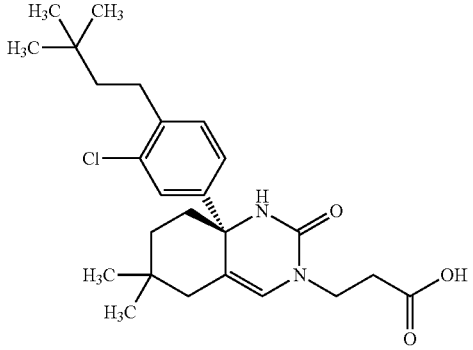 [SMILES: CC(C)(C)CCc1ccc([C@@]23CCC(C)(C)CC2=CN(CCC(=O)O)C(=O)N3)cc1Cl] | Optically active compound of Example 74 (Absolute configuration was not determined.) Enantiomer of Example 82 (>99% ee for corresponding ethyl ester derivative chiral column IA-3, Hexane/IPA = 90/10, flow 1 ml/min Retention time: 8.9 min) |
| 84 | 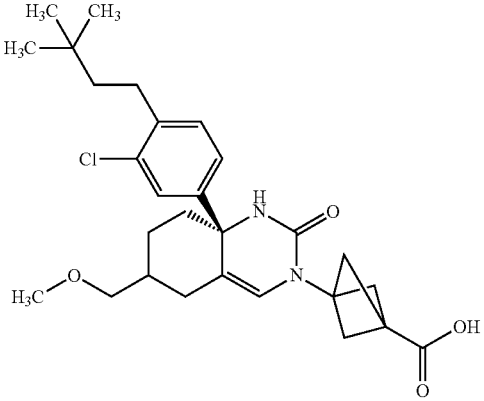 | Enantiomer of Example 85 (Absolute and relative configurations were not determined.) Analytical conditions for corresponding methyl ester derivative: chiral column IA-3, Hexane/IPA = 85/15, flow 1 ml/mm Retention time: 3.9 min |
| 85 | 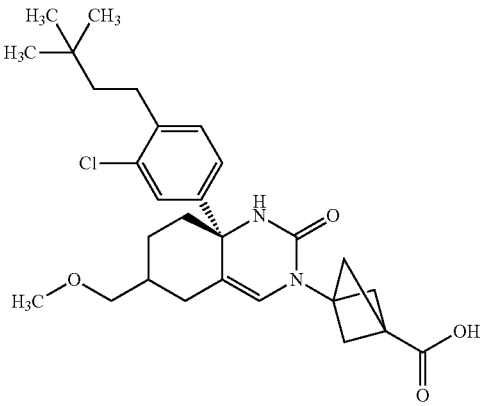 | Enantiomer of Example 84 (Absolute and relative configurations were not determined.) Analytical conditions for corresponding methyl ester derivative: chiral column IA-3, Hexane/IPA = 85/15, flow 1 ml/min Retention time: 6.3 min |
| 86 | 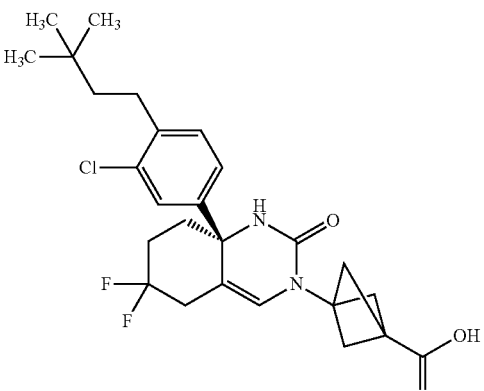 | Enantiomer of Example 87 (Absolute configuration was not determined.) Analytical conditions for corresponding methyl ester derivative: chiral column IA-3, Hexane/IPA = 80/20, flow 1 ml/min Retention time: 3.1 min |

-continued

| Example | Structure | Structural Information |
|---|---|---|
| 87 | 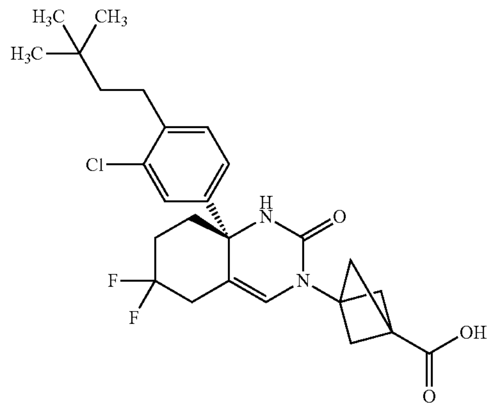 [SMILES: CC(C)(C)CCc1ccc([C@@]23CCC(F)(F)CC2=CN(C24CC(C(=O)O)(C2)C4)C(=O)N3)cc1Cl] | Enantiomer of Example 86 (Absolute configuration was not determined.) Analytical conditions for corresponding methyl ester derivative: chiral column IA-3, Hexane/IPA = 80/20, flow 1 ml/min Retention time: 5.2 min |
| 88 | 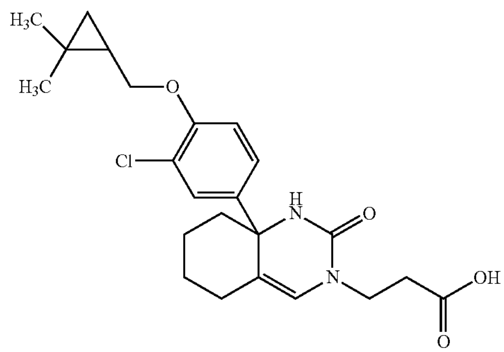 [SMILES: CC1(C)CC1COc1ccc(C23CCCCC2=CN(CCC(=O)O)C(=O)N3)cc1Cl] | Racemate 1:1 diastereomeric mixture regarding the substituents on cyclopropyl |
| 89 | 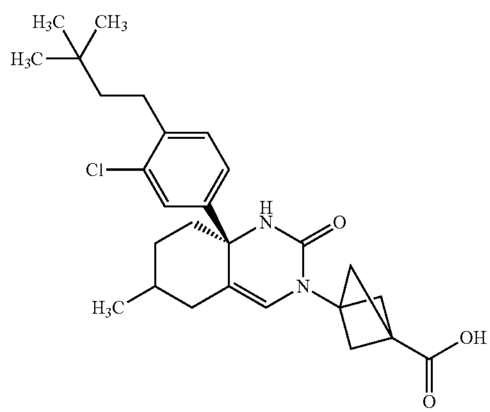 | Enantiomer of Example 90 (Absolute and relative configurations were not determined.) Analytical conditions for corresponding methyl ester derivative: chiral column IA-3, Hexane/IPA = 90/10, flow 1 ml/min Retention time: 4.6 min |
| 90 | 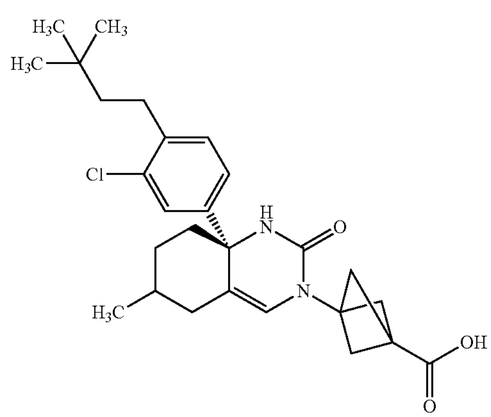 | Enantiomer of Example 89 (Absolute and relative configurations were not determined.) Analytical conditions for corresponding methyl ester derivative: chiral column IA-3, Hexane/IPA = 90/10, flow 1 ml/min Retention time: 8.4 min |

-continued

| Example | Structure | Structural Information |
|---|---|---|
| 91 | 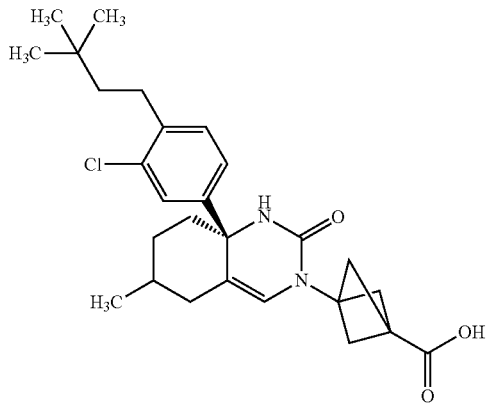 | Enantiomer of Example 92 (Absolute and relative configurations were not determined.) Analytical conditions for corresponding methyl ester derivative: chiral column IA-3, Hexane/IPA = 90/0, flow 1 ml/min Retention time: 4.1 min |
| 92 | 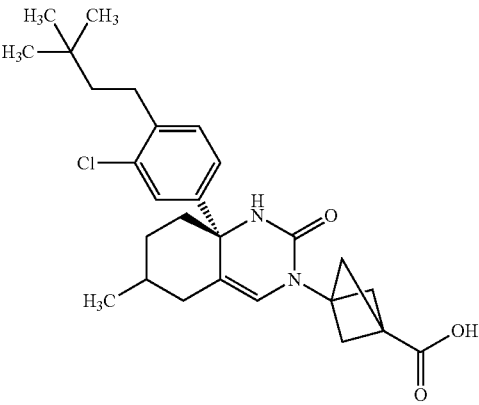 | Enantiomer of Example 91 (Absolute and relative configurations were not determined.) Analytical conditions for corresponding methyl ester derivative: chiral column IA-3, Hexane/IPA = 90/10, flow 1 ml/min Retention time: 7.8 min |
| 93 | 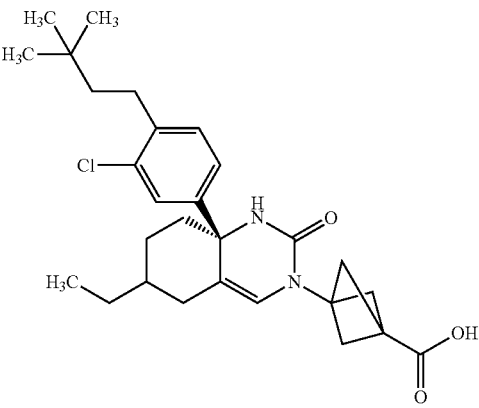 | Enantiomer of Example 94 (Absolute and relative configurations were not determined.) Analytical conditions for corresponding methyl ester derivative: chiral column IA-3, Hexane/IPA = 90/10, flow 1 ml/min Retention time: 4.1 min |

-continued
| Example | Structure | Structural Information |
|---|---|---|
| 94 | 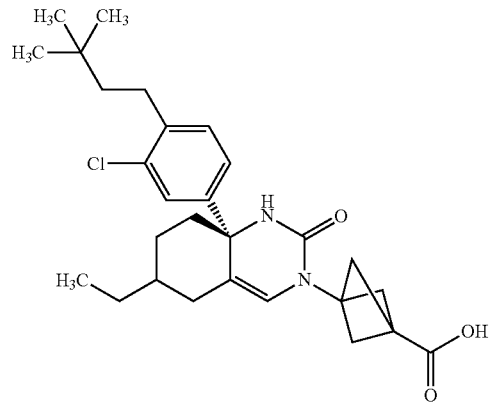 | Enantiomer of Example 93 (Absolute and relative configurations were not determined.) Analytical conditions for corresponding methyl ester derivative: chiral column IA-3, Hexane/IPA = 90/10, flow 1 ml/min Retention time: 7.3 min |
| 95 | 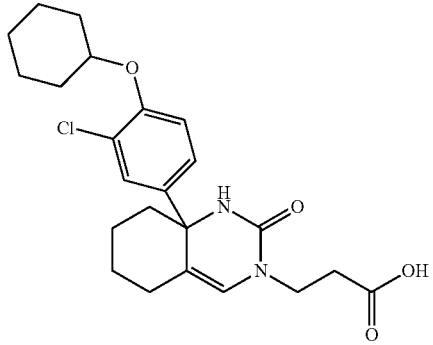 [SMILES: O=C(O)CCN1C=C2CCCCC2(c2ccc(OC3CCCCC3)c(Cl)c2)NC1=O] | Racemate |
| 96 | 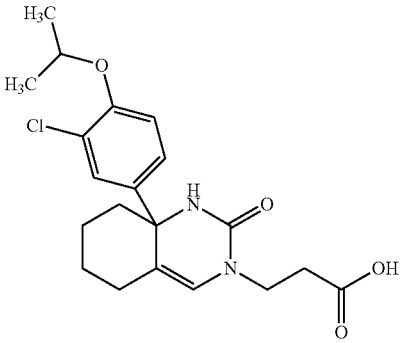 [SMILES: CC(C)Oc1ccc(C23CCCCC2=CN(CCC(=O)O)C(=O)N3)cc1Cl] | Racemate |
| 97 | 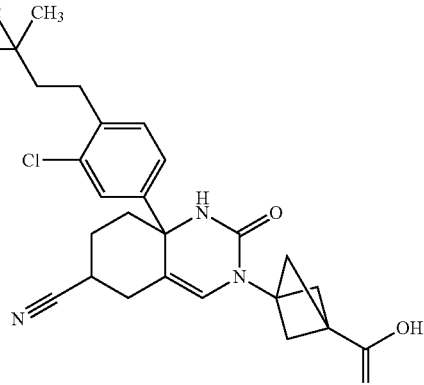 | Single diastereomer. Estimated structure. Estimated to be racemate. |

| Example | Structure | Structural Information |
|---------|-----------|------------------------|
| 98 | 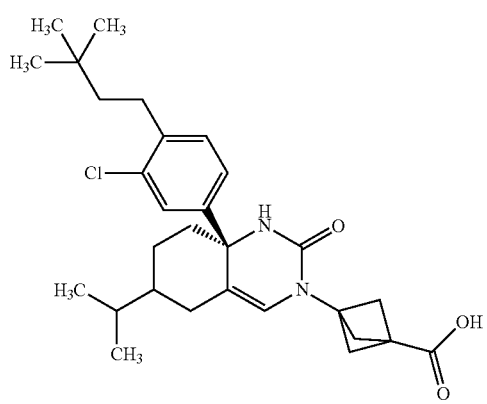 | Optically active (Absolute and relative configurations were not determined.) Analytical conditions for corresponding ethyl ester derivative: chiral column IA-3, IPA/Hex, = 10/90, flow 1 ml/min Retention time: 3.7 min |
| 99 | 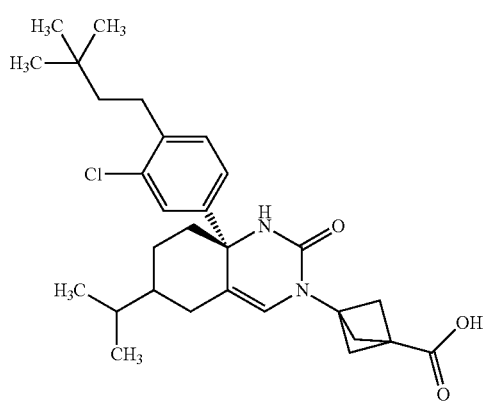 | Optically active (Absolute and relative configurations were not determined.) Analytical conditions for corresponding ethyl ester derivative: chiral column IA-3, IPA/Hex. = 10/90, flow 1 ml/min Retention time: 6.5 min |
| 100 | 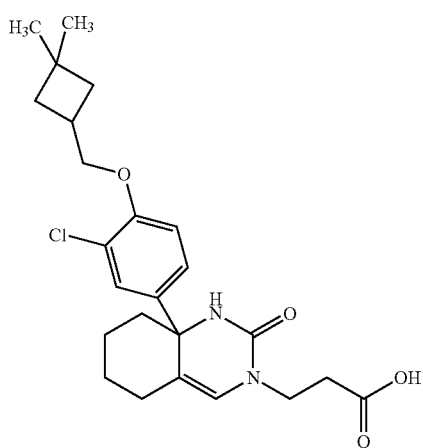 [SMILES: CC1(C)CC(COc2ccc(C34CCCCC3=CN(CCC(=O)O)C(=O)N4)cc2Cl)C1] | Racemate |

-continued

| Example | Structure | Structural Information |
|---|---|---|
| 101 | 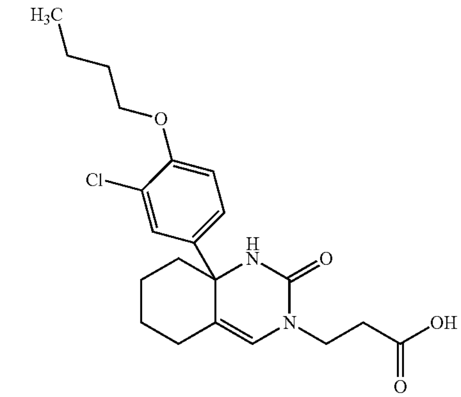 [SMILES: CCCCOc1ccc(C23CCCCC2=CN(CCC(=O)O)C(=O)N3)cc1Cl] | Racemate |
| 102 | 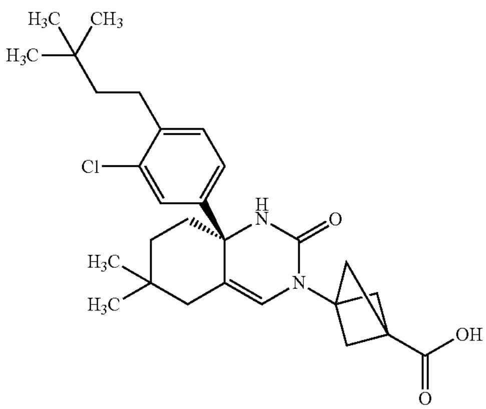 [SMILES: CC(C)(C)CCc1ccc([C@]23CCC(C)(C)CC2=CN(C24CC(C(=O)O)(C2)C4)C(=O)N3)cc1Cl] | Enantiomer of Example 103 (Absolute configuration was not determined.) Analytical conditions for corresponding methyl ester derivative: chiral column IA-3, Hexane/IPA = 90/10, flow 1 ml/min Retention time: 4.3 min |
| 103 | 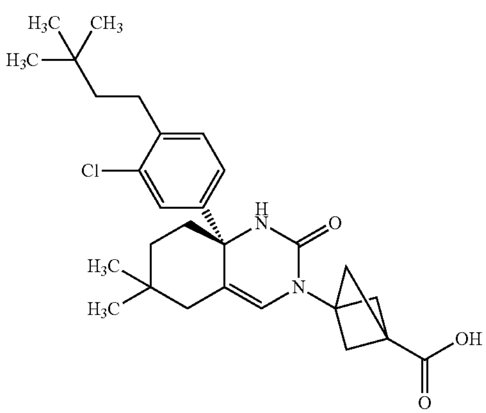 [SMILES: CC(C)(C)CCc1ccc([C@@]23CCC(C)(C)CC2=CN(C24CC(C(=O)O)(C2)C4)C(=O)N3)cc1Cl] | Enantiomer of Example 102 (Absolute configuration was not determined.) Analytical conditions for corresponding methyl ester derivative: chiral column IA-3, Hexane/IPA = 90/10, flow 1 ml/min Retention time: 9.7 min |
| 104 | 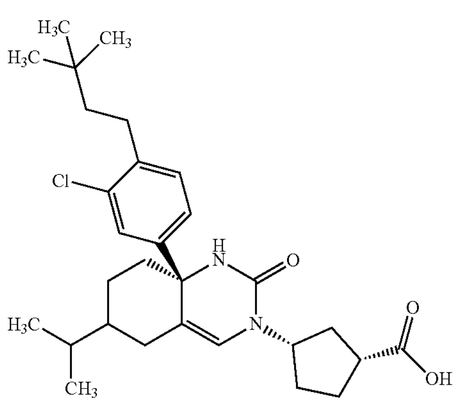 | Optically active (Absolute and relative configurations were not determined.) Analytical conditions for corresponding methyl ester derivative: chiral column AS-3R, MeCN/H$_2$O = 80/20, flow 1 ml/min Retention time: 6.8 min Cyclopentane ring moiety was induced from methyl (1R,3S)-3-aminocyclopentanecarboxy-late hydrochloride. |

-continued

| Example | Structure | Structural Information |
|---------|-----------|------------------------|
| 105 | 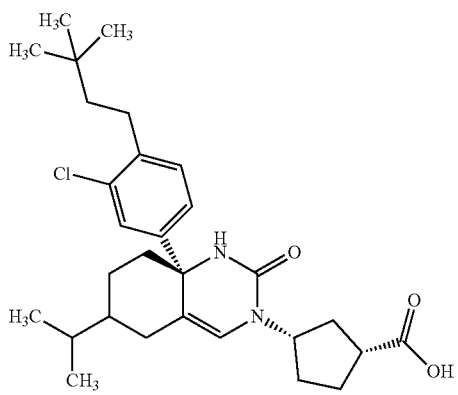 | Optically active (Absolute and relative configurations were not determined.) Analytical conditions for corresponding methyl ester derivative: chiral column AS-3R, MeCN/H$_2$O = 80/20, flow 1 ml/min Retention time: 7.5 min Cyclopentane ring moiety was induced from methyl (1R,3S)-3-aminocyclopentanecarboxylate hydrochloride. |
| 106 | 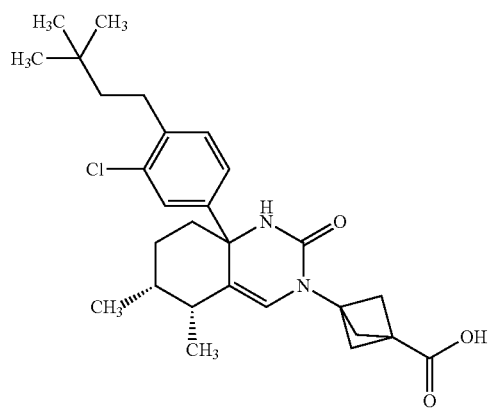 [SMILES: C[C@@H]1CCC2(c3ccc(CCC(C)(C)C)c(Cl)c3)NC(=O)N(C34CC(C(=O)O)(C3)C4)C=C2[C@@H]1C] | Optically active. (Absolute configuration was not determined.) Optical purity was not determined. Single stereoisomer. Configuration of two methyl groups on the cyclohexane ring was estimated to be cis. Configuration of the two methyl groups and 3-chloro-4-(3,3-dimethylbutyl)phenyl was estimated to be trans from NOE. |
| 107 | 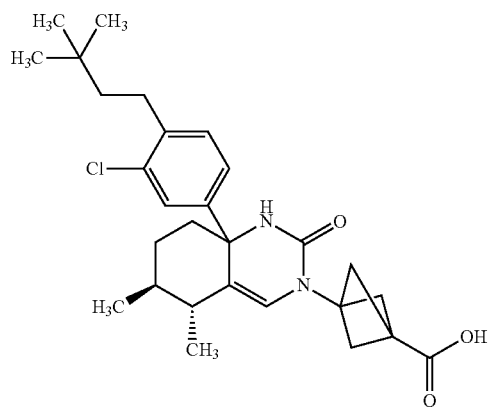 [SMILES: C[C@H]1CCC2(c3ccc(CCC(C)(C)C)c(Cl)c3)NC(=O)N(C34CC(C(=O)O)(C3)C4)C=C2[C@@H]1C] | Optically active. (Absolute configuration was not determined.) Optical purify was not determined. Single stereoisomer. Estimated structure. Configuration of two methyl groups on the cyclohexane ring was estimated to be trans. Analytical conditions for corresponding methyl ester derivative: chiral column IA-3, Hexane/IPA = 90/10, flow 1 ml/min Retention time: 9.7 min |

-continued

| Example | Structure | Structural Information |
|---|---|---|
| 108 | 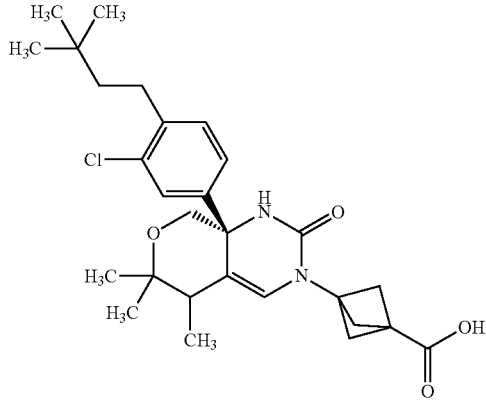 | Diastereomeric mixture (Absolute configuration was not determined.) Enantiomeric mixture of Example 109 and Example 110 (>99% ee for corresponding methyl ester derivative chiral column IA-3, Hexane/IPA = 85/15, flow 1 ml/min Retention time: 3.9 min) |
| 109 | 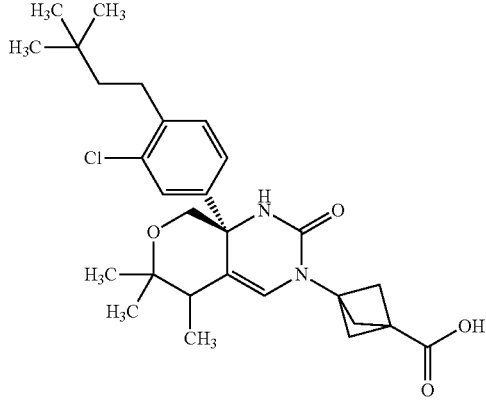 | Optically active (Absolute and relative configurations were not determined.) Enantiomer of Example 108 Diastereomer of Example 109 (>99% ee for corresponding methyl ester derivative chiral column IA-3, Hexane/IPA = 85/15, flow 1 ml/min Retention time: 7.6 min) |
| 110 | 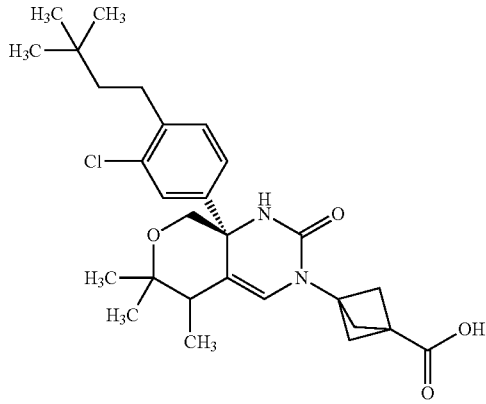 | Optically active (Absolute and relative configurations were not determined.) Enantiomer of Example 102 Diastereomer of Example 109 (>99% ee for corresponding methyl ester derivative chiral column IA-3, Hexane/ IPA = 85/15, flow 1 ml/min Retention time: 9.8 min) |
| 111 | 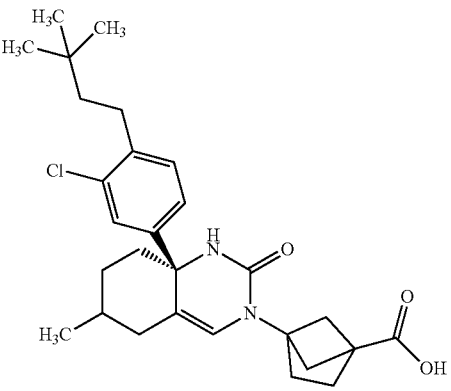 | Optically active (Absolute and relative configurations were not determined.) Analytical conditions for corresponding ethyl ester derivative: chiral column IA-3, IPA/Hex. = 10/90, flow 1 ml/min Retention time: 6.4 min |

-continued

| Example | Structure | Structural Information |
|---|---|---|
| 112 | 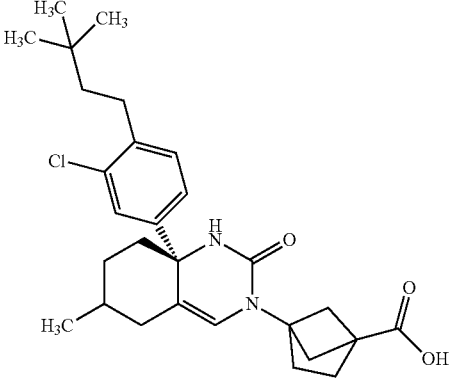 | Optically active (Absolute and relative configurations were not determined.) Analytical conditions for corresponding ethyl ester derivative: chiral column IA-3, IPA/Hex. = 10/90, flow 1 ml/min Retention time: 13.3 min |
| 113 | 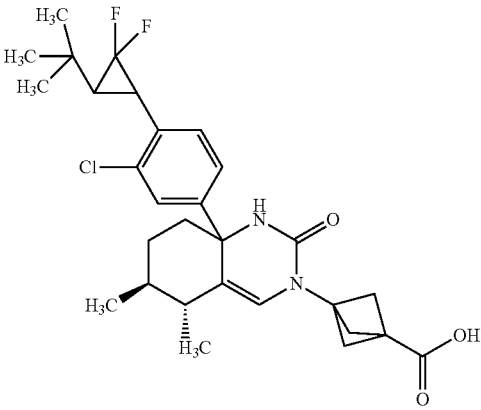 [SMILES: C[C@H]1CCC2(c3ccc(C4C(C(C)(C)C)C4(F)F)c(Cl)c3)NC(=O)N(C34CC(C(=O)O)(C3)C4)C=C2[C@@H]1C] | Optically active (Absolute and relative configurations were not determined.) Optical purity was not determined Enantiomer of Example 114 |
| 114 | 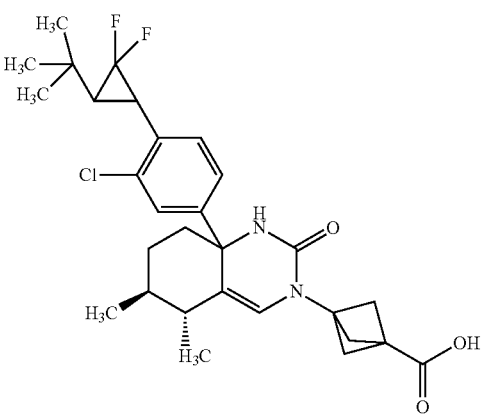 [SMILES: C[C@H]1CCC2(c3ccc(C4C(C(C)(C)C)C4(F)F)c(Cl)c3)NC(=O)N(C34CC(C(=O)O)(C3)C4)C=C2[C@@H]1C] | Optically active (Absolute and relative configurations were not determined.) Optical purity was not determined Enantiomer of Example 113 |
| 115 | 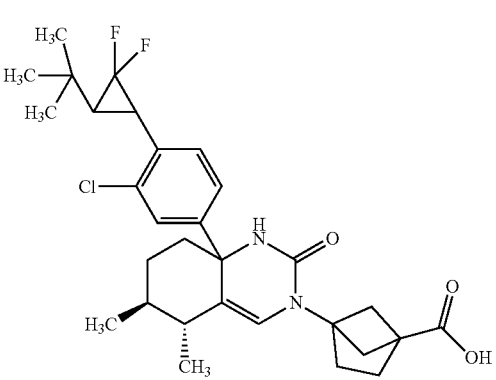 [SMILES: C[C@H]1CCC2(c3ccc(C4C(C(C)(C)C)C4(F)F)c(Cl)c3)NC(=O)N(C34CCC(C(=O)O)(C3)C4)C=C2[C@@H]1C] | Optically active (Absolute and relative configurations were not determined.) Optical purity was not determined Enantiomer of Example 116 |

-continued

| Example | Structure | Structural Information |
|---|---|---|
| 116 | 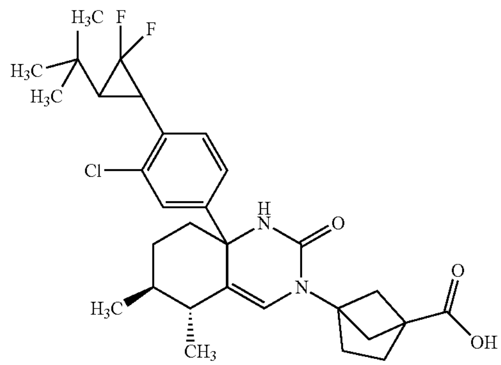 [SMILES: C[C@H]1CCC2(c3ccc(C4C(C(C)(C)C)C4(F)F)c(Cl)c3)NC(=O)N(C34CCC(C(=O)O)(C3)C4)C=C2[C@@H]1C] | Optically active (Absolute and relative configurations were not determined Optical purity was not determined Enantiomer of Example 115 |
| 117 | 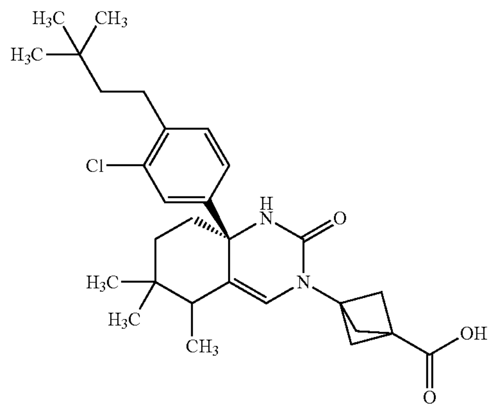 | Optically active (Absolute and relative configurations were not determined.) Single stereoisomer Enantiomer of Example 118 (>99% ee for corresponding ethyl ester derivative chiral column IA-3, Hexane/IPA = 90/10, flow 1 ml/min Retention time: 4.2 min) |
| 118 | 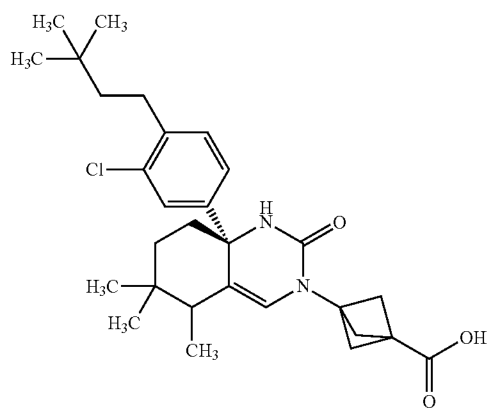 | Optically active (Absolute and relative configurations were not determined.) Single stereoisomer Enantiomer of Example 117 (>99% ee for corresponding ethyl ester derivative chiral column IA-3, Hexane/IPA = 90/10, flow 1 ml/min Retention time: 11.2 min) |
| 119 | 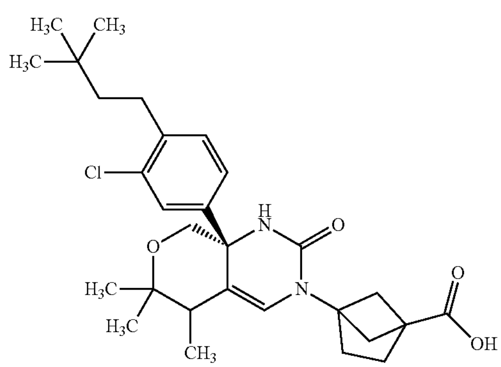 | Diastereomeric mixture (Absolute configuration was not determined.) Enantiomeric mixture of Example 120 and Example 121 (>99% ee for corresponding ethyl ester derivative chiral column IA-3, Hexane/IPA = 85/15, flow 1 ml/min Retention time: 6.6, 7.5 min) |

-continued

| Example | Structure | Structural Information |
|---|---|---|
| 120 | 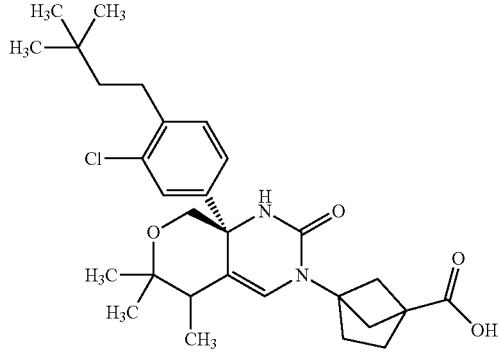 | Optically active (Absolute and relative configurations were not determined.) Single stereoisomer Enantiomer of Example 119 Diastereomer of Example 121 (>99% ee for corresponding ethyl ester derivative chiral column IA-3, Hexane/IPA = 85/15, flow 1 ml/min Retention time: 12.9 min) |
| 121 | 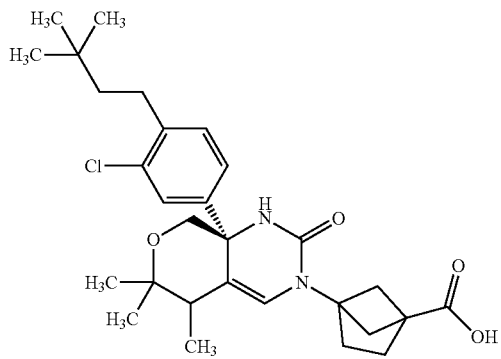 | Optically active (Absolute and relative configurations were not determined.) Single stereoisomer Enantiomer of Example 119 Diastereomer of Example 120 (>99% ee for corresponding ethyl ester derivative chiral column IA-3, Hexane/IPA = 85/15, flow 1 ml/min Retention time: 10.5 min) |

| Example | $^1$H-NMR | MS M + H | MS M − H |
|---|---|---|---|
| 1 | $^1$H-NMR (400 MHz, DMSO-$d_6$) δ: 1.02 (s, 9H), 1.47-1.60 (m, 1H), 1.78-1.88 (m, 1H), 1.99-2.07 (m, 1H), 2.13-2.19 (m, 1H), 2.53-2.64 (m, 2H), 3.69 (s, 2H), 7.09 (d, J = 8.6 Hz, 1H), 7.12 (dd, J = 8.6, 2.1 Hz, 1H), 7.36 d, J = 2.1. Hz, 1H), 8.09 (d, J = 1.8 Hz, 1H), 9.63 (d, J = 1.8 Hz, 1H). | 336 | 334 |
| 2 | $^1$H-NMR (400 MHz, DMSO-$d_6$) δ: 0.93 (s, 9H), 1.08 (s, 3H), 1.20 (s, 3H), 1.21-1.26 (m, 1H), 1.43 (ddd, J = 12.0, 7.5, 3.0 Hz, 2H), 1.46-1.51 (m, 1H), 1.53-1.63 (m, 2H), 2.00 (t, J = 8.1 Hz, 2H), 2.06 (td, J = 11.2, 5.7 Hz, 1H), 2.23 (dq, J = 12.8, 3.2 Hz, 1H), 2.45-2.49 (m, 1H), 2.99-3.06 (m, 1H), 3.55 (dt, J = 14.0, 6.6 Hz, 1H), 6.27 (s, 1H), 7.12 (d, J = 8.3 Hz, 2H), 7.30 (d, J = 8.3 Hz, 2H), 7.42 (s, 1H), 12.14 (br s, 1H). | 413 | 411 |
| 3 | $^1$H-NMR (400 MHz, DMSO-$d_6$) δ: 0.95 (s, 9H), 1.06 (s, 3H), 1.19 (s, 3H), 1.20-1.24 (m, 1H), 1.37-1.41 (m, 2H), 1.45-1.53 (m, 1H), 2.05 (dt, J = 18.3, 5.9 Hz, 1H), 2.19-2.25 (m, 1H), 2.33 (t, J = 6.8 Hz, 2H), 2.59-2.63 (m, 2H), 3.28-3.35 (m, 1H), 3.67 (dt, J = 14.2, 6.8 Hz, 1H), 6.38 (s, 1H), 7.23 (dd, J = 8.0, 1.7 Hz, 1H), 7.27 (d, J = 7.9 Hz, 1H), 7,42 (d, J = 1.6 Hz, 1H), 7.57 (s, 1H), 12.23 (br s, 1H). | 433 | 431 |
| 4 | $^1$H-NMR (400 MHz, DMSO-$d_6$) δ: 0.95 (s, 9H), 1.06 (s, 3H), 1.19 (s, 3H), 1.20-1.24 (m, 1H), 1.37-1.41 (m, 2H), 1.4 5-1.53 (m, 1H), 2.05 (dt, J = 18.3, 5.9 Hz, 1H), 2.19-2.25 (m, 1H), 2.33 (t, J = 6.8 Hz, 2H), 2.59-2.63 (m, 2H), 3.28-3.35 (m, 1H), 3.67 (dt, J = 14.2, 6.8 Hz, 1H), 6.38 (s, 1H), 7.23 (dd, J = 8.0, 1.7 Hz, 1H), 7.27 (d, J = 7.9 Hz, 1H), 7.42 (d, J = 1.6 Hz, 1H), 7.57 (s, 1H), 12.23 (br s, 1H). | 433 | 431 |
| 5 | $^1$H-NMR (400 MHz, DMSO-$d_6$) δ: 0.95 (s, 9H), 1.18 (s, 3H), 1.36 (s, 3H), 1.37-1.41 (m, 2H), 2.40 (dt, J = 10.5, 3.5 Hz, 2H), 2.62 (ddd, J = 9.3, 4.2, 3.3 Hz, 2H), 3.37 (dt, J = 14.3, 6.8 Hz, 1H), 3.69-3.76 (m, 1H), 3.83 (d, J = 8.6 Hz, 1H), 4.25 (d, J = 8.6 Hz, 1H), 6.52 (s, 1H), 7.27 (dd, J = 8.0, 1.7 Hz, 1H), 7.30 (d, J = 7.9 Hz, 1H), 7.44 (d, J = 1.6 Hz, 1H), 7.59 (s, 1H), 12.28 (br s, 1H). | 435 | 433 |
| 6 | $^1$H-NMR (400 MHz, DMSO-$d_6$) δ: 0.95 (s, 9H), 1.18 (s, 3H), 1.36 (s, 3H), 1.37-1.41 (m, 2H), 2.40 (dt, J = 10.5, 3.5 Hz, 2H), 2.62 (ddd, J = 9.3, 4.2, 3.3 Hz, 2H), 3.37 (dt, J = 14.3, 6.8 Hz, 1H), | 435 | 433 |

| Example | ¹H-NMR | MS M+H | MS M-H |
|---|---|---|---|
|  | 3.69-3.76 (m, 1H), 3.83 (d, J = 8.6 Hz, 1H), 4.25 (d, J = 8.6 Hz, 1H), 6.52 (s, 1H), 7.27 (dd, J = 8.0, 1.7 Hz, 1H), 7.30 (d, J = 7.9 Hz, 1H), 7.44 (d, J = 1.6 Hz, 1H), 7.59 (s, 1H), 12.28 (br s, 1H). |  |  |
| 7 | ¹H-NMR (400 MHz, DMSO-d₆) δ: 0.93 (s, 9H), 1.27 (s, 3H), 1.33-1.41 (m, 2H), 1.44 (s, 3H), 2.57-2.66 (m, 2H), 3.90-3.97 (m, 2H), 4.28-4.35 (m, 2H), 6.86 (br s, 1H), 7.32-7.42 (m, 2H), 7.43-7.56 (m, 3H), 7.89-7.96 (m, 2H), 8.11 (br s, 1H), 12.90 (br s, 1H). | 483 | 481 |
| 8 | ¹H-NMR (400 MHz, DMSO-d₆) δ: 0.93 (s, 9H), 1.28 (s, 3H), 1.33-1.41 (m, 2H), 2.63 (s, 3H), 3.90-3.98 (m, 2H), 4.28-4.36 (m, 2H), 7.30-7.44 (m, 2H), 7.44-7.56 (m, 3H), 7.87-7.96 (m, 2H), 8.11 (br s, 1H), 12.91 (br s, 1H). | 483 | 481 |
| 9 | ¹H-NMR (400 MHz, DMSO-d₆) δ: 0.92 (s, 9H), 1.15 (s, 3H), 1.22-1.33 (m, 4H), 1.33-1.41 (m, 2H), 1.51-1.60 (m, 1H), 2.09-2.21 (m, 1H), 2.21-2.30 (m, 1H), 2.57-2.63 (m, 2H), 6.67 (s, 1H), 7.29-7.37 (m, 2H), 7.42-7.47 (m, 2H), 7.50-7.53 (m, 1H), 7.86-7.91 (m, 2H), 8.12 (br s, 1H), 12.85 (br s, 1H). | 481 | 479 |
| 10 | ¹H-NMR (400 MHz, DMSO-d₆) δ: 0.93 (s, 9H), 1.15 (s, 3H), 1.20-1.34 (m, 4H), 1.33-1.42 (m, 2H), 1.50-1.63 (m, 1H), 2.10-2.22 (m, 1H), 2.22-2.33 (m, 1H), 2.55-2.64 (m, 2H), 6.67 (s, 1H), 7.28-7.37 (m, 2H), 7.41-7.48 (m, 2H), 7.50-7.55 (m, 1H), 7.85-7.93 (m, 2H), 8.12 (s, 1H), 12.85 (br s, 1H). | 481 | 479 |
| 11 | ¹H-NMR (400 MHz, CDCl₃) δ: 0.97 (s, 9H), 1.11 (d, J = 19.08 Hz, 3H), 1.40-1.48 (m, 2H), 1.86-2.07 (m, 2H), 2.33-2.41 (m, 1H), 2.51-2.59 (m, 2H), 2.60-2.68 (m, 2H), 2.80-2.92 (m, 1H), 3.49-3.59 (m, 1H), 3.76-3.87 (m, 1H), 6.17-6.20 (m, 1H), 6.51 (br s, 1H), 7.14-7.16 (m, 2H), 7.30 (br s, 1H). | 419 | 417 |
| 12 | ¹H-NMR (400 MHz, CDCl₃) δ: 0.97 (s, 9H), 1.11 (d, J = 19.08 Hz, 3H), 1.40-1.48 (m, 2H), 1.86-2.07 (m, 2H), 2.33-2.41 (m, 1H), 2.51-2.59 (m, 2H), 2.60-2.68 (m, 2H), 2.80-2.92 (m, 1H), 3.49-3.59 (m, 1H), 3.76-3.87 (m, 1H), 6.17-6.20 (m, 1H), 6.51 (br s, 1H), 7.14-7.16 (m, 2H), 7.30 (br s, 1H). | 419 | 417 |
| 13 | ¹H-NMR (400 MHz, CDCl₃) δ: 0.96 (s, 9H), 1.19-1.29 (m, 5H), 1.37-1.50 (m, 11H), 2.59-2.69 (m, 2H), 3.52-3.61 (m, 2H), 3.86-4.22 (m, 6H), 5.39 (br s, 1H), 6.25 (br s, 1H), 7.07-7.14 (m, 1H), 7.17-7.22 (m, 1H), 7.23-7.25 (m, 1H). | 534 | 532 |
| 14 | ¹H-NMR (400 MHz, MeOH-d₄) δ: 1.01 (s, 9H), 1.41-1.49 (m, 2H), 2.05 (s, 3H), 2.55-2.62 (m, 2H), 2.68-2.76 (m, 2H), 3.48-3.64 (m, 2H), 3.80-3.95 (m, 2H), 4.05-4.55 (m, 3H), 6.55 (br s, 1H), 7.21-7.33 (m, 2H), 7.37-7.41 (m, 1H). | 448 | 446 |
| 15 | ¹H-NMR (400 MHz, DMSO-d₆) δ: 0.94 (s, 9H), 1.33-1.38 (m, 2H), 2.35-2.40 (m, 2H), 2.57-2.61 (m, 2H), 3.35-3.41 (m, 3H), 3.65-3.72 (m, 1H), 3.77 (d, J = 8.55 Hz, 1H), 4.33 (d, J = 8.55 Hz, 1H), 4.42 (d, J = 12.95 Hz, 1H), 4.47 (d, J= 12.95 Hz, 1H), 4.74-4.78 (m, 1H), 6.56 (d, J = 1.62 Hz, 1H), 7.20-7.35 (m, 7H), 7.41 (s, 1H), 7.65 (s, 1H), 12.18 (br s, 1H). | 527 | 525 |
| 16 | ¹H-NMR (400 MHz, DMSO-d₆) δ: 0.94 (s, 9H), 1.33-1.38 (m, 2H), 2.35-2.40 (m, 2H), 2.57-2.61 (m, 2H), 3.35-3.41 (m, 3H), 3.65-3.72 (m, 1H), 3.77 (d, J = 8.55 Hz, 1H), 4.33 (d, J = 8.55 Hz, 1H), 4.42 (d, J = 12.95 Hz, 1H), 4.47 (d, J= 12.95 Hz, 1H), 4.74-4.78 (m, 1H), 6.56 (d, J = 1.62 Hz, 1H), 7.20-7.35 (m, 7H), 7.41 (s, 1H), 7.65 (s, 1H), 12.18 (br s, 1H). | 527 | 525 |
| 17 | ¹H-NMR (400 MHz, DMSO-d₆) δ: 0.94 (s, 9H), 1.35-1.39 (m, 2H), 2.39 (dd, J = 7.17, 2.77 Hz, 2H), 2.58-2.63 (m, 2H), 3.25-3.33 (m, 1H), 3.35-3.42 (m, 1H), 3.64-3.71 (m, 1H), 3.76 (d, J = 8.32 Hz, 1H), 4.29 (d, J = 8.55 Hz, 1H), 4.55 (dd, J = 7.17, 6.94 Hz, 1H), 4.87 (dd, J = 6.94, 5.78 Hz, 1H), 6.50 (d, J = 1.62 Hz, 1H), 7.26 (d, J = 8.09 Hz, 1H), 7.28 (d, J = 8.09 Hz, 1H), 7.43 (s, 1H), 7.64 (s, 1H), 12.21 (s, 1H). | 437 | 435 |
| 18 | ¹H-NMR (400 MHz, DMSO-d₆) δ: 0.94 (s, 9H), 1.35-1.39 (m, 2H), 2.39 (dd, J = 7.17, 2.77 Hz, 2H), 2.58-2.63 (m, 2H), 3.25-3.33 (m, 1H), 3.35-3.42 (m, 1H), 3.64-3.71 (m, 1H), 3.76 (d, J = 8.32 Hz, 1H), 4.29 (d, J = 8.55 Hz, 1H), 4.55 (dd, J = 7.17, 6.94 Hz, 1H), 4.87 (dd, J = 6.94, 5.78 Hz, 1H), 6.50 (d, J = 1.62 Hz, 1H), 7.26 (d, J = 8.09 Hz, 1H), 7.28 (d, J = 8.09 Hz, 1H), 7.43 (s, 1H), 7.64 (s, 1H), 12.21 (s, 1H). | 437 | 435 |
| 19 | ¹H-NMR (400 MHz, DMSO-d₆) δ: 0.94 (s, 9H), 1.36-1.40 (m, 2H), 2.31-2.45 (m, 2H), 2.59-2.63 (m, 2H), 3.18-3.25 (m, 1H), 3.21 (s, 3H), 3.27-3.33 (m, 1H), 3.35-3.42 (m, 1H), 3.64-3.71 (m, 1H), 3.76 (d, J = 8.55 Hz, 1H), 4.31 (d, J = 8.55 Hz, 1H), 4.71 (dd, J = 7.17, 4.16 Hz, 1H), 6.55 (d, J = 1.62 Hz, 1H), 7.24 (dd, J = 7.86, 1.62 Hz 1H), 7.29 (d, J = 7.86 Hz, 1H), 7.42 (d, J = 1.62 Hz, 1H), 7.67 (s, 1H), 12.22 (s, 1H). | 451 | 449 |
| 20 | ¹H-NMR (400 MHz, DMSO-d₆) δ: 0.94 (s, 9H), 1.36-1.40 (m, 2H), 2.31-2.45 (m, 2H), 2.59-2.63 (m, 2H), 3.18-3.25 (m, 1H), 3.21 (s, 3H), 3.27-3.33 (m, 1H), 3.35-3.42 (m, 1H), 3.64-3.71 (m, 1H), 3.76 (d, J = 8.55 Hz, 1H), | 451 | 449 |

| Example | ¹H-NMR | M + H | M − H |
|---|---|---|---|
|  | 4.31 (d, J = 8.55 Hz, 1H), 4.71 (dd, J = 7.17, 4.16 Hz, 1H), 6.55 (d, J = 1.62 Hz, 1H), 7.24 (dd, J = 7.86, 1.62 Hz, 1H), 7.29 (d, J = 7.86 Hz, 1H), 7.42 (d, J = 1.62 Hz, 1H), 7.67 (s, 1H), 12.22 (s, 1H). |  |  |
| 21 | ¹H-NMR (400 MHz, DMSO-d₆) δ: 0.95 (s, 9H), 1.09 (s, 9H), 1.36-1.41 (m, 2H), 2.35-2.44 (m, 2H), 2.60-2.64 (m, 2H), 3.20 (dd, J = 8.32, 5.78 Hz, 1H), 3.25-3.29 (m, 1H), 3.36-3.43 (m, 1H), 3.67-3.74 (m, 1H), 3.76 (t, J = 6.36 Hz, 1H), 4.31 (d, J = 8.32 Hz, 1H), 4.58 (dd, J = 6.24, 5.78 Hz, 1H), 6.52 (d, J = 1.85 Hz, 1H), 7.28 (d, J = 7.17 Hz, 1H), 7.30 (d, J = 7.17 Hz, 1H), 7.44 (s, 1H), 7.67 (s, 1H). | 493 | 491 |
| 22 | ¹H-NMR (400 MHz, DMSO-d₆) δ: 0.95 (s, 9H), 1.09 (s, 9H), 1.36-1.41 (m, 2H), 2.35-2.44 (m, 2H), 2.60-2.64 (m, 2H), 3.20 (dd, J = 8.32, 5.78 Hz, 1H), 3.25-3.29 (m, 1H), 3.36-3.43 (m, 1H), 3.67-3.74 (m, 1H), 3.76 (t, J = 6.36 Hz, 1H), 4.31 (d, J = 8.32 Hz, 1H), 4.58 (dd, J = 6.24, 5.78 Hz, 1H), 6.52 (d, J = 1.85 Hz, 1H), 7.28 (d, J = 7.17 Hz, 1H), 7.30 (d, J = 7.17 Hz, 1H), 7.44 (s, 1H), 7.67 (s, 1H). | 493 | 491 |
| 23 | ¹H-NMR (400 MHz, CDCl₃) δ: 0.79-0.90 (m, 1H), 0.97 (s, 9H), 1.42-1.46 (m, 2H), 1.78-1.88 (m, 1H), 2.03-2.11 (m, 1H), 2.32-2.42 (m, 2H), 2.46-2.54 (m, 1H), 2.63-2.67 (m, 2H), 5.42 (s, 1H), 6.03 (s, 1H), 6.10 (s, 1H), 7.15 (dd, J = 8.06, 1.61 Hz, 1H), 7.18 (d, J = 8.06 Hz, 1H), 7.27 (d, J = 1.61 Hz, 1H). | 333 | — |
| 24 | ¹H-NMR (400 MHz, DMSO-d₆) δ: 0.93 (s, 9H), 1.35-1.39 (m, 3H), 1.65-1.73 (m, 1H), 1.89-1.97 (m, 1H), 2.12-2.17 (m, 1H), 2.22-2.34 (m, 3H), 2.40-2.45 (m, 1H), 2.57-2.61 (m, 2H), 3.36-3.42 (m, 1H), 3.52-3.59 (m, 1H), 6.29 (s, 1H), 7.19 (dd, J = 7.86, 1.85 Hz, 1H), 7.25 (d, J = 7.86 Hz, 1H), 7.37 (d, J = 1.85 Hz, 1H), 7.61 (br s, 1H). | 405 | 403 |
| 25 | ¹H-NMR (400 MHz, DMSO-d₆) δ: 0.91-0.82 (m, 1H), 0.93 (s, 9H), 1.32-1.40 (m, 3H), 1.56-1.64 (m, 1H), 1.82-1.90 (m, 2H), 2.25-2.35 (m, 3H), 2.57-2.61 (m, 2H), 2.75-2.83 (m, 1H), 3.39-3.46 (m, 3H), 3.60-3.67 (m, 1H), 4.39 (t, J = 5.09 Hz, 1H), 6.34 (d, J = 1.85 Hz, 1H), 7.22 (dd, J = 8.09, 1.39 Hz, 1H), 7.25 (d, J = 8.09 Hz, 1H), 7.41 (d, J = 1.39 Hz, 1H), 7.56 (s, 1H), 12.20 (br s, 1H). | 449 | 447 |
| 26 | ¹H-NMR (400 MHz, CDCl₃) δ: 0.95 (s, 9H), 1.01-1.09 (m, 1H), 1.39-1.43 (m, 2H), 1.54-1.63 (m, 1H), 1.64-1.73 (m, 1H), 1.88-2.03 (m, 2H), 2.42 (dd, J = 11.21, 6.13 Hz, 1H), 2.49-2.53 (m, 2H), 2.59-2.63 (m, 2H), 2.89-2.97 (m, 1H), 3.39-3.54 (m, 3H), 3.75-3.82 (m, 1H), 4.46 (d, J = 11.79 Hz, 1H), 4.50 (d, J = 11.79 Hz, 1H), 6.04 (d, J = 1.62 Hz, 1H), 6.14 (s, 1H), 7.10 (dd, J = 8.32, 1.39 Hz, 1H), 7.12 (d, J = 8.32 Hz, 1H), 7.26-7.34 (m, 6H). | 539 | 537 |
| 27 | ¹H-NMR (400 MHz, DMSO-d₆) δ: 0.91-0.84 (m, 1H), 0.93 (s, 9H), 1.34-1.47 (m, 3H), 1.60-1.68 (m, 1H), 1.81-1.90 (m, 2H), 2.26-2.35 (m, 3H), 2.57-2.61 (m, 2H), 2.73-2.80 (m, 1H), 3.21 (s, 3H), 3.31-3.38 (m, 3H), 3.61-3.68 (m, 1H), 6.34 (d, J = 1.62 Hz, 1H), 7.22 (dd, J = 7.86, 1.39 Hz, 1H), 7.25 (d, J = 7.86 Hz, 1H), 7.41 (d, J = 1.39 Hz, 1H), 7.56 (s, 1H), 12.20 (s, 1H). | 463 | 461 |
| 28 | ¹H-NMR (400 MHz, DMSO-d₆) δ: 0.91-0.84 (m, 1H), 0.95 (s, 9H), 1.29-1.42 (m, 4H), 1.54-1.61 (m, 1H), 1.83-1.94 (m, 4H), 2.10 (s, 6H), 2.17-2.28 (m, 3H), 2.59-2.63 (m, 2H), 3.20-3.27 (m, 1H), 3.48-3.55 (m, 1H), 6.41 (d, J = 1.49 Hz, 1H), 7.26 (d, J = 8.07 Hz, 1H), 7.28 (d, J = 8.07 Hz, 1H), 7.35 (s, 1H), 7.42 (s, 1H). | 476 | 474 |
| 29 | ¹H-NMR (400 MHz, DMSO-d₆) δ: 0.92-0.86 (m, 1H), 0.93 (s, 9H), 1.35-1.40 (m, 2H), 1.77-1.92 (m, 2H), 2.27-2.35 (m, 3H), 2.57-2.61 (m, 2H), 2.79-2.87 (m, 1H), 3.17-3.37 (m, 3H), 3.57-3.64 (m, 1H), 4.65 (br s, 1H), 6.39 (d, J = 1.85 Hz, 1H), 7.24-7.26 (m, 2H), 7.42 (s, 1H), 7.57 (s, 1H). | 435 | 433 |
| 30 | ¹H-NMH (400 MHz, DMSO-d₆) δ: 0.92-0.85 (m, 1H), 0.94 (s, 9H), 1.36-1.40 (m, 2H), 1.79 (s, 3H), 1.81-1.90 (m, 2H), 2.26-2.38 (m, 3H), 2.58-2.62 (m, 2H), 2.83-2.92 (m, 2H), 3.03-3.11 (m, 1H), 3.31-3.37 (m, 1H), 3.59-3.66 (m, 1H), 6.39 (s, 1H), 7.24-7.28 (m, 2H), 7.44 (s, 1H), 7.57 (s, 1H), 7.85-7.88 (m, 1H), 12.23 (br s, 1H). | 476 | 474 |
| 31 | ¹H-NMR (400 MHz, DMSO-d₆) δ: 0.93 (s, 9H), 0.97-1.06 (m, 1H), 1.36-1.40 (m, 2H), 1.88-2.00 (m, 2H), 2.30-2.36 (m, 3H), 2.51-2.62 (m, 4H), 3.01-3.08 (m, 1H), 3.32-3.38 (m, 1H), 3.60-3.67 (m, 1H), 6.58 (d, J = 1.85 Hz, 1H), 7.21 (dd, J = 7.86, 1.85 Hz, 1H), 7.26 (d, J = 7.86 Hz, 1H), 7.43 (d, J = 1.85 Hz, 1H), 7.69 (s, 1H), 12.21 (br s, 1H). | 444 | 442 |
| 32 | ¹H-NMR (400 MHz, CDCl₃) δ: 0.95 (s, 9H), 0.99 (s, 3H), 1.10 (s, 3H), 1.38-1.45 (m, 2H), 1.96-2.02 (m, 1H), 2.13-2.23 (m, 2H), 2.26-2.33 (m, 1H), 2.54-2.66 (m, 4H), 3.45-3.56 (m, 1H), 3.79-3.92 (m, 1H), 5.70-5.76 (m, 1H), 6.14 (br s, 1H), 7.04-7.09 (m, 1H), 7.11-7.16 (m, 1H), 7.18-7.21 (m, 1H). | 433 | 431 |
| 33 | ¹H-NMR (400 MHz, CDCl₃) δ: 0.95 (s, 9H), 0.99 (s, 3H), 1.10 (s, 3H), 1.38-1.45 (m, 2H), 1.96-2.02 | 433 | 431 |

| Example | ¹H-NMR | MS M+H | M−H |
|---|---|---|---|
| | (m, 1H), 2.13-2.23 (m, 2H), 2.26-2.33 (m, 1H), 2.54-2.66 (m, 4H), 3.45-3.56 (m, 1H), 3.79-3.92 (m, 1H), 5.70-5.76 (m, 1H), 6.14 (br s, 1H), 7.04-7.09 (m, 1H), 7.11-7.16 (m, 1H), 7.18-7.21 (m, 1H). | | |
| 34 | ¹H-NMR (400 MHz, DMSO-d₆) δ: 0.65 (s, 3H), 0.84 (d, J = 6.47 Hz, 3H), 0.93 (s, 9H), 1.02 (s, 3H), 1.36-1.40 (m, 2H), 2.05 (s, 2H), 2.19 (s, 6H), 2.40 (q, J = 6.47 Hz, 1H), 2.57-2.61 (m, 2H), 6.45 (d, J = 0.92 Hz, 1H), 7.17 (dd, J = 8.09, 1.85 Hz, 1H), 7.25 (d, J = 8.09 Hz, 1H), 7.34 (d, J = 1.85 Hz, 1H), 7.52 (s, 1H), 12.43 (s, 1H). | 485 | 483 |
| 35 | ¹H-NMR (400 MHz, DMSO-d₆) δ: 0.65 (s, 3H), 0.84 (d, J = 6.47 Hz, 3H), 0.93 (s, 9H), 1.02 (s, 3H), 1.36-1.40 (m, 2H), 2.05 (s, 2H), 2.19 (s, 6H), 2.40 (q, J = 6.47 Hz, 1H), 2.57-2.61 (m, 2H), 6.45 (d, J = 0.92 Hz, 1H), 7.17 (dd, J = 8.09, 1.85 Hz, 1H), 7.25 (d, J = 8.09 Hz, 1H), 7.34 (d, J = 1.85 Hz, 1H), 7.52 (s, 1H), 12.43 (s, 1H). | 485 | 483 |
| 36 | ¹H-NMR (400 MHz, DMSO-d₆) δ: 1.02 (s, 9H), 1.15-1.08 (m, 1H), 1.40-1.48 (m, 1H), 1.61-1.65 (m, 1H), 1.73-1.81 (m, 2H), 2.08-2.18 (m, 1H), 2.41-2.55 (m, 2H), 3.71 (s, 2H), 7.11 (dd, J = 8.60, 1.76 Hz, 1H), 7.14 (d, J = 8.60 Hz, 1H), 7.30 (d, J = 1.76 Hz, 1H), 7.58 (d, J = 1.98 Hz, 1H), 9.64 (d, J = 1.98 Hz, 1H). | 350 | 348 |
| 37 | ¹H-NMR (400 MHz, CDCl₃) δ: 0.58 (s, 3H), 0.97 (s, 9H), 1.14 (s, 3H), 1.34-1.49 (m, 4H), 1.51-1.73 (m, 3H), 1.82-1.93 (m, 1H), 2.54-2.76 (m, 4H), 3.60-3.72 (m, 1H), 3.79-3.92 (m, 1H), 5.08-5.17 (br m, 1H), 6.12 (br s, 1H), 7.14-7.22 (m, 2H), 7.30-7.36 (m, 1H). | 447 | 445 |
| 38 | ¹H-NMR (400 MHz, CDCl₃) δ: 0.58 (s, 3H), 0.97 (s, 9H), 1.14 (s, 3H), 1.34-1.49 (m, 4H), 1.51-1.73 (m, 3H), 1.82-1.93 (m, 1H), 2.54-2.76 (m, 4H), 3.60-3.72 (m, 1H), 3.79-3.92 (m, 1H), 5.08-5.17 (br m, 1H), 6.12 (br s, 1H), 7.14-7.22 (m, 2H), 7.30-7.36 (m, 1H). | 447 | 445 |
| 39 | ¹H-NMR (400 MHz, DMSO-d₆) δ: 0.95 (s, 9H), 0.98-1.06 (m, 1H), 1.23-1.30 (m, 1H), 1.38-1.42 (m, 2H), 1.59-1.81 (m, 4H), 2.16-2.22 (m, 1H), 2.42 (t, J = 7.05 Hz, 2H), 2.52-2.57 (m, 1H), 2.61-2.65 (m, 2H), 3.35-3.42 (m, 1H), 3.58-3.65 (m, 1H), 6.23 (d, J = 1.62 Hz, 1H), 7.07 (s, 1H), 7.24 (dd, J = 8.09, 1.85 Hz, 1H), 7.33 (d, J = 8.09 Hz, 1H), 7.35 (d, J = 1.85 Hz, 1H), 12.24 (s, 1H). | 419 | 417 |
| 40 | ¹H-NMR (400 MHz, DMSO-d₆) δ: 0.95 (s, 9H), 0.98-1.06 (m, 1H), 1.23-1.30 (m, 1H), 1.38-1.42 (m, 2H), 1.59-1.81 (m, 4H), 2.16-2.22 (m, 1H), 2.42 (t, J = 7.05 Hz, 2H), 2.52-2.57 (m, 1H), 2.61-2.65 (m, 2H), 3.35-3.42 (m, 1H), 3.58-3.65 (m, 1H), 6.23 (d, J = 1.62 Hz, 1H), 7.07 (s, 1H), 7.24 (dd, J = 8.09, 1.85 Hz, 1H), 7.33 (d, J = 8.09 Hz, 1H), 7.35 (d, J = 1.85 Hz, 1H), 12.24 (s, 1H). | 419 | 417 |
| 41 | ¹H-NMR (400 MHz, DMSO-d₆) δ: 0.95 (s, 9H), 0.98-1.06 (m, 1H), 1.23-1.30 (m, 1H), 1.38-1.42 (m, 2H), 1.59-1.81 (m, 4H), 2.16-2.22 (m, 1H), 2.42 (t, J = 7.05 Hz, 2H), 2.52-2.57 (m, 1H), 2.61-2.65 (m, 2H), 3.35-3.42 (m, 1H), 3.58-3.65 (m, 1H), 6.23 (d, J = 1.62 Hz, 1H), 7.07 (s, 1H), 7.24 (dd, J = 8.09, 1.85 Hz, 1H), 7.33 (d, J = 8.09 Hz, 1H), 7.35 (d, J = 1.85 Hz, 1H), 12.24 (s, 1H). | 419 | 417 |
| 42 | ¹H-NMR (400 MHz, DMSO-d₆) δ: 0.95 (s, 9H), 1.00-1.06 (m, 1H), 1.23-1.31 (m, 1H), 1.37-1.42 (m, 2H), 1.55-1.74 (m, 4H), 2.00 (s, 3H), 2.15-2.23 (m, 1H), 2.32-2.44 (m, 3H), 2.59-2.64 (m, 2H), 3.52-3.59 (m, 1H), 3.77-3.84 (m, 1H), 7.15-7.18 (m, 2H), 7.28-7.31 (m, 2H), 12.19 (s, 1H). | 433 | 431 |
| 43 | ¹H-NMR (400 MHz, DMSO-d₆) δ: 0.92 (s, 9H), 0.94-1.09 (m, 2H), 1.32-1.42 (m, 3H), 1.53-1.66 (m, 5H), 2.40-2.48 (m, 3H), 2.58-2.68 (m, 3H), 3.16-3.22 (m, 1H), 3.33-3.40 (m, 1H), 3.67-3.74 (m, 1H), 4.30 (d, J = 11.79 Hz, 1H), 4.34 (d, J = 11.79 Hz, 1H), 6.14 (s, 1H), 7.00 (s, 1H), 7.25-7.28 (m, 5H), 7.31-7.35 (m, 3H), 12.31 (s, 1H). | 553 | 551 |
| 44 | ¹H-NMR (400 MHz, DMSO-d₆) δ: 0.94-0.88 (m, 2H), 0.95 (s, 9H), 1.33-1.41 (m, 3H), 1.52-1.66 (m, 4H), 2.46-2.50 (m, 3H), 2.60-2.67 (m, 3H), 3.12-3.17 (m, 1H), 3.23-3.29 (m, 1H), 3.36-3.43 (m, 1H), 3.68-3.75 (m, 1H), 4.19 (s, 1H), 6.23 (s, 1H), 6.97 (s, 1H), 7.24-7.31 (m, 3H), 12.30 (s, 1H). | 463 | 461 |
| 45 | ¹H-NMR (400 MHz, DMSO-d₆) δ: 0.95 (s, 9H), 1.20 (t, J = 7.09 Hz, 3H), 1.26-1.34 (m, 1H), 1.38-1.42 (m, 2H), 1.50-1.81 (m, 6H), 2.53 (t, J = 6.94 Hz, 2H), 2.62-2.67 (m, 3H), 2.80-2.85 (m, 1H), 3.39-3.46 (m, 1H), 3.70-3.77 (m, 1H), 4.10 (q, J = 7.09 Hz, 2H), 6.34 (s, 1H), 7.05 (s, 1H), 7.23 (dd, J = 8.09, 2.08 Hz, 1H), 7.30 (d, J = 8.09 Hz, 1H), 7.31 (d, J = 2.08 Hz, 1H), 11.97 (s, 1H). | 505 | 503 |
| 46 | ¹H-NMR (400 MHz, DMSO-d₆) δ: 0.90-1.02 (m, 2H), 0.95 (s, 9H), 1.35-1.40 (m, 3H), 1.53-1.67 (m, 4H), 2.37-2.42 (m, 1H), 2.46-2.52 (m, 2H), 2.60-2.67 (m, 3H), 3.02-3.07 (m, 1H), 3.11 (s, 3H), 3.14-3.21 (m, 1H), 3.35-3.42 (m, 1H), 3.70-3.77 (m, 1H), 6.18 (s, 1H), 7.00 (s, 1H), 7.25-7.32 (m, 3H), 12.29 (s, 1H). | 477 | 475 |
| 47 | ¹H-NMR (400 MHz, DMSO-d₆) δ: 0.93-0.98 (m, 1H), 0.96 (s, 9H), 1.21 (t, J = 7.09 Hz, 3H), 1.37-1.41 (m, 2H), 1.45-1.74 (m, | 476 | — |

| Example | ¹H-NMR | MS M+H | MS M−H |
|---|---|---|---|
| | 4H), 2.09-2.14 (m, 1H), 2.18-2.26 (m, 1H), 2.57-2.69 (m, 6H), 3.45-3.52 (m, 1H), 3.70-3.76 (m, 1H), 4.11 (q, J = 7.09 Hz, 2H), 6.36 (s, 1H), 7.16 (s, 1H), 7.25-7.34 (m, 3H), 7.51 (s, 3H). | | |
| 48 | ¹H-NMR (400 MHz, DMSO-$d_6$) δ: 0.95 (s, 9H), 1.03-1.10 (m, 1H), 1.18-1.26 (m, 1H), 1.32-1.41 (m, 3H), 1.57-1.69 (m, 4H), 2.44-2.54 (m, 3H), 2.61-2.68 (m, 3H), 3.14 (s, 3H), 3.35-3.42 (m, 1H), 3.69-3.76 (m, 1H), 3.90-3.95 (m, 1H), 4.02-4.08 (m, 1H), 6.28 (s, 1H), 7.05 (s, 1H), 7.26-7.32 (m, 3H), 12.30 (s, 1H). | 541 | 539 |
| 49 | ¹H-NMR (400 MHz, DMSO-$d_6$) δ: 0.96 (s, 9H), 1.03-1.12 (m, 1H), 1.22 (t, J = 7.17 Hz, 3H), 1.33-1.40 (m, 3H), 1.54-1.68 (m, 5H), 2.36-2.42 (m, 1H), 2.37 (s, 3H), 2.56-2.65 (m, 5H), 2.75-2.82 (m, 1H), 3.38-3.45 (m, 1H), 3.74-3.81 (m, 1H), 4.12 (q, J = 7.17 Hz, 2H), 6.33 (s, 1H), 7.10 (s, 1H), 7.24 (dd, J = 8.09, 1.85 Hz, 1H), 7.30 (d, J = 1.85 Hz, 1H), 7.31 (d, J = 8.09 Hz, 1H), 8.09 (s, 2H). | 504 | — |
| 50 | ¹H-NMR (400 MHz, DMSO-$d_6$) δ: 0.95 (s, 9H), 1.00-1.20 (m, 3H), 1.22 (t, J = 7.17 Hz, 3H), 1.30-1.70 (m, 8H), 2.33-2.68 (m, 80H), 3.40-3.47 (m, 1H), 3.72-3.80 (m, 1H), 4.12 (q, J = 7.17 Hz, 2H), 6.29 (s, 1H), 7.12 (s, 1H), 7.25-7.35 (m, 3H), 9.24 (br s, 1H). | 518 | — |
| 51 | ¹H-NMR (400 MHz, DMSO-$d_6$) δ: 0.95 (s, 9H), 1.31-1.70 (m, 6H), 2.41-2.52 (m, 5H), 2.61-2.67 (m, 3H), 2.84-2.91 (m, 1H), 3.35-3.44 (m, 1H), 3.65-3.71 (m, 1H), 6.36 (s, 1H), 6.64 (s, 1H), 7.00 (s, 1H), 7.21-7.38 (m, 3H), 12.29 (br s, 1H). | 476 | 474 |
| 52 | ¹H-NMR (400 MHz, DMSO-$d_6$) δ: 0.95 (s, 9H), 1.21-1.32 (m, 1H), 1.37-1.44 (m, 2H), 1.52-1.70 (m, 4H), 1.83 (dd, J = 16.76, 9.13 Hz, 1H), 2.13 (dd, J = 16.76, 6.82 Hz, 1H), 2.45-2.53 (m, 2H), 2.62-2.67 (m, 3H), 2.70-2.78 (m, 1H), 3.41-3.48 (m, 1H), 3.67-3.74 (m, 1H), 6.48 (s, 1H), 7.15 (s, 1H), 7.27-7.38 (m, 3H), 12.31 (br s, 1H). | 458 | 456 |
| 53 | ¹H-NMR (400 MHz, DMSO-$d_6$) δ: 0.95 (s, 9H), 0.96-1.05 (m, 1H), 1.21-1.33 (m, 1H), 1.37-1.42 (m, 2H), 1.56-1.73 (m, 3H), 1.76-1.85 (m, 1H), 2.25-2.29 (m, 1H), 2.25 (s, 6H), 2.48-2.57 (m, 1H), 2.61-2.65 (m, 2H), 6.20 (d, J = 1.47 Hz, 1H), 7.16 (s, 1H), 7.22 (dd, J = 8.07, 1.96 Hz, 1H), 7.34-7.36 (m, 2H), 12.48 (s, 1H). | 457 | 455 |
| 54 | ¹H-NMR (400 MHz, DMSO-$d_6$) δ: 0.95 (s, 9H), 0.96-1.05 (m, 1H), 1.21-1.33 (m, 1H), 1.37-1.42 (m, 2H), 1.56-1.73 (m, 3H), 1.76-1.85 (m, 1H), 2.25-2.29 (m, 1H), 2.25 (s, 6H), 2.48-2.57 (m, 1H), 2.61-2.65 (m, 2H), 6.20 (d, J = 1.47 Hz, 1H), 7.16 (s, 1H), 7.22 (dd, J = 8.07, 1.96 Hz, 1H), 7.34-7.36 (m, 2H), 12.48 (s, 1H). | 457 | 455 |
| 55 | ¹H-NMR (400 MHz, DMSO-$d_6$) δ: 0.95 (s, 9H), 1.17-1.26 (m, 1H), 1.30-1.42 (m, 3H), 1.44-1.52 (m, 1H), 1.58-1.68 (m, 1H), 1.76-1.83 (m, 1H), 2.41-2.50 (m, 2H), 2.57-2.69 (m, 4H), 2.80-2.87 (m, 1H), 3.35-3.44 (m, 1H), 3.62-3.73 (m, 1H), 4.35-4.40 (m, 1H), 6.31 (s, 1H), 7.02 (s, 1H), 7.22-7.34 (m, 3H), 12.30 (br s, 1H). | 449 | 447 |
| 56 | ¹H-NMR (400 MHz, DMSO-$d_6$) δ: 0.95 (s, 9H), 1.11-1.23 (m, 1H), 1.36-1.69 (m, 6H), 2.41-2.47 (m, 2H), 2.50-2.73 (m, 8H), 3.01 (s, 3H), 3.39-3.47 (m, 1H), 3.61-3.67 (m, 1H), 6.31 (s, 1H), 7.05 (s, 1H), 7.24-7.40 (m, 3H), 12.29 (br s, 1H). | 463 | 461 |
| 57 | ¹H-NMR (400 MHz, DMSO-$d_6$) δ: 0.60 (d, J = 7.63 Hz, 3H), 0.95 (s, 9H), 1.30-1.43 (m, 4H), 1.48-1.67 (m, 3H), 2.43-2.68 (m, 6H), 3.33-3.43 (m, 1H), 3.64-3.73 (m, 1H), 6.31 (s, 1H), 7.00 (s, 1H), 7.24-7.36 (m, 3H), 12.31 (br s, 1H). | 433 | 431 |
| 58 | ¹H-NMR (400 MHz, DMSO-$d_6$) δ: 0.96 (s, 9H), 1.35-1.42 (m, 2H), 1.97-2.08 (m, 2H), 2.43-2.50 (m, 2H), 2.58-2.67 (m, 2H), 3.34-3.46 (m, 3H), 3.65-3.72 (m, 1H), 3.88-3.95 (m, 1H), 4.32 (d, J = 11.10 Hz, 1H), 6.24 (s, 1H), 7.09 (s, 1H), 7.30-7.46 (m, 3H), 12.24 (br s, 1H). | 421 | 419 |
| 59 | ¹H-NMR (400 MHz, DMSO-$d_6$) δ: 0.94 (d, J = 5.50 Hz, 6H), 0.98-1.07 (m, 1H), 1.23-1.29 (m, 1H), 1.57-1.85 (m, 7H), 2.13-2.20 (m, 1H), 2.40 (t, J = 7.05 Hz, 2H), 2.49-2.56 (m, 1H), 3.34-3.42 (m, 1H), 3.57-3.64 (m, 1H), 4.07 (t, J = 6.47 Hz, 2H), 6.22 (s, 1H), 7.04 (s, 1H), 7.11-7.38 (m, 3H), 12.28 (s, 1H). | 421 | 419 |
| 60 | ¹H-NMR (400 MHz, DMSO-$d_6$) δ: 0.99-1.06 (m, 1H), 1.03 (s, 9H), 1.20-1.29 (m, 1H), 1.56-1.83 (m, 4H), 2.14-2.20 (m, 1H), 2.40 (t, J = 6.94 Hz, 2H), 2.47-2.56 (m, 1H), 3.34-3.41 (m, 1H), 3.57-3.65 (m, 1H), 3.70 (s, 2H), 6.22 (s, 1H), 7.04 (s, 1H), 7.09 (d, J = 8.55 Hz, 1H), 7.23 (dd, J = 8.55, 2.31 Hz, 1H), 7.37 (d, J = 2.31 Hz, 1H), 12.26 (br s, 1H). | 421 | 419 |
| 61 | ¹H-NMR (400 MHz, DMSO-$d_6$) δ: 0.95-1.08 (m, 1H), 0.97 (s, 9H), 1.20-1.35 (m, 2H), 1.56-1.82 (m, 6H), 2.13-2.21 (m, 1H), 2.42 (t, J = 6.90 Hz, 2H), 2.48-2.56 (m, 1H), 3.33-3.42 (m, 1H), 3.58-3.66 (m, 1H), 4.10 (t, J = 6.90 Hz, 2H), 6.22 (d, J = 1.39 Hz, 1H), 7.05 (s, 1H), 7.15 (d, J = 8.73 Hz, 1H), 7.24 (dd, J = 8.73, 2.14 Hz, 1H), 7.36 (d, J = 2.14 Hz, 1H), 12.20 (br s, 1H). | 435 | 433 |
| 62 | ¹H-NMR (400 MHz, DMSO-$d_6$) δ: 0.96-1.07 (m, 1H), 1.20-1.31 (m, 1H), 1.55-1.87 (m, 10H), 2.01-2.09 (m, 2H), 2.13-2.20 (m, 1H), 2.39 (t, J = 7.05 Hz, 2H), 2.42-2.47 (m, 1H), 2.49-2.55 (m, 1H), 3.34-3.41 (m, 1H), 3.56-3.65 (m, 1H), 3.98 (t, J = 6.36 Hz, 2H), 6.22 (d, J = 1.62 Hz, 1H), 7.03 (s, 1H), 7.10 (d, J = 8.55 Hz, | 433 | 431 |

| Example | ¹H-NMR | MS M+H | MS M−H |
|---|---|---|---|
| | 1H), 7.23 (dd, J = 8.55, 2.31 Hz, 1H), 7.36 (d, J = 2.31 Hz, 1H), 12.29 (br s, 1H). | | |
| 63 | ¹H-NMR (400 MHz, DMSO-d₆) δ: 0.95 (s, 9H), 1.38-1.59 (m, 3H), 1.88-1.97 (m, 1H), 2.00-2.34 (m, 2H), 2.41-2.46 (m, 2H), 2.59-2.74 (m, 4H), 3.37-3.45 (m, 1H), 3.62-3.70 (m, 1H), 6.46 (d, J = 1.85 Hz, 1H), 7.25-7.41 (m, 4H), 12.28 (br s, 1H). | 455 | 453 |
| 64 | ¹H-NMR (400 MHz, CDCl₃) δ: 0.38 (s, 3H), 0.91 (s, 3H), 0.96 (s, 9H), 1.23-1.40 (m, 2H), 1.40-1.47 (m, 2H), 1.80-1.89 (m, 1H), 2.15-2.23 (m, 2H), 2.32-2.40 (m, 1H), 2.55-2.69 (m, 4H), 3.53-3.65 (m, 1H), 3.65-3.76 (m, 1H), 5.57 (br s, 1H), 6.12 (br s, 1H), 7.10-7.19 (m, 2H), 7.24-7.26 (m, 1H). | 447 | 445 |
| 65 | ¹H-NMR (400 MHz, DMSO-d₆) δ: 0.97-1.13 (m, 5H), 1.21-1.29 (m, 1H), 1.56-1.82 (m, 4H), 2.14-2.20 (m, 1H), 2.39-2.43 (m, 2H), 2.49-2.59 (m, 1H), 3.34-3.42 (m, 1H), 3.58-3.65 (m, 1H), 4.19 (s, 2H), 6.22 (d, J = 1.62 Hz, 1H), 7.06 (br s, 1H), 7.12 (d, J = 8.79 Hz, 1H), 7.24 (dd, J = 8.67, 2.20 Hz, 1H), 7.38 (d, J = 2.31 Hz, 1H), 12.25 (br s, 1H). | 473 | 471 |
| 66 | ¹H-NMR (400 MHz, DMSO-d₆) δ: 0.90-0.99 (m, 12H), 1.28-1.43 (m, 4H), 1.81-2.05 (m, 4H), 2.22-2.34 (m, 1H), 2.39-2.45 (m, 2H), 2.58-2.67 (m, 2H), 3.34-3.43 (m, 1H), 3.59-3.67 (m, 1H), 6.19 (s, 1H), 7.07 (br s, 1H), 7.22-7.37 (m, 3H), 12.21 (br s, 1H). | 433 | 431 |
| 67 | ¹H-NMR (400 MHz, CDCl₃) δ: 0.95 (s, 9H), 1.07-1.27 (m, 1H), 1.38-1.47 (m, 2H), 1.75-2.06 (m, 2H), 2.45-2.61 (m, 2H), 2.60-2.69 (m, 4H), 3.18-3.27 (m, 1H), 3.30 (s, 3H), 3.57-3.68 (m, 1H), 3.71-3.82 (m, 1H), 5.40 (br s, 1H), 6.07 (br s, 1H), 7.08-7.21 (m, 2H), 7.27-7.31 (m, 1H). | 449 | 447 |
| 68 | ¹H-NMR (400 MHz, CDCl₃) δ: 0.95 (s, 9H), 1.07-1.27 (m, 1H), 1.38-1.47 (m, 2H), 1.75-2.06 (m, 2H), 2.45-2.61 (m, 2H), 2.60-2.69 (m, 4H), 3.18-3.27 (m, 1H), 3.30 (s, 3H), 3.57-3.68 (m, 1H), 3.71-3.82 (m, 1H), 5.40 (br s, 1H), 6.07 (br s, 1H), 7.08-7.21 (m, 2H), 7.27-7.31 (m, 1H). | 449 | 447 |
| 69 | ¹H-NMR (400 MHz, DMSO-d₆) δ: 0.65-0.78 (m, 4H), 0.77 (d, J = 7.51 Hz, 3H), 0.96 (s, 9H), 1.36-1.60 (m, 5H), 1.70-1.80 (m, 1H), 2.14-2.23 (m, 1H), 2.38-2.44 (m, 2H), 2.52-2.59 (m, 1H), 2.59-2.67 (m, 2H), 3.35-3.43 (m, 1H), 3.57-3.64 (m, 1H), 6.24 (s, 1H), 7.11 (s, 1H), 7.20-7.36 (m, 3H), 12.27 (br s, 1H). | 433 | 431 |
| 70 | ¹H-NMR (400 MHz, DMSO-d₆) δ: 0.95 (s, 9H), 1.18 (d, J = 6.80 Hz, 3H), 1.36-1.42 (m, 2H), 1.83 (d, J = 13.64 Hz, 1H), 2.15-2.22 (m, 1H), 2.46 (t, J = 6.94 Hz, 2H), 2.60-2.66 (m, 2H), 3.39-3.47 (m, 1H), 3.65-3.78 (m, 2H), 3.96 (d, J = 11.79 Hz, 1H), 4.03-4.12 (m, 1H), 6.20 (d, J = 1.62 Hz, 1H), 7.10 (s, 1H), 7.31-7.33 (m, 2H), 7.41-7.43 (m, 1H), 12.27 (br s, 1H). | 435 | 433 |
| 71 | ¹H-NMR (400 MHz, DMSO-d₆) δ: 0.95 (s, 9H), 1.18 (d, J = 6.80 Hz, 3H), 1.36-1.42 (m, 2H), 1.83 (d, J = 13.64 Hz, 1H), 2.15-2.22 (m, 1H), 2.46 (t, J = 6.94 Hz, 2H), 2.60-2.66 (m, 2H), 3.39-3.47 (m, 1H), 3.65-3.78 (m, 2H), 3.96 (d, J = 11.79 Hz, 1H), 4.03-4.12 (m, 1H), 6.20 (d, J = 1.62 Hz, 1H), 7.10 (s, 1H), 7.31-7.33 (m, 2H), 7.41-7.43 (m, 1H), 12.27 (br s, 1H). | 435 | 433 |
| 72 | ¹H-NMR (400 MHz, DMSO-d₆) δ: 0.95 (s, 9H), 1.18 (d, J = 6.47 Hz, 3H), 1.36-1.41 (m, 2H), 1.92 (d, J = 13.18 Hz, 1H), 2.18-2.27 (m, 1H), 2.28 (s, 6H), 2.60-2.66 (m, 2H), 3.73 (d, J = 11.79 Hz, 1H), 3.96 (d, J = 11.79 Hz, 1H), 4.05-4.14 (m, 1H), 6.19 (d, J = 1.85 Hz, 1H), 7.17 (s, 1H), 7.26-7.42 (m, 3H), 12.46 (br s, 1H). | 473 | 471 |
| 73 | ¹H-NMR (400 MHz, DMSO-d₆) δ: 0.58 (d, J = 7.40 Hz, 3H), 0.95 (s, 9H), 1.34-1.41 (m, 5H), 1.49-1.66 (m, 3H), 2.23 (s, 6H), 2.59-2.68 (m, 3H), 6.25 (s, 1H), 7.02 (s, 1H), 7.21-7.34 (m, 3H). | 471 | 469 |
| 74 | ¹H-NMR (400 MHz, DMSO-d₆) δ: 0.79 (s, 3H), 0.90 (s, 3H), 0.95 (s, 9H), 1.25-1.32 (m, 1H), 1.36-1.43 (m, 2H), 1.63 (d, J = 13.76 Hz, 1H), 1.78 (dd, J = 13.76, 1.50 Hz, 1H), 1.83-1.93 (m, 1H), 2.37-2.51 (m, 2H), 2.40-2.44 (m, 2H), 2.59-2.66 (m, 2H), 3.36-3.44 (m, 1H), 3.59-3.67 (m, 1H), 6.19 (d, J = 1.39 Hz, 1H), 7.10 (s, 1H), 7.21-7.36 (m, 3H), 12.21 (br s, 1H). | 447 | 445 |
| 75 | ¹H-NMR (400 MHz, CDCl₃) δ: 0.97 (s, 9H), 1.39-1.48 (m, 2H), 1.53-1.65 (m, 1H), 1.90-2.00 (m, 1H), 2.15-2.35 (m, 5H), 2.41 (br s, 6H), 2.61-2.69 (m, 2H), 5.60-5.76 (br m, 1H), 6.03 (br s, 1H), 7.11-7.16 (m, 1H), 7.19-7.26 (m, 2H). | 525 | 523 |
| 76 | ¹H-NMR (400 MHz, DMSO-d₆) δ: 0.94 (s, 9H), 1.34-1.41 (m, 2H), 1.53-1.64 (m, 1H), 1.65-1.77 (m, 1H), 1.84-1.94 (m, 1H), 2.24 (br s, 6H), 2.51-2.73 (m, 5H), 3.11-3.22 (m, 4H), 6.27-6.31 (m, 1H), 7.17-7.27 (m, 2H), 7.30-7.37 (m, 2H), 12.45 (br s, 1H). | 487 | 435 |
| 77 | ¹H-NMR (400 MHz, DMSO-d₆) δ: 0.94 (s, 9H), 1.34-1.41 (m, 2H), 1.53-1.64 (m, 1H), 1.65-1.77 (m, 1H), 1.84-1.94 (m, 1H), 2.24 (br s, 6H), 2.51-2.73 (m, 5H), 3.11-3.22 (m, 4H), 6.27-6.31 (m, 1H), 7.17-7.27 (m, 2H), 7.30-7.37 (m, 2H), 12.45 (br s, 1H). | 487 | 485 |
| 78 | ¹H-NMR (400 MHz, DMSO-d₆) δ: 0.58 (d, J = 7.40 Hz, 3H), 0.95 (s, 9H), 1.34-1.41 (m, 5H), 1.49-1.66 (m, 3H), 2.23 (s, 6H), 2.59-2.68 (m, 3H), 6.25 (s, 1H), 7.02 (s, 1H), 7.21-7.34 (m, 3H). | 471 | 469 |

| Example | ¹H-NMR | M + H | M − H |
|---|---|---|---|
| 79 | ¹H-NMR (400 MHz, DMSO-d₆) δ: 0.58 (d, J = 7.40 Hz, 3H), 0.95 (s, 9H), 1.34-1.41 (m, 5H), 1.49-1.66 (m, 3H), 2.23 (s, 6H), 2.59-2.68 (m, 3H), 6.25 (s, 1H), 7.02 (s, 1H), 7.21-7.34 (m, 3H). | 471 | 469 |
| 80 | ¹H-NMR (400 MHz, DMSO-d₆) δ: 0.65-0.78 (m, 4H), 0.77 (d, J = 7.51 Hz, 3H), 0.96 (s, 9H), 1.36-1.60 (m, 5H), 1.70-1.80 (m, 1H), 2.14-2.23 (m, 1H), 2.38-2.44 (m, 2H), 2.52-2.59 (m, 1H), 2.59-2.67 (m, 2H), 3.35-3.43 (m, 1H), 3.57-3.64 (m, 1H), 6.24 (s, 1H), 7.11 (s, 1H), 7.20-7.36 (m, 3H), 12.27 (br s, 1H). | 433 | 431 |
| 81 | ¹H-NMR (400 MHz, DMSO-d₆) δ: 0.65-0.78 (m, 4H), 0.77 (d, J = 7.51 Hz, 3H), 0.96 (s, 9H), 1.36-1.60 (m, 5H), 1.70-1.80 (m, 1H), 2.14-2.23 (m, 1H), 2.38-2.44 (m, 2H), 2.52-2.59 (m, 1H), 2.59-2.67 (m, 2H), 3.35-3.43 (m, 1H), 3.57-3.64 (m, 1H), 6.24 (s, 1H), 7.11 (s, 1H), 7.20-7.36 (m, 3H), 12.27 (br s, 1H). | 433 | 431 |
| 82 | ¹H-NMR (400 MHz, DMSO-d₆) δ: 0.79 (s, 3H), 0.90 (s, 3H), 0.95 (s, 9H), 1.25-1.32 (m, 1H), 1.36-1.43 (m, 2H), 1.63 (d, J = 13.76 Hz, 1H), 1.78 (dd, J = 13.76, 1.50 Hz, 1H), 1.83-1.93 (m, 1H), 2.37-2.51 (m, 2H), 2.40-2.44 (m, 2H), 2.59-2.66 (m, 2H), 3.36-3.44 (m, 1H), 3.59-3.67 (m, 1H), 6.19 (d, J = 1.39 Hz, 1H), 7.10 (s, 1H), 7.21-7.36 (m, 3H), 12.21 (br s, 1H). | 447 | 445 |
| 83 | ¹H-NMR (400 MHz, DMSO-d₆) δ: 0.79 (s, 3H), 0.90 (s, 3H), 0.95 (s, 9H), 1.25-1.32 (m, 1H), 1.36-1.43 (m, 2H), 1.63 (d, J = 13.76 Hz, 1H), 1.78 (dd, J = 13.76, 1.50 Hz, 1H), 1.83-1.93 (m, 1H), 2.37-2.51 (m, 2H), 2.40-2.44 (m, 2H), 2.59-2.66 (m, 2H), 3.36-3.44 (m, 1H), 3.59-3.67 (m, 1H), 6.19 (d, J = 1.39 Hz, 1H), 7.10 (s, 1H), 7.21-7.36 (m, 3H), 12.21 (br s, 1H). | 447 | 445 |
| 84 | ¹H-NMR (400 MHz, DMSO-d₆) δ: 0.66-0.80 (m, 1H), 0.94 (s, 9H), 1.33-1.43 (m, 2H), 1.44-1.80 (m, 4H), 2.24 (s, 6H), 2.29-2.37 (m, 1H), 2.53-2.69 (m, 3H), 2.97-3.10 (m, 2H), 3.15 (s, 3H), 6.23 (s, 1H), 7.14-7.23 (m, 2H), 7.29-7.37 (m, 2H), 12.41 (br s, 1H). | 501 | 499 |
| 85 | ¹H-NMR (400 MHz, DMSO-d₆) δ: 0.66-0.80 (m, 1H), 0.94 (s, 9H), 1.33-1.43 (m, 2H), 1.44-1.80 (m, 4H), 2.24 (s, 6H), 2.29-2.37 (m, 1H), 2.53-2.69 (m, 3H), 2.97-3.10 (m, 2H), 3.15 (s, 3H), 6.23 (s, 1H), 7.14-7.23 (m, 2H), 7.29-7.37 (m, 2H), 12.41 (br s, 1H). | 501 | 499 |
| 86 | ¹H-NMR (400 MHz, DMSO-d₆) δ: 0.93 (s, 9H), 1.34-1.43 (m, 2H), 1.43-1.56 (m, 1H), 1.84-1.95 (m, 1H), 1.98-2.09 (m, 1H), 2.15-2.30 (m, 7H), 2.59-2.68 (m, 3H), 2.74-2.86 (m, 1H), 6.42-6.45 (m, 1H), 7.22-7.27 (m, 1H), 7.34-7.43 (m, 3H). | 493 | 491 |
| 87 | ¹H-NMR (400 MHz, DMSO-d₆) δ: 0.93 (s, 9H), 1.34-1.43 (m, 2H), 1.43-1.56 (m, 1H), 1.84-1.95 (m, 1H), 1.98-2.09 (m, 1H), 2.15-2.30 (m, 7H), 2.59-2.68 (m, 3H), 2.74-2.86 (m, 1H), 6.42-6.45 (m, 1H), 7.22-7.27 (m, 1H), 7.34-7.43 (m, 3H). | 493 | 491 |
| 88 | ¹H-NMR (400 MHz, DMSO-d₆) δ: 0.31 (t, J = 4.74 Hz, 1H), 0.56 (dd, J = 8.67, 4.28 Hz, 1H), 0.99-1.09 (m, 2H), 1.07 (s, 3H), 1.09 (s, 3H), 1.23-1.31 (m, 1H), 1.57-1.83 (m, 4H), 2.14-2.19 (m, 1H), 2.41 (t, J = 7.05 Hz, 2H), 2.49-2.55 (m, 1H), 3.35-3.42 (m, 1H), 3.57-3.65 (m, 1H), 3.88-3.95 (m, 1H), 4.17-4.24 (m, 1H), 6.22 (d, J = 1.62 Hz, 1H), 7.04 (s, 1H), 7.13 (d, J = 8.55 Hz, 1H), 7.21-7.25 (m, 1H), 7.35-7.37 (m, 1H), 12.25 (br s, 1H). | 433 | 431 |
| 89 | ¹H-NMR (400 MHz, DMSO-d₆) δ: 0.61-0.74 (m, 1H), 0.74-0.79 (m, 2H), 0.94 (s, 9H), 1.35-1.41 (m, 2H), 1.42-1.51 (m, 2H), 1.50-1.59 (m, 1H), 1.66-1.78 (m, 1H), 2.19-2.28 (m, 7H), 2.51-2.58 (m, 1H), 2.58-2.64 (m, 2H), 6.19 (br s, 1H), 7.16 (br s, 1H), 7.18-7.22 (m, 1H), 7.30-7.35 (m, 2H), 12.46 (br s, 1H). | 471 | 469 |
| 90 | ¹H-NMR (400 MHz, DMSO-d₆) δ: 0.61-0.74 (m, 1H), 0.74-0.79 (m, 2H), 0.94 (s, 9H), 1.35-1.41 (m, 2H), 1.42-1.51 (m, 2H), 1.50-1.59 (m, 1H), 1.66-1.78 (m, 1H), 2.19-2.28 (m, 7H), 2.51-2.58 (m, 1H), 2.58-2.64 (m, 2H), 6.19 (br s, 1H), 7.16 (br s, 1H), 7.18-7.22 (m, 1H), 7.30-7.35 (m, 2H), 12.46 (br s, 1H). | 471 | 469 |
| 91 | ¹H-NMR (400 MHz, DMSO-d₆) δ: 0.89-0.97 (m, 12H), 1.24-1.34 (m, 2H), 1.34-1.42 (m, 2H), 1.81-1.97 (m, 3H), 1.98-2.09 (m, 1H), 2.19-2.33 (m, 7H), 2.56-2.64 (m, 2H), 6.12-6.16 (m, 1H), 7.11 (s, 1H), 7.18-7.24 (m, 1H), 7.30-7.35 (m, 2H), 12.44 (br s, 1H). | 471 | 469 |
| 92 | ¹H-NMR (400 MHz, DMSO-d₆) δ: 0.89-0.97 (m, 12H), 1.24-1.34 (m, 2H), 1.34-1.42 (m, 2H), 1.81-1.97 (m, 3H), 1.98-2.09 (m, 1H), 2.19-2.33 (m, 7H), 2.56-2.64 (m, 2H), 6.12-6.16 (m, 1H), 7.11 (s, 1H), 7.18-7.24 (m, 1H), 7.30-7.35 (m, 2H), 12.44 (br s, 1H). | 471 | 469 |
| 93 | ¹H-NMR (400 MHz, DMSO-d₆) δ: 0.58-0.71 (m, 1H), 0.75-0.81 (m, 3H), 0.94 (s, 9H), 1.02-1.12 (m, 2H), 1.18-1.32 (m, 1H), 1.34-1.42 (m, 2H), 1.56-1.65 (m, 1H), 1.65-1.77 (m, 1H), 2.23 (s, 6H), 2.27-2.36 (m, 1H), 2.52-2.65 (m, 3H), 6.21 (br s, 1H), 7.16 (br s, 1H), 7.18-7.22 (m, 1H), 7.28-7.35 (m, 2H), 12.45 (br s, 1H). | 485 | 483 |
| 94 | ¹H-NMR (400 MHz, DMSO-d₆) δ: 0.58-0.71 (m, 1H), 0.75-0.81 (m, 3H), 0.94 (s, 9H), 1.02-1.12 (m, 2H), 1.18-1.32 (m, 1H), 1.34-1.42 (m, 2H), 1.56-1.65 (m, 1H), 1.65-1.77 (m, 1H), 2.23 (s, 6H), 2.27-2.36 (m, 1H), 2.52-2.65 (m, | 485 | 483 |

| Example | $^1$H-NMR | MS M + H | MS M − H |
|---|---|---|---|
|  | 3H), 6.21 (br s, 1H), 7.16 (br s, 1H), 7.18-7.22 (m, 1H), 7.28-7.35 (m, 2H), 12.45 (br s, 1H). |  |  |
| 95 | $^1$H-NMR (400 MHz, CDCl$_3$) δ: 0.80-0.87 (m, 1H), 1.24-1.30 (m, 1H), 1.33-1.42 (m, 2H), 1.53-1.97 (m, 12H), 2.11-2.16 (m, 1H), 2.47-2.51 (m, 1H), 2.59-2.72 (m, 2H), 3.59-3.66 (m, 1H), 3.70-3.78 (m, 1H), 4.26-4.32 (m, 1H), 5.10 (s, 1H), 6.00 (d, J = 1.47 Hz, 1H), 6.93 (d, J = 8.80 Hz, 1H), 7.17 (dd, J = 8.80, 2.45 Hz, 1H), 7.33 (d, J = 2.45 Hz, 1H). | 433 | 431 |
| 96 | $^1$H-NMR (400 MHz, CDCl$_3$) δ: 1.43-1.21 (m, 2H), 1.38 (d, J = 6.11 Hz, 6H), 1.63-1.74 (m, 2H), 1.87-1.97 (m, 2H), 2.11-2.15 (m, 1H), 2.47-2.53 (m, 1H), 2.56-2.67 (m, 2H), 3.61 (dt, J = 14.43, 6.36 Hz, 1H), 3.73 (dt, J = 13.94, 6.36 Hz, 1H), 4.50-4.59 (m, 1H), 5.81 (s, 1H), 6.01 (d, J = 1.47 Hz, 1H), 6.92 (d, J = 8.56 Hz, 1H), 7.19 (dd, J = 8.56, 2.45 Hz, 1H), 7.34 (d, J = 2.45 Hz, 1H). | 393 | 391 |
| 97 | $^1$H-NMR (400 MHz, DMSO-d$_6$) δ: 0.96 (s, 9H), 1.13-1.29 (m, 1H), 1.37-1.45 (m, 2H), 1.71-1.81 (m, 1H), 1.94-2.05 (m, 2H), 2.22 (s, 6H), 2.55-2.74 (m, 4H), 2.78-2.89 (m, 1H), 6.35-6.38 (m, 1H), 7.19-7.23 (m, 1H), 7.30 (s, 1H), 7.33-7.40 (m, 2H). | 482 | 480 |
| 98 | $^1$H-NMR (400 MHz, CDCl$_3$) δ: 0.81 (dd, J = 6.60, 2.45 Hz, 6H), 0.97-0.93 (m, 1H), 0.98 (s, 9H), 1.19-1.34 (m, 2H), 1.44-1.48 (m, 2H), 1.58-1.65 (m, 1H), 1.71-1.76 (m, 1H), 1.90-1.98 (m, 1H), 2.18-2.23 (m, 1H), 2.47 (s, 6H), 2.54-2.59 (m, 1H), 2.64-2.69 (m, 2H), 5.15 (3, 1H), 5.97 (d, J = 1.47 Hz, 1H), 7.14 (dd, J = 7.83, 2.20 Hz, 1H), 7.20 (d, J = 7.83 Hz, 1H), 7.27 (d, J = 2.20 Hz, 1H). | 499 | 497 |
| 99 | $^1$H-NMR (400 MHz, CDCl$_3$) δ: 0.81 (dd, J = 6.60, 2.45 Hz, 6H), 0.97-0.93 (m, 1H), 0.98 (s, 9H), 1.19-1.34 (m, 2H), 1.44-1.48 (m, 2H), 1.58-1.65 (m, 1H), 1.71-1.76 (m, 1H), 1.90-1.98 (m, 1H), 2.18-2.23 (m, 1H), 2.47 (s, 6H), 2.54-2.59 (m, 1H), 2.64-2.69 (m, 2H), 5.15 (s, 1H), 5.97 (d, J = 1.47 Hz, 1H), 7.14 (dd, J = 7.83, 2.20 Hz, 1H), 7.20 (d, J = 7.83 Hz, 1H), 7.27 (d, J = 2.20 Hz, 1H). | 499 | 497 |
| 100 | $^1$H-NMR (400 MHz, CDCl$_3$) δ: 1.10 (s, 3H), 1.18 (s, 3H), 1.24-1.39 (m, 2H), 1.78-1.68 (m, 4H), 1.87-1.98 (m, 4H), 2.10-2.16 (m, 1H), 2.48-2.54 (m, 1H), 2.58-2.76 (m, 3H), 3.63 (dt, J = 14.35, 7.34 Hz, 1H), 3.75 (dt, J = 14.35, 6.24 Hz, 1H), 3.95 (d, J = 6.11 Hz, 2H), 5.48 (s, 1H), 6.01 (d, J = 1.71 Hz, 1H), 6.88 (d, J = 8.56 Hz, 1H), 7.19 (dd, J = 8.56, 2.20 Hz, 1H), 7.35 (d, J = 2.20 Hz, 1H). | 447 | 445 |
| 101 | $^1$H-NMR (400 MHz, CDCl$_3$) δ: 0.99 (t, J = 7.34 Hz, 3H), 1.24-1.30 (m, 1H), 1.32-1.37 (m, 1H), 1.48-1.58 (m, 2H), 1.67-1.73 (m, 2H), 1.78-1.85 (m, 2H), 1.89-1.99 (m, 2H), 2.12-2.16 (m, 1H), 2.47-2.53 (m, 1H), 2.64-2.73 (m, 2H), 3.61-3.68 (m, 1H), 3.73-3.80 (m, 1H), 4.03 (t, J = 6.48 Hz, 2H), 4.95 (s, 1H), 6.01 (d, J = 1.71 Hz, 1H), 6.90 (d, J = 8.56 Hz, 1H), 7.19 (dd, J = 8.56, 2.45 Hz, 1H), 7.34 (d, J = 2.45 Hz, 1H). | 407 | 405 |
| 102 | $^1$H-NMR (400 MHz, DMSO-d$_6$) δ: 0.78 (s, 3H), 0.88 (s, 3H), 0.90-1.06 (m, 10H), 1.20-1.32 (m, 1H), 1.35-1.43 (m, 2H), 1.61-1.70 (m, 1H), 1.79-1.92 (m, 2H), 2.24 (s, 6H), 2.33-2.42 (m, 1H), 2.58-2.65 (m, 2H), 6.15 (br s, 1H), 7.15 (s, 1H), 7.17-7.22 (m, 1H), 7.30-7.35 (m, 2H), 12.41 (br s, 1H). | 485 | 483 |
| 103 | $^1$H-NMR (400 MHz, DMSO-d$_6$) δ: 0.78 (s, 3H), 0.88 (s, 3H), 0.90-1.06 (m, 10H), 1.20-1.32 (m, 1H), 1.35-1.43 (m, 2H), 1.61-1.70 (m, 1H), 1.79-1.92 (m, 2H), 2.24 (s, 6H), 2.33-2.42 (m, 1H), 2.58-2.65 (m, 2H), 6.15 (br s, 1H), 7.15 (s, 1H), 7.17-7.22 (m, 1H), 7.30-7.35 (m, 2H), 12.41 (br s, 1H). | 485 | 483 |
| 104 | $^1$H-NMR (400 MHz, DMSO-d$_6$) δ: 0.67-0.76 (m, 1H), 0.78 (dd, J = 6.60, 1.71 Hz, 6H), 0.95 (s, 9H), 1.13-1.30 (m, 2H), 1.37-1.42 (m, 2H), 1.48-1.55 (m, 1H), 1.59-1.99 (m, 8H), 2.35-2.39 (m, 1H), 2.58-2.64 (m, 3H), 2.68-2.76 (m, 1H), 4.57-4.66 (m, 1H), 6.35 (d, J = 1.22 Hz, 1H), 7.11 (s, 1H), 7.21 (dd, J = 7.95, 1.83 Hz, 1H), 7.32-7.34 (m, 2H), 12.18 (br s, 1H). | 501 | 499 |
| 105 | $^1$H-NMR (400 MHz, DMSO-d$_6$) δ: 0.67-0.76 (m, 1H), 0.78 (dd, J = 6.60, 1.71 Hz, 6H), 0.95 (s, 9H), 1.13-1.30 (m, 2H), 1.37-1.42 (m, 2H), 1.48-1.55 (m, 1H), 1.59-1.99 (m, 8H), 2.35-2.39 (m, 1H), 2.58-2.64 (m, 3H), 2.68-2.76 (m, 1H), 4.57-4.66 (m, 1H), 6.35 (d, J = 1.22 Hz, 1H), 7.11 (s, 1H), 7.21 (dd, J = 7.95, 1.83 Hz, 1H), 7.32-7.34 (m, 2H), 12.18 (br s, 1H). | 501 | 499 |
| 106 | $^1$H-NMR (400 MHz, DMSO-d$_6$) δ: 0.79 (d, J = 6.80 Hz, 3H), 0.95-0.98 (m, 3H), 0.95 (s, 9H), 1.36-1.45 (m, 4H), 1.70-1.74 (m, 1H), 1.85-1.93 (m, 1H), 2.09-2.15 (m, 1H), 2.28 (s, 6H), 2.30-2.37 (m, 1H), 2.59-2.65 (m, 2H), 5.89 (d, J = 1.62 Hz, 1H), 7.12 (s, 1H), 7.20 (dd, J = 8.09, 1.85 Hz, 1H), 7.31-7.35 (m, 2H), 12.44 (br s, 1H). | 485 | 483 |
| 107 | $^1$H-NMR (400 MHz, DMSO-d$_6$) δ: 0.57-0.62 (m, 3H), 0.91-0.97 (m, 12H), 1.21-1.30 (m, 1H), 1.34-1.41 (m, 2H), 1.46-1.66 (m, 2H), 1.79-1.91 (m, 1H), 2.12-2.20 (m, 1H), 2.27 (s, 6H), 2.29-2.37 (m, 1H), 2.58-2.64 (m, 2H), 6.21 (s, 1H), 7.01 (s, 1H), 7.18-7.25 (m, 1H), 7.28-7.32 (m, 2H), 12.41 (br s, 1H). | 485 | 483 |

| Example | ¹H-NMR | MS M + H | M − H |
|---|---|---|---|
| 108 | ¹H-NMR (400 MHz, DMSO-d₆) δ: 0.44 (d, J = 7.29 Hz, 1.89H), 0.88 (d, J = 6.94 Hz, 1.11H), 0.95 (s, 9H), 1.02 (s, 1.89H), 1.04 (s, 1.11H), 1.11 (s, 1.11H), 1.25 (s, 1.89H), 1.34-1.41 (m, 2H), 1.94-1.99 (m, 0.37H), 2.13 (q, J = 7.29 Hz, 0.63H), 2.30 (s, 2.22H), 2.31 (s, 3.88H), 2.59-2.66 (m, 2H), 3.66 (d, J = 12.02 Hz, 0.63H), 3.69 (d, J = 11.90 Hz, 0.37H), 4.06 (d, J = 11.90 Hz, 0.37H), 4.23 (d, J = 12.25 Hz, 0.63H), 5.88 (d, J = 1.85 Hz, 0.37H), 6.21 (s, 0.63H), 7.06 (s, 0.63H), 7.16 (s, 0.37H), 7.26-7.42 (m, 3H), 12.50 (br s, 1H). | 501 | 499 |
| 109 | ¹H-NMR (400 MHz, DMSO-d₆) δ: 0.88 (d, J = 6.94 Hz, 3H), 0.95 (s, 9H), 1.04 (s, 3H), 1.11 (s, 3H), 1.37-1.41 (m, 2H), 1.94-1.99 (m, 1H), 2.30 (s, 6H), 2.60-2.65 (m, 2H), 3.69 (d, J = 11.90 Hz, 1H), 4.06 (d, J = 11.90 Hz, 1H), 5.88 (d, J = 1.85 Hz, 1H), 7.16 (s, 1H), 7.28-7.42 (m, 3H), 12.50 (br s, 1H). | 501 | 499 |
| 110 | ¹H-NMR (400 MHz, DMSO-d₆) δ: 0.44 (d, J = 7.29 Hz, 3H), 0.95 (s, 9H), 1.02 (s, 3H), 1.25 (s, 3H), 1.34-1.41 (m, 2H), 2.13 (q, J = 7.29 Hz, 1H), 2.31 (s, 6H), 2.59-2.66 (m, 2H), 3.66 (d, J = 12.02 Hz, 1H), 4.23 (d, J = 12.25 Hz, 1H), 6.21 (s, 1H), 7.06 (s, 1H), 7.26-7.38 (m, 3H), 12.49 (br s, 1H). | 501 | 499 |
| 111 | ¹H-NMR (400 MHz, CDCl₃) δ: 0.83 (d, J = 5.38 Hz, 3H), 0.98-0.92 (m, 1H), 0.99 (s, 9H), 1.45-1.49 (m, 2H), 1.54-1.67 (m, 3H), 1.95-2.07 (m, 9H), 2.11-2.14 (m, 1H), 2.52-2.56 (m, 1H), 2.65-2.69 (m, 2H), 5.38 (s, 1H), 5.92 (s, 1H), 7.15 (dd, J = 8.07, 1.96 Hz, 1H), 7.20 (d, J = 8.07 Hz, 1H), 7.29 (d, J = 1.96 Hz, 1H). | 485 | 483 |
| 112 | ¹H-NMR (400 MHz, CDCl₃) δ: 0.83 (d, J = 5.38 Hz, 3H), 0.98-0.92 (m, 1H), 0.99 (s, 9H), 1.45-1.49 (m, 2H), 1.54-1.67 (m, 3H), 1.95-2.07 (m, 9H), 2.11 2.14 (m, 1H), 2.52-2.56 (m, 1H), 2.65-2.69 (m, 2H), 5.38 (s, 1H), 5.92 (s, 1H), 7.15 (dd, J = 8.07, 1.96 Hz, 1H), 7.20 (d, J = 8.07 Hz, 1H), 7.29 (d, J = 1.96 Hz, 1H). | 485 | 483 |
| 113 | ¹H-NMR (400 MHz, DMSO-d₆) δ: 0.62 (d, J = 7.40 Hz, 3H), 0.96 (d, J = 6.80 Hz, 3H), 1.09 (s, 9H), 1.24-1.31 (m, 1H), 1.49-1.65 (m, 2H), 1.84-1.92 (m, 1H), 2.06-2.22 (m, 2H), 2.26-2.37 (m, 1H), 2.29 (s, 6H), 2.89 (dd, J = 14.33, 9.25 Hz, 1H), 6.25 (s, 1H), 7.10 (s, 1H), 7.29-7.35 (m, 2H), 7.40-7.43 (m, 1H), 12.44 (br s, 1H). | 533 | 531 |
| 114 | ¹H-NMR (400 MHz, DMSO-d₆) δ: 0.62 (d, J = 7.40 Hz, 3H), 0.96 (d, J = 6.80 Hz, 3H), 1.09 (s, 9H), 1.24-1.31 (m, 1H), 1.49-1.65 (m, 2H), 1.84-1.92 (m, 1H), 2.06-2.22 (m, 2H), 2.26-2.37 (m, 1H), 2.29 (s, 6H), 2.89 (dd, J = 14.33, 9.25 Hz, 1H), 6.25 (s, 1H), 7.10 (s, 1H), 7.29-7.35 (m, 2H), 7.40-7.43 (m, 1H), 12.44 (br s, 1H). | 533 | 531 |
| 115 | ¹H-NMR (400 MHz, DMSO-d₆) δ: 0.63 (d, J = 7.60 Hz, 3H), 0.96 (d, J = 7.20 Hz, 3H), 1.10 (s, 9H), 1.24-1.31 (m, 1H), 1.48-1.64 (m, 2H), 1.80-1.96 (m, 9H), 2.06-2.22 (m, 2H), 2.87-2.93 (m, 1H), 6.19 (s, 1H), 6.98 (s, 1H), 7.32-7.35 (m, 2H), 7.43-7.46 (m, 1H), 12.25 (br s, 1H). | 547 | 545 |
| 116 | ¹H-NMR (400 MHz, DMSO-d₆) δ: 0.63 (d, J = 7.60 Hz, 3H), 0.96 (d, J = 7.20 Hz, 3H), 1.10 (s, 9H), 1.24-1.31 (m, 1H), 1.48-1.64 (m, 2H), 1.80-1.96 (m, 9H), 2.06-2.22 (m, 2H), 2.87-2.93 (m, 1H), 6.19 (s, 1H), 6.98 (s, 1H), 7.32-7.35 (m, 2H), 7.43-7.46 (m, 1H), 12.25 (br s, 1H). | 547 | 545 |
| 117 | ¹H-NMR (400 MHz, DMSO-d₆) δ: 0.39 (d, J = 7.28 Hz, 3H), 0.75 (s, 3H), 0.95 (s, 9H), 0.97 (s, 3H), 1.10-1.26 (m, 2H), 1.35-1.46 (m, 3H), 1.77-1.85 (m, 1H), 1.99-2.05 (m, 1H), 2.29 (s, 6H), 2.59-2.66 (m, 2H), 6.18 (s, 1H), 7.04 (s, 1H), 7.20-7.35 (m, 3H). | 499 | 497 |
| 118 | ¹H-NMR (400 MHz, DMSO-d₆) δ: 0.39 (d, J = 7.28 Hz, 3H), 0.75 (s, 3H), 0.95 (s, 9H), 0.97 (s, 3H), 1.10-1.26 (m, 2H), 1.35-1.46 (m, 3H), 1.77-1.85 (m, 1H), 1.99-2.05 (m, 1H), 2.29 (s, 6H), 2.59-2.66 (m, 2H), 6.18 (s, 1H), 7.04 (s, 1H), 7.20-7.35 (m, 3H). | 499 | 497 |
| 119 | ¹H-NMR (400 MHz, DMSO-d₆) δ: 0.45 (d, J = 7.40 Hz, 1.77H), 0.87 (d, J = 6.70 Hz, 1.23H), 0.95 (s, 9H), 1.01 (s, 1.77H), 1.05 (s, 1.23H), 1.11 (s, 1.23H), 1.25 (s, 1.77H), 1.36-1.41 (m, 2H), 1.80-1.98 (m, 8.41H), 2.09-2.14 (m, 0.59H), 2.59-2.66 (m, 2H), 3.67 (d, J = 12.25 Hz, 0.59H), 3.70 (d, J = 12.02 Hz, 0.41H), 4.06 (d, J = 11.79 Hz, 0.41H), 4.24 (d, J = 12.25 Hz, 0.59H), 5.82 (d, J = 1.85 Hz, 0.41H), 6.15 (s, 0.59H), 6.95 (s, 0.59H), 7.05 (s, 0.41H), 7.31-7.44 (m, 3H), 12.30 (br s, 1H). | 545 | 513 |
| 120 | ¹H-NMR (400 MHz, DMSO-d₆) δ: 0.45 (d, J = 7.40 Hz, 3H), 0.95 (s, 9H), 1.01 (s, 3H), 1.25 (s, 3H), 1.36-1.41 (m, 2H), 1.80-1.97 (m, 8H), 2.09-2.14 (m, 1H), 2.59-2.66 (m, 2H), 3.67 (d, J = 12.25 Hz, 1H), 4.24 (d, J = 12.25 Hz, 1H), 6.15 (s, 1H), 6.95 (s, 1H), 7.31-7.41 (m, 3H), 12.31 (s, 1H). | 545 | 513 |
| 121 | ¹H-NMR (400 MHz, DMSO-d₆) δ: 0.87 (d, J = 6.70 Hz, 3H), 0.95 (s, 9H), 1.05 (s, 3H), 1.11 (s, 3H), 1.37-1.41 (m, 2H), 1.80-1.98 (m, 9H), 2.59-2.66 (m, 2H), 3.70 (d, J = 12.02 Hz, 1H), 4.06 (d, J = 11.79 Hz, 1H), 5.82 (d, J = 1.85 Hz, 1H), 7.05 (s, 1H), 7.31-7.35 (m, 2H), 7.41-7.44 (m, 1H), 12.30 (br s, 1H). | 545 | 513 |

Test Example 1

In-Vitro Assay for Inhibitory Activity Against RORγ Transcription

Inhibitory activity against RORγ transcription was assessed for test compounds by either of the following Test Method A or B of reporter gene assay.

(Test Method A)

cDNAs encoding human and mouse RORγ ligand binding domains (LBD) were obtained based on the sequences of human RORγ (Genbank registered number NM_005060.3) and mouse RORγ (Genbank registered number NM_011281.2) (LBD sequences: from Ser253 to Lys518 for human RORγ; from Ile251 to Lys516 for mouse RORγ).

LBD cDNAs of human and mouse RORγ were inserted into pFA-CMV vector (Stratagene), which expresses GAL4-DNA binding domain fusion protein. The resulting plasmids are hereinafter referred to as GAL4-hRORγ plasmid and GAL4-mRORγ plasmid, respectively.

GAL4-hRORγ plasmid or GAL4-mRORγ plasmid was transiently co-transfected into Chinese hamster ovary cells (CHO cells) with pG5-Luc (Promega), reporter plasmid expressing firefly luciferase in a GAL4-dependent manner.

TransIT (Registered trademark) CHO Transfection Kit (Mirus) was used to co-transfect CHO cells with the plasmids. One day prior to the assay, CHO cells were suspended in HAM F-12 Nutrient medium containing 10% (v/v) fetal bovine serum and seeded at $6 \times 10^6$ cells per 175 cm$^2$ cell culture flask each. 54 µL of TransIT (Registered trademark) CHO reagent was added into a 15 mL tube containing 1.16 mL of HAM F-12 Nutrient medium without fetal bovine serum, and then mixed and incubated at room temperature for 10 minutes. 36 µL of a plasmid solution containing 400 ng of GAL4-hRORγ plasmid, 9000 ng of pG5-Luc plasmid, and 8600 ng of pcDNA3 plasmid were added into the tube and mixed gently. In the case of mouse assay, a plasmid solution containing 250 ng of GAL4-mRORγ plasmid, 9000 ng of pG5-Luc plasmid, and 8750 ng of pcDNA3 plasmid was added, instead. The mixture was incubated at room temperature for 10 minutes. 9 µL each of CHO Mojo Reagent were then added into each tube and mixed gently. The mixture was incubated at room temperature for 10 minutes. The resulting transfection reagent was applied to the cell culture. After incubation at 37° C., 5% CO$_2$ for 4 hours, the plasmid-transfected CHO cells were harvested by trypsin treatment. The collected cells were resuspended in culture medium and plated into a 384-well-white plate at 8,000 cells/50 µL/well. The plate was let stand at room temperature for 1 hour and then further incubated at 37° C., 5% CO$_2$ for 3 hours. A test compound was dissolved in DMSO to obtain a concentration of 10 mM. Each solution was serially diluted with DMSO and further diluted with culture medium just before use. The test compound solutions were added to the cells in the plate at 8 different concentrations. The final concentration of DMSO was 0.2% (v/v). After the addition of test compound, the cells were incubated at 31° C., 5% CO$_2$ for 2 days.

Cell viability was tested by fluorescence method with Resazurin (Invitrogen). Two days after the addition of test compound, Resazurin was diluted to 20 µM with a medium. 10 µL each of the diluted solution of Resazurin was added into the 384-well-plate. Just after the addition, fluorescence at 615 nm was measured with a 570-nm excitation wavelength (0-hour value). After incubation at 37° C., 5% CO$_2$ for 2 hours, fluorescence at 615 nm was measured with the 570-nm excitation wavelength (2-hour value). A fluorescence count (2 h–0 h) was calculated by deducting the 0-hour value from the 2-hour value. The fluorescence count (2 h–0 h) in the cells treated with 0.2% DMSO alone was defined as 100%, and the cell viability after treatment with the test compound was calculated as a percentage, %-of-control, based on the value of 0.2% DMSO alone. When the cell viability was 70% or less, a test compound was assessed to have cytotoxicity.

RORγ transcriptional activity was detected as the intracellular luciferase activity using SteadyLite HTS Reporter Gene Assay System (Perkin Elmer). SteadyLite Reagent was diluted five-fold with Extension buffer (10 mM Tricine, 0.2% (w/v) bovine serum albumin, 0.02% (v/v) Tween-20) to obtain a luciferase substrate solution. After the measurement of the cell viability with Resazurin, the medium was removed in the plate and the luciferase substrate solution was added thereto. After the incubation at room temperature for 10 minutes, luminescence of each well was measured with a microplate reader. The luciferase activity derived from the luminescence count in a vehicle-control well treated with 0.2% DMSO alone was defined as 100%, and the luciferase activity after treatment with the test compound was calculated as a percentage, %-of-control, based on the value of the vehicle-control. An $EC_{50}$ value of the test compound was calculated by curve fitting with GraphPad Prism. The luminescence counts at the concentration of test compound where cytotoxicity was observed were excluded from data analysis.

(Test Method B)

cDNAs encoding human and mouse RORγ ligand binding domains (LBD) were obtained based on the sequences of human RORγ (Genbank registered number NM_005060.3) and mouse RORγ (Genbank registered number NM_011281.2) (LBD sequences: from Ser253 to Lys518 for human RORγ; from Ile251 to Lys516 for mouse RORγ).

LBD cDNAs of human and mouse RORγ were inserted into pFA-CMV vector (Agilent Technologies, Inc.), which expresses GAL4-DNA binding domain fusion protein. The resulting plasmids are hereinafter referred to as pFA/hRORγ plasmid and pFA/mRORγ plasmid, respectively.

pFA/hRORγ plasmid or pFA/mRORγ plasmid was transiently co-transfected into Chinese hamster ovary cells (CHO cells) with pG5-Luc (Promega), reporter plasmid expressing firefly luciferase in a GAL4-dependent manner.

TransIT (Registered trademark) CHO Transfection Kit (Mirus) was used to co-transfect CHO cells with the plasmids. One day prior to the assay, CHO cells were suspended in HAM F-12 Nutrient medium containing 10% (v/v) fetal bovine serum and seeded at $5.5 \times 10^6$ cells per 225 cm$^2$ cell culture flask each. 72 µL of TransIT (Registered trademark) CHO reagent was added into a 2 mL tube containing 1.55 mL of Opti-MEM, and then mixed and incubated at room temperature for 10 minutes. 50.4 µL of a plasmid solution containing 300 ng of pFA/hRORγ plasmid, 12000 ng of pG5-Luc plasmid, and 11700 ng of pcDNA3.1 plasmid were added into the tube and mixed gently. In the case of mouse assay, a plasmid solution containing 300 ng of pFA/mRORγ plasmid, 12000 ng of pG5-Luc plasmid, and 11700 ng of pcDNA3.1 plasmid was added, instead. The mixture was incubated at room temperature for 10 minutes. 12 µL each of CHO Mojo Reagent were then added into each tube and mixed gently. The mixture was incubated at room temperature for 10 minutes. The resulting transfection reagent was applied to the cell culture. After incubation at 37° C., 5% CO$_2$ for 4 hours, the plasmid-transfected CHO cells were harvested by trypsin treatment. The collected cells were resuspended in culture medium and plated into a 384-well-white plate at 8,000 cells/35 µL/well. The plate was let stand at room temperature for 1 hour and then further incubated at 37° C., 5% $CO_2$ for 3 hours. A test compound was dissolved in dimethyl sulfoxide (DMSO) to obtain a concentration of 10 mM. Each solution was serially diluted with DMSO and further diluted with culture medium just before use. The test compound solutions were added to the cells in the plate at 6 different concentrations. The final concentration of DMSO was 0.2% (v/v). After the addition of test compound, the cells were incubated at 37° C., 5% $CO_2$ for 2 days.

Cell viability was tested by luminescence method with CellTiter-Glo (Promega). Two days after the addition of test compound, 40 μL each of CellTiter-Glo was added into the 384-well-plate. Ten minutes after the addition, luminescence was measured for each well with a microplate reader. The luminescence count in the cells treated with 0.2% DMSO alone was defined as 100%, and the cell viability after treatment with the test compound was calculated as a percentage, %-of-control, based on the value of 0.2% DMSO alone. When the cell viability was 70% or less, a test compound was assessed to have cytotoxicity.

RORγ transcriptional activity was detected as the intracellular luciferase activity using SteadyLite HTS Reporter Gene Assay System (Perkin Elmer). SteadyLite Reagent was diluted 2.5-fold with Extension buffer (10 mM Tricine, 0.2% (w/v) bovine serum albumin, 0.02% (v/v) Tween-20) to obtain a luciferase substrate solution. Two days after the addition of test compound, 40 μL each of the luciferase substrate solution was added into the 384-well-plate. After the incubation at room temperature for 10 minutes, luminescence of each well was measured with a microplate reader. The luciferase activity derived from the luminescence count in a vehicle-control well treated with 0.2% DMSO alone was defined as 100%, and the luciferase activity after treatment of the test compound was calculated as a percentage, %-of-control, based on the value of the vehicle-control. An $EC_{50}$ value of the test compound was calculated by curve fitting. The luminescence counts at the concentration of test compound where cytotoxicity was observed were excluded from data analysis.

The results are shown in the table below.

The value with (%) is the activity after treatment with a test compound which was calculated as a %-of-control value based on 100% of the vehicle-control treated with 0.2% DMSO alone.

| Example | LUC $EC_{50}$ (μM) hRORγ | LUC $EC_{50}$ (μM) mRORγ | Test Method |
|---|---|---|---|
| 1 | 1.693 | 0.536 | A |
| 2 | 0.030 | 0.022 | A |
| 3 | 0.008 | 0.013 | A |
| 4 | 1.022 | 1.014 | A |
| 5 | 0.007 | 0.009 | A |
| 6 | 0.554 | 0.714 | A |
| 7 | 0.009 | 0.011 | A |
| 8 | 0.427 | 0.381 | A |
| 9 | 0.819 | 1.466 | A |
| 10 | 0.016 | 0.030 | A |
| 11 | 0.021 | 0.022 | A |
| 12 | 2.584 | 3.429 | A |
| 13 | 5.701 | 5.374 | A |
| 14 | 2.878 | 3.805 | A |
| 15 | >8 (71%) | >8 (69%) | A |
| 16 | 0.755 | 0.774 | A |
| 17 | >20 (65%) | >20 (78%) | A |
| 18 | 0.773 | 0.452 | A |
| 19 | 17.130 | 15.590 | A |
| 20 | 0.025 | 0.025 | A |
| 21 | 2.263 | 1.270 | A |
| 22 | 16.170 | >8 (74%) | A |
| 23 | 0.224 | 0.106 | A |
| 24 | 0.332 | 0.126 | A |
| 25 | 0.092 | 0.105 | A |
| 26 | 0.351 | 0.243 | A |
| 27 | 0.027 | 0.039 | A |
| 28 | >20 (64%) | >20 (73%) | A |
| 29 | 0.173 | 0.103 | A |
| 30 | >20 (60%) | >20 (54%) | A |
| 31 | 0.048 | 0.048 | A |
| 32 | 0.021 | 0.018 | A |
| 33 | 2.964 | >3.2 (52%) | A |
| 34 | 0.087 | 0.169 | B |
| 35 | 4.193 | 4.974 | B |
| 36 | 0.435 | 0.071 | A |
| 37 | 3.870 | 5.508 | A |
| 38 | 0.011 | 0.021 | A |
| 39 | 0.032 | 0.021 | A |
| 40 | 4.638 | 5.328 | A |
| 41 | 0.017 | 0.013 | A |
| 42 | 0.290 | 0.139 | A |
| 43 | 0.043 | 0.159 | A |
| 44 | 1.274 | 0.482 | A |
| 45 | 1.627 | 0.840 | A |
| 46 | 0.302 | 0.211 | A |
| 47 | >8 (51%) | 8.828 | A |
| 48 | 1.990 | 1.867 | A |
| 49 | >3.2 (85%) | >3.2 (87%) | A |
| 50 | >8 (51%) | 7.479 | A |
| 51 | 4.971 | 1.796 | A |
| 52 | 0.018 | 0.029 | A |
| 53 | >3.2 (69%) | 2.732 | A |
| 54 | 0.064 | 0.035 | A |
| 55 | 0.093 | 0.058 | A |
| 56 | 0.020 | 0.029 | A |
| 57 | 0.034 | 0.021 | A |
| 58 | 0.033 | 0.020 | A |
| 59 | 0.279 | 0.149 | A |
| 60 | 0.118 | 0.072 | A |
| 61 | 0.106 | 0.068 | A |
| 62 | 0.151 | 0.099 | A |
| 63 | 0.022 | 0.022 | A |
| 64 | 0.034 | 0.052 | A |
| 65 | 1.159 | 0.160 | A |
| 66 | 0.024 | 0.030 | A |
| 67 | 4.719 | 8.341 | A |
| 68 | 0.015 | 0.016 | A |
| 69 | 0.015 | 0.027 | A |
| 70 | 0.541 | 0.516 | A |
| 71 | 0.010 | 0.007 | A |
| 72 | 0.028 | 0.015 | A |
| 73 | 0.014 | 0.027 | A |
| 74 | 0.016 | 0.024 | A |
| 75 | 0.061 | 0.038 | A |
| 76 | 2.406 | 3.031 | A |
| 77 | 0.024 | 0.031 | A |
| 78 | 2.203 | >3.2 (51%) | A |
| 79 | 0.018 | 0.022 | A |
| 80 | >10 (64%) | >10 (61%) | A |
| 81 | 0.013 | 0.019 | A |
| 82 | 9.866 | 9.792 | A |
| 83 | 0.014 | 0.018 | A |
| 84 | >10 (61%) | >10 (74%) | A |
| 85 | 0.033 | 0.073 | A |
| 86 | 4.942 | 4.366 | B |
| 87 | 0.038 | 0.029 | B |
| 88 | 0.751 | 0.169 | B |
| 89 | 3.707 | 4.191 | B |
| 90 | 0.022 | 0.023 | B |
| 91 | 0.111 | 0.185 | B |
| 92 | 0.042 | 0.019 | B |
| 93 | 3.968 | 4.231 | B |
| 94 | 0.046 | 0.082 | B |
| 95 | 2.344 | 0.455 | B |
| 96 | >10 (84%) | >10 (84%) | B |

-continued

| Example | LUC EC$_{50}$ (µM) hRORγ | mRORγ | Test Method |
|---|---|---|---|
| 97 | 0.110 | 0.156 | B |
| 98 | 4.359 | 5.107 | B |
| 99 | 0.053 | 0.146 | B |
| 100 | 0.206 | 0.055 | B |
| 101 | 7.284 | 1.390 | B |
| 102 | 3.954 | 4.572 | B |
| 103 | 0.026 | 0.046 | B |
| 104 | 5.261 | 5.278 | B |
| 105 | 0.102 | 0.113 | B |
| 106 | 4.398 | 4.778 | B |
| 107 | 0.027 | 0.032 | B |
| 108 | 4.689 | 5.053 | B |
| 109 | 0.033 | 0.036 | B |
| 110 | 0.010 | 0.012 | B |
| 111 | 3.449 | 3.660 | B |
| 112 | 0.035 | 0.038 | B |
| 113 | 0.033 | 0.037 | B |
| 114 | 0.027 | 0.050 | B |
| 115 | 0.031 | 0.049 | B |
| 116 | 0.044 | 0.101 | B |
| 117 | 4.679 | 5.296 | B |
| 118 | 0.033 | 0.082 | B |
| 119 | >10 | >10 | B |
| 120 | 0.013 | 0.020 | B |
| 121 | 0.035 | 0.040 | B |

Formulation Examples

Formulation Examples in the present invention include, for example, the following formulations. The present invention, however, is not intended to be limited to these Formulation Examples.

Formulation Example 1

Preparation of a Capsule

| 1) | Example 1 Compound | 30 mg |
|---|---|---|
| 2) | Microcrystalline cellulose | 10 mg |
| 3) | Lactose | 19 mg |
| 4) | Magnesium stearate | 1 mg |

Ingredients 1), 2), 3), and 4) are mixed to be filled in a gelatin capsule.

Formulation Example 2

Preparation of a Tablet

| 1) | Example 1 Compound | 10 g |
|---|---|---|
| 2) | Lactose | 50 g |
| 3) | Cornstarch | 15 g |
| 4) | Carmellose calcium | 44 g |
| 5) | Magnesium stearate | 1 g |

The total amount of ingredients 1), 2), and 3) and 30 g of Ingredient 4) are combined with water, dried in vacuo, and then granulated. The resulted granules are mixed with 14 g of Ingredient 4) and 1 g of Ingredient 5), and tabletted with a tableting machine. In this manner, 1000 tablets comprising 10 mg of Example 1 Compound per each are obtained.

INDUSTRIAL APPLICABILITY

A compound of Formula [I] or a pharmaceutically acceptable salt thereof is expected to be useful for treating or preventing autoimmune diseases, allergic diseases, dry eye, fibrosis, cancers, metabolic disease, ischemia, cardiomyopathy, hypertension, and periodontal disease.

The invention claimed is:
1. A compound of Formula [I]:

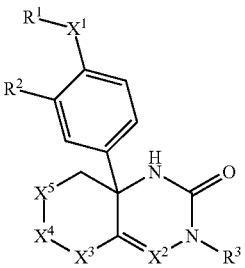

wherein R$^1$ is
(1) C$_{1-8}$ alkyl,
(2) halo-C$_{1-8}$ alkyl,
(3) C$_{3-8}$ cycloalkyl optionally substituted with the same or different 1 to 3 substituents selected from Group A$^1$, or
(4) C$_{3-8}$ cycloalkyl-C$_{1-4}$ alkyl wherein the C$_{3-8}$ cycloalkyl moiety may be optionally substituted with the same or different 1 to 3 substituents selected from Group A$^1$,
Group A$^1$ is
(1) halogen,
(2) C$_{1-4}$ alkyl, or
(3) halo-C$_{1-4}$ alkyl,
X$^1$ is
(1) a bond, or
(2) —O—,
R$^2$ is
(1) hydrogen, or
(2) halogen,
R$^3$ is
(1) hydrogen, or
(2) —Y$^3$—COO—R$^{30}$,
Y$^3$ is
(1) C$_{1-8}$ alkylene,
(2) C$_{3-8}$ cycloalkylene,
(3) bridged C$_{5-8}$ cycloalkylene, or
(4) C$_{6-14}$ arylene,
R$^{30}$ is
(1) hydrogen, or
(2) C$_{1-4}$ alkyl,
X$^2$ is
(1) =C(R$^4$)—, or
(2) =N—,
R$^4$ is
(1) hydrogen, or
(2) C$_{1-4}$ alkyl,
X$^3$ is
(1) —C(R$^5$)(R$^6$)—, $X^4$ is
(1) a bond, or
(2) —C($R^7$)($R^8$)—,
$X^5$ is
(1) —C($R^9$)($R^{10}$)—,
(2) —N($R^{11}$)—, or
(3) —O—,
$R^5$ and $R^6$ are each independently
(1) hydrogen,
(2) $C_{1-4}$ alkyl,
(3) halo-$C_{1-4}$ alkyl,
(4) cyano-$C_{1-4}$ alkyl, or
(5) $C_{1-4}$ alkyl substituted with one substituent selected from the group consisting of —O—$R^{51}$, —CO—$R^{61}$, —COO—$R^{52}$, —N($R^{71}$)($R^{72}$), —CO—N($R^{73}$)($R^{74}$), —N($R^{75}$)—CO—$R^{62}$, —N($R^{76}$)—COO—$R^{53}$, and —O—S(O)$_2$—$R^{63}$,
$R^7$, $R^8$, $R^9$, and $R^{10}$ are each independently
(1) hydrogen,
(2) halogen,
(3) cyano,
(4) hydroxy,
(5) $C_{1-4}$ alkyl,
(6) halo-$C_{1-4}$ alkyl,
(7) cyano-$C_{1-4}$ alkyl,
(8) $C_{1-4}$ alkoxy, or
(9) $C_{1-4}$ alkyl substituted with one substituent selected from the group consisting of —O—$R^{51}$, —CO—$R^{61}$, —COO—$R^{52}$, —N($R^{71}$)($R^{72}$), —CO—N($R^{73}$)($R^{74}$), —N($R^{75}$)—CO—$R^{62}$, —N($R^{76}$)—COO—$R^{53}$, and —O—S(O)$_2$—$R^{63}$,
$R^{51}$, $R^{52}$, and $R^{53}$ are each independently
(1) hydrogen,
(2) $C_{1-4}$ alkyl, or
(3) $C_{6-14}$ aryl-$C_{1-4}$ alkyl,
$R^{61}$, $R^{62}$, and $R^{63}$ are each independently
(1) $C_{1-4}$ alkyl,
$R^{71}$, $R^{72}$, $R^{73}$, $R^{74}$, $R^{75}$, and $R^{76}$ are each independently
(1) hydrogen, or
(2) $C_{1-4}$ alkyl,
$R^{11}$ is
(1) —CO—$R^{111}$, or
(2) —COO—$R^{112}$,
$R^{111}$ is
(1) $C_{1-4}$ alkyl, and
$R^{112}$ is
(1) $C_{1-4}$ alkyl, or a pharmaceutically acceptable salt thereof.

2. The compound according to claim 1, having a structure of Formula [II]:

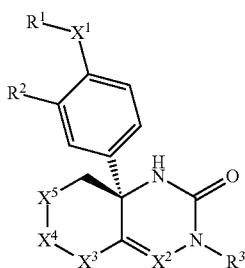

[II]

wherein each variable is defined as defined in claim 1, or a pharmaceutically acceptable salt thereof.

3. The compound according to claim 1, wherein $X^2$ is =N—, or a pharmaceutically acceptable salt thereof.

4. The compound according to claim 1, wherein $X^2$ is =C($R^4$)— and $R^4$ is hydrogen, or a pharmaceutically acceptable salt thereof.

5. The compound according to claim 1, wherein $R^3$ is hydrogen, or a pharmaceutically acceptable salt thereof.

6. The compound according to claim 1, wherein $R^3$ is —$Y^3$—COO—$R^{30}$,
$Y^3$ is
(1) $C_{1-8}$ alkylene,
(2) $C_{3-8}$ cycloalkylene, or
(3) bridged $C_{5-8}$ cycloalkylene, and
$R^{30}$ is hydrogen or $C_{1-4}$ alkyl, or a pharmaceutically acceptable salt thereof.

7. The compound according to claim 1, wherein $R^2$ is halogen, or a pharmaceutically acceptable salt thereof.

8. The compound according to claim 1, wherein $R^1$ is $C_{1-8}$ alkyl and $X^1$ is a bond, or a pharmaceutically acceptable salt thereof.

9. The compound according to claim 1, wherein $R^5$ and $R^6$ are each independently hydrogen or $C_{1-4}$ alkyl, or a pharmaceutically acceptable salt thereof.

10. The compound according to claim 1, wherein $X^4$ is a bond or —C($R^7$)($R^8$)— and both of $R^7$ and $R^8$ are hydrogen, or a pharmaceutically acceptable salt thereof.

11. The compound according to claim 1, wherein $X^5$ is —C($R^9$)($R^{10}$)— or —O— and both of $R^9$ and $R^{10}$ are hydrogen, or a pharmaceutically acceptable salt thereof.

12. A pharmaceutical composition comprising a compound according to claim 1 or a pharmaceutically acceptable salt thereof and a pharmaceutically acceptable carrier.

13. The compound according to claim 1, having a structure:

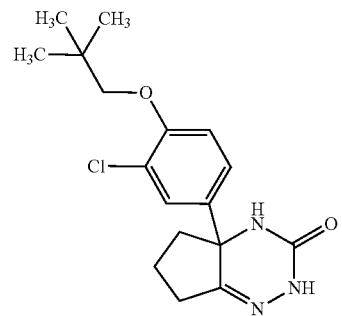 [SMILES: CC(C)(C)COc1ccc(C23CCCC2=NNC(=O)N3)cc1Cl]

or a pharmaceutically acceptable salt thereof.

14. The compound according to claim 1, having a structure:

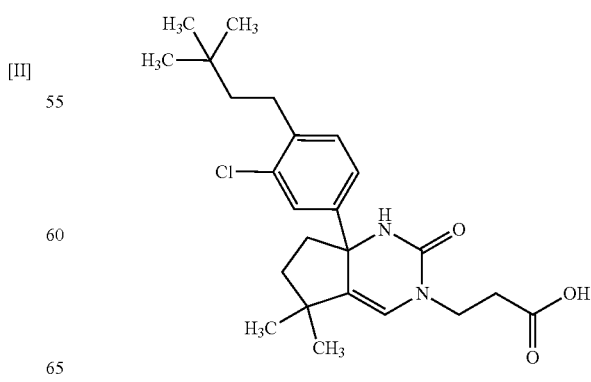

or a pharmaceutically acceptable salt thereof.

15. The compound according to claim 1, having a structure:

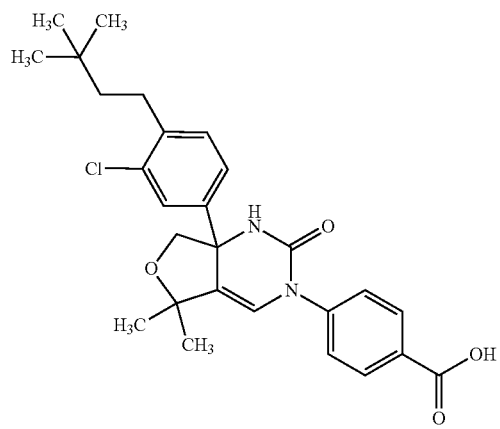 [SMILES: CC(C)(C)CCc1ccc(C23COC(C)(C)C2=CN(c2ccc(C(=O)O)cc2)C(=O)N3)cc1Cl]

or a pharmaceutically acceptable salt thereof.

16. The compound according to claim 1, having a structure:

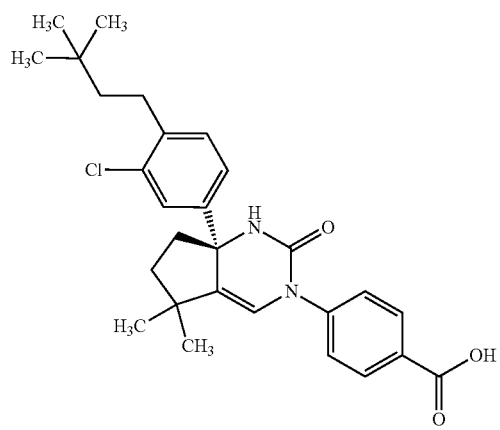 [SMILES: CC(C)(C)CCc1ccc([C@@]23CCC(C)(C)C2=CN(c2ccc(C(=O)O)cc2)C(=O)N3)cc1Cl]

or a pharmaceutically acceptable salt thereof.

17. The compound according to claim 1, having a structure:

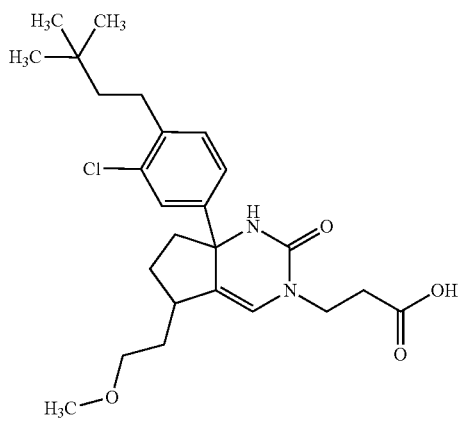 [SMILES: COCCC1CCC2(c3ccc(CCC(C)(C)C)c(Cl)c3)NC(=O)N(CCC(=O)O)C=C12]

or a pharmaceutically acceptable salt thereof.

18. The compound according to claim 1, having a structure:

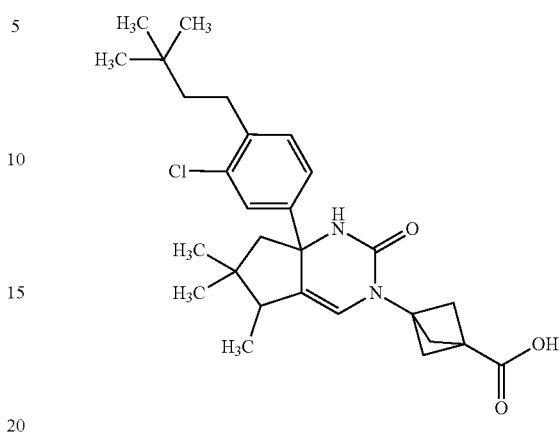

or a pharmaceutically acceptable salt thereof.

19. The compound according to claim 1, having a structure:

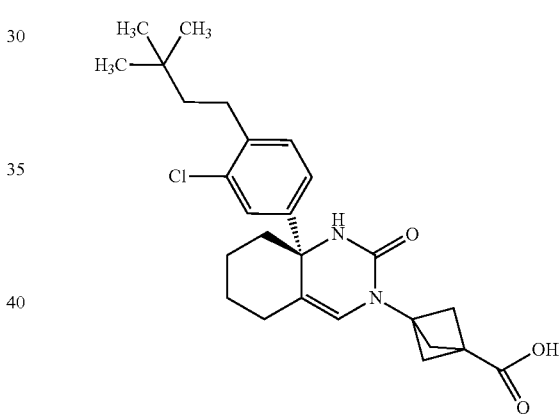

or a pharmaceutically acceptable salt thereof.

20. The compound according to claim 1, having a structure:

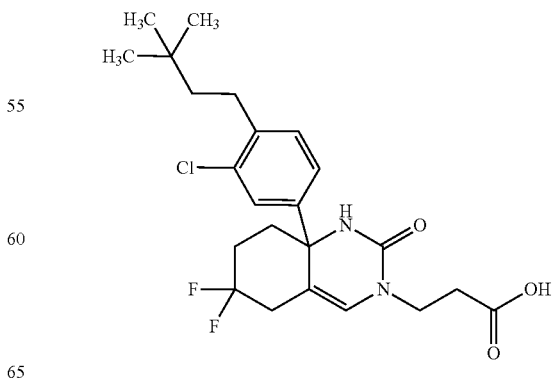

or a pharmaceutically acceptable salt thereof.

21. The compound according to claim 1, having a structure:

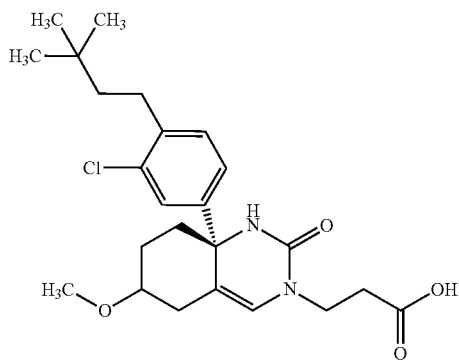

or a pharmaceutically acceptable salt thereof.

22. The compound according to claim 1, having a structure:

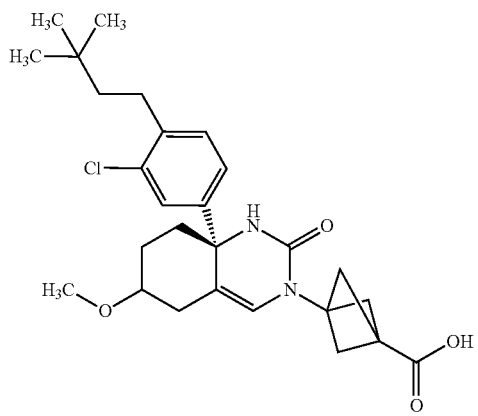

or a pharmaceutically acceptable salt thereof.

23. The compound according to claim 1, having a structure:

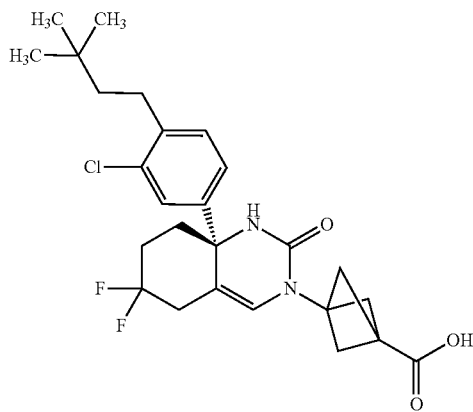 [SMILES: CC(C)(C)CCc1ccc([C@@]23CCC(F)(F)CC2=CN(C24CC(C(=O)O)(C2)C4)C(=O)N3)cc1Cl]

or a pharmaceutically acceptable salt thereof.

24. The compound according to claim 1, having a structure:

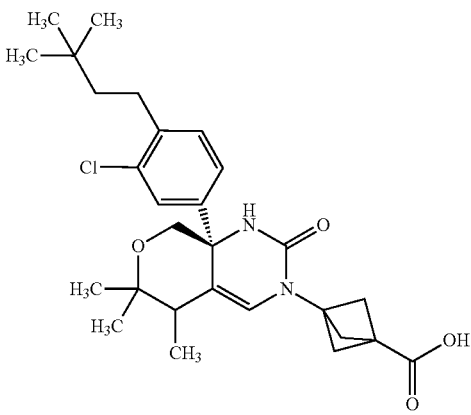

or a pharmaceutically acceptable salt thereof.

25. The compound according to claim 1, having a structure:

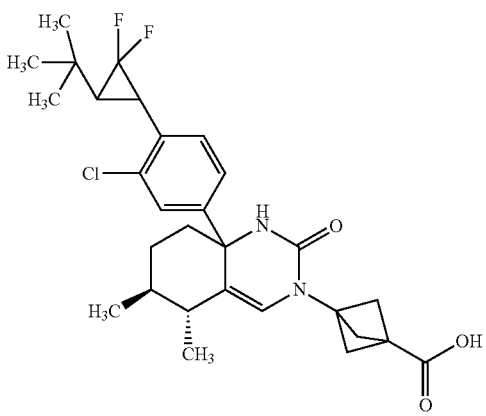 [SMILES: C[C@H]1CCC2(c3ccc(C4C(C(C)(C)C)C4(F)F)c(Cl)c3)NC(=O)N(C34CC(C(=O)O)(C3)C4)C=C2[C@@H]1C]

or a pharmaceutically acceptable salt thereof.

26. The compound according to claim 1, having a structure:

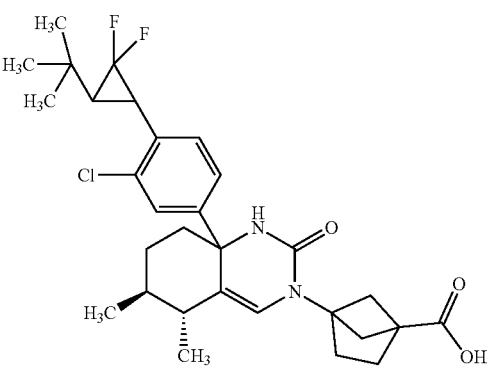 [SMILES: C[C@H]1CCC2(c3ccc(C4C(C(C)(C)C)C4(F)F)c(Cl)c3)NC(=O)N(C34CCC(C(=O)O)(C3)C4)C=C2[C@@H]1C]

or a pharmaceutically acceptable salt thereof.

27. The compound according to claim 1, having a structure:
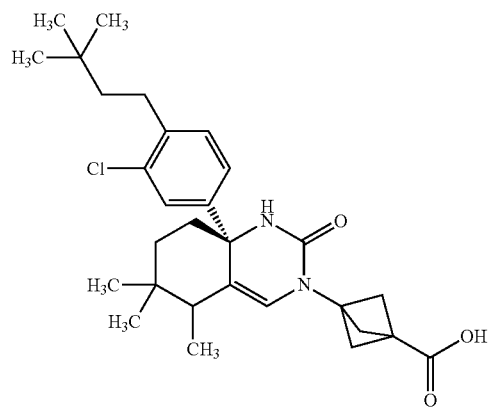
or a pharmaceutically acceptable salt thereof.
28. The compound according to claim 1, having a structure:
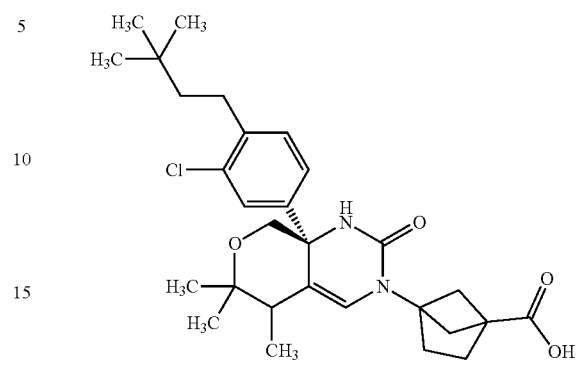
or a pharmaceutically acceptable salt thereof.
* * * * *